United States Patent
Spergel et al.

(10) Patent No.: US 11,866,414 B2
(45) Date of Patent: Jan. 9, 2024

(54) SUBSTITUTED HETEROCYCLIC COMPOUNDS

(71) Applicant: BRISTOL-MYERS SQUIBB COMPANY, Princeton, NJ (US)

(72) Inventors: Steven H. Spergel, Warrington, PA (US); Ryan M. Moslin, Princeton, NJ (US); Michael Edward Mertzman, New Hope, PA (US); Zili Xiao, East Windsor, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 17/743,557

(22) Filed: May 13, 2022

(65) Prior Publication Data

US 2022/0411384 A1  Dec. 29, 2022

Related U.S. Application Data

(60) Provisional application No. 63/318,149, filed on Mar. 9, 2022, provisional application No. 63/188,498, filed on May 14, 2021.

(51) Int. Cl.
*C07D 249/04* (2006.01)
*A61P 25/28* (2006.01)
*A61P 25/16* (2006.01)
*A61K 31/501* (2006.01)

(52) U.S. Cl.
CPC .......... *C07D 249/04* (2013.01); *A61K 31/501* (2013.01); *A61P 25/16* (2018.01); *A61P 25/28* (2018.01)

(58) Field of Classification Search
CPC ........ C07D 249/04; A61P 25/28; A61P 25/16; A61K 31/501
See application file for complete search history.

(56) References Cited

U.S. PATENT DOCUMENTS 9,505,748 B2 * 11/2016 Moslin ................ C07D 417/14

FOREIGN PATENT DOCUMENTS

WO    2014/074661 A1    5/2014

* cited by examiner

*Primary Examiner* — Timothy R Rozof
(74) *Attorney, Agent, or Firm* — Elliott Korsen

(57) ABSTRACT

There are disclosed compounds of the following formula I:

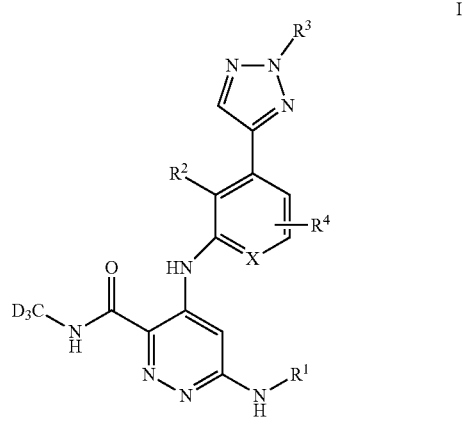

or a stereoisomer or pharmaceutically acceptable salt thereof, wherein all substituents are as defined herein, which are useful in the modulation of IL-12, IL-23 and/or IFNα, by acting on Tyk-2 to cause signal transduction inhibition. The compounds of the invention may be useful for treating neurodegenerative diseases or disorders.

23 Claims, 1 Drawing Sheet

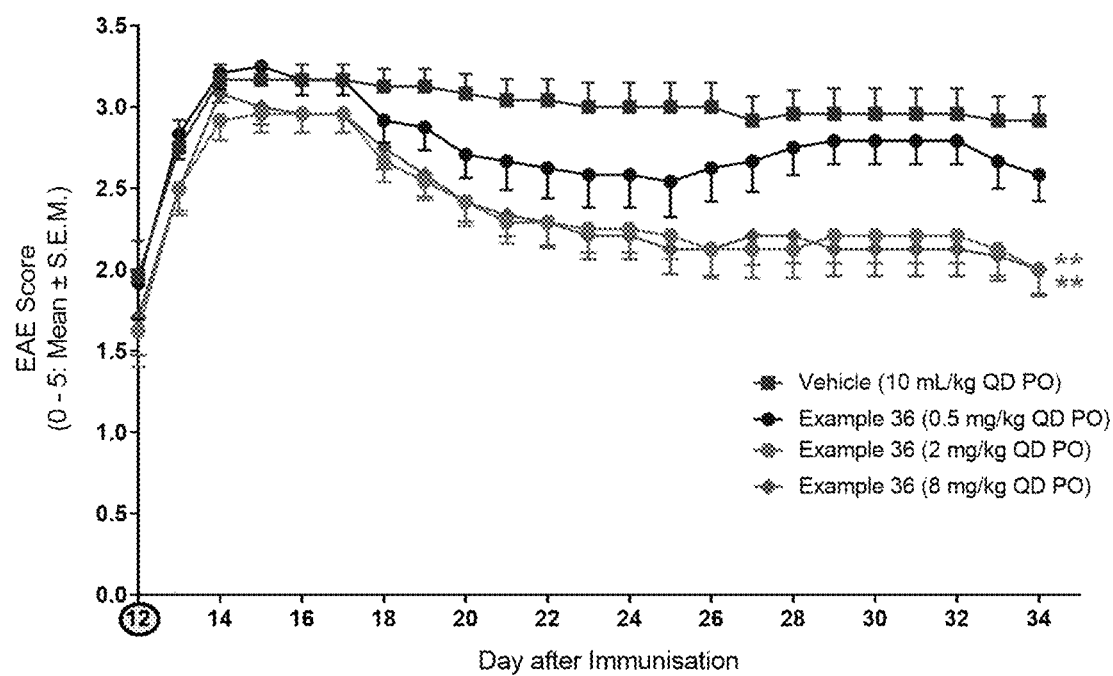

SUBSTITUTED HETEROCYCLIC COMPOUNDS

CROSS-REFERENCE TO RELATED APPLICATIONS

This application claims the benefit of U.S. Provisional Application No. 63/188,498, filed May 14, 2021, and U.S. Provisional Application No. 63/318,148, filed Mar. 9, 2022, the disclosures of which are incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are -substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal. In particular, this invention relates to compounds which show utility against neurodegenerative diseases.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR).

Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7: e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", Rheumatology (Oxford), 46:927-930 (2007); Eyre, S. et al., "High-density genetic mapping identifies new susceptibility loci for rheumatoid arthritis", *Nat. Genet.*, 44:1336-1340 (2012)).

TYK2 inhibition may also be utilized in both solid tumors and hematologic malignancies both as a monotherapy and in combination with existing standards of care including immunotherapy.

Ex vivo studies in T-cell acute lymphoblastic leukemia (T-ALL) have shown that TYK2 is required for the survival of T-ALL, suggesting a potential direct cancer killing mechanism for TYK2 inhibitors in this indication, Sanda, T. et al. TYK2-STAT1-BCL2 Pathway Dependence in T-cell Acute Lymphoblastic Leukemia. *Cancer Discov.* 3, 564-577 (2013). Multiple TYK2 activating mutations in T-ALL cell lines have been detected and characterized. NPM1-TYK2 gene fusions have also been identified in a subset of cutaneous T-cell lymphomas (CTCL), and TYK2 was shown to be an oncogenic driver of transformation, Kuravi, S. et al. Functional characterization of NPM1-TYK2 fusion oncogene. *Npj Precis. Oncol.* 6, 3 (2022). Loss of TYK2 signaling could inhibit this transformational potential.

Effective TYK2 inhibitors have been described; however, these compounds tend to be highly polar compounds subject to high efflux ratios in standard efflux models, Wrobleski, S. T. et al. Highly selective inhibition of Tyrosine Kinase 2 (TYK2) for the treatment of autoimmune diseases: Discovery of the allosteric inhibitor BMS-986165. *J. Med. Chem.* 62, 8973-8995 (2019). It is well established that one pathway for multidrug resistance is increased expression of efflux transporters, Gottesman, M. M. et al. Multidrug Resistance in Cancer: Role of ATP-Dependent Transporters. *Nature Rev. Cancer* 2, 48-58 (2002), Fletcher, J. I. et al. ABC transporters in cancer: more than just drug efflux pumps. *Nature Rev. Cancer* 10, 147-156 (2010).

Therefore, compounds with lower efflux ratios in in vitro models could potentially have a greater chance of effectively treating some oncogenic indications.

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating neurodegenerative diseases, comprising administering to a host in need of such treatment a therapeutically effective amount of at least one of the compounds of the present invention.

The present invention also provides the compounds of the present invention for use in therapy.

These and other features of the invention will be set forth in the expanded form as the disclosure continues.

BRIEF DESCRIPTION OF THE DRAWINGS

FIG. 1 shows a graph of the Disease Score in EAE $MOG_{1-125}$ model for the compound of Example 36

DETAILED DESCRIPTION OF THE EMBODIMENTS OF THE INVENTION

In a first aspect of the present invention, there is provided a compound of the formula

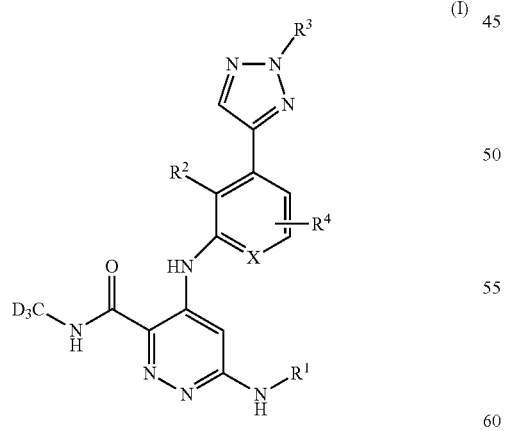

(I)

or a stereoisomer or pharmaceutically acceptable salt thereof, wherein
X is —N— or —CH—;
$R^1$ is —C(O)$R^{1a}$; or a 5-8 membered heterocycle containing 1-2 heteroatoms selected from N, O, and S, each heterocycle substituted with 0-2 $R^{1b}$;

$R^{1a}$ is COO$C_{1-3}$ alkyl, or $C_{3-6}$ cycloalkyl, said cycloalkyl group substituted with 0-2 $R^{1b}$;
$R^{1b}$ is independently at each occurrence, F or $C_{1-3}$ alkyl;
$R^2$ is OMe or OCHF$_2$.
$R^3$ is CD$_3$, $C_{1-3}$ alkyl, $C_{3-6}$ cycloalkyl or (CH$_2$)F; and
$R^4$ is hydrogen, halo, $C_{1-4}$ alkyl, $C_{1-4}$ alkoxy or $C_{3-6}$ cycloalkyl.

In a second aspect of the invention, there is provided the compound of formula II

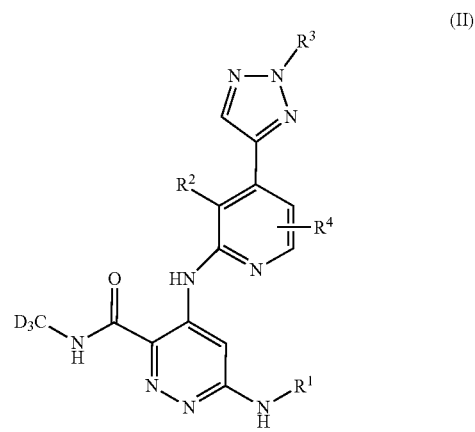

(II)

or a stereoisomer or pharmaceutically acceptable salt thereof, wherein
$R^1$ is —C(O)$R^{1a}$; or a 5-8 membered heterocycle containing 1-2 heteroatoms selected from N, O, and S, each heterocycle substituted with 0-2 $R^{1b}$;
$R^{1a}$ is COO$C_{1-3}$ alkyl, or $C_{3-6}$ cycloalkyl, said cycloalkyl group substituted with 0-2 $R^{1b}$;
$R^{1b}$ is independently at each occurrence, F or $C_{1-3}$ alkyl;
$R^2$ is OMe or OCHF$_2$.
$R^3$ is CD$_3$, $C_{1-3}$ alkyl, $C_{3-6}$ cycloalkyl or (CH$_2$)F; and
$R^4$ is hydrogen, halo, $C_{1-4}$ alkyl, $C_{1-4}$ alkoxy or $C_{3-6}$ cycloalkyl.

In a third aspect of the invention, there is provided the compound of formula II

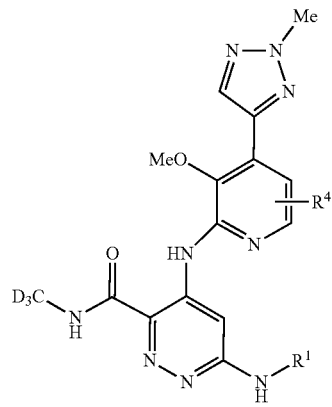

or a stereoisomer or pharmaceutically acceptable salt thereof, wherein
$R^1$ is —C(O)$R^{1a}$; or a 5-8 membered heterocycle containing 1-2 heteroatoms selected from N, O, and S, each heterocycle substituted with 0-2 $R^{1b}$;

$R^{1a}$ is COOC$_{1-3}$ alkyl, or C$_{3-6}$ cycloalkyl, said cycloalkyl group substituted with 0-2 $R^{1b}$;
$R^{1b}$ is independently at each occurrence, F or C$_{1-3}$ alkyl;
$R^4$ is hydrogen, F or CH$_3$.

In a fourth aspect of the invention, there is provided the compound of formula III

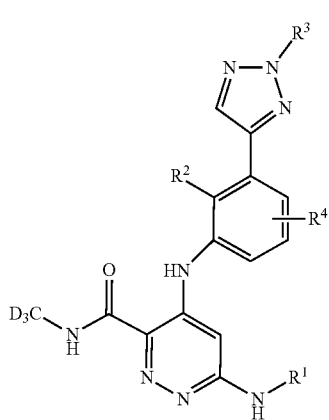

(III)

or a stereoisomer or pharmaceutically acceptable salt thereof, wherein
$R^1$ is —C(O)$R^{1a}$; or a 5-8 membered heterocycle containing 1-2 heteroatoms selected from N, O, and S, each heterocycle substituted with 0-2 $R^{1b}$;
$R^{1a}$ is COOC$_{1-3}$ alkyl, or C$_{3-6}$ cycloalkyl, said cycloalkyl group substituted with 0-2 $R^{1b}$;
$R^{1b}$ is independently at each occurrence, F or C$_{1-3}$ alkyl;
$R^2$ is OMe or OCHF$_2$.
$R^3$ is CD$_3$, C$_{1-3}$ alkyl, C$_{3-6}$ cycloalkyl or (CH$_2$)F; and
$R^4$ is hydrogen, halo, C$_{1-4}$ alkyl, C$_{1-4}$ alkoxy or C$_{3-6}$ cycloalkyl.

In a fifth aspect of the invention, there is provided the compound of the formula

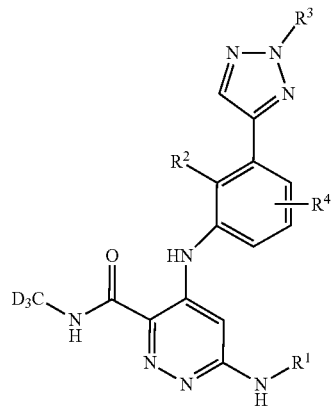

or a stereoisomer or pharmaceutically acceptable salt thereof, wherein
$R^1$ is —C(O)$R^{1a}$; or a 5-8 membered heterocycle containing 1-2 heteroatoms selected from N, O, and S, each heterocycle substituted with 0-2 $R^{1b}$;
$R^{1a}$ is COOC$_{1-3}$ alkyl, or C$_{3-6}$ cycloalkyl, said cycloalkyl group substituted with 0-2 $R^{1b}$;
$R^{1b}$ is independently at each occurrence, F or C$_{1-3}$ alkyl;
$R^4$ is hydrogen, F or CH$_3$.

In another aspect, there is provided a compound selected from the exemplified examples within the scope of the first aspect, or a pharmaceutically acceptable salt thereof.

In another aspect, there is provided a compound selected from any subset list of compounds within the scope of any of the above aspects.

In another aspect, there is provided a compound (IUPAC naming convention) or a pharmaceutically acceptable salt thereof, selected from
6-cyclopropaneamido-4-{[3-(2-ethyl-2H-1,2,3-triazol-4-yl)-2-methoxyphenyl]amino}-N—($^2$H3)methylpyridazine-3-carboxamide,
4-{[2-methoxy-3-(2-methyl-2H-1,2,3-triazol-4-yl)phenyl]amino}-6-[(6-methoxypyridazin-3-yl)amino]-N—($^2$H3)methylpyridazine-3-carboxamide,
6-cyclopropaneamido-4-{[5-fluoro-2-methoxy-3-(2-methyl-2H-1,2,3-triazol-4-yl)phenyl]amino}-N—($^2$H3)methylpyridazine-3-carboxamide,
4-{[2-methoxy-3-(2-methyl-2H-1,2,3-triazol-4-yl)phenyl]amino}-N—($^2$H3)methyl-6-[(pyridin-2-yl)amino]pyridazine-3-carboxamide,
methyl N-(5-{[2-methoxy-3-(2-methyl-2H-1,2,3-triazol-4-yl)phenyl]amino}-6-[($^2$H3)methylcarbamoyl]pyridazin-3-yl)carbamate,
6-[(1,5-dimethyl-1H-pyrazol-3-yl)amino]-4-{[2-methoxy-3-(2-methyl-2H-1,2,3-triazol-4-yl)phenyl]amino}-N—($^2$H3)methylpyridazine-3-carboxamide,
4-{[2-methoxy-3-(2-methyl-2H-1,2,3-triazol-4-yl)phenyl]amino}-N—($^2$H3)methyl-6-[(1R)-spiro[2.2]pentane-1-amido]pyridazine-3-carboxamide,
6-cyclopropaneamido-4-{[3-(2-cyclopropyl-2H-1,2,3-triazol-4-yl)-2-methoxyphenyl]amino}-N—($^2$H3)methylpyridazine-3-carboxamide,
6-cyclopropaneamido-4-{[3-(2-cyclopropyl-2H-1,2,3-triazol-4-yl)-5-fluoro-2-methoxyphenyl]amino}-N—($^2$H3)methylpyridazine-3-carboxamide,
6-cyclopropaneamido-4-{[3-(2-ethyl-2H-1,2,3-triazol-4-yl)-4-fluoro-2-methoxyphenyl]amino}-N—($^2$H3)methylpyridazine-3-carboxamide,
6-cyclopropaneamido-4-{[4-(2-cyclopropyl-2H-1,2,3-triazol-4-yl)-3-methoxypyridin-2-yl]amino}-N—($^2$H3)methylpyridazine-3-carboxamide,
6-cyclopropaneamido-4-({3-[2-(2-fluoroethyl)-2H-1,2,3-triazol-4-yl]-2-methoxyphenyl}amino)-N—($^2$H3)methylpyridazine-3-carboxamide,
6-cyclopropaneamido-4-({3-[2-(2,2-difluoroethyl)-2H-1,2,3-triazol-4-yl]-2-methoxyphenyl}amino)-N—($^2$H3)methylpyridazine-3-carboxamide,
6-cyclopropaneamido-4-{[2-methoxy-5-methyl-3-(2-methyl-2H-1,2,3-triazol-4-yl)phenyl]amino}-N—($^2$H3)methylpyridazine-3-carboxamide,
6-cyclopropaneamido-4-{[3-(2-cyclopropyl-2H-1,2,3-triazol-4-yl)-2-methoxy-5-methylphenyl]amino}-N—($^2$H3)methylpyridazine-3-carboxamide,
4-{[5-chloro-3-(2-ethyl-2H-1,2,3-triazol-4-yl)-2-methoxyphenyl]amino}-6-cyclopropaneamido-N—($^2$H3)methylpyridazine-3-carboxamide,
6-cyclopropaneamido-4-{[3-(2-cyclopropyl-2H-1,2,3-triazol-4-yl)-4-fluoro-2-methoxyphenyl]amino}-N—($^2$H3)methylpyridazine-3-carboxamide,
6-cyclopropaneamido-4-{[4-fluoro-2-methoxy-3-(2-methyl-2H-1,2,3-triazol-4-yl)phenyl]amino}-N—($^2$H3)methylpyridazine-3-carboxamide,
6-cyclopropaneamido-4-{[5-fluoro-2-methoxy-4-methyl-3-(2-methyl-2H-1,2,3-triazol-4-yl)phenyl]amino}-N—($^2$H3)methylpyridazine-3-carboxamide, 6-cyclopropaneamido-4-{[3-methoxy-4-(2-methyl-2H-1,2,3-triazol-4-yl)pyridin-2-yl]amino}-N—($^2$H3)methylpyridazine-3-carboxamide, 6-cyclopropaneamido-4-{[3-(5-ethyl-2-methyl-2H-1,2,3-triazol-4-yl)-2-methoxyphenyl]amino}-N—($^2$H3)methylpyridazine-3-carboxamide, 6-cyclopropaneamido-4-{[5-ethyl-2-methoxy-3-(2-methyl-2H-1,2,3-triazol-4-yl)phenyl]amino}-N—($^2$H3)methylpyridazine-3-carboxamide, 6-cyclopropaneamido-4-{[6-fluoro-2-methoxy-3-(2-methyl-2H-1,2,3-triazol-4-yl)phenyl]amino}-N—($^2$H3)methylpyridazine-3-carboxamide, methyl 3-({6-cyclopropaneamido-3-[($^2$H3)methylcarbamoyl]pyridazin-4-yl}amino)-4-methoxy-5-(2-methyl-2H-1,2,3-triazol-4-yl)benzoate, 6-cyclopropaneamido-4-({2-methoxy-3-[2-($^2$H3)methyl-2H-1,2,3-triazol-4-yl]phenyl}amino)-N—($^2$H3)methylpyridazine-3-carboxamide, 6-cyclopropaneamido-4-{[3-(2,5-dimethyl-2H-1,2,3-triazol-4-yl)-2-methoxyphenyl]amino}-N—($^2$H3)methylpyridazine-3-carboxamide, 6-cyclopropaneamido-4-{[2,5-dimethoxy-3-(2-methyl-2H-1,2,3-triazol-4-yl)phenyl]amino}-N—($^2$H3)methylpyridazine-3-carboxamide, 4-{[2-methoxy-3-(2-methyl-2H-1,2,3-triazol-4-yl)phenyl]amino}-N—($^2$H3)methyl-6-[(1-methyl-1H-pyrazol-3-yl)amino]pyridazine-3-carboxamide, 4-{[2-methoxy-3-(2-methyl-2H-1,2,3-triazol-4-yl)phenyl]amino}-N—($^2$H3)methyl-6-[(1R,2S)-2-methylcyclopropaneamido]pyridazine-3-carboxamide, 4-{[2-methoxy-3-(2-methyl-2H-1,2,3-triazol-4-yl)phenyl]amino}-N—($^2$H3)methyl-6-[(1R,2S)-2-methylcyclopropaneamido]pyridazine-3-carboxamide, 6-cyclopropaneamido-4-{[3-(2-cyclopropyl-5-methyl-2H-1,2,3-triazol-4-yl)-2-methoxyphenyl]amino}-N—($^2$H3)methylpyridazine-3-carboxamide, 4-{[2-methoxy-3-(2-methyl-2H-1,2,3-triazol-4-yl)phenyl]amino}-N—($^2$H3)methyl-6-[2-oxo-3-(propan-2-yl)imidazolidin-1-yl]pyridazine-3-carboxamide, 6-cyclopropaneamido-4-{[2-methoxy-4-methyl-3-(2-methyl-2H-1,2,3-triazol-4-yl)phenyl]amino}-N—($^2$H3)methylpyridazine-3-carboxamide, 6-cyclopropaneamido-4-{[3-methoxy-6-methyl-4-(2-methyl-2H-1,2,3-triazol-4-yl)pyridin-2-yl]amino}-N—($^2$H3)methylpyridazine-3-carboxamide, ethyl N-(5-{[2-methoxy-3-(2-methyl-2H-1,2,3-triazol-4-yl)phenyl]amino}-6-[($^2$H3)methylcarbamoyl]pyridazin-3-yl)carbamate, 6-[(1S,2R)-2-fluorocyclopropaneamido]-4-{[2-methoxy-3-(2-methyl-2H-1,2,3-triazol-4-yl)phenyl]amino}-N—($^2$H3)methylpyridazine-3-carboxamide, 4-{[2-methoxy-3-(2-methyl-2H-1,2,3-triazol-4-yl)phenyl]amino}-N—($^2$H3)methyl-6-[(1S,2R)-2-methylcyclopropaneamido]pyridazine-3-carboxamide, 6-[(1S,2S)-2-fluorocyclopropaneamido]-4-{[3-methoxy-4-(2-methyl-2H-1,2,3-triazol-4-yl)pyridin-2-yl]amino}-N—($^2$H3)methylpyridazine-3-carboxamide, 6-cyclopropaneamido-4-{[4-cyclopropyl-2-methoxy-3-(2-methyl-2H-1,2,3-triazol-4-yl)phenyl]amino}-N—($^2$H3)methylpyridazine-3-carboxamide, 6-(2,2-difluorocyclopropaneamido)-4-{[2-methoxy-3-(2-methyl-2H-1,2,3-triazol-4-yl)phenyl]amino}-N—($^2$H3)methylpyridazine-3-carboxamide, 6-[(azetidine-1-carbonyl)amino]-4-{[2-methoxy-3-(2-methyl-2H-1,2,3-triazol-4-yl)phenyl]amino}-N—($^2$H3)methylpyridazine-3-carboxamide, 6-cyclopropaneamido-4-({2-methoxy-3-[2-(oxetan-3-yl)-2H-1,2,3-triazol-4-yl]phenyl}amino)-N—($^2$H3)methylpyridazine-3-carboxamide, 4-{[3-(2-cyclobutyl-2H-1,2,3-triazol-4-yl)-2-methoxyphenyl]amino}-6-cyclopropaneamido-N—($^2$H3)methylpyridazine-3-carboxamide, 6-(2,2-dimethylcyclopropaneamido)-4-{[3-methoxy-4-(2-methyl-2H-1,2,3-triazol-4-yl)pyridin-2-yl]amino}-N—($^2$H3)methylpyridazine-3-carboxamide, 6-cyclopropaneamido-4-{[2-(difluoromethoxy)-3-(2-methyl-2H-1,2,3-triazol-4-yl)phenyl]amino}-N—($^2$H3)methylpyridazine-3-carboxamide, 6-[(dimethylcarbamoyl)amino]-4-{[3-methoxy-4-(2-methyl-2H-1,2,3-triazol-4-yl)pyridin-2-yl]amino}-N—($^2$H3)methylpyridazine-3-carboxamide, 4-{[3-methoxy-4-(2-methyl-2H-1,2,3-triazol-4-yl)pyridin-2-yl]amino}-N—($^2$H3)methyl-6-[(1S,2R)-2-methylcyclopropaneamido]pyridazine-3-carboxamide, 4-{[3-methoxy-4-(2-methyl-2H-1,2,3-triazol-4-yl)pyridin-2-yl]amino}-N—($^2$H3)methyl-6-[(1R,2R)-2-methylcyclopropaneamido]pyridazine-3-carboxamide, 6-(4-fluorobutanamido)-4-{[3-methoxy-4-(2-methyl-2H-1,2,3-triazol-4-yl)pyridin-2-yl]amino}-N—($^2$H3)methylpyridazine-3-carboxamide, 6-cyclopropaneamido-4-{[3-(difluoromethoxy)-4-(2-methyl-2H-1,2,3-triazol-4-yl)pyridin-2-yl]amino}-N—($^2$H3)methylpyridazine-3-carboxamide, {[(6E)-6-(cyclopropanecarbonylimino)-4-{[3-methoxy-4-(2-methyl-2H-1,2,3-triazol-4-yl)pyridin-2-yl]amino}-3-[($^2$H3)methylcarbamoyl]-1,6-dihydropyridazin-1-yl]methoxy}phosphonic acid, 4-{[3-methoxy-4-(2-methyl-2H-1,2,3-triazol-4-yl)pyridin-2-yl]amino}-N—($^2$H3)methyl-6-[(1S,2S)-2-methylcyclopropaneamido]pyridazine-3-carboxamide, 6-[(1R,2R)-2-ethylcyclopropaneamido]-4-{[3-methoxy-4-(2-methyl-2H-1,2,3-triazol-4-yl)pyridin-2-yl]amino}-N—($^2$H3)methylpyridazine-3-carboxamide, 4-{[4-(2-cyclopropyl-2H-1,2,3-triazol-4-yl)-3-methoxypyridin-2-yl]amino}-6-[(1S,2S)-2-fluorocyclopropaneamido]-N—($^2$H3)methylpyridazine-3-carboxamide, 4-{[3-methoxy-4-(2-methyl-2H-1,2,3-triazol-4-yl)pyridin-2-yl]amino}-N—($^2$H3)methyl-6-{[methyl(propan-2-yl)carbamoyl]amino}pyridazine-3-carboxamide, 6-{[ethyl(methyl)carbamoyl]amino}-4-{[3-methoxy-4-(2-methyl-2H-1,2,3-triazol-4-yl)pyridin-2-yl]amino}-N—($^2$H3)methylpyridazine-3-carboxamide, 4-{[4-(2-cyclopropyl-2H-1,2,3-triazol-4-yl)-3-methoxypyridin-2-yl]amino}-6-[(dimethylcarbamoyl)amino]-N—($^2$H3)methylpyridazine-3-carboxamide, propan-2-yl 3-({6-cyclopropaneamido-3-[($^2$H3)methylcarbamoyl]pyridazin-4-yl}amino)-4-methoxy-5-(2-methyl-2H-1,2,3-triazol-4-yl)benzoate, 6-cyclopropaneamido-4-{[2-methoxy-5-(methoxymethyl)-3-(2-methyl-2H-1,2,3-triazol-4-yl)phenyl]amino}-N—($^2$H3)methylpyridazine-3-carboxamide, 6-cyclopropaneamido-4-{[6-fluoro-3-methoxy-4-(2-methyl-2H-1,2,3-triazol-4-yl)pyridin-2-yl]amino}-N—($^2$H3)methylpyridazine-3-carboxamide, 6-cyclopropaneamido-4-({3-methoxy-4-[2-($^2$H3)methyl-2H-1,2,3-triazol-4-yl]pyridin-2-yl}amino)-N—($^2$H3)methylpyridazine-3-carboxamide, 4-{[3-methoxy-6-methyl-4-(2-methyl-2H-1,2,3-triazol-4-yl)pyridin-2-yl]amino}-N—($^2$H3)methyl-6-[(1R,2R)-2-methylcyclopropaneamido]pyridazine-3-carboxamide, 4-{[3-methoxy-6-methyl-4-(2-methyl-2H-1,2,3-triazol-4-yl)pyridin-2-yl]amino}-N—($^2$H3)methyl-6-[(1S,2S)-2-methylcyclopropaneamido]pyridazine-3-carboxamide, 4-{[3-methoxy-4-(2-methyl-2H-1,2,3-triazol-4-yl)pyridin-2-yl]amino}-N—($^2$H3)methyl-6-[(pyridin-2-yl)amino]pyridazine-3-carboxamide, 6-[(2,6-dimethylpyrimidin-4-yl)amino]-4-{[3-methoxy-4-(2-methyl-2H-1,2,3-triazol-4-yl)pyridin-2-yl]amino}-N—($^2$H3)methylpyridazine-3-carboxamide, 6-{[5-(2-hydroxypropan-2-yl)pyridin-2-yl]amino}-4-{[3-methoxy-4-(2-methyl-2H-1,2,3-triazol-4-yl)pyridin-2-yl]amino}-N—($^2$H3)methylpyridazine-3-carboxamide, 4-{[3-methoxy-4-(2-methyl-2H-1,2,3-triazol-4-yl)pyridin-2-yl]amino}-N—($^2$H3)methyl-6-{[5-(morpholin-4-yl)pyridin-2-yl]amino}pyridazine-3-carboxamide, 6-{[4-(2-hydroxypropan-2-yl)pyridin-2-yl]amino}-4-{[3-methoxy-4-(2-methyl-2H-1,2,3-triazol-4-yl)pyridin-2-yl]amino}-N—($^2$H3)methylpyridazine-3-carboxamide, and 6-[(1,5-dimethyl-1H-pyrazol-3-yl)amino]-4-{[3-methoxy-4-(2-methyl-2H-1,2,3-triazol-4-yl)pyridin-2-yl]amino}-N—($^2$H3)methylpyridazine-3-carboxamide, and 6-((1S,2S)-2-fluorocyclopropane-1-carboxamido)-4-((3-methoxy-6-methyl-4-(2-methyl-2H-1,2,3-triazol-4-yl)pyridin-2-yl)amino)-N-(methyl-d3)pyridazine-3-carboxamide.

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating neurodegenerative disease (or use of the compounds of the present invention for the manufacture of a medicament for the treatment of said diseases), comprising administering to a patient in need of such treatment a therapeutically-effective amount of a compound of Formula I, wherein the disease is selected from as Alzheimer's disease, Parkinson's disease, ALS, Multiple Sclerosis (RMS and/or progressive MS, including CIS, optic neuritis, neuromyelitis optica).

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating an IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating an IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}<1000$ nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 and/or IFNα, and particularly the selective inhibition of function of IL-23, IL-12 and/or IFNα, by acting on Tyk2 to mediate signal transduction. Such conditions include IL-23-, IL-12- or IFNα-associated diseases in which pathogenic mechanisms are mediated by these cytokines and the subsequent activation of the Tyk2 pathway with subsequent pro-inflammatory responses which may occur in the peripheral and/or central compartments.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting or slowing its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and/or IFNα-stimulated cellular responses, compounds of Formula I are useful in treating TL-23-, IL-12- and/or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, ALS, Multiple Sclerosis (RMS and/or progressive MS, including CIS, optic neuritis, neuromyelitis optica), cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic 3-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, Multiple Sclerosis (RMS and/or progressive MS, including CIS, optic neuritis, neuromyelitis optica), cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Alzheimer's disease, Parkinson's disease, ALS, Multiple Sclerosis (RMS and/or progressive MS, including CIS, optic neuritis, neuromyelitis optica), When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934@). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

The key intermediates shown in FIG. 1 can be assembled to give compound 1 in a variety of ways known to one skilled in the art of synthetic organic chemistry.

FIG 1

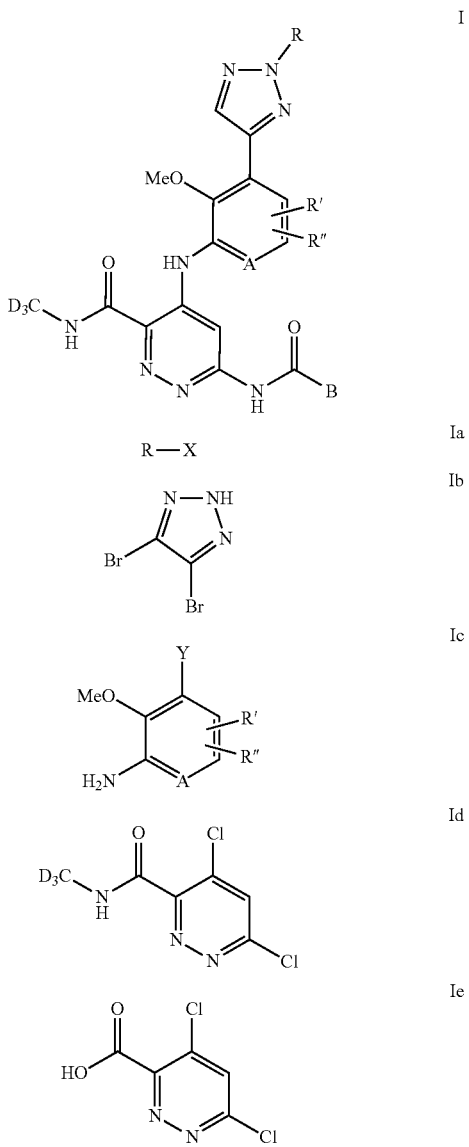

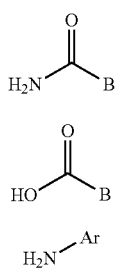

Scheme 1 shows how intermediate Ia, where X=halogen, such as iodide, in the cases where R=simple alkyl (methyl, ethyl, etc) and intermediate Ib can be combined in the presence of an appropriate base, preferably potassium carbonate, in an appropriate solvent, preferably DMF to give intermediates of formula II. In the case where R=cyclopropyl, Ib can be treated with cyclopropylboronic acid in the presence of copper (II) acetate, 2,2'-bipyridine and sodium carbonate in dichloroethane at elevated temperatures.

II can then be mono-debrominated in the presence of a strong reducing base, particularly isopropylmagnesium bromide, THF solution in ether at low temperature to give intermediates of formula IIa. II can also be used, as is, to make more highly substituted 1,2,3-triazoles. IIa can be used, as is, or can be converted to the corresponding boronic acid (IIb) a metal halogen exchange followed by quenching with a trialkylborate, specifically trimethylborate or triisopropylborate. A preferred base for the metal halogen exchange could be isopropylmagnesium chloride-lithium chloride complex in THF at low temperature.

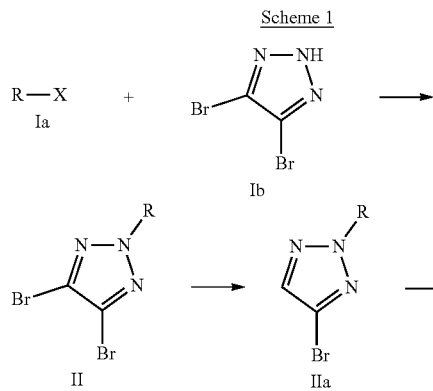

Scheme 2 shows how one skilled in the art can combine intermediate IIa or IIb with intermediate Ic, where Y=boronate, in the case of reaction with IIa, or halide, in the case of reaction with IIb to provide intermediates of general formula III. (Intermediates of general formula Ic are commercially available or can be prepared using methods well known to those skilled in the art of organic synthesis.) The transformation can be achieved by those skill in the art using transition metal catalyzed coupling of the appropriate boronate with the appropriate halide. More specifically, this transformation can be achieved using a Suzuki type coupling with PdCl$_2$(dppf)[DCM] as the catalyst and aqueous tribasic potassium phosphate as the base in solvents like 1,4-dioxane at elevated temperatures. Similar chemistry can be done with intermediate II to produce fully substituted 1,2,3-triazoles (intermediates of general formula IIa). It is necessary in these cases to take the corresponding bromo-triazole and subject it to additional palladium catalyzed coupling with alkyl or alkenyl boronates (in this case followed by olefin reduction using methods known in the art, i.e.—catalytic hydrogenation).

Scheme 2

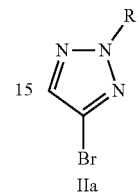
+
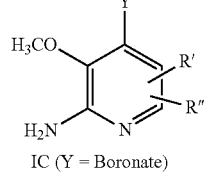
→
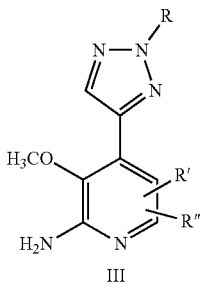

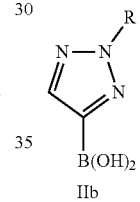
+
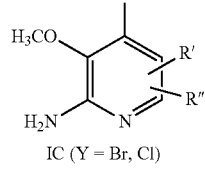
→
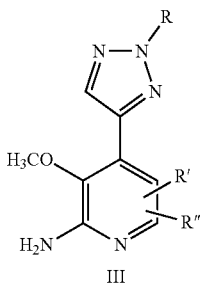

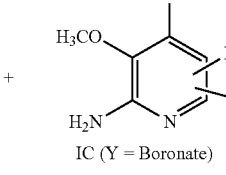
+
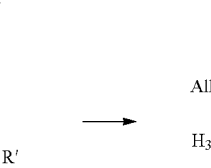
→

Scheme 3 shows how one skilled in the art of organic synthesis can couple intermediates of general formula Id (refer to Moslin, et. al., *J. Med. Chem* 2019, 62, 8953-8972 or U.S. Pat. No. 9,505,748) and Ie (refer to patent: U.S. Pat. No. 10,899,745) with intermediates of general formula III to provide intermediates of general formula IV or IVa. The reaction involves mixing the two reagents in an appropriate aprotic solvent, particularly THF or 2-methyl-THF at between 0° C. and 50° C. depending on the particular III and adding the appropriate base, particularly, lithium hexamethyldisilazide, sodium hexamethyldisilazide, potassium hexamethyldisilazide or sodium hydride. In the case of IVa, the trideuteromethylamide can be installed in a subsequent step.

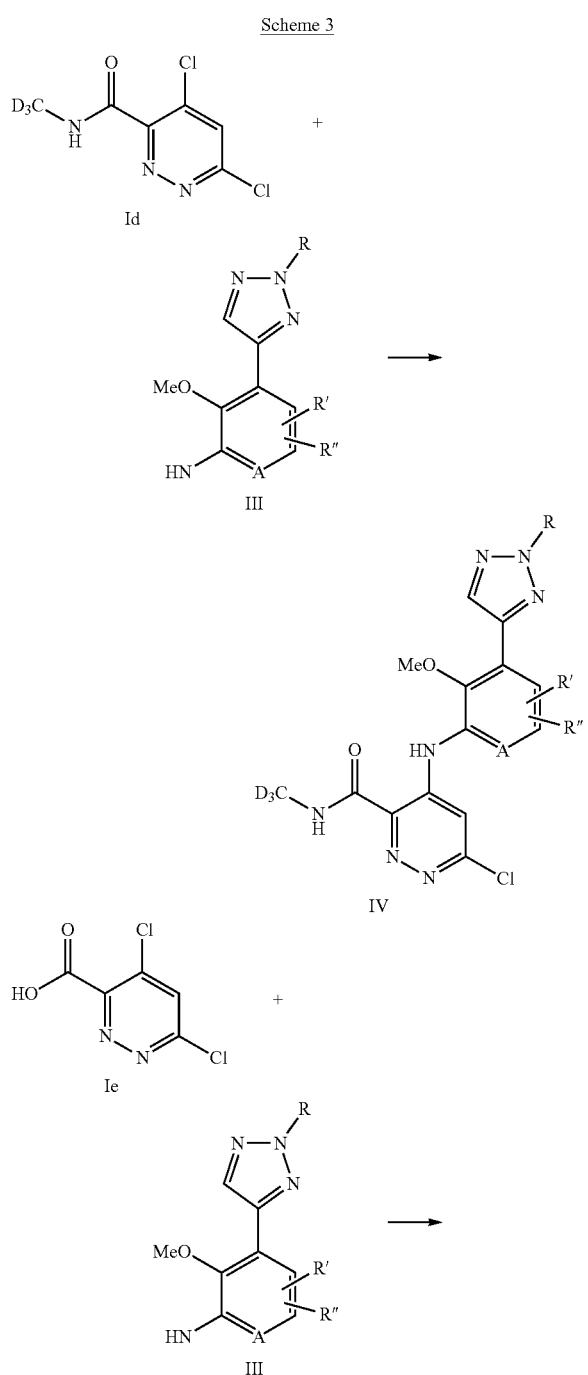

-continued

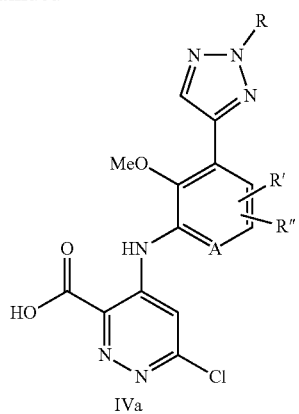

Scheme 4 shows how one skilled in the art of organic synthesis can couple compound IV to the appropriate substrate, in one or one steps, to produce compounds of general formula 1. The one step process involves the coupling of compounds of general formula IV with primary amides of general formula Ig or aromatic amines of general formula Ih, under transition metal catalyzed conditions. In particular, favorable conditions for this reaction involve employing a Buchwald type coupling, using $Pd_2(dba)_3$, as catalyst, xantphos as the ligand and $Cs_2CO_3$ as the base in 1,4-dioxane as solvent, at elevated temperatures. This catalyst/ligand/base system can be altered in ways known to those skilled in the art. Alternatively, compounds of general formula IV can be treated with primary amines, that can give a product that can be deprotected to afford the corresponding primary amines of general formula V, at elevated temperature in an appropriate solvent, particularly 4-methoxybenzylamine. The product of this reaction can be deprotected to afford V with TFA at elevated temperature. Subsequently, compounds of general formula I can be prepared from V by coupling with an appropriate carboxylic acid under amide coupling conditions known by those skilled in the art.

23
-continued

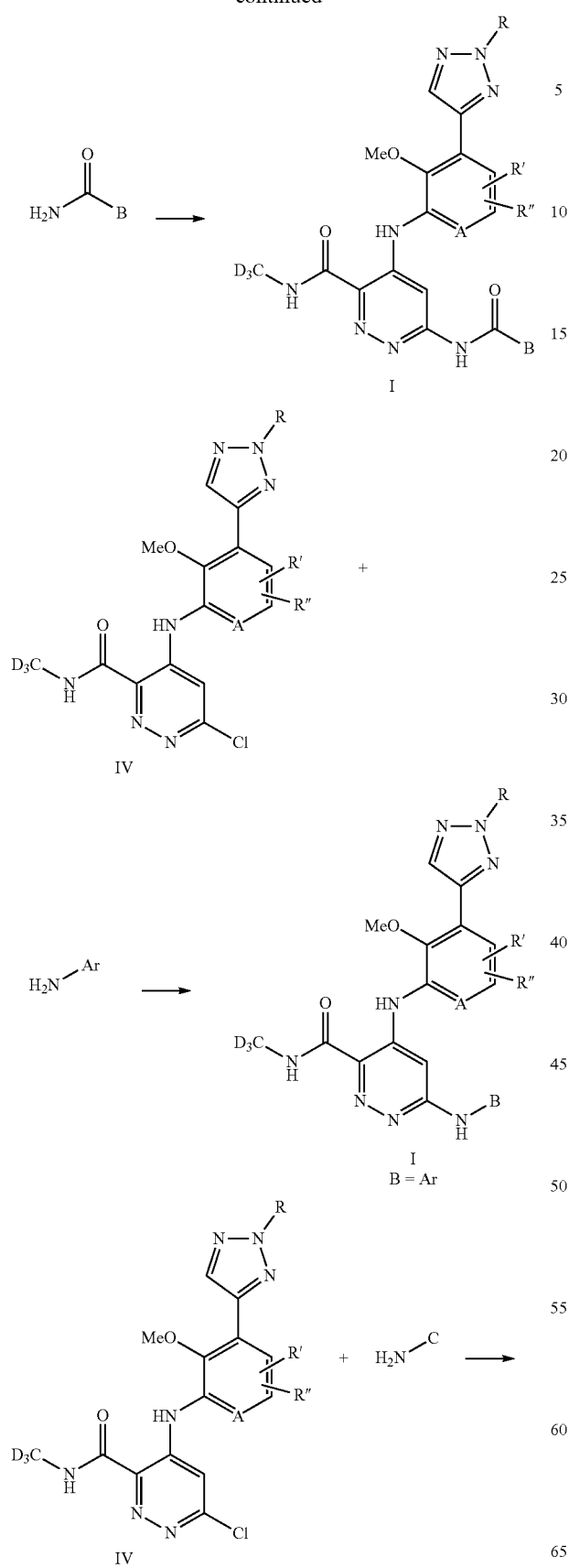

24
-continued

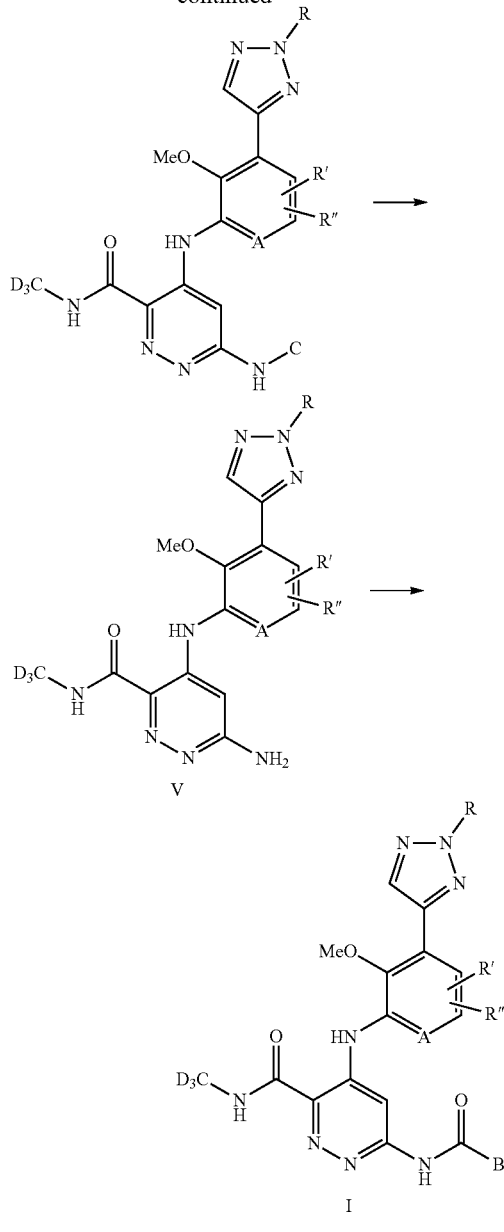

Scheme 5 shows an alternative synthesis of compounds of general formula I, where A=nitrogen. Compound Ie can be coupled to compounds of general formula III, where A=nitrogen, as described above to give compounds of general formula IVa. These compounds can then be used to prepare compounds of general formula VI using a Buchwald type coupling (as described above) with the appropriate primary amide of general formula 1f. Compounds of general formula VI can then be treated with a amide bond coupling reagent system known to those skilled in the art of synthetic organic chemistry, particularly N-(3-dimethylaminopropyl)-N'-ethylcarbodiimide hydrochloride and HOBT in an appropriate solvent, particularly NMP/AcCN at elevated temperature to produce compounds of general formula VII. These compounds can then be treated with trideuteromethylamine hydrochloride, in an appropriate solvent, particularly DMSO, in the presence of a base, in particular diisopropylethylamine at elevated temperature.

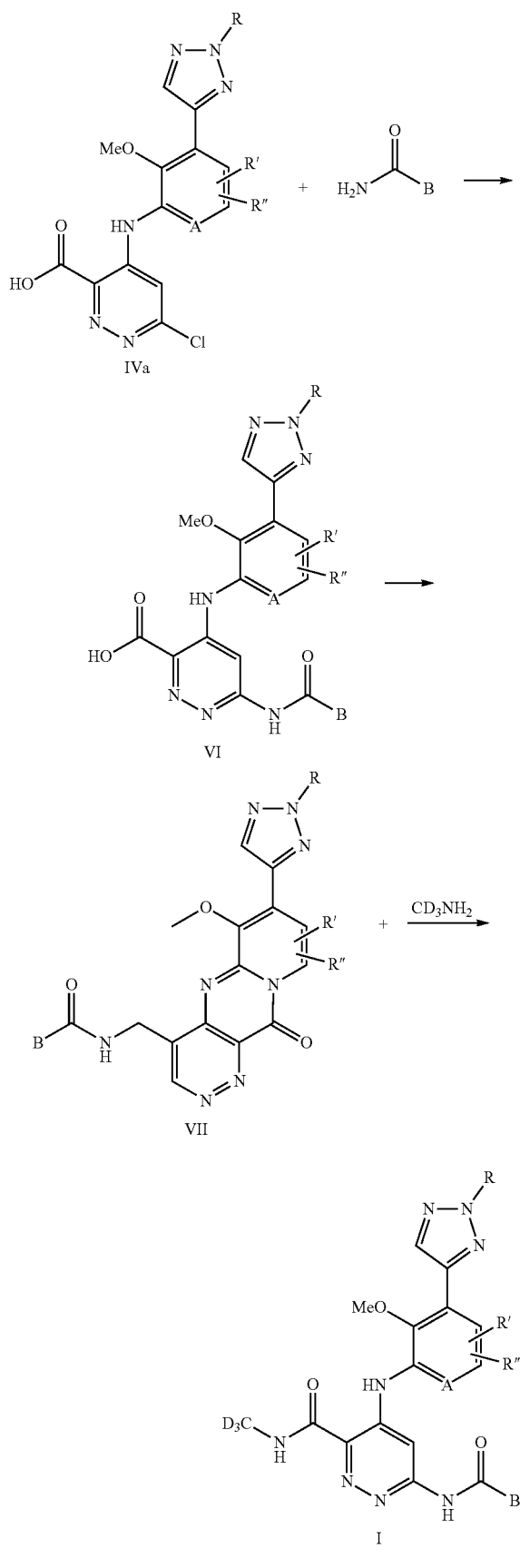

Preparation

All reagents purchased from commercial sources were used without further purification unless otherwise noted. All reactions involving air or moisture sensitive reagents were performed under an inert atmosphere. Proton and carbon magnetic resonance ($^1H$ and $^{13}C$ NMR) spectra were recorded either on a Bruker Avance 400 or a JEOL Eclipse 500 spectrometer and are reported in ppm relative to the reference solvent of the sample in which they were run. HPLC and LCMS analyses were conducted using a Shimadzu LC-10AS liquid chromatograph and a SPDUV-vis detector at 220 or 254 nm with the MS detection performed with a Micromass Platform LC spectrometer. GCMS analyses were conducted using a GC (7890B)-MS (5977B) from Agilent technologies.

Method A:
  Linear gradient of 20% to 100% solvent B over 4 minutes with 0.6-minute hold at 100% B and
  followed by 0.1-minute gradient to 20% B and a 0.3-minute hold at 20% B
  Solvent A: 5 mm Ammonium formate pH 3.3:ACN (98:02)
  Solvent: B: ACN:Buffer (98:02)
  Flow Rate: 1.0 ml/min
  Column: Kinetex XB-C18 (75×3.0) mm, 2.6 μm
  Ultraviolet ("UV") visualization at 220 nanometers ("nm").

Method B:
  Linear gradient of 5% to 95% solvent B over 2.5 minutes with 1.5-minute hold at 95% B and
  followed by 0.5-minute gradient to 5% B and a 1.5-minute hold at 5% B
  Solvent A: 0.1% TFA in $H_2O$
  Solvent: B: 0.1% TFA in ACN
  Flow Rate: 1.5 ml/min
  Column: XBridge C8 (50×4.6) mm, 3.5 μm
  Ultraviolet ("UV") visualization at 220 nanometers ("nm").

Method C:
  Linear gradient of 0 to 100% solvent B over 2 minutes ("min"), with 0.5 minute ("min") hold at 100% B
  Ultraviolet ("UV") visualization at 254 nanometers ("nm")
  Column: Acquity UPLC® BEH C18 1.7 μM
  Flow rate: 1 milliliters ("mL")/min
  Solvent A: 0.05% trifluoroacetic acid, 95% water, 5% acetonitrile
  Solvent B: 0.05% trifluoroacetic acid, 5% water, 95% acetonitrile Method D:
  Linear gradient of 2 to 98% solvent B over 1 minute ("min"), with 0.5 minute ("min") hold at 98% B
  Ultraviolet ("UV") visualization at 254 nanometers ("nm")
  Column: Acquity UPLC® BEH C18 1.7 μM
  Flow rate: 0.8 milliliters ("mL")/min
  Solvent A: water
  Solvent B: acetonitrile Method E:
  Linear gradient of 0 to 100% solvent B over 1 minute ("min"), with 0.5 minute ("min") hold at 100% B
  Ultraviolet ("UV") visualization at 254 nanometers ("nm")
  Column: Acquity UPLC® BEH C18 1.7 μM
  Flow rate: 1 milliliters ("mL")/min Solvent A: 0.05% trifluoroacetic acid, 95% water, 5% acetonitrile
Solvent B: 0.05% trifluoroacetic acid, 5% water, 95% acetonitrile Method F:
Linear gradient of 5% to 95% solvent B over 2.5 minutes ("min"), with 1.5 minute ("min") hold at 95% B followed by 0.5 minute gradient to 5% B and a 1 minute hold at 5% B.
Ultraviolet ("UV") visualization at 220 nanometers ("nm")
Column: Zorbax XDB C-18 (50×4.6 mm) 3.5 µM
Flow rate: 1.5 milliliters ("mL")/min
Solvent A: 0.1% formic acid, 95% water, 5% acetonitrile
Solvent B: acetonitrile Method G:
Linear gradient of 0 to 100% solvent B over 3 minutes ("min"), with 0.5 minute ("min") hold at 100% B
Ultraviolet ("UV") visualization at 220 nanometers ("nm")
Column: Waters XBridge C18 (2.1 mm×50 mm) 1.7 µM
Flow rate: 1 milliliters ("mL")/min
Solvent A: 95% 10 mM ammonium acetate (in water) 5% acetonitrile
Solvent B: 5% 10 mM ammonium acetate (in water), 95% acetonitrile Method H:
Linear gradient of 0 to 100% solvent B over 1 minute ("min"), with 0.5 minute ("min") hold at 100% B
Ultraviolet ("UV") visualization at 254 nanometers ("nm")
Column: Acquity UPLC® BEH C18 1.7 µM
Flow rate: 1 milliliters ("mL")/min
Solvent A: 0.1% trifluoroacetic acid, 95% water, 5% acetonitrile
Solvent B: 0.1% trifluoroacetic acid, 5% water, 95% acetonitrile Method I:
Linear gradient of 0 to 100% solvent B over 3 minute ("min"), with 0.5 minute ("min") hold at 100% B
Ultraviolet ("UV") visualization at 254 nanometers ("nm")
Column: Acquity UPLC® BEH C18 1.7 µM (2.1×50 mm)
Flow rate: 1 milliliters ("mL")/min
Solvent A: 0.05% trifluoroacetic acid, 95% water, 5% acetonitrile
Solvent B: 0.05% trifluoroacetic acid, 5% water, 95% acetonitrile Method J:
Linear gradient of 20% to 98% solvent B over 1.5 minutes with 0.5-minute hold at 98% B and followed by 0.1-minute gradient to 20% B and a 0.5-minute hold at 20% B
Solvent A 5 mm Ammonium formate pH 3.3:ACN (98:02)
Solvent: B: ACN:Buffer (98:02)
Flow Rate: 0.7 ml/min
Column: Kinetex XB-C18 (75×3.0) mm, 2.6 µm
Ultraviolet ("UV") visualization at 220 nanometers ("nm").

Method K:
Linear gradient of 2% to 40% solvent B over 4 minutes with 0.6-minute hold at 100% B and followed by 0.1-minute gradient to 20% B and a 0.3-minute hold at 20% B.
Solvent A: 5 mM Ammonium formate pH 3.3:ACN (98:02)
Solvent: B: ACN:Buffer (98:02)
Flow Rate: 1.0 ml/min
Column: Kinetex XB-C18 (75×3.0) mm, 2.6 µm
Ultraviolet ("UV") visualization at 220 nanometers ("nm").

GCMS Method
Chromatographic column: HP-5 (3 m×320 µm×0.25 nm)
Column length 3 m, internal diameter 032 n, thickness 0.25 µm
Inlet temperature: 250° C.; Carrier gas: He. Detector temperature: 300° C.; Column flow 2 mL/min; Air-flow 400) $H_2$ flow 40 mL/min. Heating schedule: 120° C. hold time 3 min; Then raise to 300° C. with a 40° C./min speed and hold for 2 min., source temperature: 230° C.

| Abbreviation | Meaning |
| --- | --- |
| ACN | Acetonitrile |
| DIPEA | Diisopropylamine |
| LiHMDS | Lithium bis(trimethylsilyl)amide |
| EtOH | Ethanol |
| EtOAc | Ethyl acetate |
| THF | Tetrahydrofuran |
| 2Me-THF | 2-Methyltetrahydrofuran |
| DCM | Dichloromethane |
| TBAF | Tetra-n-butylammonium fluoride |
| DMF | N,N'-Dimethylformamide |
| TFA | Trifluoroacetic acid |
| DAST | Diethylaminosulfur trifluoride |
| $Tf_2O$ | Trifluoromethanesulphonic anhydride |
| dba | dibenzylideneacetone |
| Xantphos | 4,5-Bis(diphenylphosphino)-9,9-dimethylxanthene |
| dcpf | 1,1'-Bis(dicyclohexylphosphino)ferrocene |
| dppf | 1,1'-Bis(diphenylphosphino)ferrocene |
| MeOH | Methanol |
| DIC | N,N'-Diisopropylcarbodiimide |
| HPLC | high pressure liquid chromatography |
| DIAD | Diisopropyl azodicarboxylate |
| LC | liquid chromatography |
| MS | mass spectrometry |
| rt | Room temperature |
| Pd/C | palladium on carbon |
| Et | Ethyl |
| Me | Methyl |
| h | hours |
| ° C. | ° Celsius |
| PBSF | Perfluorobutanesulfonyl fluoride |
| HATU | 1-[Bis(dimethylamino)methylene]-1H-1,2,3-triazolo[4,5-b]pyridinium 3-oxid hexafluorophosphate |
| DMA | dimethylacetamide |
| MW | microwave |
| AcOH | Acetic acid |
| DMAP | 4-dimethyl aminopyridine |
| Boc | Tert-butoxy carbonyl |
| AcCl | Acetyl chloride |
| min | minutes |
| MHz | megahertz |
| m-CPBA | meta-Chloroperoxybenzoic acid |
| DBU | 1,8-Diazabicyclo[5.4.0]undec-7-ene |
| dtbpf | 1,1'-Bis(di-tert-butylphosphino)ferrocene |

Intermediate 1

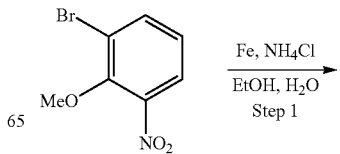

Step 1

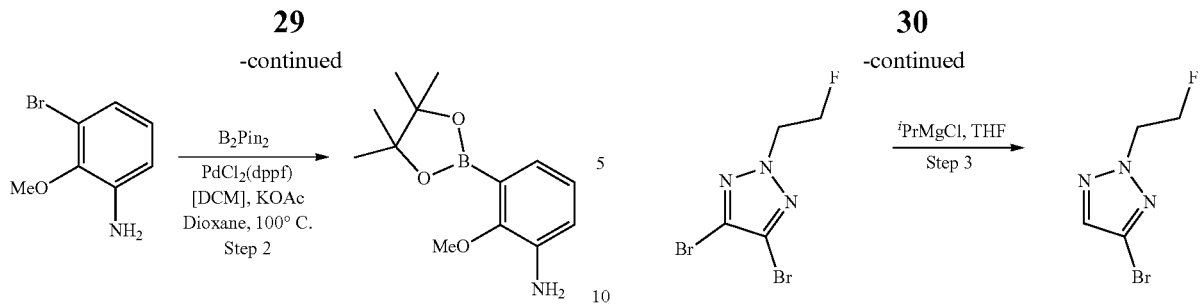

Step 2

To a solution of 1-bromo-2-methoxy-3-nitrobenzene (2.0 g, 8.62 mmol) in Ethanol (20 mL) and water (5 mL) was added iron (3.37 g, 60.3 mmol) and ammonium chloride (2.3 g, 43.3 mmol). The reaction was stirred at 60° C. for 3 h, diluted with ethanol (50 mL) and filtered through celite pad. The filtrate was concentrated under reduced pressure to afford crude product (2.5 g). The crude residue was diluted with EtOAc (100 mL) and washed with water (2×20 mL) and brine (2×20 mL). Combined organic layer was dried over anhydrous sodium sulfate and concentrated under reduced pressure to afford 3-bromo-2-methoxyaniline (1.8 g, 8.55 mmol, 99% yield) as a brown liquid.

MS (M+1) m/z: 202.0 (M+H)$^+$. LC retention time 1.84 [A].

Step 2

To a stirred solution of 3-bromo-2-methoxyaniline (1.80 g, 8.91 mmol) in Dioxane (15 mL) in a sealed tube was added bis(pinacolato)diborone (3.39 g, 13.36 mmol) and potassium acetate (2.62 g, 26.7 mmol). Purged the reaction with nitrogen gas for 5 min and then added PdCl$_2$(dppf).[DCM] (0.73 g, 0.89 mmol). The reaction mixture was stirred at 90° C. for 5 h, then cooled to rt and diluted with EtOAc (100 mL). Reaction mixture was filtered through celite pad and the filtrate was washed with water (2×50 mL) and brine (2×50 mL). Collected organic extract was dried over Na$_2$SO$_4$ and concentrated under reduced pressure to afford crude product which was purified by silica gel column chromatography (25% ethyl acetate in pet ether) to afford 2-methoxy-3-(4,4,5,5-tetramethyl-1,3,2-dioxaborolan-2-yl)aniline (1.8 g, 6.88 mmol, 77% yield) as a pale brown solid. MS (M+1) m/z: 250.4 (M+H)$^+$. LC retention time 2.11 [A].

Intermediate 2

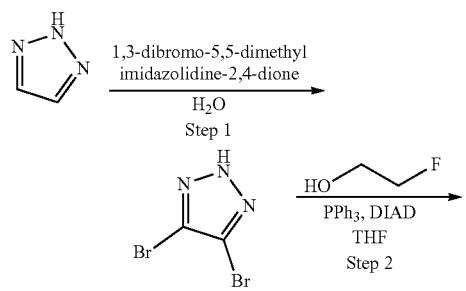

Step 1

To a stirred solution of 1,3-dibromo-5,5-dimethylimidazolidine-2,4-dione (53.8 g, 188 mmol) in H$_2$O (150 mL) at 0° C. was added 2H-1,2,3-triazole (10 g, 145 mmol) in portion wise. After completion of addition the reaction mixture was stirred at 0° C. for 1 h. The reaction mixture was filtered, and the residue was washed with water and dried under vacuo to afford 4,5-dibromo-2H-1,2,3-triazole (26 g, 115 mmol, 79% yield) as pale yellow solid.

GCMS: 226.8 [M], retention time=3.40.

Step 2

To a solution of triphenylphosphine (1.52 g, 5.78 mmol) in THF (8 mL) was added DIAD (0.95 mL, 4.89 mmol) at −10° C. After 10 min 4,5-dibromo-2H-1,2,3-triazole (1 g, 4.45 mmol) was added in portion wise followed by addition of 2-fluoroethan-1-ol (0.4 g, 6.23 mmol). The reaction mixture was allowed to reach to rt and stirred for 2 h. Quenched the reaction mixture with saturated aqueous NaHCO$_3$ solution and extracted with diethyl ether (2×40 mL). The organic layer was dried over anhydrous Na$_2$SO$_4$ and concentrated under reduced pressure. The crude residue was purified by column chromatography (5% ethyl acetate in pet ether) to obtained 4,5-dibromo-2-(2-fluoroethyl)-2H-1,2,3-triazole (730 mg, 2.69 mmol, 60.6% yield) as yellow liquid. GCMS: =272.9 [M], retention time=3.63.

Step 3

To a solution of 4,5-dibromo-2-(2-fluoroethyl)-2H-1,2,3-triazole (0.7 g, 2.57 mmol) in THF (10 mL) was added isopropylmagnesium chloride (3.85 mL, 7.70 mmol) drop wise at 0° C. and stirred for 1 h at 0° C. The reaction mixture was quenched with saturated aqueous NH$_4$Cl solution (10 mL) and extracted with diethyl ether (2×30 ml). Collected organic extract was dried under anhydrous Na$_2$SO$_4$ and concentrated under low vacuo to obtain desired product as brown liquid. This was used as such without further purification. GCMS: 193.0, retention time=5.84.

Intermediate 3

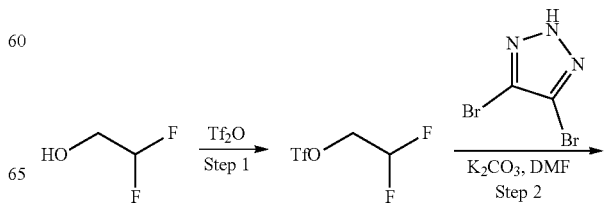

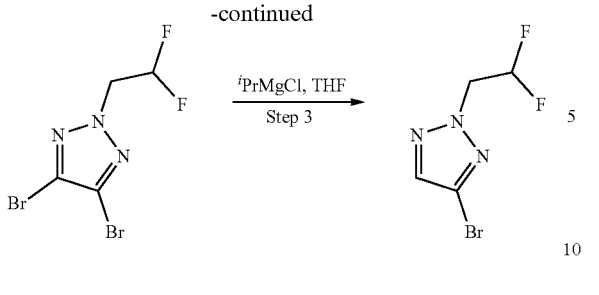

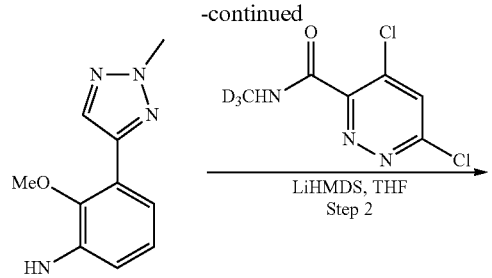

Step 1

2,2-difluoroethan-1-ol (2.0 g, 24.38 mmol) was cooled at 0° C. in a sealed tube and was added Tf$_2$O (5.77 ml, 34.1 mmol) drop wise. The reaction vessel was sealed and heated at 80° C. for 1 h. The reaction mixture was cooled to rt and poured into a cooled 10% NaHCO$_3$ solution (50 mL). The aqueous layer was extracted with diethyl ether (2×50 mL), dried over Na$_2$SO$_4$ and concentrated under reduced pressure. The crude 2,2-difluoroethyl trifluoromethanesulfonate (5.1 g, 23.82 mmol, 98% yield) was used as such without further purification.

$^1$H NMR (CDCl$_3$): 6.22-5.92 (m, 1H), 4.64-4.57 (m, 2H).

Step 2

To a stirred solution of 2,2-difluoroethyl trifluoromethanesulfonate (5.0 g, 23.35 mmol) and 4,5-dibromo-2H-1,2,3-triazole (6.36 g, 28.0 mmol) in DMF (20 mL) was added K$_2$CO$_3$ (6.45 g, 46.7 mmol) at 0° C. The reaction was allowed to reach to rt and stirred for 16 h. The reaction mixture was quenched with cold water (100 mL) and extracted with DCM (2×100 mL). Combined organic layer dried over anhydrous Na$_2$SO$_4$ and concentrated under reduce pressure. The crude residue was purified using silica gel column chromatography (10% ethyl acetate in pet ether) to afford 4,5-dibromo-2-(2,2-difluoroethyl)-2H-1,2,3-triazole (2.3 g, 7.91 mmol, 33.9% yield) as colorless liquid.

$^1$H NMR (CDCl$_3$): 6.36-6.06 (m, 1H), 4.78-4.71 (m, 2H).

Step 3

To a solution of 4,5-dibromo-2-(2,2-difluoroethyl)-2H-1,2,3-triazole (1.5 g, 5.16 mmol) in THF (20 mL) was added isopropylmagnesium chloride (9 ml, 18.00 mmol, 2M solution in THF) drop wise at 0° C. The reaction mixture was stirred at this temperature for 1.5 h. The reaction mixture was quenched with saturated NH$_4$Cl solution (20 mL) and extracted with diethyl ether (2×50 mL). Organic extract was dried over anhydrous Na$_2$SO$_4$ and concentrated under low vacuum to afford crude 4-bromo-2-(2,2-difluoroethyl)-2H-1,2,3-triazole (1.05 g) as deep red oil. The crude product was used as such without further purification. GCMS: 210.9, retention time=5.37.

Intermediate 4

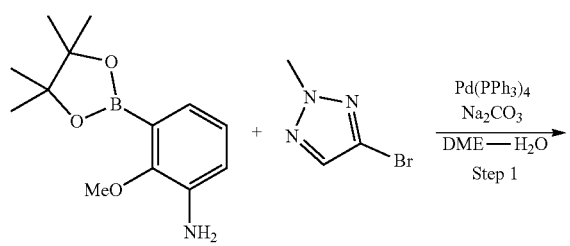

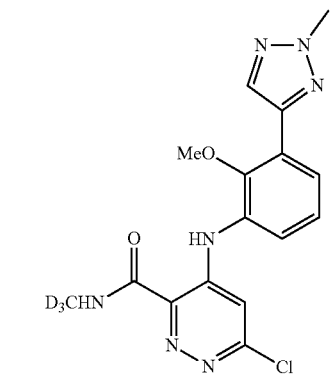

Step 1

To a stirred solution of 2-methoxy-3-(4,4,5,5-tetramethyl-1,3,2-dioxaborolan-2-yl) aniline (2.31 g, 9.26 mmol) and 4-bromo-2-methyl-2H-1,2,3-triazole (1.50 g, 9.26 mmol) in DME (15 mL) and water (5 mL) was added sodium carbonate (2.45 mg, 23.15 mmol). The reaction mixture was purged with nitrogen for 5 mins and Pd(Ph$_3$P)$_4$ (1.07 g, 0.93 mmol) was added under nitrogen. The reaction mixture was stirred at 90° C. for 6 h. Filtered the reaction mixture through celite pad and washed with methanol (50 mL). Filtrate was then concentrated under reduced pressure. The crude residue was partitioned between ethyl acetate (150 mL) and water (150 mL). Collected organic layer was dried over anhydrous Na$_2$SO$_4$ and concentrated. The crude residue was purified by silica gel column chromatography (50% ethyl acetate in pet ether) to obtain desired 2-methoxy-3-(2-methyl-2H-1,2,3-triazol-4-yl) aniline (1.70 g, 7.67 mmol, 83% yield) as brown crystalline solid. MS (M+1) m/z: 205.2 (M+H)+. LC retention time 1.20 [A]

Step 2

To a solution of 4,6-dichloro-N-(methyl-d3)pyridazine-3-carboxamide (refer to Moslin, et. al., *J. Med. Chem* 2019, 62, 8953-8972) (0.35 g, 1.67 mmol) and 2-methoxy-3-(2-methyl-2H-1,2,3-triazol-4-yl) aniline (0.41 g, 2.01 mmol) in THF (10 mL) at 0° C. was added LiHMDS (6.70 mL, 6.70 mmol, 1M solution in THF) dropwise and stirred at rt for 2 h. The reaction mixture was quenched with saturated ammonium chloride solution and extracted with EtOAc (2×30 mL). Combined organic layer was dried over anhydrous sodium sulfate and concentrated under reduced pressure. The crude residue was purified by silica gel column chromatography (40% ethyl acetate in pet ether) to afford desired 6-chloro-4-((2-methoxy-3-(2-methyl-2H-1,2,3-triazol-4-yl) phenyl)amino)-N-(methyl-d3)pyridazine-3-carboxamide (0.37 g, 0.97 mmol, 58.2% yield) as a light brown solid. MS (M+1) m/z: 377.2 (M+H)$^+$. LC retention time 2.167 [A].

The following intermediates (4a-4e) were prepared in a similar manner to the preparation of intermediate 4.

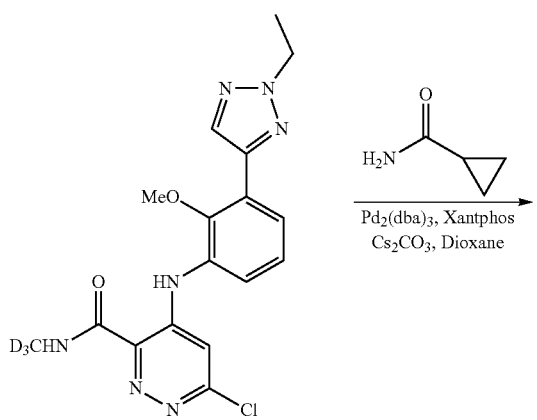

| Intermediate (4a-4e) | R¹ | R² | m/z [M + H]⁺ | Rt (min) [Method] |
|---|---|---|---|---|
| 4a | H | Et | 391.1 | 2.15 [A] |
| 4b | H | CH₂CH₂F | 409.3 | 1.69 [A] |
| 4c | H | CH₂CHF₂ | 426.8 | 2.09 [A] |
| 4d | F | CH₃ | 395.1 | 2.34 [A] |
| 4e | F | CH₂CH₃ | 409.6 | 2.24 [A] |

Example 1

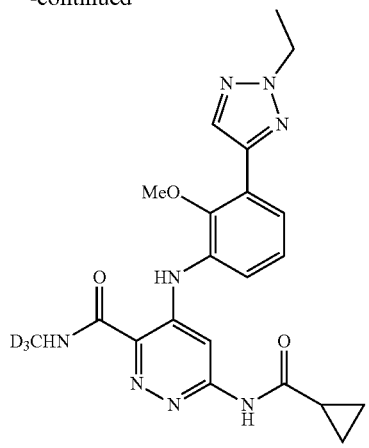

To a solution of 6-chloro-4-((2-methoxy-3-(2-ethyl-2H-1,2,3-triazol-4-yl)phenyl)amino)-N-(methyl-d3)pyridazine-3-carboxamide (101 mg, 0.26 mmol), cyclopropanecarboxamide (110 mg, 1.29 mmol) in dioxane (2.5 mL) and the reaction mixture was purged under $N_2$ for 5 mins. To this solution was added xantphos (30 mg, 0.052 mmol), $Pd_2dba_3$ (24 mg, 0.026 mmol) and cesium carbonate (337 mg, 1.03 mmol) and the mixture was stirred at 130° C. for 45 minutes. After cooling to room temperature, the reaction mixture was purified using a 12 gm isco silica gel cartridge, eluted with a 0-10% MeOH/DCM gradient. The pure fractions were concentrated to afford 6-(cyclopropanecarboxamido)-4-((2-methoxy-3-(2-ethyl-2H-1,2,3-triazol-4-yl)phenyl)amino)-N-(methyl-d3)pyridazine-3-carboxamide (79 mg, 66%) as an off white solid. MS (M+1) m/z: 440.2 [M+H]⁺, LC retention time 1.53 min [I]. ¹H NMR (400 MHz, DMSO-d6) δ 11.33 (s, 1H), 11.01 (s, 1H), 9.16 (s, 1H), 8.14 (d, J=7.9 Hz, 2H), 7.72 (dd, J=7.9, 1.5 Hz, 1H), 7.47 (dd, J=8.0, 1.5 Hz, 1H), 7.30 (t, J=8.0 Hz, 1H), 4.52 (q, J=7.3 Hz, 2H), 3.66 (s, 3H), 2.13-2.05 (m, 1H), 1.52 (t, J=7.3 Hz, 3H), 0.87-0.78 (m, 4H).

The following examples 2-8 were prepared in a similar manner to the preparation of Example 1.

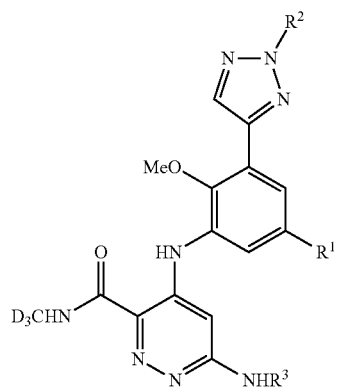

| Example | m/z | Rt (min) |
|---|---|---|

-continued

| No. | $R^1$ | $R^2$ | $R^3$ | MW | $[M + H]^+$ | [Method] |
|---|---|---|---|---|---|---|
| $2^{a,b}$ | H | $CH_2CH_2F$ | cyclopropyl ketone | 457.4 | 458.0 | 2.32 [A] |
| $3^a$ | H | $CH_2CHF_2$ | cyclopropyl ketone | 475.4 | 476.2 | 2.33 [B] |
| 4 | F | $CH_3$ | cyclopropyl ketone | 443.4 | 444.2 | 2.54 [A] |
| 5 | H | $CH_3$ | 6-methoxypyridazin-3-yl | 465.4 | 466.4 | 1.572 [A] |
| 6 | H | $CH_3$ | 1,5-dimethyl-1H-pyrazol-3-yl | 451.5 | 452.2 | 1.58 [A] |
| 7 | H | $CH_3$ | methyl ester | 415.4 | 416.2 | 2.00 [A] |
| 8 | H | $CH_3$ | pyridin-2-yl | 434.5 | 435.4 | 1.372 [A] |

$^a$= depf ligand, 100° C., 2h, MW.
$^b$= Purified by silica gel column chromatography.

Intermediate 5

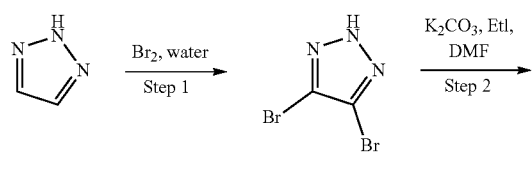

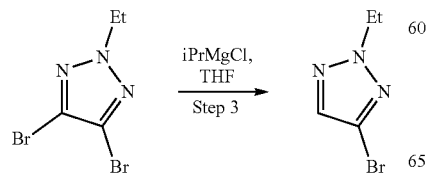

Step 1

To a solution of 1H-1,2,3-triazole (0.52 mL, 9 mmol) in water (5 mL) at 50° C. was added bromine (0.62 mL, 12 mmol). The reaction mixture was stirred at 50° C. for 90 minutes, whereupon the precipitated product was isolated via filtration. The precipitate was air-dried on the filter. To the filtrate was added additional bromine (0.62 mL, 12 mmol) and this mixture was then stirred at room temperature overnight. The subsequent slurry was filtered and the solid was combined with the previously obtained precipitate to provide 4,5-dibromo-1H-1,2,3-triazole (1.83 g, 87% yield).

Step 2 (*Org. Lett.* 2010, 12, 4632-4635)

To a cooled (−10° C.) solution of 4,5-dibromo-1H-1,2,3-triazole (2.3 g, 10 mmol) in DMF (23 mL) was added potassium carbonate (2.80 g, 20.3 mmol). The reaction mixture was stirred for 15 minutes and then iodoethane (1.2 mL, 15 mmol) was added dropwise. Stirring was maintained for 30 minutes and then 10 mL of water was added. The crude product was extracted with EtOAc (2×50 mL) and the combined organic layers were washed with 10% (aq.) LiCl solution and brine. The organic layer was dried over sodium sulfate, filtered and concentrated under reduced pressure. The crude product was purified using ISCO automated chromatography eluting with 0-100% EtOAc in hexanes yielding 4,5-dibromo-2-ethyl-2H-1,2,3-triazole (1.1 g, 46% yield) as a white solid. Product did not ionize under LCMS conditions. $^1$H NMR (400 MHz, CHLOROFORM-d) δ 4.43 (q, J=7.3 Hz, 2H), 1.60-1.54 (m, 3H).

Step 3 (*Org. Lett.* 2010, 12, 4632-4635)

To a cooled (−20° C.) solution of 4,5-dibromo-2-ethyl-2H-1,2,3-triazole (1.11 g, 4.35 mmol) in THF (6 mL) was slowly added isopropylmagnesium chloride (2M in THF, 6.5 mL, 13 mmol). The reaction was stirred for 30 minutes with the −20° C. cold bath maintained and then allowed to warm to 0° C. over 2 hours. The reaction was quenched via the addition of saturated (aq.) ammonium chloride. The product was extracted using EtOAc (2×50 mL). The combined EtOAc layers were washed with brine solution and then dried over anhydrous sodium sulfate. The desiccant was filtered off and the filtrate concentrated under reduced pressure, yielding Intermediate 5 as a yellow oil (627 mg, 82% yield). Product did not ionize under LCMS conditions. $^1$H NMR (400 MHz, CHLOROFORM-d) δ 7.53 (s, 1H), 4.46 (q, J=7.3 Hz, 2H), 1.56 (t, J=7.4 Hz, 3H).

Intermediate 6

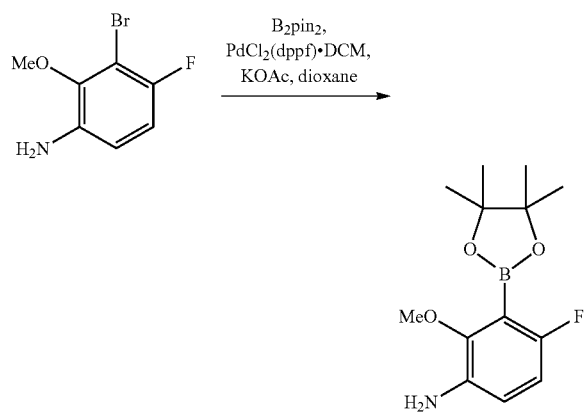

A sealed vessel containing 3-bromo-4-fluoro-2-methoxyaniline (1.0 g, 4.5 mmol), 4,4,4',4',5,5,5',5'-octamethyl-2,2'-bi(1,3,2,-dioxaborolane) (1.50 g, 5.91 mmol), PdCl$_2$(dppf)·DCM (0.186 g, 0.227 mmol) and potassium acetate (1.34 g, 13.6 mmol) in dioxane (22 mL) was heated to 105° C. Heating was continued overnight at which point the reaction was cooled to room temperature, absorbed onto Celite®, and dried under reduced pressure. The crude material was then purified using automated chromatography (solid loading) eluting with 0-50% EtOAc/hexanes. Product containing fractions were combined and concentrated under reduced pressure yielding Intermediate 6 as a pale yellow solid (244 mg, 20% yield). MS (M+1) m/z: 268.3 (MW). LC retention time 1.05 min [C].

Intermediate 7

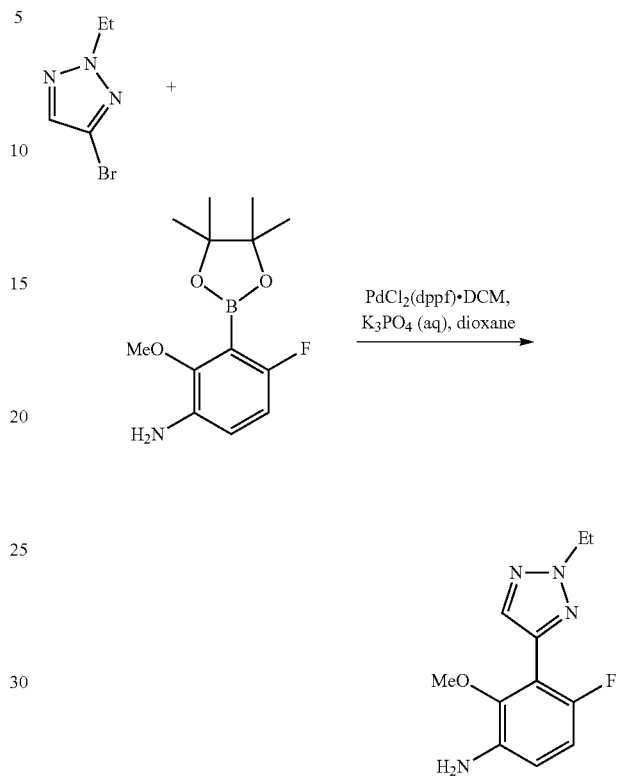

A stirred solution of Intermediate 5 (241 mg, 1.37 mmol), Intermediate 6 (244 mg, 0.91 mmol) and PdCl$_2$(dppf)·DCM (37 mg, 0.046 mmol) in dioxane (4 mL) was degassed by bubbling nitrogen through the mixture for 5 minutes. An aqueous solution of K$_3$PO$_4$ (2M, 1.4 mL, 2.8 mmol) was subsequently added and the reaction mixture heated at 100° C. for 15 minutes. The reaction was cooled to room temperature and diluted with EtOAc (75 mL). The resulting solution was dried over sodium sulfate, filtered and concentrated under reduced pressure. The crude product was then purified using automated chromatography (0-100% EtOAc/hexanes). Combined pure fractions were concentrated to afford Intermediate 7 (124 mg, 56% yield) as a colorless oil. MS (M+1) m/z: 237.3 (MH$^+$). LC retention time 1.04 min [C]. $^1$H NMR (400 MHz, CHLOROFORM-d) δ 7.88 (d, J=2.0 Hz, 1H), 6.85-6.77 (m, 1H), 6.75-6.67 (m, 1H), 4.58 (q, J=7.3 Hz, 2H), 3.77 (br s, 2H), 3.62 (s, 3H), 1.63 (t, J=7.3 Hz, 3H).

Intermediate 8

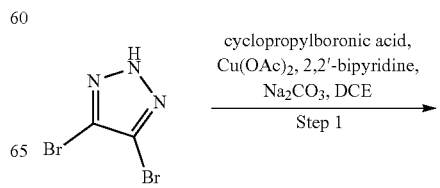

39
-continued

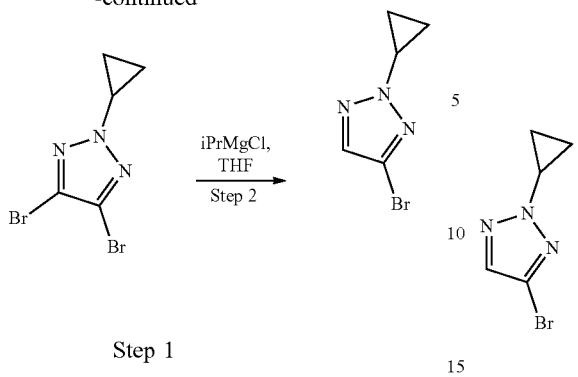

Step 1

A stirred solution of 4,5-dibromo-1H-1,2,3-triazole (3.0 g, 13 mmol), copper(II) acetate (2.88 g, 15.9 mmol), 2,2'-bipyridine (2.48 g, 15.9 mmol) and sodium carbonate (2.80 g, 26.4 mmol) in dichloroethane (40 mL) was degassed by bubbling nitrogen through the reaction mixture for 5 minutes. To the degassed mixture was added cyclopropylboronic acid (3.41 g, 39.7 mmol). The reaction was heated to 85° C. overnight. The reaction was cooled to room temperature and then partitioned between 200 mL EtOAc and a 100 mL mixture (1:1) of saturated (aq.) ammonium chloride and concentrated ammonium hydroxide. The layers were separated and the aq. layer was extracted 2×75 mL with EtOAc. The combined EtOAc layers were then washed with saturated (aq.) ammonium chloride and with brine. The EtOAc layer was then dried over sodium sulfate, filtered and concentrated under reduced pressure. The crude product was purified using automated chromatography (0-70% EtOAc/hexanes). The pure fractions were combined and concentrated under reduced pressure to provide 4,5-dibromo-2-cyclopropyl-2-H-1,2,3-triazole (979 mg, 28% yield). Product did not ionize under LCMS conditions. $^1$H NMR (400 MHz, chloroform-d) δ 4.03-3.95 (m, 1H), 1.38-1.32 (m, 2H), 1.16-1.09 (m, 2H)

Step 2

To a cooled (−20° C.) solution of 4,5-dibromo-2-cyclopropyl-2H-1,2,3-triazole (0.950 g, 3.56 mmol) in THF (5 mL) was slowly added isopropylmagnesium chloride (2M in THF, 5.3 mL, 10.7 mmol). The reaction was stirred for 30 minutes with the −20° C. cold bath maintained and then allowed to warm to 0° C. over 2 hours. The reaction was quenched via the addition of saturated (aq.) ammonium chloride. The product was extracted using EtOAc (2×50 mL). The combined EtOAc layers were washed with brine solution and then dried over anhydrous sodium sulfate. The desiccant was removed via filtration and the filtrate concentrated under reduced pressure, yielding Intermediate 8 as a yellow oil (605 mg, 81% yield). Product did not ionize under LCMS conditions. $^1$H NMR (400 MHz, chloroform-d) δ 7.51 (s, 1H), 3.99 (tt, J=7.5, 3.8 Hz, 1H), 1.39-1.32 (m, 2H), 1.15-1.07 (m, 2H).

40
Intermediate 9

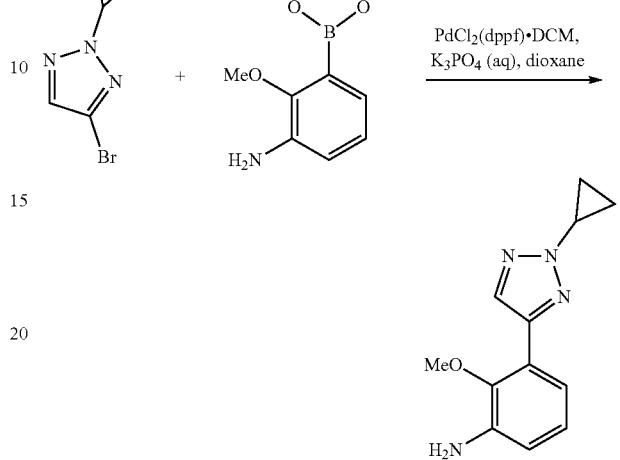

A stirred solution of Intermediate 8 (249 mg, 1.32 mmol), Intermediate 3 (220 mg, 0.88 mmol) and PdCl$_2$(dppf)·DCM (36 mg, 0.044 mmol) in dioxane (4 mL) was degassed by bubbling nitrogen through the mixture for 5 minutes. An aqueous solution of K$_3$PO$_4$ (2M, 1.3 mL, 2.6 mmol) was subsequently added and the reaction mixture heated at 80° C. for 30 minutes. The reaction was cooled to room temperature and diluted with EtOAc (75 mL). The resulting solution was dried over sodium sulfate, filtered and concentrated under reduced pressure. The crude product was then purified using automated chromatography (0-100% EtOAc/hexanes). Combined pure fractions were concentrated to afford Intermediate 9 as a colorless oil (153 mg, 71% yield). MS (M+1) m/z: 231.1 (MH$^+$). LC retention time 1.07 min [C]. $^1$H NMR (400 MHz, CHLOROFORM-d) δ 8.01 (s, 1H), 7.31-7.27 (m, 1H), 6.99 (t, J=7.9 Hz, 1H), 6.76 (dd, J=7.9, 1.6 Hz, 1H), 4.05 (tt, J=7.5, 3.9 Hz, 1H), 3.94-3.79 (m, 2H), 3.73-3.61 (m, 3H), 1.45-1.39 (m, 2H), 1.17-1.09 (m, 2H).

Intermediate 10

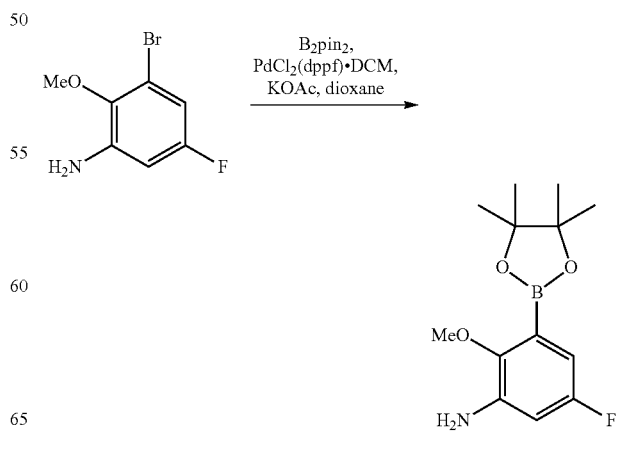

A sealed vessel containing 3-bromo-5-fluoro-2-methoxyaniline (hydrochloride salt) (4.5 g, 17.5 mmol), 4,4,4',4',5,5,5',5'-octamethyl-2,2'-bi(1,3,2,-dioxaborolane) (5.79 g, 22.8 mmol), PdCl$_2$(dppf)·DCM (0.716 g, 0.877 mmol) and potassium acetate (6.03 g, 61.4 mmol) in dioxane (100 mL) was heated to 105° C. Heating was continued overnight at which point the reaction was cooled to room temperature, absorbed onto Celite®, and dried under reduced pressure. The crude material was then purified using automated chromatography (solid loading) eluting with 0-50% EtOAc/hexanes. Product containing fractions were combined and concentrated under reduced pressure yielding Intermediate 10 as a pale yellow solid (2.55 g, 54% yield). MS (M+1) m/z: 268.3 (MW). LC retention time 1.50 min [C].

Intermediate 11

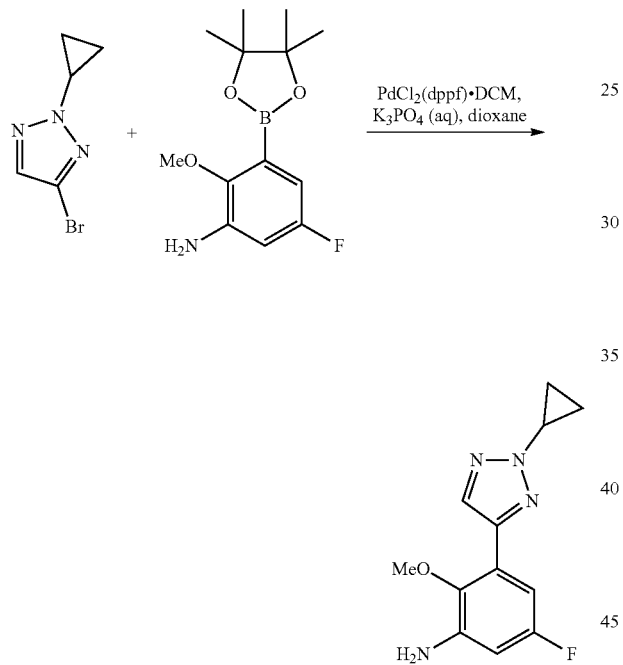

A stirred solution of Intermediate 8 (348 mg, 1.85 mmol), Intermediate 10 (330 mg, 1.24 mmol) and PdCl$_2$(dppf)·DCM (50.4 mg, 0.062 mmol) in dioxane (6 mL) was degassed by bubbling nitrogen through the mixture for 5 minutes. An aqueous solution of K$_3$PO$_4$ (2M, 1.85 mL, 3.7 mmol) was subsequently added and the reaction mixture heated at 50° C. for 30 minutes. The reaction was cooled to room temperature and diluted with EtOAc (75 mL). The resulting solution was dried over sodium sulfate, filtered and concentrated under reduced pressure. The crude product was then purified using automated chromatography (0-100% EtOAc/hexanes). Pure fractions were combined and concentrated under reduced pressure to provide Intermediate 11 as a colorless oil (188 mg, 61% yield). MS (M+1) m/z: 249.2 (MH$^+$). LC retention time 1.40 min [C]. $^1$H NMR (400 MHz, chloroform-d) δ 8.03 (s, 1H), 7.00 (dd, J=9.6, 3.0 Hz, 1H), 6.46 (dd, J=9.5, 3.0 Hz, 1H), 4.11-4.04 (m, 1H), 4.04-3.97 (m, 2H), 3.67 (s, 3H), 1.47-1.40 (m, 2H), 1.19-1.12 (m, 2H).

Intermediate 12

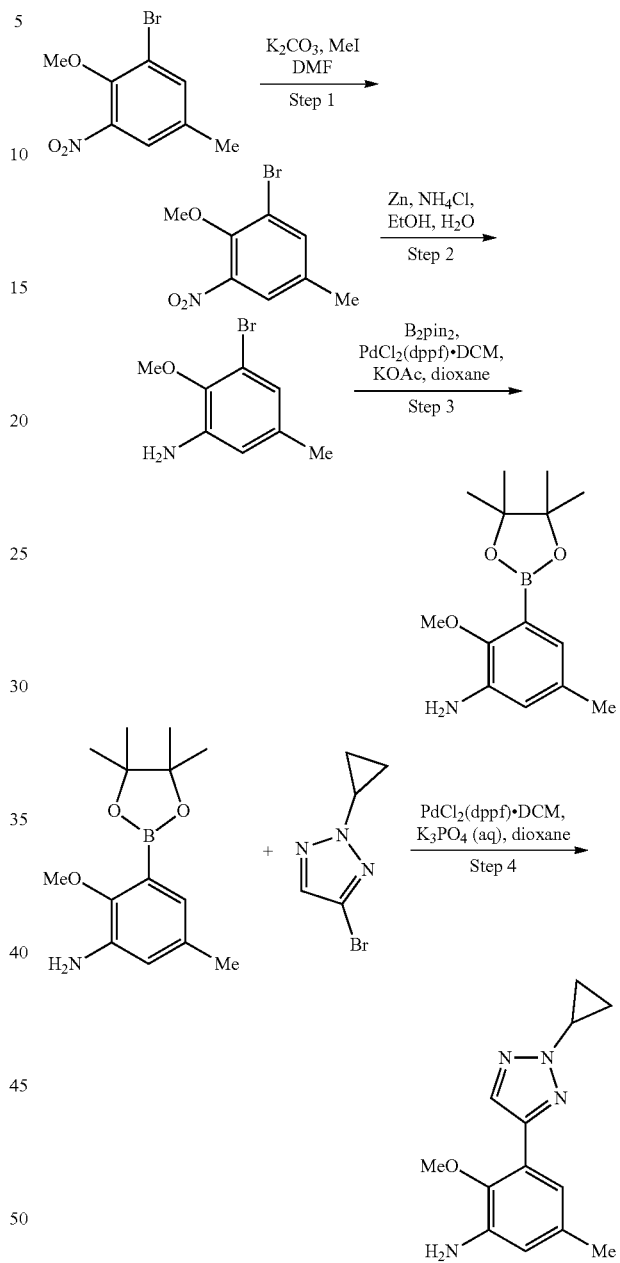

Step 1

2-Bromo-4-methyl-6-nitrophenol (1.00 g, 4.31 mmol) was combined potassium carbonate (1.19 g, 8.62 mmol) and iodomethane (0.40 mL, 6.5 mmol) in DMF (15 mL) and stirred at room temperature overnight. Ethyl acetate (50 mL) and water (50 mL) were added to the reaction and the two layers were separated. The EtOAc layer was washed with 1 N NaOH (aq.), 10% LiCl (aq.) and brine solutions. The EtOAc layer was then dried over anhydrous sodium sulfate, filtered and then concentrated under reduced pressure. The crude product was then purified using automated chromatography (0-30% EtOAc/hexanes) to afford 1-bromo-2- methoxy-5-methyl-3-nitrobenzene. Product did not ionize. $^1$H NMR (400 MHz, chloroform-d) δ 7.61 (d, J=2.0 Hz, 1H), 7.56 (d, J=1.5 Hz, 1H), 3.98 (s, 3H), 2.37 (s, 3H).

Step 2

1-Bromo-2-methoxy-5-methyl-3-nitrobenzene (0.979 g, 3.98 mmol) was combined with ammonium chloride (2.13 g, 39.8 mmol) in ethanol (21 mL) and water (3 mL). To this was added zinc (2.60 g, 39.8 mmol) in a portion wise manner over 10 minutes. The resulting heterogeneous mixture was stirred overnight at room temperature. Dichloromethane (200 mL) was added to the reaction, which was then filtered through celite-collecting the filtrate. The filtrate was washed with water (100 mL) and dried over sodium sulfate. The desiccant was removed via filtration and the crude product concentrated under reduced pressure. Purification was accomplished using automated chromatography (0-50% EtOAc/hexanes) yielding 3-bromo-2-methoxy-5-methylaniline (0.763 g, 89% yield) as a colorless oil. MS (M+1) m/z: 216.1 (MH$^+$). LC retention time 0.90 min [E]. $^1$H NMR (400 MHz, DMSO-d) δ 6.64 (d, J=8.1 Hz, 1H), 6.30 (dt, J=8.0, 1.1 Hz, 1H), 4.56 (bs, 2H), 3.70 (s, 3H), 3.31 (s, 3H).

Step 3

A sealed vessel containing 3-bromo-2-methoxy-5-methylaniline (150 mg, 0.694 mmol), 4,4,4',4',5,5,5',5'-octamethyl-2,2'-bi(1,3,2,-dioxaborolane) (229 mg, 0.90 mmol), PdCl$_2$(dppf)·DCM (28 mg, 0.035 mmol) and potassium acetate (204 mg, 2.08 mmol) in dioxane (4 mL) was heated to 100° C. Heating was continued overnight at which point partial conversion was observed. Additional 4,4,4',4',5,5,5',5'-octamethyl-2,2'-bi(1,3,2,-dioxaborolane) (229 mg, 0.90 mmol), PdCl$_2$(dppf)·DCM (28 mg, 0.035 mmol) and potassium acetate (204 mg, 2.08 mmol) were added and heating was continued for 2 hours. The reaction mixture was used as is in the subsequent step. MS (M+1) m/z: 264.1 (MH$^+$). LC retention time 0.82 min [E].

Step 4

To the reaction mixture from step 3 was added Intermediate 8 (170 mg, 0.904 mmol) and the mixture was degassed by bubbling through nitrogen for 5 minutes. To this K$_3$PO$_4$ (2M aq. 1.04 mL, 2.09 mmol) was rapidly added. The mixture was heated at 100° C. for 1 hour and then cooled to room temperature. The reaction was partitioned between EtOAc (30 mL) and brine solution (20 mL). The EtOAc layer was dried over anhydrous sodium sulfate, filtered and concentrated under reduced pressure. The crude product was purified using automated chromatography (0-70% EtOAc/hexanes). The pure fractions were collected and concentrated to provide Intermediate 12 as a yellow oil (87 mg, 51% yield over two steps). MS (M+1) m/z: 245.1 (MH$^+$). LC retention time 0.80 min [E].

Intermediate 13

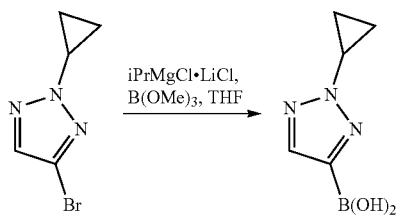 [SMILES: Brc1cnn(C2CC2)n1 ; OB(O)c1cnn(C2CC2)n1]

To a chilled (10° C.) stirred solution of Intermediate 8 (712 mg, 3.79 mmol) in THF (10 mL) was slowly added isopropylmagnesium chloride lithium chloride complex (1.3 M in THF, 3.5 mL, 4.5 mmol). The reaction was stirred for 2 hours at 10° C. and then further cooled to −20° C. To this solution was then added trimethyl borate (0.64 mL, 5.7 mmol). The reaction was stirred at −20° C. for 1 hour and then quenched via the addition of 1 N (aq) HCl. The product was extracted with EtOAc (×2) and the combined organic layers were washed with brine solution and then dried over anhydrous sodium sulfate. The desiccant was removed via filtration and the filtrate concentrated under reduced pressure to afford solid Intermediate 13 (499 mg, 73% yield). Material used as recovered.

Intermediate 14

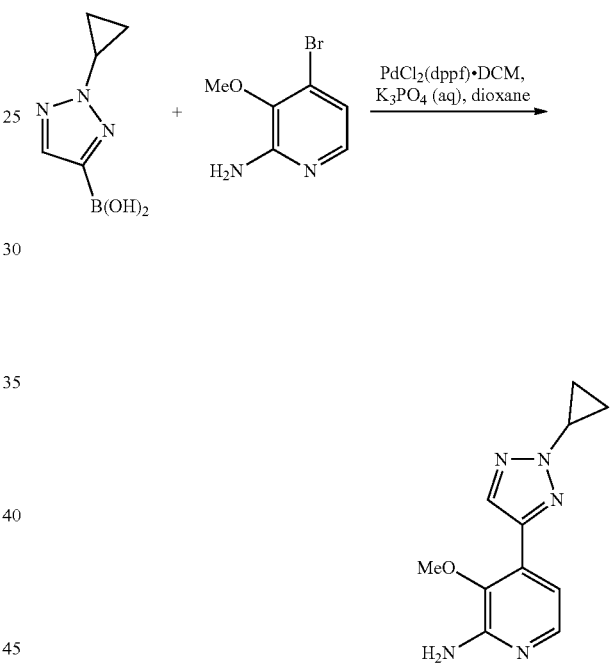

A stirred solution of Intermediate 13 (245 mg, 1.60 mmol), 4-bromo-3-methoxypyridin-2-amine (250 mg, 1.23 mmol) and PdCl$_2$(dppf)·DCM (50.3 mg, 0.062 mmol) in dioxane (3 mL) was degassed by bubbling nitrogen through the mixture for 5 minutes. An aqueous solution of K$_3$PO$_4$ (2M, 1.85 mL, 3.7 mmol) was subsequently added and the reaction mixture heated at 100° C. for 45 minutes. The reaction was cooled to room temperature and diluted with EtOAc (75 mL). The resulting solution was dried over sodium sulfate, filtered and concentrated under reduced pressure. The crude product was then purified using automated chromatography (0-100% EtOAc/hexanes). Pure fractions were combined and concentrated under reduced pressure to provide Intermediate 14 as an off-white crystalline solid (155 mg, 54% yield). MS (M+1) m/z: 232.3 (MH$^+$). LC retention time 0.83 min [C]. $^1$H NMR (400 MHz, CHLOROFORM-d) δ 8.08 (s, 1H), 7.87 (d, J=5.3 Hz, 1H), 7.19 (d, J=5.3 Hz, 1H), 4.71 (br s, 2H), 4.09 (dt, J=7.5, 3.7 Hz, 1H), 3.73 (s, 3H), 1.49-1.39 (m, 2H), 1.21-1.12 (m, 2H).

Intermediate 15

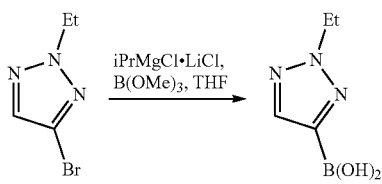 [SMILES: CCn1ncc(Br)n1 ; CCn1ncc(B(O)O)n1]

To a chilled (10° C.) stirred solution of Intermediate 5 (244 mg, 1.39 mmol) in THF (3.3 mL) was slowly added isopropylmagnesium chloride lithium chloride complex (1.3 M in THF, 1.3 mL, 1.7 mmol). The reaction was stirred for 2 hours at 10° C. and then further cooled to −20° C. To this solution was then added trimethyl borate (0.23 mL, 2.1 mmol). The reaction was stirred at −20° C. for 1 hour and then quenched via the addition of 1 N (aq) HCl. The product was extracted with EtOAc (×2) and the combined organic layers were washed with brine solution and then dried over anhydrous sodium sulfate. The desiccant was removed via filtration and the filtrate concentrated under reduced pressure to afford solid Intermediate 15 (115 mg, 50% yield). MS (M+1) m/z: 142.3 (MH$^+$). LC retention time 0.37 min [C]. $^1$H NMR (400 MHz, DMSO-d6) δ 7.92 (s, 1H), 4.45 (q, J=7.3 Hz, 2H), 1.44 (t, J=7.3 Hz, 3H).

Intermediate 16

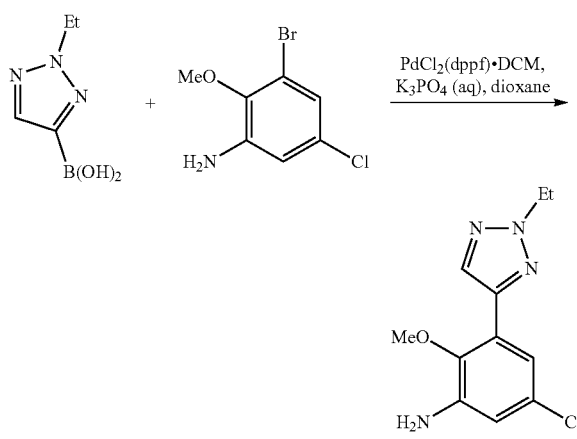

A stirred solution of Intermediate 15 (99 mg, 0.23 mmol), 3-bromo-5-chloro-2-methoxyaniline (50 mg, 0.21 mmol) and PdCl$_2$(dppf)·DCM (8.6 mg, 0.010 mmol) in dioxane (1.5 mL) was degassed by bubbling nitrogen through the mixture for 5 minutes. An aqueous solution of K$_3$PO$_4$ (2M, 0.32 mL, 0.63 mmol) was subsequently added and the reaction mixture stirred at room temperature for 90 minutes and then heated at 50° C. for 30 minutes and then overnight at room temperature. The reaction was diluted with EtOAc (75 mL). The resulting solution was dried over sodium sulfate, filtered and concentrated under reduced pressure. The crude product was then purified using automated chromatography (0-100% EtOAc/hexanes). Pure fractions were combined and concentrated under reduced pressure to provide Intermediate 16 as yellow oil (23 mg, 43% yield). MS (M+1) m/z: 253.1 (MH$^+$). LC retention time 1.34 min [C].

Intermediate 17

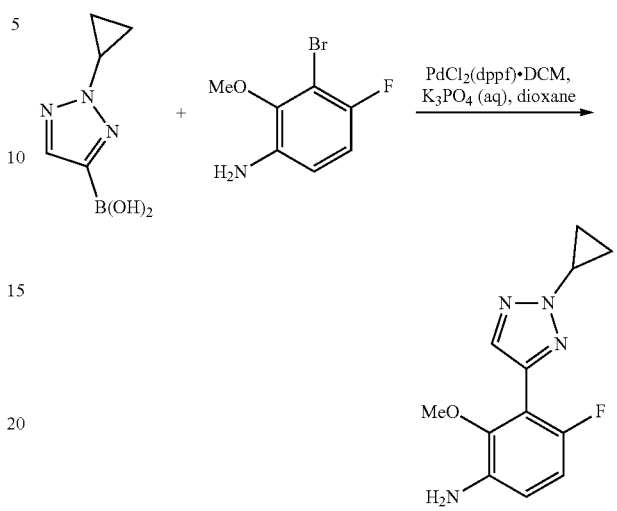

A stirred solution of Intermediate 13 (60.3 mg, 0.394 mmol), 3-bromo-4-fluoro-2-methoxyaniline (62 mg, 0.28 mmol) and PdCl$_2$(dppf)·DCM (11.5 mg, 0.014 mmol) in dioxane (5 mL) was degassed by bubbling nitrogen through the mixture for 5 minutes. An aqueous solution of K$_3$PO$_4$ (2M, 0.42 mL, 0.84 mmol) was subsequently added and the reaction mixture heated at 100° C. for 30 minutes. The reaction was cooled to room temperature and diluted with EtOAc (75 mL). The resulting solution was dried over sodium sulfate, filtered and concentrated under reduced pressure. The crude product was then purified using automated chromatography (0-100% EtOAc/hexanes). Pure fractions were combined and concentrated under reduced pressure to provide Intermediate 17 as a yellow oil (35 mg, 50% yield). MS (M+1) m/z: 249.1 (MH$^+$). LC retention time 1.01 min [C].

Intermediate 18

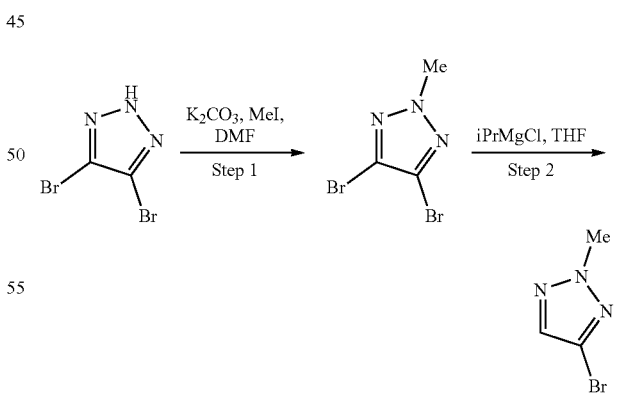

Step 1

To a cooled (−10° C.) solution of 4,5-dibromo-1H-1,2,3-triazole (2.0 g, 8.8 mmol) in DMF (20 mL) was added potassium carbonate (2.68 g, 19.4 mmol). The reaction mixture was stirred for 15 minutes and then iodomethane (1.10 mL, 17.6 mmol) was added dropwise. Stirring was maintained overnight and then 10 mL of water was added. The crude product was extracted with EtOAc (2×50 mL) and the combined organic layers were washed with 10% (aq.) LiCl solution and brine. The organic layer was dried over sodium sulfate, filtered and concentrated under reduced pressure. The crude product was purified using ISCO automated chromatography eluting with 0-100% EtOAc in hexanes yielding 4,5-dibromo-2-methyl-2H-1,2,3-triazole (1.33 g, 63% yield) as a white solid. Product did not ionize under LCMS conditions. LC retention time 1.26 min [C].

Step 2

To a cooled (−20° C.) solution of 4,5-dibromo-2-methyl-2H-1,2,3-triazole (1.33 g, 5.52 mmol) in diethyl ether (6 mL) was slowly added isopropylmagnesium chloride (2M in THF, 8.28 mL, 16.6 mmol). The reaction was stirred for 30 minutes with the −20° C. cold bath maintained and then allowed to warm to 0° C. over 2 hours. The reaction was quenched via the addition of saturated (aq.) ammonium chloride. The product was extracted using EtOAc (2×50 mL). The combined EtOAc layers were washed with brine solution and then dried over anhydrous sodium sulfate. The desiccant was filtered off and the filtrate concentrated under reduced pressure, yielding Intermediate 18 (31) as a colorless oil (627 mg, 82% yield). Product did not ionize under LCMS conditions. LC retention time 0.81 min [C]. $^1$H NMR (400 MHz, CHLOROFORM-d) δ 7.54 (s, 1H), 4.19 (s, 3H).

Intermediate 19

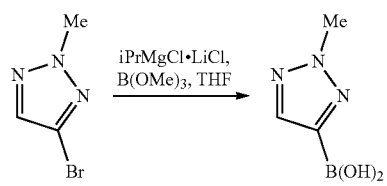

To a solution of 4-bromo-2-methyl-2H-1,2,3-triazole (0.896 g, 5.53 mmol) in THF (12 mL) cooled to 10° C. was slowly added isopropylmagnesium chloride lithium chloride complex, 1.3 in THF (8.51 mL, 11.06 mmol). The reaction was stirred 2 hr cold. Then cooled to −20° C. Trimethyl borate (1.854 mL, 16.59 mmol) was added and the mixture was stirred 1 hour. At this time, the reaction mixture was quenched with 1N HCl, transferred to a separatory funnel and extracted with EtOAc (2×). The combined organic were washed brine and then dried over anhydrous sodium sulfate. Filtration and concentration afforded (2-methyl-2H-1,2,3-triazol-4-yl)boronic acid (533 mg, 3.78 mmol, 68.3% yield) as a white solid. $^1$H NMR (400 MHz, DMSO-d6) δ 8.31 (br s, 2H), 7.89 (s, 1H), 4.16 (s, 3H).

Intermediate 20

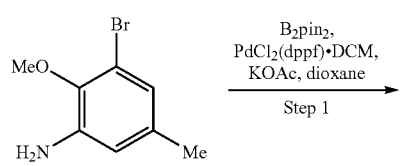

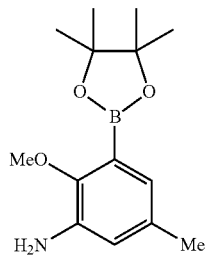

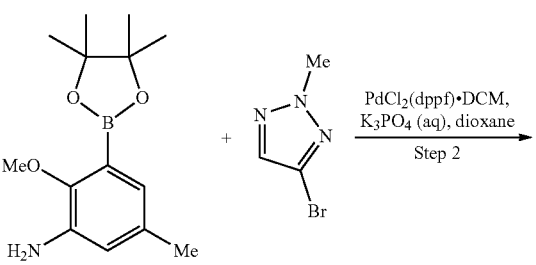

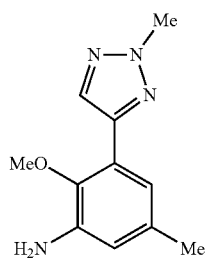

Step 1

A sealed vessel containing 3-bromo-2-methoxy-5-methylaniline (150 mg, 0.694 mmol), 4,4,4',4',5,5,5',5'-octamethyl-2,2'-bi(1,3,2,-dioxaborolane) (229 mg, 0.90 mmol), PdCl$_2$(dppf)·DCM (28 mg, 0.035 mmol) and potassium acetate (204 mg, 2.08 mmol) in dioxane (4 mL) was heated to 100° C. for 8 hours. The reaction mixture was used as is in the subsequent step. MS (M+1) m/z: 264.1 (MH$^+$). LC retention time 0.82 min [E].

Step 2

To the reaction mixture from step 1 was added Intermediate 18 (146 mg, 0.904 mmol) and the mixture was degassed by bubbling through nitrogen for 5 minutes. To this K$_3$PO$_4$ (2M aq. 1.04 mL, 2.09 mmol) was rapidly added. The mixture was heated at 100° C. for 1 hour and then cooled to room temperature. The reaction was partitioned between EtOAc (30 mL) and brine solution (20 mL). The EtOAc layer was dried over anhydrous sodium sulfate, filtered and concentrated under reduced pressure. The crude product was purified using automated chromatography (0-70% EtOAc/hexanes). The pure fractions were collected and concentrated to provide Intermediate 20 as a yellow oil (120 mg, 79% yield over two steps). MS (M+1) m/z: 219.3 (MH$^+$). LC retention time 0.71 min [E].

Intermediate 21

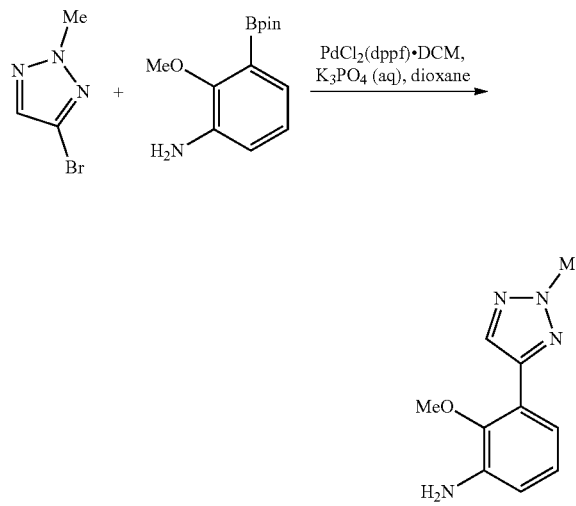

To a stirred solution of Intermediate 18 (100 mg, 0.62 mmol) in dioxane (3 mL) was added Intermediate 3 (185 mg, 0.74 mmol) and potassium carbonate (256 mg, 1.85 mmol). The reaction mixture was degassed by bubbling nitrogen through the mixture for 10 minutes. PdCl$_2$(dppf)·DCM (25 mg, 0.031 mmol) was then added and the mixture degassed again via bubbling nitrogen through the mixture for 10 minutes. The reaction was heated to 110° C. in the microwave for 2 hours. The reaction was cooled to room temperature, filtered and concentrated. The crude product was then purified using reverse phase chromatography (A: 0.1% formic acid in water; B: 100% acetonitrile) to give Intermediate 21 as a brown amorphous solid (70 mg, 55% yield). MS (M+1) m/z: 205.1 (MH$^+$). LC retention time 1.25 min [F]. $^1$H NMR (400 MHz, DMSO-d) δ 8.02 (s, 1H), 7.02 (dd, J=8.0, 1.6 Hz, 1H), 6.89 (t, J=8.0 Hz, 1H), 6.70 (dd, J=8.0, 1.6 Hz, 1H), 5.06 (br s, 2H), 4.19 (s, 3H), 3.59 (s, 3H).

Example 9

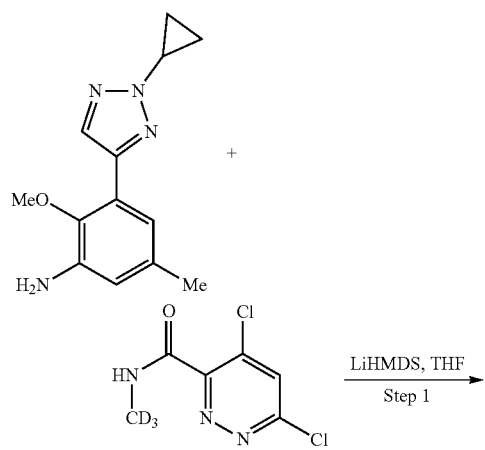

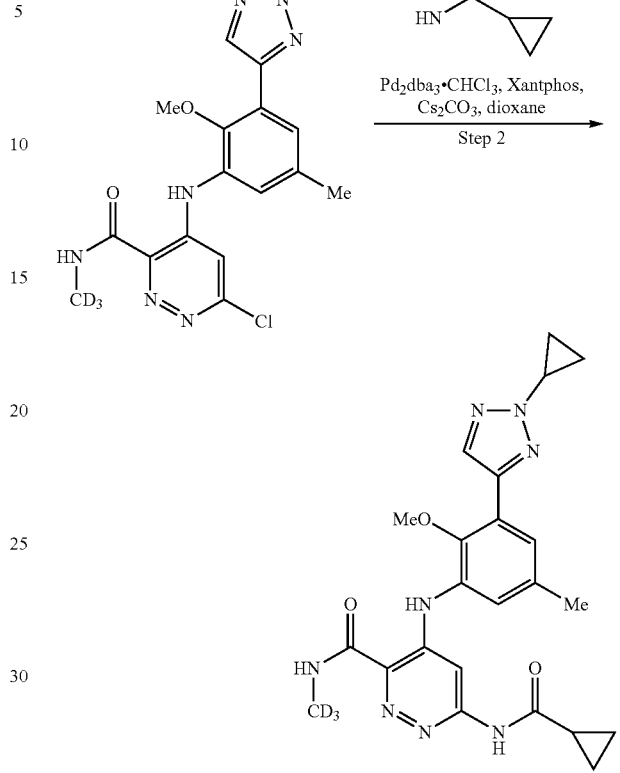

Step 1

4,6-Dichloro-N-(methyl-d3)pyridazine-3-carboxamide (73 mg, 0.35 mmol) and Intermediate 22 (96 mg, 0.35 mmol) were combined in THF (3 mL) at room temperature. To this was added LiHMDS (1M in THF, 1.2 mL, 1.2 mmol) dropwise over 10 minutes. The reaction was stirred at room temperature for 30 minutes and then quenched via the addition of 2 mL of saturated aqueous ammonium chloride solution. The reaction mixture was partitioned between EtOAc (30 mL) and saturated aqueous ammonium chloride solution (20 mL). The organic layer was washed with brine solution (20 mL), dried over anhydrous sodium sulfate, filtered and concentrated to afford a crude brown solid. This was purified using automated chromatography (0-100% EtOAc/hexanes). Pure fractions were combined to afford 6-chloro-4-((3-(2-cyclopropyl-2H-1,2,3-triazol-4-yl)-2-methoxy-5-methylphenyl)amino)-N-(methyl-d3) pyridazine-3-carboxamide (72 mg, 50% yield) as a light yellow solid. MS (M+1) m/z: 417.1 (MH$^+$). LC retention time 1.09 min [E].

Step 2

A mixture of 6-chloro-4-((3-(2-cyclopropyl-2H-1,2,3-triazol-4-yl)-2-methoxy-5-methylphenyl)amino)-N-(methyl-d3)pyridazine-3-carboxamide (72 mg, 0.17 mmol), cyclopropanecarboxamide (29 mg, 0.34 mmol), tris (dibenzylideneacetone)dipalladium(0) chloroform adduct (17.8 mg, 0.017 mmol), 4,5-bis(diphenylphosphino)-9,9'-dimethylxanthene (Xantphos) (20 mg, 0.035 mmol) and cesium carbonate (225 mg, 0.69 mmol) in dioxane (0.7 mL) was degassed by bubbling nitrogen through the mixture for 5 minutes. The reaction vessel was then sealed and heated to 130° C. for 45 minutes. The reaction was cooled to room temperature, diluted with DMF, filtered through a 0.45 micron nylon filter and then purified using preparative HPLC purification to provide 47 (26.7 mg, 33% yield). MS (M+1) m/z: 466.2 (MH+). LC retention time 1.94 min [G]. $^1$H NMR (500 MHz, DMSO-d6) δ 11.27 (s, 1H), 10.89 (s, 1H), 9.11 (s, 1H), 8.07 (d, J=1.4 Hz, 2H), 7.52 (s, 1H), 7.27 (s, 1H), 4.18 (dt, J=7.5, 3.8 Hz, 1H), 3.59 (s, 3H), 2.32 (s, 3H), 2.17-2.00 (m, 1H), 1.35-1.18 (m, 2H), 1.18-1.06 (m, 2H), 0.88-0.73 (in, 4H).

The following Examples were prepared in a similar manner to the preparation of Example 9 using described intermediates and commercial reagents allowing for some minor modifications to solvent, reaction time, etc.

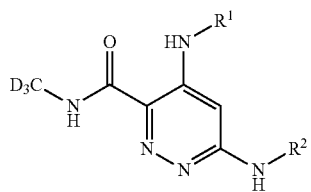

TABLE 1

| Example No. | R$^1$ | R$^2$ | MW | m/z [M + H]$^+$ | Rt (min) [Method] |
|---|---|---|---|---|---|
| 10 | Et-triazole-(MeO, F-phenyl) | cyclopropyl ketone | 457.2 | 457.9 | 1.68 [G] |
| 11 | cyclopropyl-triazole-(MeO-phenyl) | cyclopropyl ketone | 451.2 | 452.3 | 1.67 [G] |
| 12 | cyclopropyl-triazole-(MeO, F-phenyl) | cyclopropyl ketone | 469.2 | 470.2 | 2.06 [G] |
| 13 | Me-triazole-(MeO-phenyl) | spiropentyl ketone | 451.5 | 452.2 | 1.47 [C] |

TABLE 1-continued

| | | | | | |
|---|---|---|---|---|---|
| 14 | (cyclopropyl-triazole-methoxypyridine structure) | (cyclopropyl ketone) | 452.2 | 453.1 | 1.92 [G] |
| 15 | (ethyl-triazole-methoxy-chlorophenyl structure) | (cyclopropyl ketone) | 473.2 | 474.1 | 2.16 [G] |
| 16 | (cyclopropyl-triazole-methoxy-fluorophenyl structure) | (cyclopropyl ketone) | 469.2 | 470.2 | 1.95 [G] |
| 17 | (methyl-triazole-methoxy-methylphenyl structure) | (cyclopropyl ketone) | 439.2 | 440.2 | 1.71 [G] |
| 18 | (methyl-triazole-methoxy-fluorophenyl structure) | (cyclopropyl ketone) | 443.2 | 444.1 | 1.73 [G] |

| Example No. | $^1$H NMR |
|---|---|
| 2 | $^1$H-NMR (400 MHz, DMSO-$d_6$): δ 11.34 (s, 1H), 11.02 (s, 1H), 9.16 (s, 1H), 8.20 (s, 1H), 8.16 (s, 1H), 7.72 (dd, J = 7.8, 1.20 Hz, 1H), 7.49 (dd, J = 7.8, 1.6 Hz, 1H), 7.31 (t, J = 8.00 Hz, 1H), 5.03-5.01 (m, 1H), 4.91-4.86 (m, 2H), 4.82-4.79 (m, 1H), 3.67 (s, 3H), 2.14-2.05 (m, 1H), 0.84-0.82 (m, 4H). |
| 3 | $^1$H NMR (CD$_3$OD): 8.22 (s, 1H), 7.91 (dd, J = 7, 3 Hz, 1H), 7.57-7.52 (m, 3H), 7.36 (t, J = 8 Hz, 1H), 6.55-6.25 (m, 1H), 4.98-4.95 (m, 2H), 3.75 (s, 3H), 1.89-1.87 (m, 1H), 1.08-1.02 (m, 2H), 1.01-0.97 (m, 2H). |
| 4 | $^1$H-NMR (400 MHz, DMSO-$d_6$): δ 11.41 (s, 1H), 11.21 (s, 1H), 9.21 (s, 1H), 8.26 (s, 1H), 8.19 (s, 1H), 7.41 (d, J = 10.4 Hz, 1H), 7.38 (d, |

TABLE 1-continued

| | |
|---|---|
| | J = 10.8 Hz, 1H), 4.25 (s, 3H), 3.68 (s, 3H), 2.00-2.10 (m, 1H), 1.18-1.20 (m, 4H). |
| 5 | $^1$H-NMR (400 MHz, DMSO-d$_6$): δ 11.06 (s, 1H), 10.28 (s, 1H), 9.15 (s, 1H), 8.16 (s, 1H), 7.97-7.92 (m, 2H), 7.69 (dd, J = 1.20, 7.80 Hz, 1H), 7.57 (dd, J = 1.20, 8.00 Hz, 1H), 7.32-7.30 (m, 1H), 7.24-7.21 (m, 1H), 4.25 (s, 3H), 3.95 (s, 3H), 3.68 (s, 3H). |
| 6 | $^1$H-NMR (400 MHz, DMSO-d$_6$): δ 10.99 (s, 1H), 9.71 (s, 1H), 9.03 (s, 1H), 8.14 (s, 1H), 7.79-7.58 (m, 3H), 7.35-7.31 (m, 1H), 5.96 (d, J = Hz, 1H), 4.24 (s, 3H), 3.67 (s, 3H), 3.58 (s, 3H), 2.20 (s, 3H). |
| 7 | $^1$H-NMR (400 MHz, DMSO-d$_6$): 11.00 (s, 1H), 10.83 (s, 1H), 9.13 (d, J = Hz, 1H), 8.14 (s, 1H), 7.89 (s, 1H), 7.72 (d, J = 1.60 Hz, 1H), 7.50 (d, J = 1.60 Hz, 1H), 7.31-7.29 (m, 1H), 4.24 (s, 3H), 3.67 (s, 6H). |
| 8 | $^1$H-NMR (400 MHz, DMSO-d$_6$): δ 11.04 (s, 1H), 10.20 (s, 1H), 9.13 (s, 1H), 8.20 (d, J = 1.20 Hz, 1H), 8.18-8.15 (m, 2H), 7.60-7.69 (m, 4H), 7.37-7.33 (m, 1H), 6.95-6.91 (m, 1H), 4.24 (s, 3H), 3.67 (s, 3H). |
| 10 | 1H NMR (500 MHz, DMSO-d6) δ 11.30 (s, 1H), 10.76 (s, 1H), 9.12 (s, 1H), 8.01 (s, 1H), 7.96 (s, 1H), 7.52 (dd, J = 8.7, 5.6 Hz, 1H), 7.24 (t, J = 9.3 Hz, 1H), 4.54 (q, J = 7.2 Hz, 2H), 3.58 (s, 3H), 2.12-2.04 (m, 1H), 1.51 (t, J = 7.3 Hz, 3H), 0.88-0.78 (m, 4H) |
| 11 | $^1$H NMR (500 MHz, DMSO-d6) δ 11.30 (s, 1H), 10.97 (s, 1H), 9.12 (s, 1H), 8.11 (d, J = 9.8 Hz, 2H), 7.70 (dd, J = 7.9, 1.2 Hz, 1H), 7.46 (br d, J = 6.7 Hz, 1H), 7.29 (t, J = 7.9 Hz, 1H), 4.27-4.13 (m, 1H), 3.64 (s, 3H), 2.06 (br d, J = 4.9 Hz, 1H), 1.31-1.22 (m, 2H), 1.20-1.07 (m, 2H), 0.87-0.77 (m, 4H). |
| 12 | 1H NMR (500 MHz, DMSO-d6) δ 11.39 (s, 1H), 11.19 (s, 1H), 9.17 (s, 1H), 8.24 (s, 1H), 8.17 (s, 1H), 7.47-7.39 (m, 1H), 7.40-7.33 (m, 1H), 4.22 (tt, J = 7.4, 3.8 Hz, 1H), 3.66 (s, 3H), 2.18-2.06 (m, 1H), 1.34-1.25 (m, 2H), 1.19-1.08 (m, 2H), 0.85 (br d, J = 6.1 Hz, 4H). |
| 13 | $^1$H NMR (400 MHz, DMSO-d$_6$) δ 11.13 (s, 1H), 11.03 (s, 1H), 9.14 (s, 1H), 8.17 (s, 1H), 8.12 (s, 1H), 7.70 (dd, J = 7.8, 1.6 Hz, 1H), 7.48 (dd, J = 8.0, 1.5 Hz, 1H), 7.31 (t, J = 1.9 Hz, 1H), 4.23 (s, 3H), 3.65 (s, 3H), 2.43 (dd, J = 7.4, 4.3 Hz, 1H), 1.38 (t, J = 3.8 Hz, 1H), 1.36-1.31 (m, 1H), 0.94-0.79 (m, 3H), 0.77-0.67 (m, 1H) |
| 14 | 1H NMR (500 MHz, DMSO-d6) δ 12.40 (s, 1H), 11.32 (s, 1H), 9.85 (s, 1H), 9.23 (br s, 1H), 8.29 (s, 1H), 8.14 (d, J = 5.3 Hz, 1H), 7.46 (d, J = 5.3 Hz, 1H), 4.25 (tt, J = 7.4, 3.8 Hz, 1H), 3.80 (s, 3H), 2.12 (br d, J = 4.0 Hz, 1H), 1.33-1.25 (m, 2H), 1.24-1.09 (m, 2H), 0.95-0.82 (m, 4H). |
| 15 | 1H NMR (500 MHz, DMSO-d6) δ 11.37 (s, 1H), 11.13 (s, 1H), 9.18 (s, 1H), 8.17 (d, J = 8.8 Hz, 2H), 7.68 (d, J = 2.1 Hz, 1H), 7.55 (d, J = 2.1 Hz, 1H), 4.53 (q, J = 7.3 Hz, 2H), 3.68 (s, 3H), 2.10 (br t, J = 5.2 Hz, 1H), 1.52 (t, J = 7.3 Hz, 3H), 0.93-0.77 (m, 4H). |
| 16 | $^1$H NMR (500 MHz, DMSO-d$_6$) δ 11.30 (s, 1H), 10.76 (s, 1H), 9.12 (s, 1H), 7.99 (s, 1H), 7.95 (s, 1H), 7.51 (dd, J = 8.9, 5.8 Hz, 1H), 7.24 (t, J = 9.3 Hz, 1H), 4.22 (tt, J = 7.4, 3.6 Hz, 1H), 3.57 (s, 3H), 2.11-2.02 (m, 1H), 1.28-1.22 (m, 2H), 1.17-1.09 (m, 2H), 0.86-0.77 (m, 4H). |
| 17 | 1H NMR (500 MHz, DMSO-d6) δ 11.28 (s, 1H), 10.90 (s, 1H), 9.12 (s, 1H), 8.09 (d, J = 6.1 Hz, 2H), 7.52 (d, J = 0.9 Hz, 1H), 7.38-7.10 (m, 1H), 4.22 (s, 3H), 3.60 (s, 3H), 2.32 (s, 3H), 2.07 (br t, J = 5.0 Hz, 1H), 0.90-0.68 (m, 4H). |
| 18 | $^1$H NMR (500 MHz, DMSO-d$_6$) δ 11.28 (s, 1H), 10.74 (s, 1H), 9.10 (s, 1H), 7.99 (s, 1H), 7.94 (s, 1H), 7.51 (dd, J = 9.0, 5.6 Hz, 1H), 7.23 (t, J = 9.2 Hz, 1H), 4.24 (s, 3H), 3.56 (s, 3H), 2.12-1.98 (m, 1H), 0.90-0.76 (m, 4H). |

Example 19

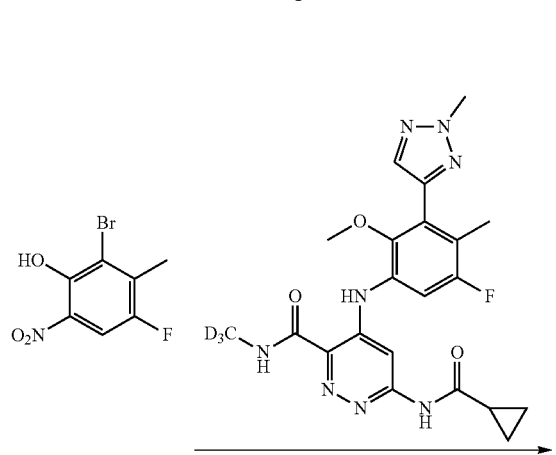

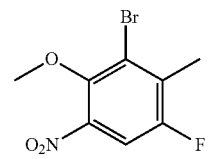

Step 1

To a solution of 2-bromo-4-fluoro-3-methyl-6-nitrophenol (266 mg, 1.064 mmol) in DMF (4 ml) was added potassium carbonate (441 mg, 3.19 mmol). The mixture was stirred for 15 minutes and then iodomethane (0.133 ml, 2.128 mmol) was added. The resulting mixture was stirred at rt overnight. LCMS indicated complete conversion to product. Cold water was added (75 mL), the mixture was stirred and then sonicated before the solid was collected with filtration. This material was then dissolved in EtOAc (150 mL). This solution was washed 1×10% LiCl, 1× brine, dried over anhydrous sodium sulfate, filtered and the filtrated was concentrated. The residue was loaded onto a 12 g silica gel column and purified by flash chromatography eluting with 0-50% EtOAc in hexanes. Concentration of the pure fractions afforded a pale yellow solid, 3-bromo-1-fluoro-4-methoxy-2-methyl-5-nitrobenzene (231 mg, 0.875 mmol, 82% yield).

MS (M+1) m/z: n/a (M+H)+. LC retention time 1.572 [C] [the nitro product does not ionize]

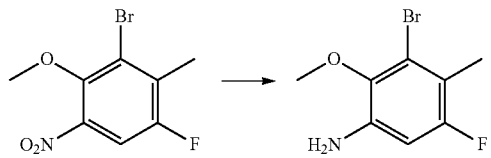

Step 2

A mixture of 3-bromo-1-fluoro-4-methoxy-2-methyl-5-nitrobenzene (230 mg, 0.871 mmol) and tin(II) chloride, dihydrate (786 mg, 3.48 mmol) in ethyl acetate (8.5 mL) was stirred at reflux for 1 hr. After cooling to rt, the reaction was then diluted with ethyl acetate (100 ml). The solution was washed 3× with 2.5N NaOH, 1× water and 1× brine. Drying over anhydrous sodium sulfate and concentration afforded 3-bromo-5-fluoro-2-methoxy-4-methylaniline (136 mg, 0.581 mmol, 66.7% yield) as a light brown oil. MS (M+1) m/z: 235.9 (M+H)+. LC retention time 1.37 [C].

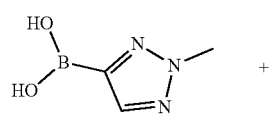    +

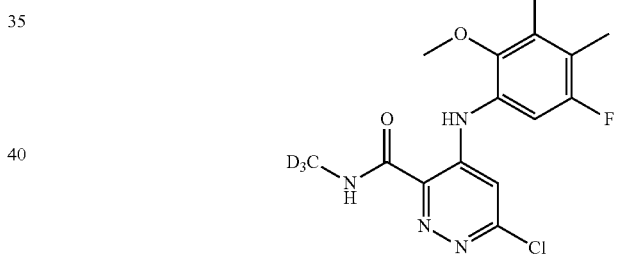

Step 3

A stirred mixture of (2-methyl-2H-1,2,3-triazol-4-yl)boronic acid (65.1 mg, 0.513 mmol), 3-bromo-5-fluoro-2-methoxy-4-methylaniline (60 mg, 0.256 mmol) and PdCl$_2$(dppf)-dichloromethane adduct (10.47 mg, 0.013 mmol) in dioxane (3 mL) was degassed by bubbling nitrogen through the mixture for 5 minutes. 2M K$_3$PO$_4$ (aq) (0.385 mL, 0.769 mmol) was quickly added and the reaction mixture heated to 100° C. for 30 minutes. The reaction turned dark almost immediately. LC-MS showed complete consumption of the starting material. The reaction mixture was cooled to room temperature, then diluted with EtOAc (75 mL). This solution was then dried over anhydrous sodium sulfate, filtered, concentrated and purified by flash chromatography, eluting with 0-100% EtOAc in hexanes to afford 5-fluoro-2-methoxy-4-methyl-3-(2-methyl-2H-1,2,3-triazol-4-yl) aniline (44 mg, 0.186 mmol, 72.7% yield) as a yellow oil.

MS (M+1) m/z: 237.2 (M+H)+. LC retention time 1.08 [C]. $^1$H NMR (400 MHz, chloroform-d) δ 7.69 (s, 1H), 6.52 (d, J=10.6 Hz, 1H), 4.28 (s, 3H), 3.84 (br s, 2H), 3.43 (s, 3H), 2.05 (d, J=2.3 Hz, 3H).

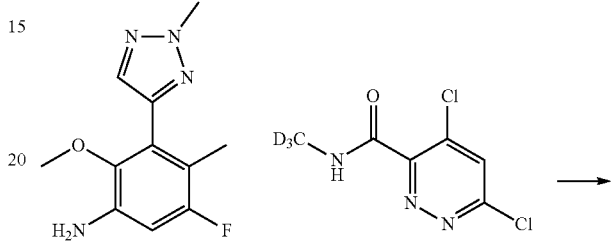

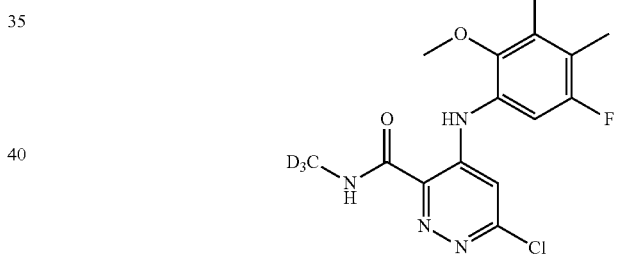

Step 4

To a solution of 4,6-dichloro-N-(methyl-d3)pyridazine-3-carboxamide (38 mg, 0.182 mmol) and 5-fluoro-2-methoxy-4-methyl-3-(2-methyl-2H-1,2,3-triazol-4-yl) aniline (42.9 mg, 0.182 mmol) in tetrahydrofuran (1.5 mL) was added lithium bis(trimethylsilyl)amide (1M in THF, 0.454 mL, 0.454 mmol) in a dropwise manner using a syringe and the reaction was stirred until complete by LCMS (~15 min). Saturated aqueous ammonium chloride was added to quench the residual base. Then the reaction was partitioned between EtOAc and water. The water layer was extracted 1× with ethyl acetate, and then the combined organic layers were washed 1× with saturated ammonium chloride solution and 1× with brine. The combined organic layer was then dried over anhydrous sodium sulfate, filtered and concentrated. The material was used directly as is in the next step. 6-chloro-4-((5-fluoro-2-methoxy-4-methyl-3-(2-methyl-2H-1,2,3-triazol-4-yl)phenyl)amino)-N-(methyl-d3) pyridazine-3-carboxamide (56 mg, 0.137 mmol, 75% yield). MS (M+1) m/z: 409.1 (M+H)+. LC retention time 1.35 [C]

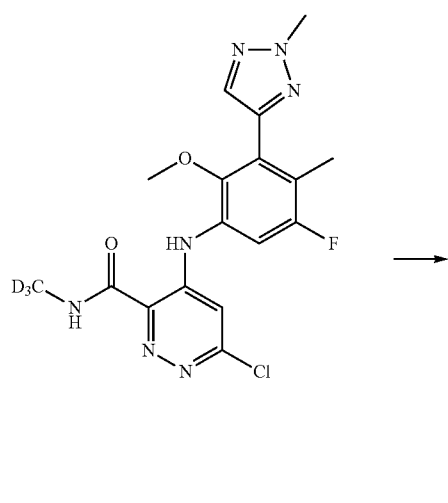

→

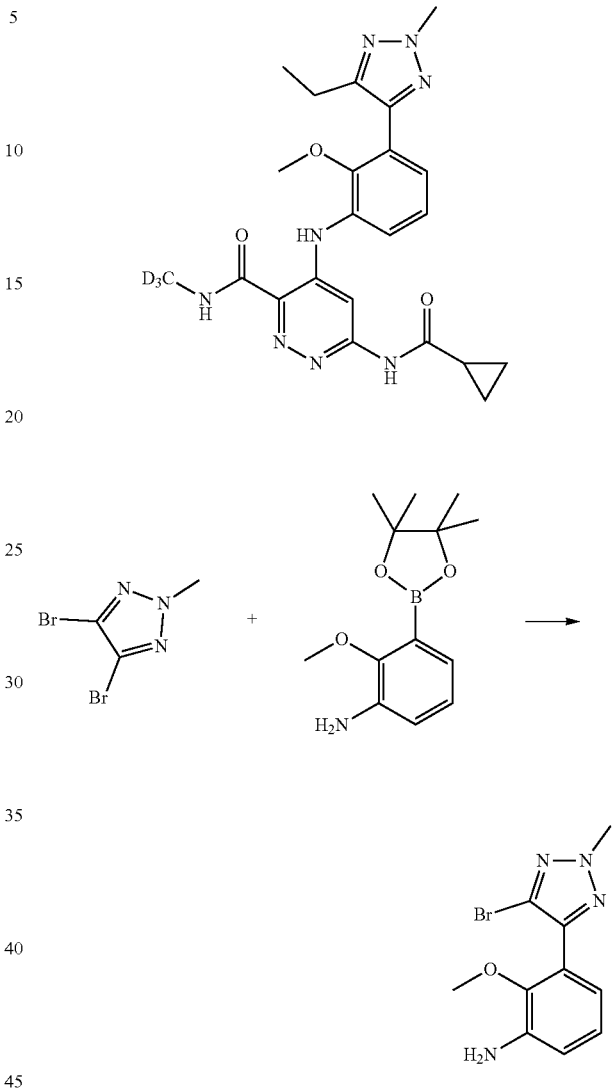

Example 20

Step 1

A stirred mixture of 4,5-dibromo-2-methyl-2H-1,2,3-triazole (0.273 g, 1.133 mmol), 2-methoxy-3-(4,4,5,5-tetramethyl-1,3,2-dioxaborolan-2-yl) aniline (0.268 g, 1.077 mmol) and PdCl$_2$(dppf)-dichloromethane adduct (0.046 g, 0.057 mmol) in dioxane (8 mL) was degassed by bubbling nitrogen through the mixture for 5 minutes. 2M K$_3$PO$_4$ (aq) (1.700 mL, 3.40 mmol) was quickly added and the reaction mixture heated at 50° C. for 25 minutes. LC-MS showed complete consumption of the starting material. The reaction mixture was cooled to room temperature, then diluted with EtOAc (75 mL). This solution was then dried over sodium sulfate, filtered, concentrated and purified by flash chromatography, eluting with 0-100% EtOAc in hexanes to afford 3-(5-bromo-2-methyl-2H-1,2,3-triazol-4-yl)-2-methoxyaniline (144 mg, 0.509 mmol, 44.9% yield) as a yellow oil. MS (M+1) m/z: 282.8/284.8 (M+H)+. LC retention time 1.05 [C]

Step 5

A mixture of 6-chloro-4-((5-fluoro-2-methoxy-4-methyl-3-(2-methyl-2H-1,2,3-triazol-4-yl)phenyl)amino)-N-(methyl-d3)pyridazine-3-carboxamide (37 mg, 0.091 mmol), xantphos (10.47 mg, 0.018 mmol), and cyclopropanecarboxamide (38.5 mg, 0.453 mmol) in dioxane (1.5 mL) was degassed by bubbling N$_2$ through it for 5 minutes. Then Cs$_2$CO$_3$ (118 mg, 0.362 mmol) and Pd$_2$(dba)$_3$ (8.29 mg, 9.05 µmol) were added, the vessel was sealed, and the reaction was stirred at 130° C. for 2 hr. The reaction was complete by LC-MS and was diluted to 2 mL with DMF and was then purified by prep HPLC to afford 6-(cyclopropanecarboxamido)-4-((5-fluoro-2-methoxy-4-methyl-3-(2-methyl-2H-1,2,3-triazol-4-yl)phenyl)amino)-N-(methyl-d3) pyridazine-3-carboxamide (17.8 mg, 0.039 mmol, 43.0% yield). MS (M+1) m/z: 458.1 (M+H)+. LC retention time 1.25 [C]. $^1$H NMR (500 MHz, DMSO-d6) δ 11.35 (s, 1H), 10.97 (s, 1H), 9.14 (s, 1H), 8.17 (s, 1H), 7.91 (s, 1H), 7.40 (d, J=10.7 Hz, 1H), 4.25 (s, 3H), 2.55 (s, 3H), 2.09 (br d, J=1.8 Hz, 4H), 0.85 (br d, J=6.1 Hz, 4H).

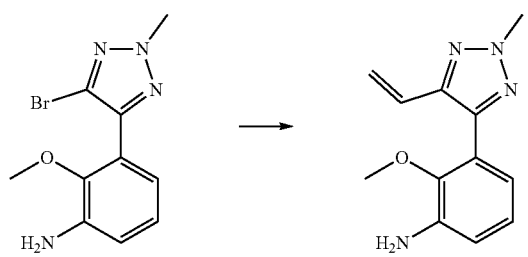 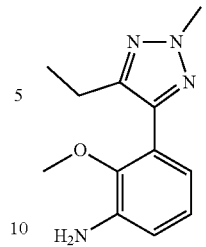

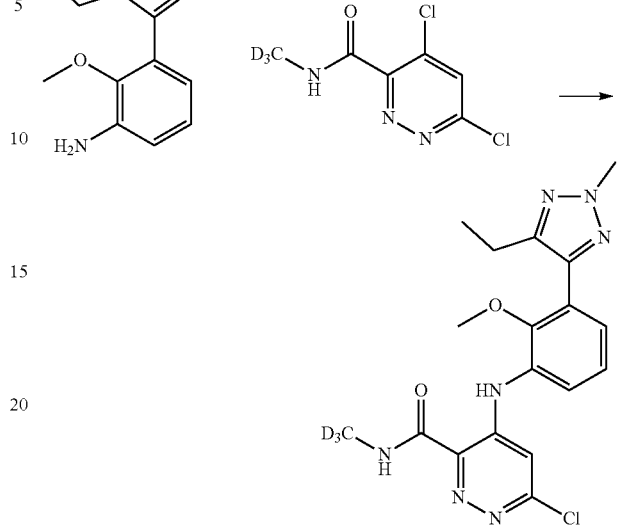

Step 4

Step 2

A mixture of 3-(5-bromo-2-methyl-2H-1,2,3-triazol-4-yl)-2-methoxyaniline (144 mg, 0.509 mmol), dicyclohexyl (2',6'-dimethoxy-[1,1'-biphenyl]-2-yl)phosphine [S-Phos] (22.97 mg, 0.056 mmol), palladium(II) acetate (5.71 mg, 0.025 mmol) and 4,4,5,5-tetramethyl-2-vinyl-1,3,2-dioxaborolane (196 mg, 1.272 mmol) in dioxane (3 mL) was purged with nitrogen for 1 minute. 2M $K_3PO_4$ (aq.)(1.399 mL, 2.80 mmol) was added and the reaction mixture was heated to 100° C. for 1 h. LCMS indicated that SM was consumed. The mixture was concentrated and then purified by flash chromatography, using a 24 g silica gel column, eluting with 0-50% EtOAc in hexanes to afford 2-methoxy-3-(2-methyl-5-vinyl-2H-1,2,3-triazol-4-yl) aniline (111 mg, 0.434 mmol, 85% yield) MS (M+1) m/z: 231.0 (M+H)$^+$. LC retention time 0.93 [C]

To a solution of 4,6-dichloro-N-(methyl-d3)pyridazine-3-carboxamide (113 mg, 0.542 mmol) and 3-(5-ethyl-2-methyl-2H-1,2,3-triazol-4-yl)-2-methoxyaniline (105 mg, 0.452 mmol) (re-purified) in THF (4 mL) was added lithium bis(trimethylsilyl)amide, 1M in THF (1.582 mL, 1.582 mmol) in a dropwise manner (<5 min), using a syringe, and the reaction stirred until complete by LCMS (~15 min). Sat. ammonium chloride (aq.) was added to quench the residual base. Then the reaction was partitioned between EtOAc and water. The water layer was extracted 1× with ethyl acetate, and then the combined organic layer was washed 1× with sat. ammonium chloride (aq.) and 1× with brine. The combined organic layer was then dried over anhydrous sodium sulfate, filtered and concentrated to afford a residue that was chromatographed on a 12 g ISCO column eluted with 0-100% EtOAc in hexanes to afford 6-chloro-4-((3-(5-ethyl-2-methyl-2H-1,2,3-triazol-4-yl)-2-methoxyphenyl)amino)-N-(methyl-d3)pyridazine-3-carboxamide (122 mg, 0.301 mmol, 66.7% yield) as an pale yellow solid.

MS (M+1) m/z: 405.1 (M+H)+. LC retention time 1.43 [C]

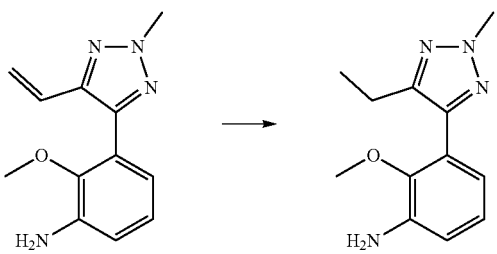 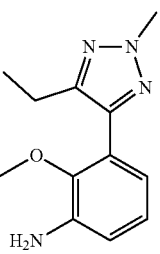

Step 3

Palladium on carbon, 10% (5.13 mg, 0.048 mmol) was added to a solution of 2-methoxy-3-(2-methyl-5-vinyl-2H-1,2,3-triazol-4-yl) aniline (111 mg, 0.482 mmol) in ethanol (5 ml). The resulting mixture was degassed by vacuum then stirred at rt overnight under a hydrogen atmosphere. After stirring overnight, the mixture was filtered and the filtrate was concentrated to afford 3-(5-ethyl-2-methyl-2H-1,2,3-triazol-4-yl)-2-methoxyaniline (115 mg, 0.446 mmol, 92% yield), a waxy white solid. $^1$H NMR (400 MHz, chloroform-d) δ 7.01-6.94 (m, 1H), 6.80 (dd, J=7.9, 1.6 Hz, 1H), 6.75 (dd, J=7.6, 1.6 Hz, 1H), 4.20 (s, 3H), 3.91 (br s, 2H), 3.50 (s, 3H), 2.71 (q, J=7.6 Hz, 2H), 1.21 (t, J=7.6 Hz, 3H).

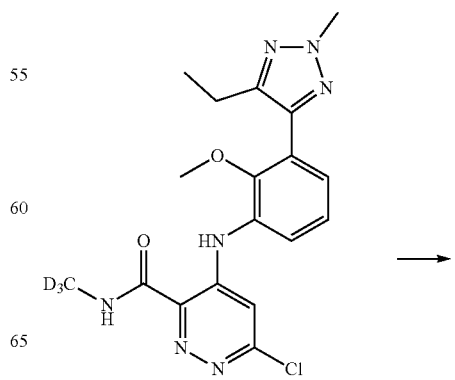

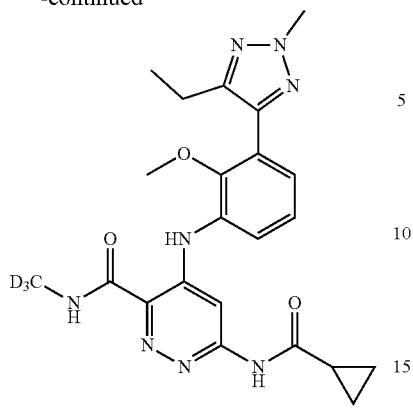

Step 5

A mixture of 6-chloro-4-((3-(5-ethyl-2-methyl-2H-1,2,3-triazol-4-yl)-2-methoxyphenyl)amino)-N-(methyl-d3) pyridazine-3-carboxamide (40 mg, 0.099 mmol), xantphos (11.43 mg, 0.020 mmol), and cyclopropanecarboxamide (42.0 mg, 0.494 mmol) in dioxane (1.3 mL) was degassed by bubbling nitrogen through it for 5 minutes. Then cesium carbonate (129 mg, 0.395 mmol) and Pd₂(dba)₃ (9.05 mg, 9.88 μmol) were added, the vessel was sealed, and the reaction was stirred at 130° C. for 2 h. The reaction was complete by LC-MS and was diluted to 2 mL with DMF, filtered and purified by prep HPLC to afford 6-(cyclopropanecarboxamido)-4-((3-(5-ethyl-2-methyl-2H-1,2,3-triazol-4-yl)-2-methoxyphenyl)amino)-N-(methyl-d3) pyridazine-3-carboxamide (17.8 mg, 0.039 mmol, 39.7% yield). MS (M+1) m/z: 454.1 (M+H)⁺. LC retention time 1.23 [C]. ¹H NMR (500 MHz, DMSO-d6) δ 11.31 (s, 1H), 10.95 (s, 1H), 9.12 (s, 1H), 8.13 (s, 1H), 7.51 (d, J=7.6 Hz, 1H), 7.28 (t, J=7.8 Hz, 1H), 7.20 (d, J=7.6 Hz, 1H), 4.15 (s, 3H), 3.42 (s, 3H), 2.60 (q, J=7.4 Hz, 2H), 2.12-2.06 (m, 1H), 1.12 (t, J=7.6 Hz, 3H), 0.88-0.80 (m, 4H).

Example 21

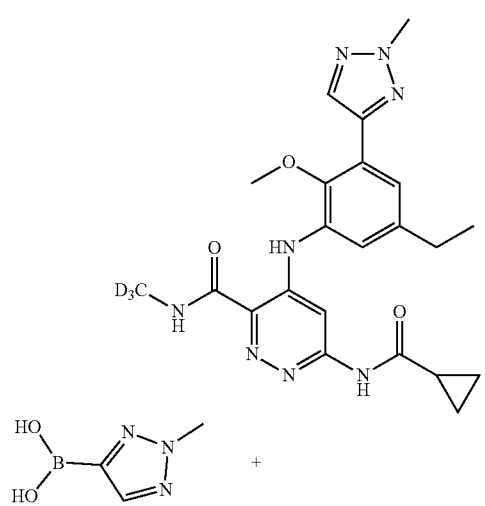

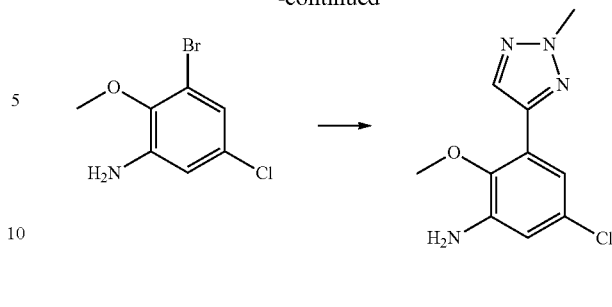

Step 1

A stirred mixture of (2-methyl-2H-1,2,3-triazol-4-yl)boronic acid (209 mg, 1.649 mmol), 3-bromo-5-chloro-2-methoxyaniline (300 mg, 1.269 mmol) and PdCl₂(dppf)-dichloromethane adduct (51.8 mg, 0.063 mmol) in dioxane (3 mL) was degassed by bubbling nitrogen through the mixture for 5 minutes. 2M K₃PO₄ (aq) (1.903 mL, 3.81 mmol) was quickly added and the reaction mixture heated at 50° C. for 30 minutes. LC-MS showed incomplete consumption of the starting material. The reaction mixture was cooled to room temperature, then diluted with EtOAc (75 mL). This solution was then dried over anhydrous sodium sulfate, filtered, concentrated and purified by flash chromatography, eluting with 0-100% EtOAc in hexanes to afford 5-chloro-2-methoxy-3-(2-methyl-2H-1,2,3-triazol-4-yl) aniline (101 mg, 0.423 mmol, 33.4% yield) as an off-white solid. MS (M+1) m/z: 239.0 (M+H)+. LC retention time 1.20 [C].

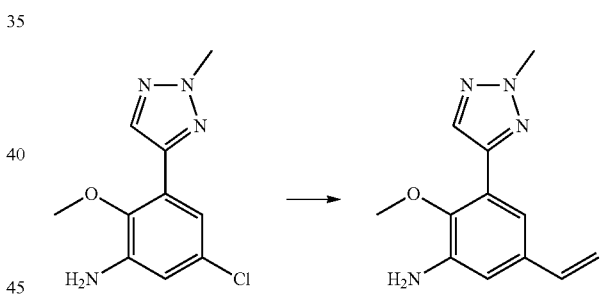

Step 2

A mixture of 5-chloro-2-methoxy-3-(2-methyl-2H-1,2,3-triazol-4-yl) aniline (101 mg, 0.423 mmol), dicyclohexyl(2',6'-dimethoxy-[1,1'-biphenyl]-2-yl)phosphine [S-Phos] (19.11 mg, 0.047 mmol), palladium(II) acetate (4.75 mg, 0.021 mmol) and 4,4,5,5-tetramethyl-2-vinyl-1,3,2-dioxaborolane (163 mg, 1.058 mmol) in dioxane (3 mL) was purged with nitrogen for 1 minute. 2M K₃PO₄ (aq.) (1.164 mL, 2.327 mmol) was added and the reaction mixture was heated to 100° C. overnight. LC-MS indicated that SM was consumed. The reaction mixture was concentrated and purified by flash chromatography, eluting with 0-50% EtOAc in hexanes to afford 2-methoxy-3-(2-methyl-2H-1,2,3-triazol-4-yl)-5-vinylaniline (100 mg, 0.391 mmol, 92% yield). MS (M+1) m/z: 231.0 (M+H)⁺. LC retention time 1.04 [C].

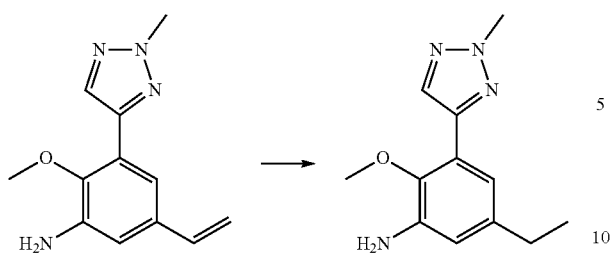

Step 3

Pd on Carbon, 10% (4.62 mg, 0.043 mmol) was added to a solution of 2-methoxy-3-(2-methyl-2H-1,2,3-triazol-4-yl)-5-vinylaniline (100 mg, 0.434 mmol) in ethanol (5 ml). The resulting mixture was degassed by vacuum and then stirred at room temperature overnight under a hydrogen atmosphere. LCMS indicated complete conversion to product. Filtration of the and concentration afforded 5-ethyl-2-methoxy-3-(2-methyl-2H-1,2,3-triazol-4-yl) aniline (100 mg, 0.387 mmol, 89% yield), a colorless oil. MS (M+1) m/z: 233.1 (M+H)+. LC retention time 1.06 [C].

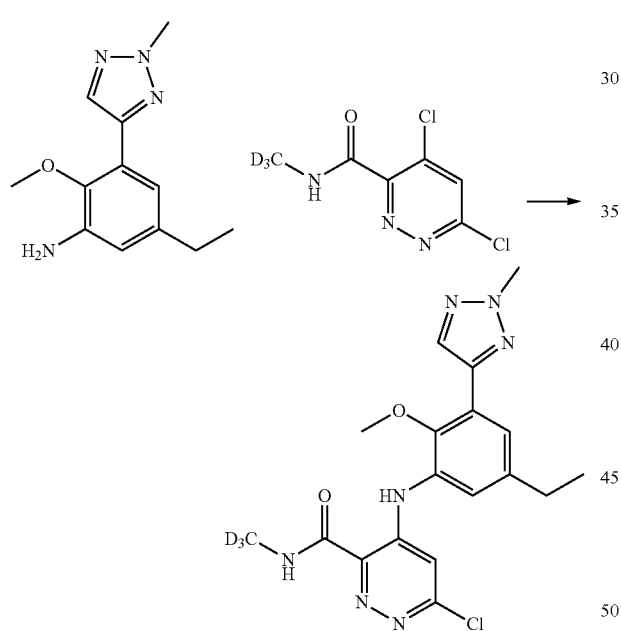

Step 4

To a mixture of 4,6-dichloro-N-(methyl-d3)pyridazine-3-carboxamide (108 mg, 0.517 mmol) and 5-ethyl-2-methoxy-3-(2-methyl-2H-1,2,3-triazol-4-yl) aniline (100 mg, 0.431 mmol) in THF (4 mL) was added lithium bis(trimethylsilyl)amide, 1M in THF (1.507 mL, 1.507 mmol) in a dropwise manner (<5 min) using a syringe and the reaction was stirred until complete by LCMS (~15 min). Sat. ammonium chloride (aq.) was added to quench the residual base. Then the reaction was partitioned between EtOAc and water. The water layer was extracted 1× with ethyl acetate, and then the combined organic layer was washed 1× with sat. ammonium chloride (aq.) and 1× with brine. It was then dried over anhydrous sodium sulfate, filtered and concentrated to a residue that was chromatographed on a 12 g silica gel cartridge eluted with 0-100% EtOAc in hexanes to afford 6-chloro-4-((5-ethyl-2-methoxy-3-(2-methyl-2H-1,2,3-triazol-4-yl)phenyl)amino)-N-(methyl-d3)pyridazine-3-carboxamide (94 mg, 0.232 mmol, 53.9% yield) as a pale yellow solid. MS (M+1) m/z: 405.0 (M+H)+. LC retention time 1.54 [C].

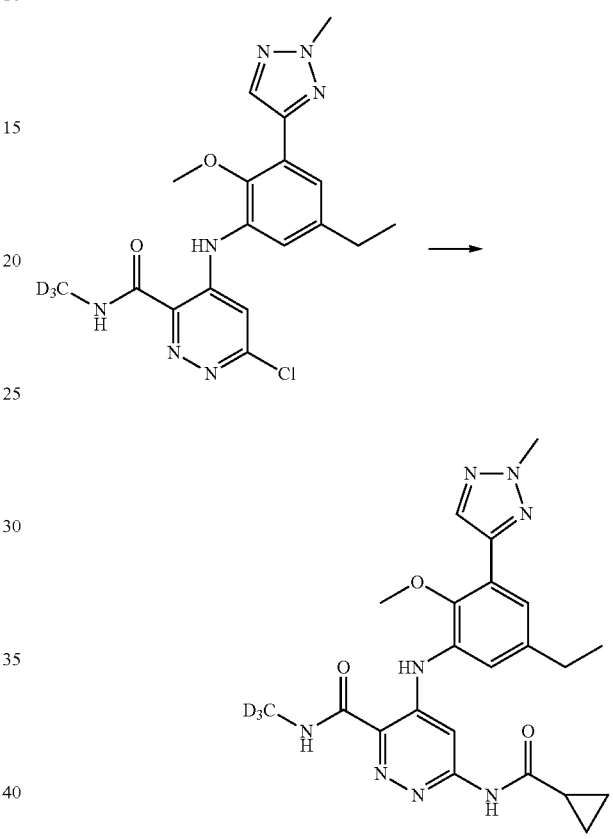

Step 5

A mixture of 6-chloro-4-((5-ethyl-2-methoxy-3-(2-methyl-2H-1,2,3-triazol-4-yl)phenyl)amino)-N-(methyl-d3) pyridazine-3-carboxamide (40 mg, 0.099 mmol), xantphos (11.43 mg, 0.020 mmol), and cyclopropanecarboxamide (42.0 mg, 0.494 mmol) in dioxane (1.3 mL) was degassed by bubbling nitrogen through it for 5 minutes. Then cesium carbonate (129 mg, 0.395 mmol) and Pd$_2$(dba)$_3$ (9.05 mg, 9.88 μmol) were added, the vessel was sealed, and the reaction was stirred at 130° C. for 2 h. The reaction was complete by LC-MS and was diluted to 2 mL with DMF, filtered and purified by prep HPLC to afford 6-(cyclopropanecarboxamido)-4-((5-ethyl-2-methoxy-3-(2-methyl-2H-1,2,3-triazol-4-yl)phenyl)amino)-N-(methyl-d3)pyridazine-3-carboxamide (9.7 mg, 0.021 mmol, 21.65% yield). MS (M+1) m/z: 454.3 (M+H)+. LC retention time 1.25 [C]. $^1$H NMR (500 MHz, DMSO-d6) δ 11.30 (s, 1H), 10.95 (s, 1H), 9.13 (s, 1H), 8.19 (s, 1H), 8.10 (s, 1H), 7.53 (s, 1H), 7.33 (s, 1H), 4.23 (s, 3H), 3.62 (s, 3H), 2.62 (q, J=7.6 Hz, 2H), 2.12-2.05 (m, 1H), 1.22 (t, J=7.6 Hz, 3H), 0.88-0.77 (m, 4H).

Example 22

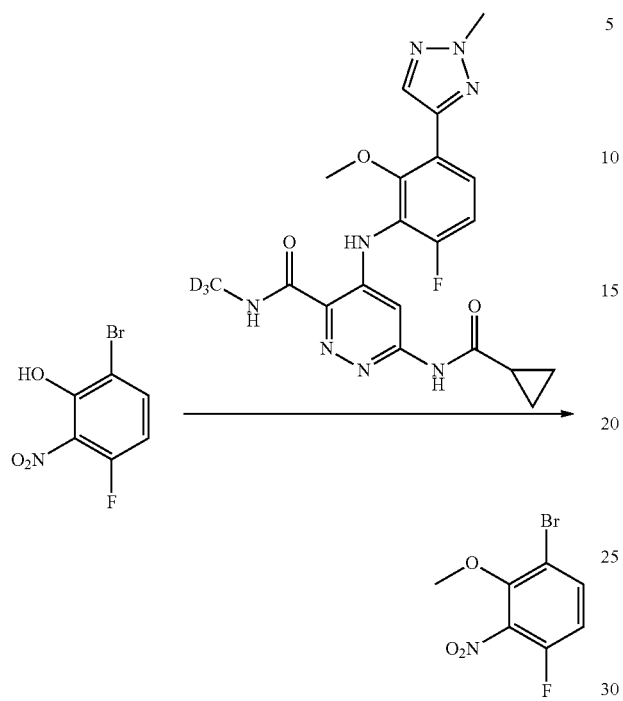

Step 1

To a solution of 6-bromo-3-fluoro-2-nitrophenol (262 mg, 1.110 mmol) in DMF (3 ml) was added potassium carbonate (460 mg, 3.33 mmol). The mixture was stirred for 15 minutes and then iodomethane (0.193 ml, 2.20 mmol) was added. The resulting mixture was stirred at room temperature overnight. LCMS indicated complete conversion to product. Cold water was added (75 mL), the mixture was stirred and then sonicated before the solid was collected by filtration. The material was then dissolved in EtOAc (150 mL) transferred to a separatory funnel and washed 1× with 10% LiCl and 1× with brine. Drying over anhydrous sodium sulfate and concentration afforded a residue that was purified by flash chromatography, on a silica gel column, eluting with 0-50% EtOAc in hexanes to afford 1-bromo-4-fluoro-2-methoxy-3-nitrobenzene (278 mg, 1.001 mmol, 90% yield) as a yellow oil. MS (M+1) m/z: n/a (M+H)⁺. LC retention time 1.54 [C].

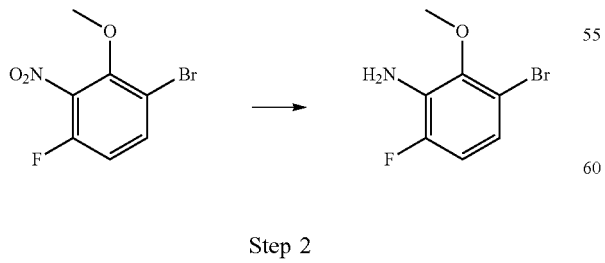

Step 2

A mixture of 1-bromo-4-fluoro-2-methoxy-3-nitrobenzene (278 mg, 1.112 mmol) and tin(II) chloride dihydrate (1004 mg, 4.45 mmol) in EtOAc (10 mL) was stirred at reflux for 1 h. The reaction was then diluted with ethyl acetate (100 ml) and washed with 2.5N NaOH 3×50 ml), water (50 ml) and brine (50 ml). drying over anhydrous sodium sulfate and concentration afforded 3-bromo-6-fluoro-2-methoxyaniline (149 mg, 0.677 mmol, 60.9% yield) as a maroon colored oil. MS (M+1) m/z: 219.9/221.9 (M+H)⁺. LC retention time 1.276 [C].

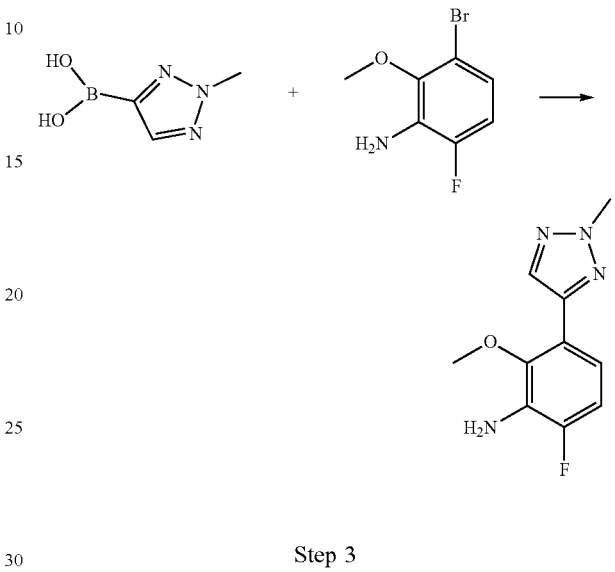

Step 3

A stirred mixture of (2-methyl-2H-1,2,3-triazol-4-yl)boronic acid (59.6 mg, 0.470 mmol), 3-bromo-6-fluoro-2-methoxyaniline (94 mg, 0.427 mmol) and PdCl$_2$(dppf)-dichloromethane adduct (17.44 mg, 0.021 mmol) in dioxane (3 mL) was degassed by bubbling nitrogen through the mixture for 5 minutes. 2M K$_3$PO$_4$ (aq) (0.641 mL, 1.282 mmol) was quickly added and the reaction mixture heated at 50° C. for 30 minutes. LC-MS showed complete consumption of the starting material. The reaction mixture was cooled to room temperature and diluted with EtOAc (75 mL). This solution was then dried over sodium sulfate, filtered, concentrated and purified by flash chromatography, on a silica gel column, eluting with 0-100% EtOAc in hexanes to afford 6-fluoro-2-methoxy-3-(2-methyl-2H-1,2,3-triazol-4-yl) aniline (52 mg, 0.234 mmol, 54.8% yield) as an off-white solid. MS (M+1) m/z: 223.1 (M+H)⁺. LC retention time 1.02 [C].

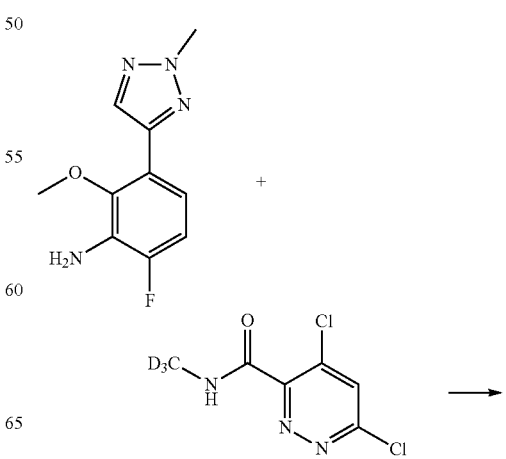

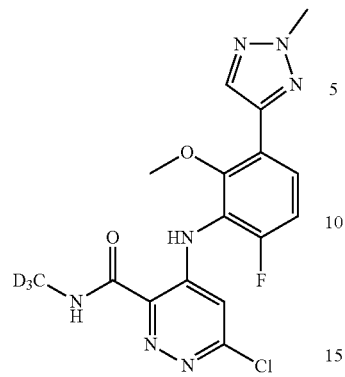

Step 4

To a solution of 4,6-dichloro-N-(methyl-d3)pyridazine-3-carboxamide (51.4 mg, 0.246 mmol) and 6-fluoro-2-methoxy-3-(2-methyl-2H-1,2,3-triazol-4-yl) aniline (52 mg, 0.234 mmol) in THF (2 mL) was added lithium bis(trimethylsilyl)amide, 1M in THF (0.585 mL, 0.585 mmol) in a dropwise manner (<5 min) using a syringe. The reaction was stirred until complete by LCMS (~15 min). Sat. ammonium chloride (aq.) was added to quench the residual base. Then the reaction was partitioned between EtOAc and water. The water layer was extracted 1× with ethyl acetate, and then the combined organic layer was washed 1× with sat. ammonium chloride (aq.) and 1× with brine. The mixture was dried over anhydrous sodium sulfate, filtered and concentrated to afford a residue that was chromatographed on a silica gel column, eluted with 0-100% EtOAc in hexanes to afford 6-chloro-4-((6-fluoro-2-methoxy-3-(2-methyl-2H-1,2,3-triazol-4-yl)phenyl)amino)-N-(methyl-d3)pyridazine-3-carboxamide (67 mg, 0.170 mmol, 72.5% yield) as an off-white solid. MS (M+1) m/z: 395.1 (M+H)⁺. LC retention time 1.29 [C].

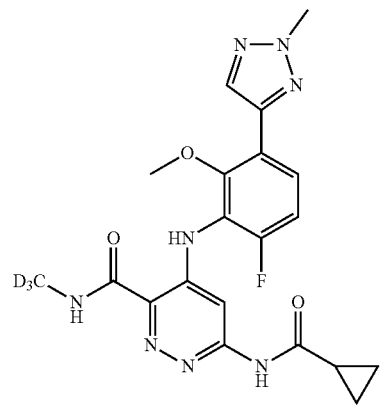

Step 5

A mixture of 6-chloro-4-((6-fluoro-2-methoxy-3-(2-methyl-2H-1,2,3-triazol-4-yl)phenyl)amino)-N-(methyl-d3) pyridazine-3-carboxamide (40 mg, 0.101 mmol), xantphos (11.72 mg, 0.020 mmol), and cyclopropanecarboxamide (43.1 mg, 0.507 mmol) in dioxane (1.3 mL) was degassed by bubbling nitrogen through it for 5 minutes. Then cesium carbonate (132 mg, 0.405 mmol) and Pd₂(dba)₃ (9.28 mg, 10.13 μmol) were added, the vessel was sealed, and the reaction was stirred at 130° C. for 2 h. The reaction was complete by LC-MS and was diluted to 2 mL with DMF, filtered and purified by prep HPLC to afford 6-(cyclopropanecarboxamido)-4-((6-fluoro-2-methoxy-3-(2-methyl-2H-1,2,3-triazol-4-yl)phenyl)amino)-N-(methyl-d3) pyridazine-3-carboxamide (6.6 mg, 0.015 mmol, 14.69% yield). MS (M+1) m/z: 444.2 (M+H)⁺. LC retention time 1.195 [C]. ¹H NMR (500 MHz, DMSO-d6) δ 11.39-11.25 (m, 1H), 10.55 (s, 1H), 9.17 (s, 1H), 8.07 (s, 1H), 7.85 (dd, J=8.9, 6.4 Hz, 1H), 7.52 (d, J=3.4 Hz, 1H), 7.30 (t, J=9.3 Hz, 1H), 4.23 (s, 3H), 3.67 (s, 3H), 2.11-1.99 (m, 1H), 0.84-0.71 (m, 4H).

Example 23

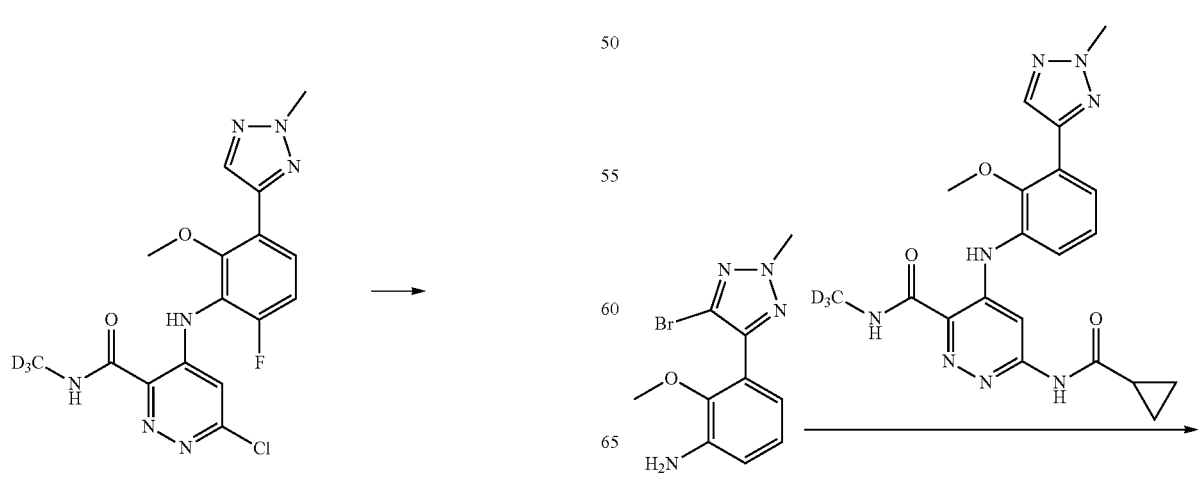

-continued

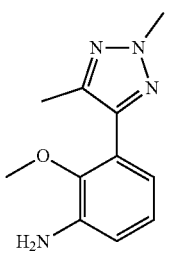

Step 1

A mixture of 3-(5-bromo-2-methyl-2H-1,2,3-triazol-4-yl)-2-methoxyaniline (180 mg, 0.636 mmol), tricyclohexylphosphine (19.61 mg, 0.070 mmol), palladium(II) acetate (7.14 mg, 0.032 mmol) and 2,4,4,5,5-pentamethyl-1,3,2-dioxaborolane (253 mg, 1.780 mmol) in toluene (3 mL) was purged with nitrogen for 1 minute. 2M K$_3$PO$_4$ (aq.) (1.748 mL, 3.50 mmol) was added and the reaction mixture was heated to 100° C. overnight. LCMS indicated that SM is consumed. Concentration and purification by flash chromatography, on a silica gel column, eluting with 0-50% EtOAc in hexanes afforded 3-(2,5-dimethyl-2H-1,2,3-triazol-4-yl)-2-methoxyaniline (124 mg, 0.511 mmol, 80% yield). MS (M+1) m/z: 219.2 (M+H)$^+$. LC retention time 0.91 [C]. $^1$H NMR (400 MHz, chloroform-d) δ 6.99 (t, J=7.4 Hz, 1H), 6.81 (t, J=9.0 Hz, 2H), 4.31-4.20 (m, 3H), 3.93 (br s, 2H), 3.55-3.49 (m, 3H), 2.32 (s, 3H).

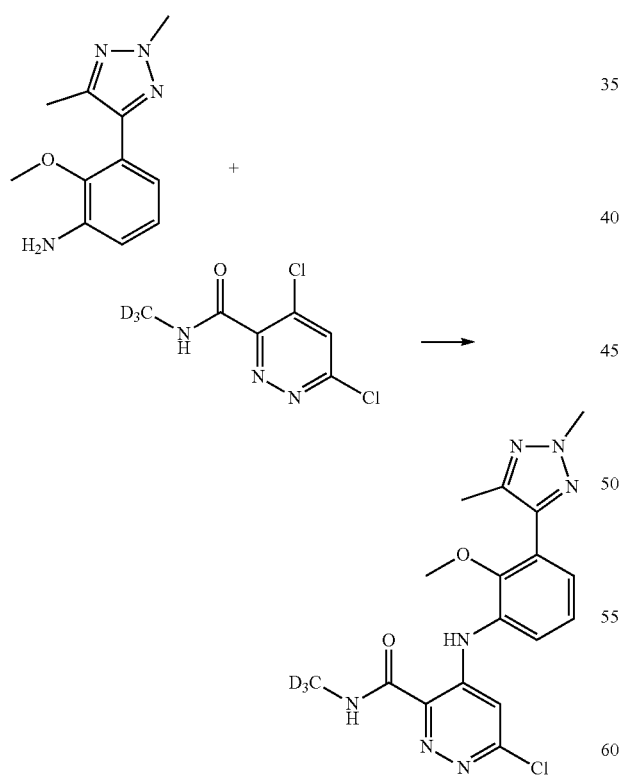

Step 2

To a solution of 4,6-dichloro-N-(methyl-d3)pyridazine-3-carboxamide (130 mg, 0.620 mmol) and 3-(2,5-dimethyl-2H-1,2,3-triazol-4-yl)-2-methoxyaniline (123 mg, 0.564 mmol) in THF (3 mL) was added lithium bis(trimethylsilyl)amide (1.578 mL, 1.578 mmol) in a dropwise manner (<5 min) using a syringe and the reaction was stirred until complete by LCMS (~15 min). Sat. ammonium chloride (aq.) was added to quench the residual base. Then the reaction was partitioned between EtOAc and water. The water layer was extracted 1× with ethyl acetate, and then the combined organic layer was washed 1× with sat. ammonium chloride (aq.) and 1× with brine. The combined organic layer was dried over anhydrous sodium sulfate, filtered and concentrated to afford a residue that was chromatographed on a silica gel column, eluted with 0-100% EtOAc in hexanes to afford 6-chloro-4-((3-(2,5-dimethyl-2H-1,2,3-triazol-4-yl)-2-methoxyphenyl)amino)-N-(methyl-d3)pyridazine-3-carboxamide as an pale yellow solid. (109 mg, 0.251 mmol, 44.5% yield) MS (M+1) m/z: 391.1 (M+H)$^+$. LC retention time 1.24 [C].

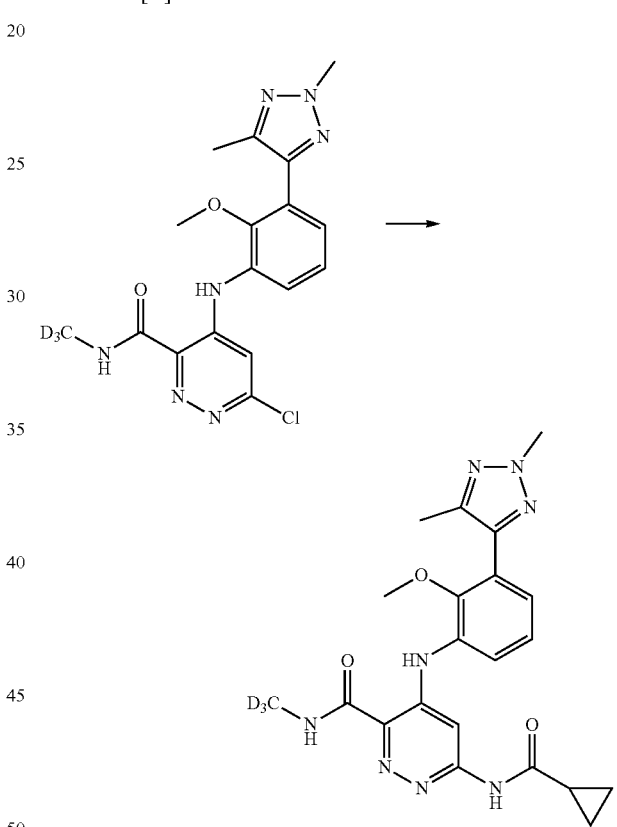

Step 3

A mixture of 6-chloro-4-((3-(2,5-dimethyl-2H-1,2,3-triazol-4-yl)-2-methoxyphenyl)amino)-N-(methyl-d3)pyridazine-3-carboxamide (40 mg, 0.102 mmol), xantphos (11.84 mg, 0.020 mmol), and cyclopropanecarboxamide (43.5 mg, 0.512 mmol) in dioxane (1.3 mL) was degassed by bubbling nitrogen through it for 5 minutes. Then cesium carbonate (133 mg, 0.409 mmol) and Pd$_2$(dba)$_3$ (9.37 mg, 10.23 μmol) were added, the vessel was sealed, and the reaction was stirred at 130° C. for 2 h. The reaction was complete by LC-MS and was diluted to 2 mL with DMF, then filtered and purified by prep. HPLC to afford 6-(cyclopropane-carboxamido)-4-((3-(2,5-dimethyl-2H-1,2,3-triazol-4-yl)-2-methoxyphenyl)amino)-N-(methyl-d3)

pyridazine-3-carboxamide (34.9 mg, 0.079 mmol, 78% yield). MS (M+1) m/z: 440.2 (M+H)⁺. LC retention time 1.17 [C]. ¹H NMR (500 MHz, DMSO-d6) δ 11.30 (s, 1H), 10.94 (s, 1H), 9.10 (s, 1H), 8.14 (s, 1H), 7.51 (br d, J=7.3 Hz, 1H), 7.32-7.25 (m, 1H), 7.25-7.19 (m, 1H), 4.14 (s, 3H), 3.42 (s, 3H), 2.23-2.14 (m, 3H), 2.10-2.02 (m, 1H), 0.88-0.79 (m, 4H).

Example 24

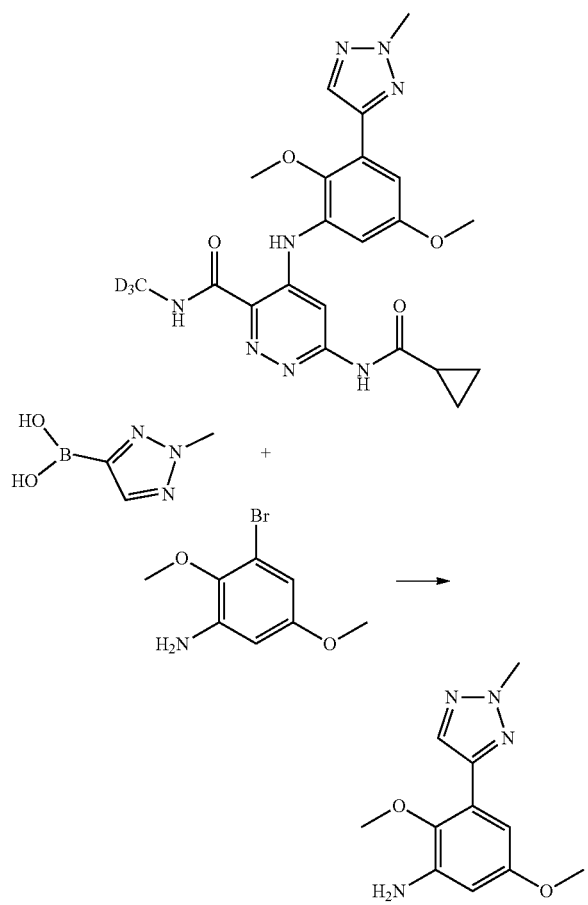

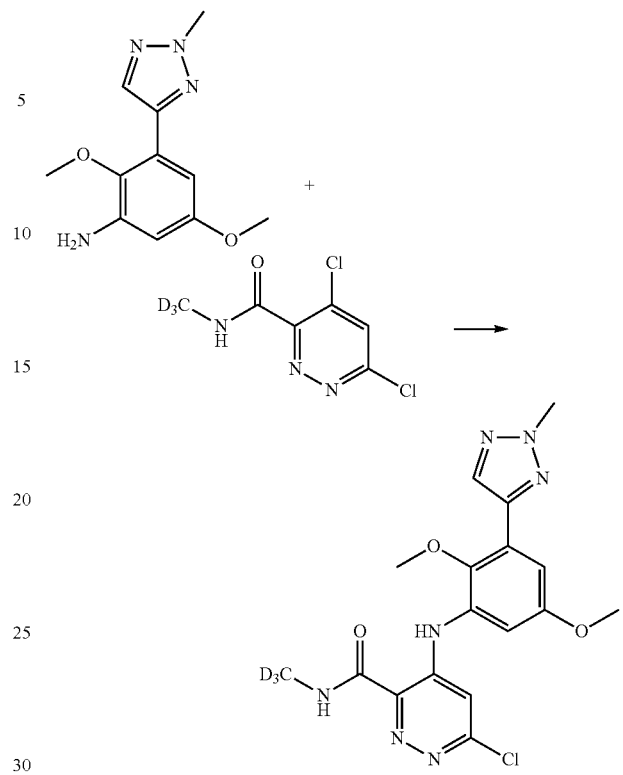

Step 1

A stirred mixture of (2-methyl-2H-1,2,3-triazol-4-yl)boronic acid (48.1 mg, 0.379 mmol), 3-bromo-2,5-dimethoxyaniline (80 mg, 0.345 mmol) and PdCl₂(dppf)-dichloromethane adduct (14.08 mg, 0.017 mmol) in dioxane (2.5 mL) was degassed by bubbling nitrogen through the mixture for 5 minutes. 2M K₃PO₄ (aq) (0.517 mL, 1.034 mmol) was quickly added and the reaction mixture heated at 50° C. for 30 minutes. LC-MS showed complete consumption of the starting material. The reaction mixture was cooled to room temperature, then diluted with EtOAc (75 mL). This solution was then dried over sodium sulfate, filtered, concentrated and purified by flash chromatography, eluting with 0-100% EtOAc in hexanes to afford 2,5-dimethoxy-3-(2-methyl-2H-1,2,3-triazol-4-yl) aniline (63 mg, 0.269 mmol, 78% yield) as an off-white solid.

MS (M+1) m/z: 235.2 (M+H)⁺. LC retention time 0.99 [C].

Step 2

To a solution of 2,5-dimethoxy-3-(2-methyl-2H-1,2,3-triazol-4-yl) aniline (63 mg, 0.269 mmol) and 4,6-dichloro-N-(methyl-d3)pyridazine-3-carboxamide (59.0 mg, 0.282 mmol) in THF (1.3 mL) at room temperature was slowly added lithium bis(trimethylsilyl)amide, 1M in THF (0.807 mL, 0.807 mmol). After 15 min, LC-MS indicated that the reaction was complete. The reaction mixture was quenched with sat. aq. ammonium chloride and then extracted 2× with EtOAc. The combined organic layer was washed 1× with brine and then dried over anhydrous sodium sulfate. Filtration and concentration afforded 6-chloro-4-((2,5-dimethoxy-3-(2-methyl-2H-1,2,3-triazol-4-yl)phenyl)amino)-N-(methyl-d3)pyridazine-3-carboxamide (101 mg, 0.223 mmol, 83% yield) as a tan solid. MS (M+1) m/z: 407.2 (M+H)⁺. LC retention time 1.296 [C].

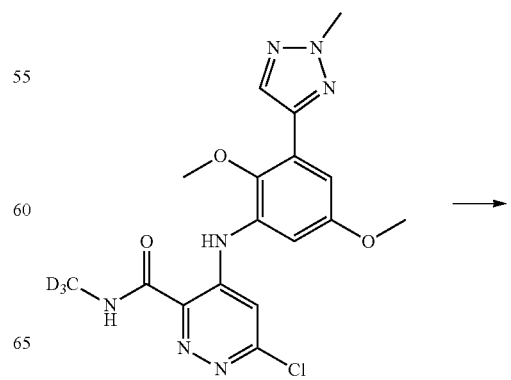

-continued

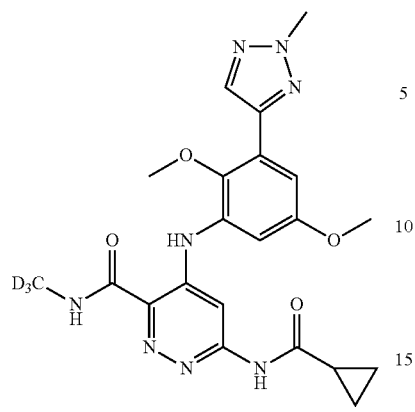

Step 3

A mixture of 6-chloro-4-((2,5-dimethoxy-3-(2-methyl-2H-1,2,3-triazol-4-yl)phenyl)amino)-N-(methyl-d3) pyridazine-3-carboxamide (40 mg, 0.098 mmol), xantphos (11.38 mg, 0.020 mmol), and cyclopropanecarboxamide (41.8 mg, 0.492 mmol) in dioxane (1.3 mL) was degassed by bubbling nitrogen through it for 5 minutes. Then cesium carbonate (128 mg, 0.393 mmol) and Pd$_2$(dba)$_3$ (9.00 mg, 9.83 μmol) were added, the vessel was sealed, and the reaction was stirred at 130° C. for 2 h. The reaction was complete by LC-MS and was diluted to 2 mL with DMF, then filtered and purified by prep HPLC to afford 6-(cyclopropane-carboxamido)-4-((2,5-dimethoxy-3-(2-methyl-2H-1,2,3-triazol-4-yl)phenyl)amino)-N-(methyl-d3)pyridazine-3-carboxamide (16.1 mg, 0.035 mmol, 35.4% yield) MS (M+1) m/z: 456.2 (M+H)$^+$. LC retention time 1.13 [C]. $^1$H NMR (500 MHz, DMSO-d6) δ 11.35 (s, 1H), 11.08 (s, 1H), 9.15 (s, 1H), 8.29 (s, 1H), 8.13 (s, 1H), 7.18 (d, J=2.4 Hz, 1H), 7.08 (d, J=2.4 Hz, 1H), 4.24 (s, 3H), 3.81 (s, 3H), 3.61 (s, 3H), 2.16-2.03 (m, 1H), 0.84 (br s, 4H).

Example 25

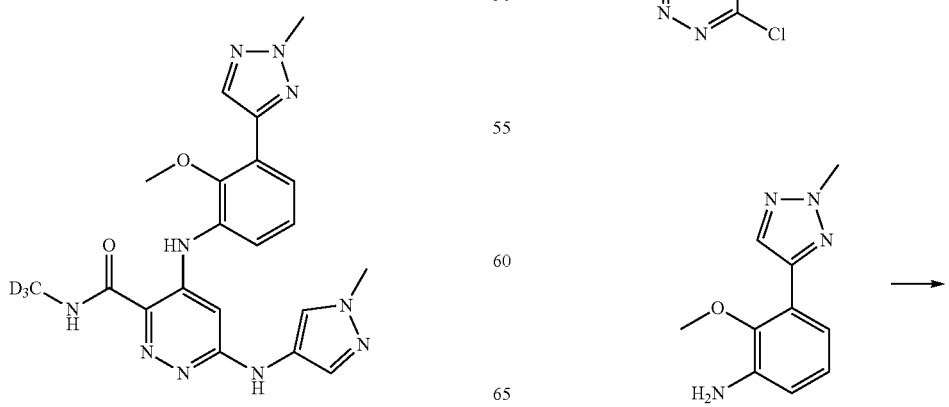

-continued

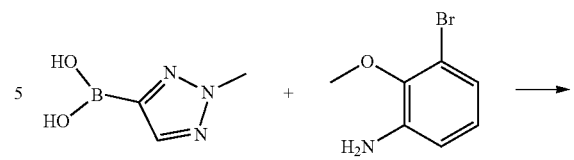

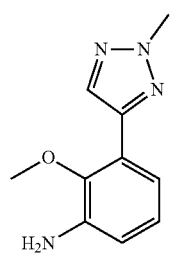

Step 1

A stirred mixture of (2-methyl-2H-1,2,3-triazol-4-yl)boronic acid (182 mg, 1.437 mmol), 3-bromo-2-methoxyaniline (264 mg, 1.307 mmol) and PdCl$_2$(dppf)-dichloromethane adduct (53.4 mg, 0.065 mmol) in dioxane (5 mL) was degassed by bubbling nitrogen through the mixture for 5 minutes. 2M K$_3$PO$_4$ (aq) (1.960 mL, 3.92 mmol) was quickly added and the reaction mixture heated at 50° C. for 30 minutes. LC-MS showed complete consumption of the starting material. The reaction mixture was cooled to room temperature, then diluted with EtOAc (75 mL). This solution was then dried over sodium sulfate, filtered, concentrated and purified by flash chromatography eluting with 0-100% EtOAc in hexanes to afford 2-methoxy-3-(2-methyl-2H-1,2,3-triazol-4-yl) aniline (211 mg, 1.033 mmol, 79% yield) as an colorless oil. MS (M+1) m/z: 205.2 (M+H)$^+$. LC retention time 0.93 [C].

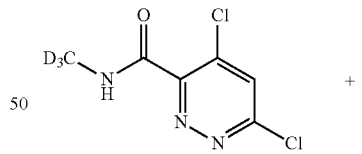

-continued

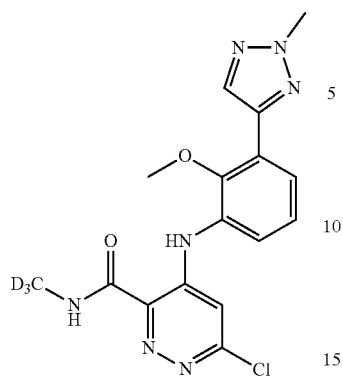

-continued

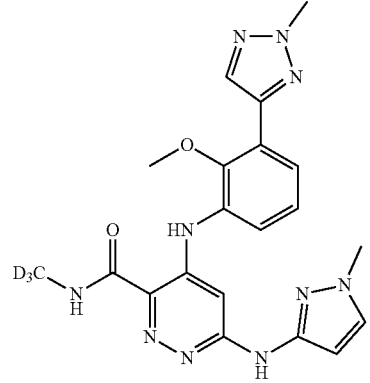

Step 2

To a solution of 4,6-dichloro-N-(methyl-d3)pyridazine-3-carboxamide (238 mg, 1.136 mmol) and 2-methoxy-3-(2-methyl-2H-1,2,3-triazol-4-yl) aniline (211 mg, 1.033 mmol) in THF (7 mL) was added lithium bis(trimethylsilyl)amide, 1M in THF (2.58 mL, 2.58 mmol) in a dropwise manner (<5 min), using a syringe, and the reaction was stirred until complete by LCMS (~15 min). Sat. ammonium chloride (aq.) was added to quench the residual base. Then the reaction was partitioned between EtOAc and water. The water layer was extracted 1× with ethyl acetate and the combined organic layer was washed 1× with sat. ammonium chloride (aq.) and 1× with brine. Drying over anhydrous sodium sulfate and concentration afforded a residue that was chromatographed on a silica gel column eluted with 0-100% EtOAc in hexanes to afford 6-chloro-4-((2-methoxy-3-(2-methyl-2H-1,2,3-triazol-4-yl)phenyl)amino)-N-(methyl-d3) pyridazine-3-carboxamide (420 mg, 1.003 mmol, 97% yield) as an pale yellow solid. MS (M+1) m/z: 377.3 (M+H)$^+$. LC retention time 1.33 [C].

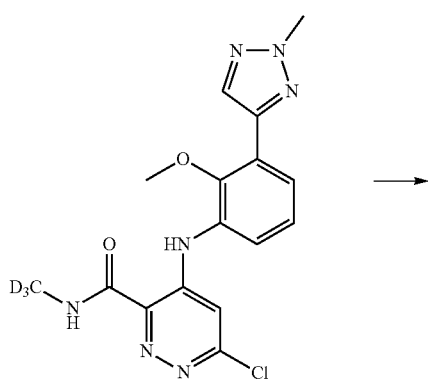

→

Step 3

A mixture of 6-chloro-4-((2-methoxy-3-(2-methyl-2H-1,2,3-triazol-4-yl)phenyl)amino)-N-(methyl-d3)pyridazine-3-carboxamide (40 mg, 0.106 mmol), xantphos (12.28 mg, 0.021 mmol), and 1-methyl-1H-pyrazol-3-amine, HCl (35.4 mg, 0.265 mmol) in dioxane (1.3 mL) was degassed by bubbling nitrogen through it for 5 minutes. Then cesium carbonate (138 mg, 0.425 mmol) and Pd$_2$(dba)$_3$ (9.72 mg, 10.62 μmol) were added, the vessel was sealed, and the reaction was stirred at 130° C. for 6 h. LC-MS indicated complete reaction. The reaction mixture was diluted to 2 mL with DMF, filtered and purified by prep HPLC to afford 4-((2-methoxy-3-(2-methyl-2H-1,2,3-triazol-4-yl)phenyl) amino)-N-(methyl-d3)-6-((1-methyl-1H-pyrazol-3-yl) amino)pyridazine-3-carboxamide (7.7 mg, 0.016 mmol, 14.87% yield). MS (M+1) m/z: 438.2 (M+H)$^+$. LC retention time 1.05 [C]. $^1$H NMR (500 MHz, DMSO-d6) δ 11.04 (s, 1H), 10.18 (br s, 1H), 9.06 (s, 1H), 8.14 (s, 1H), 7.72 (br d, J=7.6 Hz, 1H), 7.64-7.54 (m, 3H), 7.35 (t, J=7.8 Hz, 1H), 6.14 (br s, 1H), 4.24 (s, 3H), 3.73 (s, 3H), 3.69 (s, 3H).

Example 26

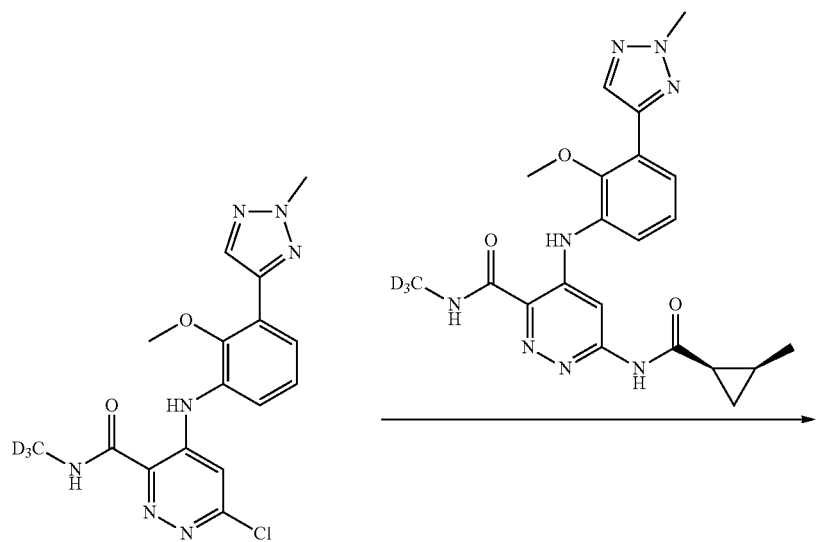

Step 1:

A mixture of 6-chloro-4-((2-methoxy-3-(2-methyl-2H-1,2,3-triazol-4-yl)phenyl)amino)-N-(methyl-d3)pyridazine-3-carboxamide (420 mg, 1.115 mmol), (4-methoxyphenyl)methan-amine (765 mg, 5.57 mmol), and potassium fluoride (194 mg, 3.34 mmol) in NMP (2.5 mL) was stirred at 120° C. for 2 h. The reaction was complete by LC-MS and was diluted to 150 mL with ethyl acetate, washed 1× with water, 2× with 10% aq. LiCl and 1× with brine. After drying over anhydrous sodium sulfate, the organic layer was filtered and concentrated to afford a residue that was chromatographed on a 40 g ISCO column, eluting with 0-100% EtOAc in hexanes. Concentration of the pure fractions afforded 4-((2-methoxy-3-(2-methyl-2H-1,2,3-triazol-4-yl)phenyl)amino)-6-((4-methoxybenzyl)amino)-N-(methyl-d3)pyridazine-3-carboxamide (265 mg, 0.555 mmol, 49.8% yield) as an off-white solid. MS (M+1) m/z: 478.4 (M+H)⁺. LC retention time 1.10 [C]. ¹H NMR (400 MHz, chloroform-d) δ 10.84-10.67 (m, 1H), 8.11 (s, 1H), 8.06 (s, 1H), 7.72 (dd, J=6.7, 2.8 Hz, 1H), 7.26-7.25 (m, 1H), 7.25-7.22 (m, 1H), 7.13-7.06 (m, 2H), 6.88 (d, J=8.7 Hz, 2H), 6.09 (s, 1H), 5.24 (br s, 1H), 4.43 (d, J=5.6 Hz, 2H), 4.27 (s, 3H), 3.85-3.81 (m, 3H), 3.70 (s, 3H).

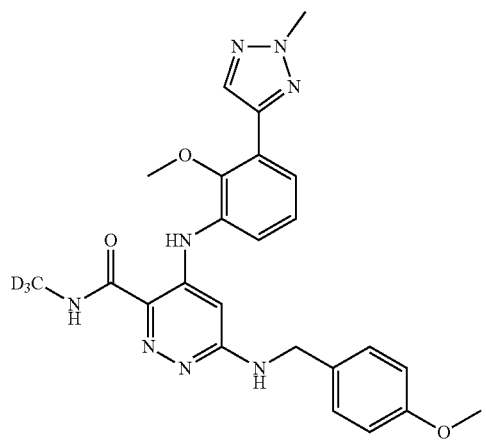

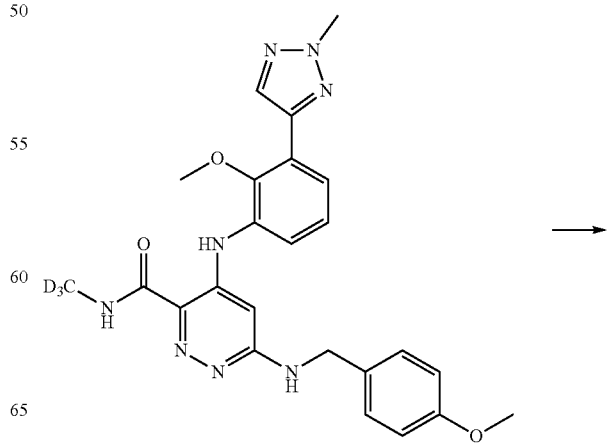

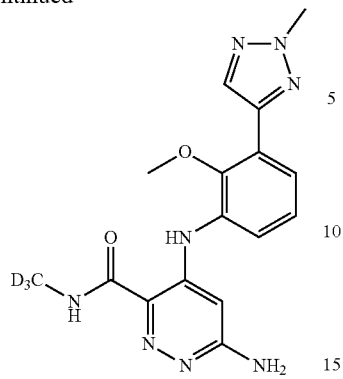

Step 2

A mixture of 4-((2-methoxy-3-(2-methyl-2H-1,2,3-triazol-4-yl)phenyl)amino)-6-((4-methoxybenzyl)amino)-N-(methyl-d3)pyridazine-3-carboxamide (265 mg, 0.555 mmol) in 1,2-dichloroethane (3 mL) and trifluoroacetic acid (1.5 mL) was warmed to 60° C. and stirred for 120 minutes. The mixture was concentrated to a solid and co-evaporated 3× from dichloroethane. The residue was dissolved in 150 mL DCM and the solution was transferred to a separatory funnel and was washed 2× with 1.5M potassium phosphate solution and 1× with brine. Drying over anhydrous sodium sulfate and concentration afforded 6-amino-4-((2-methoxy-3-(2-methyl-2H-1,2,3-triazol-4-yl)phenyl)amino)-N-(methyl-d3)pyridazine-3-carboxamide (169 mg, 0.449 mmol, 81% yield) as a light tan solid that was used without further purification. MS (M+1) m/z: 358.2 (M+H)⁺. LC retention time 0.92 [C].

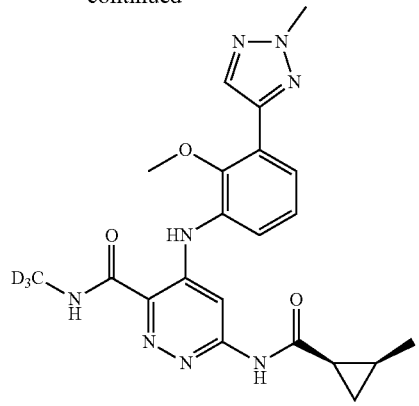

Step 3

A solution of 6-amino-4-((2-methoxy-3-(2-methyl-2H-1,2,3-triazol-4-yl)phenyl)amino)-N-(methyl-d3)pyridazine-3-carboxamide (26 mg, 0.073 mmol), cis-2-methylcyclopropane-carboxylic acid (9.47 mg, 0.095 mmol), and 1-propanephosphonic anhydride, in 50% DMF solution (139 mg, 0.218 mmol) and TEA (0.051 mL, 0.364 mmol) in DMF (1 mL) was stirred at 40° C. overnight whereupon LC-MS indicated the reaction was complete. The mixture was diluted to 2 mL with DMF, filtered and purified by prep HPLC to afford 4-((2-methoxy-3-(2-methyl-2H-1,2,3-triazol-4-yl)phenyl)amino)-N-(methyl-d3)-6-((1R,2S)-2-methylcyclopropane-1-carboxamido)pyridazine-3-carboxamide (3.5 mg, 7.96 μmol, 10.95% yield) MS (M+1) m/z: 440.2 (M+H)⁺. LC retention time 1.16[C]. ¹H NMR (500 MHz, DMSO-d6) δ 11.20 (s, 1H), 11.02 (s, 1H), 9.13 (s, 1H), 8.17 (s, 1H), 8.12 (s, 1H), 7.70 (d, J=7.3 Hz, 1H), 7.49 (d, J=7.0 Hz, 1H), 7.31 (t, J=8.1 Hz, 1H), 4.24 (s, 3H), 3.66 (s, 3H), 2.13-2.06 (m, 1H), 1.35-1.27 (m, 1H), 1.07 (d, J=6.4 Hz, 3H), 0.99 (td, J=8.0, 3.8 Hz, 1H), 0.81-0.76 (m, 1H).

Example 27

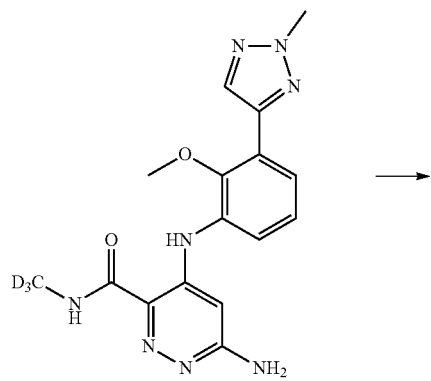

→

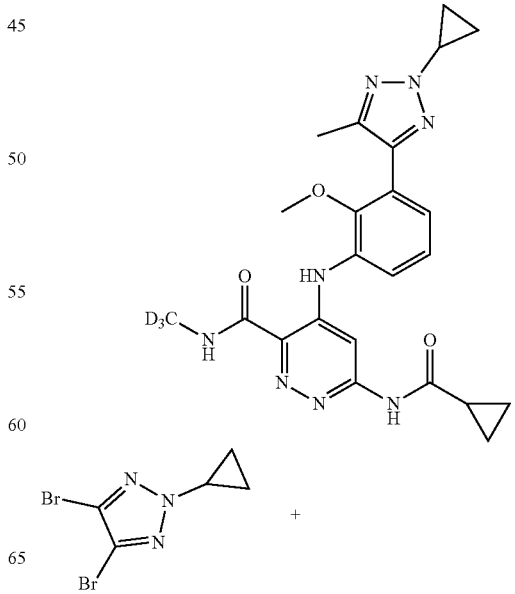

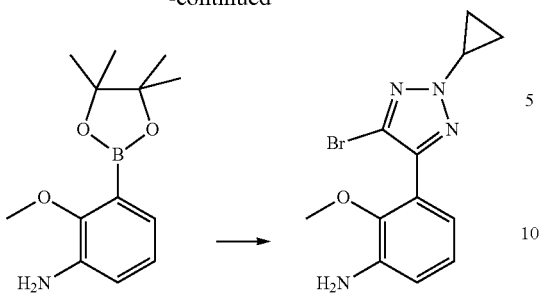

Step 1

A stirred mixture of 4,5-dibromo-2-cyclopropyl-2H-1,2,3-triazole, Intermediate 8, step 1 (545 mg, 2.043 mmol), 2-methoxy-3-(4,4,5,5-tetramethyl-1,3,2-dioxaborolan-2-yl)aniline (509 mg, 2.043 mmol) and $PdCl_2$(dppf)-dichloromethane adduct (83 mg, 0.102 mmol) in dioxane (12 mL) was degassed by bubbling nitrogen through the mixture for 5 minutes. 2M $K_3PO_4$ (aq) (3.06 mL, 6.13 mmol) was quickly added and the reaction mixture heated at 100° C. for 120 minutes. After 2 h, LC-MS showed complete consumption of the starting material. The reaction mixture was cooled to room temperature, then diluted with EtOAc (75 mL). This solution was then dried over anhydrous sodium sulfate, filtered, concentrated and purified by silica gel chromatography, eluting with 0-100% EtOAc in hexanes. Concentration of the pure fractions afforded 3-(5-bromo-2-cyclopropyl-2H-1,2,3-triazol-4-yl)-2-methoxyaniline as a yellow oil. The material was taken on directly into the next step. MS (M+1) m/z: 309.0/311.0 $(M+H)^+$. LC retention time 1.19 [C]

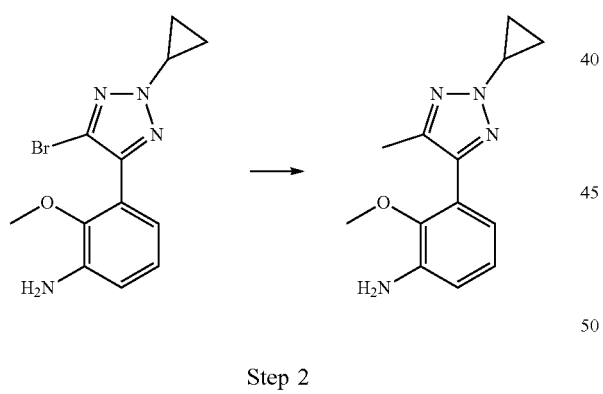

Step 2

A mixture of 3-(5-bromo-2-cyclopropyl-2H-1,2,3-triazol-4-yl)-2-methoxyaniline (126 mg, 0.408 mmol), tricyclohexylphosphane (12.57 mg, 0.045 mmol), palladium(II) acetate (4.57 mg, 0.020 mmol) and 2,4,4,5,5-pentamethyl-1,3,2-dioxaborolane (162 mg, 1.141 mmol) in toluene (3 mL) was purged with nitrogen for 1 minute. 2M $K_3PO_4$ (aq.)(1.121 mL, 2.242 mmol) was added and the reaction mixture was heated to 100° C. for 36 h. The organic layer was concentrated onto celite and chromatographed using a 12 g ISCO column, eluting with 0-50% EtOAc in hexanes. Concentration of the pure fractions afforded 3-(2-cyclopropyl-5-methyl-2H-1,2,3-triazol-4-yl)-2-methoxyaniline (51 mg, 0.209 mmol, 51.2% yield, 2 steps). MS (M+1) m/z: 245.2 $(M+H)^+$. LC retention time 1.01 [C]

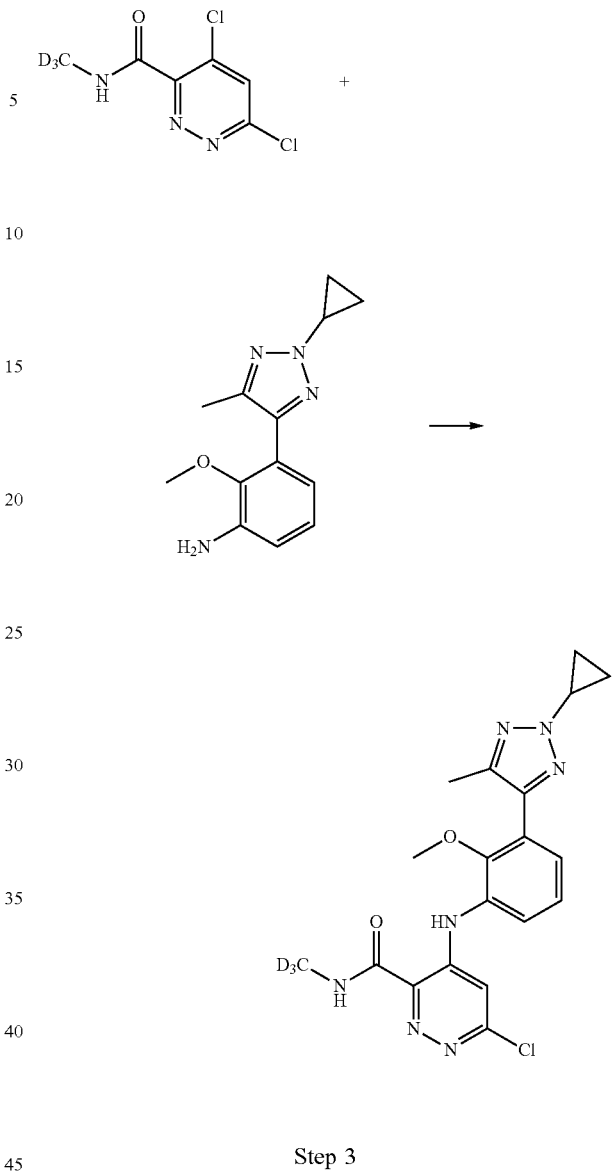

Step 3

To a solution of 4,6-dichloro-N-(methyl-d3)pyridazine-3-carboxamide (48.0 mg, 0.230 mmol) and 3-(2-cyclopropyl-5-methyl-2H-1,2,3-triazol-4-yl)-2-methoxyaniline (51 mg, 0.209 mmol) in THF (2.3 mL) was added lithium bis(trimethylsilyl)amide (0.626 mL, 0.626 mmol) in a dropwise manner (<5 min) using a syringe and the reaction stirred until complete by LCMS (~15 min). Sat. ammonium chloride (aq.) was added to quench the residual base. Then the reaction was partitioned between EtOAc and water. The water layer was extracted 1× with ethyl acetate, and then the combined organic layer was washed 1× with sat. ammonium chloride (aq.) and 1× with brine. After drying over anhydrous sodium sulfate and concentrated, the residue was chromatographed on a 12 g ISCO column, eluted with 0-100% EtOAc in hexanes. Concentration of the pure fractions afforded 6-chloro-4-((3-(2-cyclopropyl-5-methyl-2H-1,2,3-triazol-4-yl)-2-methoxyphenyl)amino)-N-(methyl-d3)pyridazine-3-carboxamide (27 mg, 0.065 mmol, 31.0% yield) as an pale yellow solid. MS (M+1) m/z: 417.1 $(M+H)^+$. LC retention time 1.510 [C]

Example 28

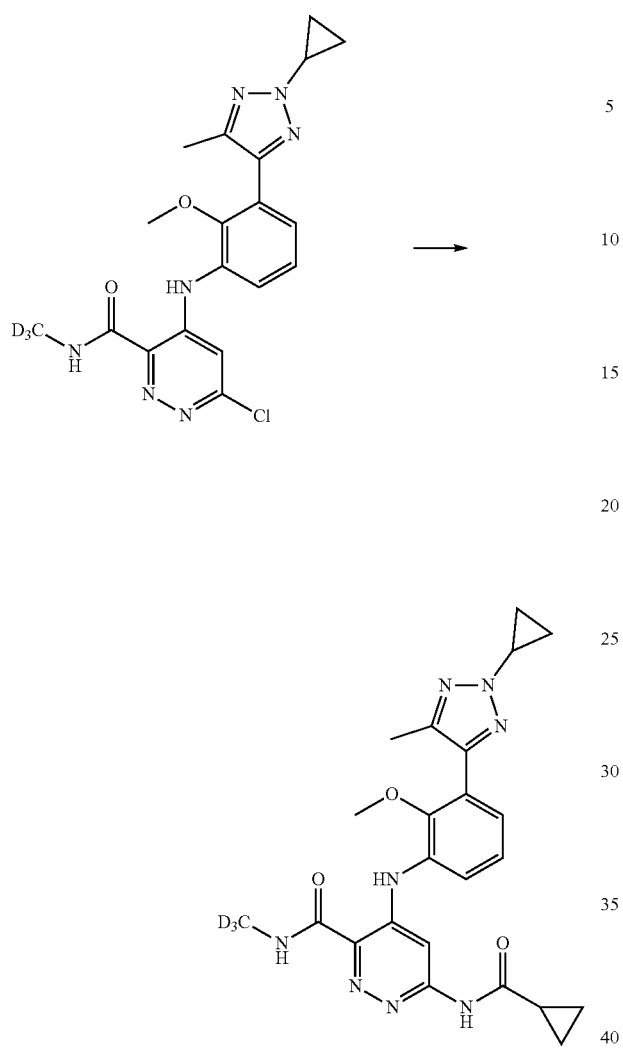

Step 4

A mixture of 6-chloro-4-((3-(2-cyclopropyl-5-methyl-2H-1,2,3-triazol-4-yl)-2-methoxyphenyl)amino)-N-(methyl-d3)pyridazine-3-carboxamide (27 mg, 0.065 mmol), xantphos (7.49 mg, 0.013 mmol), and cyclopropanecarboxamide (27.6 mg, 0.324 mmol) in dioxane (1.3 mL) was degassed by bubbling N2 through it for 5 minutes. Cesium carbonate (84 mg, 0.259 mmol) and Pd$_2$(dba)$_3$ (5.93 mg, 6.48 μmol) were added, the vessel was sealed, and the reaction was stirred at 130° C. for 2 h. The reaction was complete by LC-MS. The mixture was diluted to 2 mL with DMF, filtered and purified by prep HPLC. Concentration of pure fractions afforded 6-(cyclopropanecarboxamido)-4-((3-(2-cyclopropyl-5-methyl-2H-1,2,3-triazol-4-yl)-2-methoxyphenyl)amino)-N-(methyl-d3)pyridazine-3-carboxamide (6.7 mg, 0.014 mmol, 22.22% yield). MS (M+1) m/z: 466.3 (M+H)$^+$. LC retention time 1.19 [C] $^1$H NMR (500 MHz, DMSO-d6) δ 11.30 (s, 1H), 10.93 (s, 1H), 9.10 (s, 1H), 8.13 (s, 1H), 7.51 (d, J=7.3 Hz, 1H), 7.30-7.25 (m, 1H), 7.23-7.20 (m, 1H), 4.11-4.06 (m, 1H), 3.42 (s, 3H), 2.19 (s, 3H), 2.11-2.02 (m, 1H), 1.23-1.18 (m, 2H), 1.11-1.05 (m, 2H), 0.82 (br d, J=5.5 Hz, 4H).

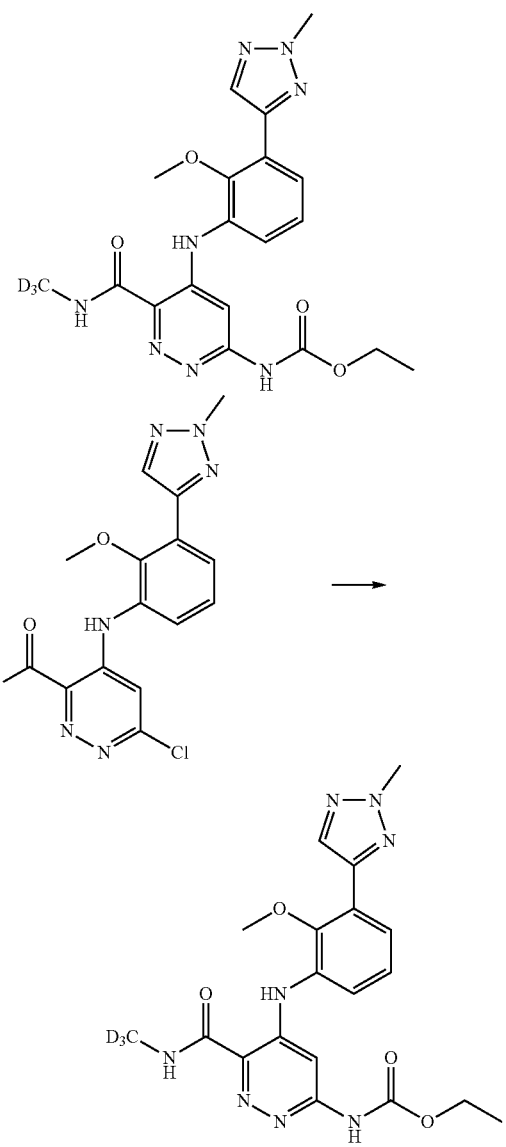

A mixture of 6-chloro-4-((2-methoxy-3-(2-methyl-2H-1,2,3-triazol-4-yl)phenyl)amino)-N-(methyl-d3)pyridazine-3-carboxamide (44 mg, 0.117 mmol), xantphos (13.51 mg, 0.023 mmol), and ethyl carbamate (52.0 mg, 0.584 mmol) in dioxane (1.3 mL) was degassed by bubbling nitrogen through it for 5 minutes. Then cesium carbonate (152 mg, 0.467 mmol) and Pd$_2$(dba)$_3$ (10.69 mg, 0.012 mmol) were added, the vessel was sealed, and the reaction was stirred at 130° C. for 2 h. The reaction was complete by LC-MS. The mixture was diluted to 2 mL with DMF, then filtered and purified by prep HPLC. Concentration of the pure fractions afforded ethyl (5-((2-methoxy-3-(2-methyl-2H-1,2,3-triazol-4-yl)phenyl)amino)-6-((methyl-d3)carbamoyl)pyridazin-3-yl)carbamate (9.2 mg, 0.021 mmol, 18.35% yield). MS (M+1) m/z: 430.1 (M+H)$^+$. LC retention time 1.11 [C] $^1$H NMR (500 MHz, DMSO-d6) δ 10.99 (s, 1H), 10.72 (s, 1H), 9.12 (s, 1H), 8.13 (s, 1H), 7.87 (s, 1H), 7.71 (d, J=7.9 Hz, 1H), 7.50 (br d, J=7.3 Hz, 1H), 7.31 (t, J=7.9 Hz, 1H), 4.24 (s, 3H), 4.13 (q, J=7.2 Hz, 2H), 3.67 (s, 3H), 1.22 (t, J=7.0 Hz, 3H).

Example 29

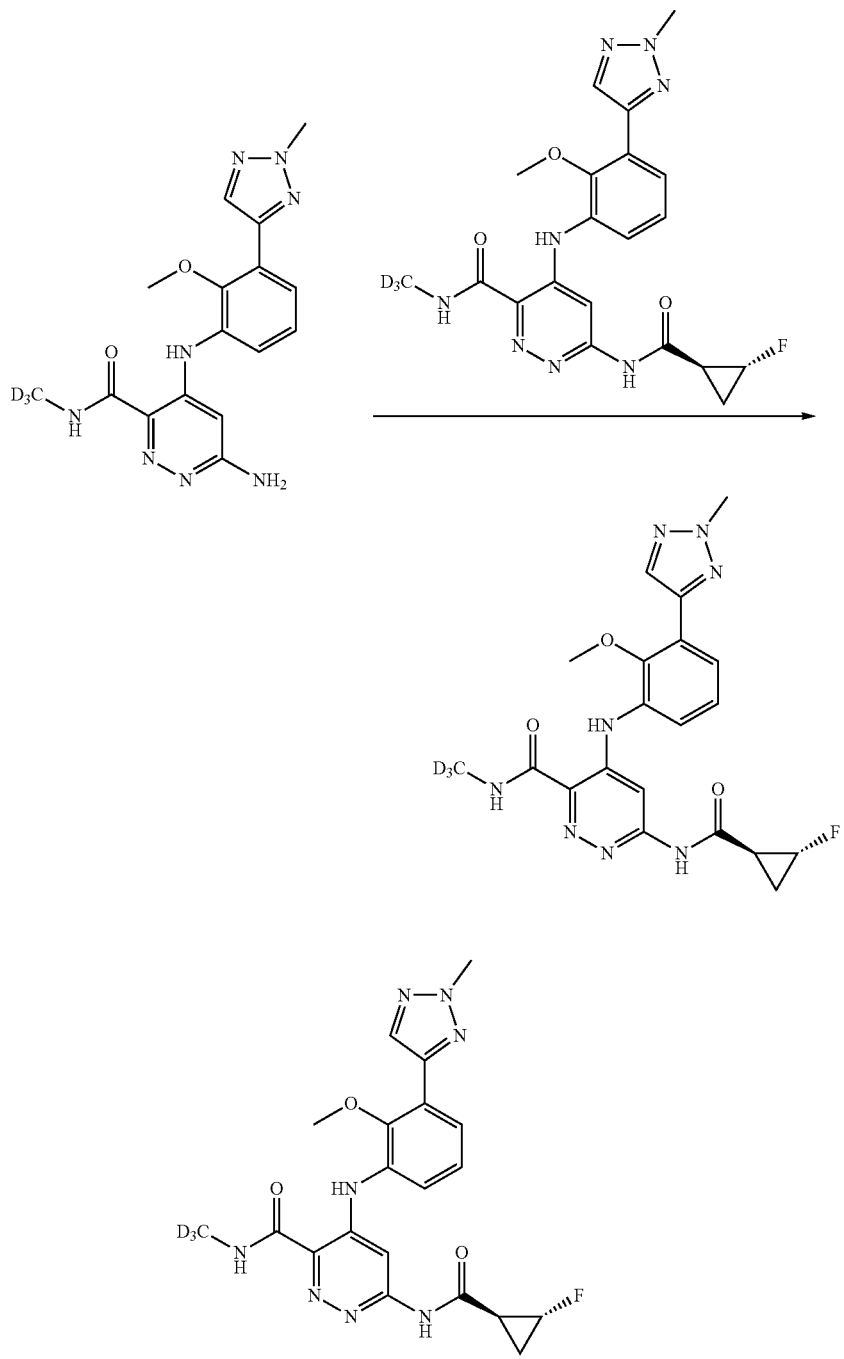

To a solution of 6-amino-4-((2-methoxy-3-(2-methyl-2H-1,2,3-triazol-4-yl)phenyl)amino)-N-(methyl-d3)pyridazine-3-carboxamide (20 mg, 0.056 mmol), and 1-propanephosphonic anhydride, in 50% DMF solution (107 mg, 0.168 mmol) in DMF (1 mL) and TEA (0.039 mL, 0.280 mmol) was added to (1S,2R)-2-fluorocyclopropane-1-carboxylic acid (11.65 mg, 0.112 mmol) and then stirred at 60° C. for 2 h., whereupon LC-MS indicated the reaction was complete. The mixture was diluted to 2 mL with DMF, filtered and purified by prep HPLC. Concentration of afforded 6-((1S,2R)-2-fluorocyclopropane-1-carboxamido)-4-((2-methoxy-3-(2-methyl-2H-1,2,3-triazol-4-yl)phenyl)amino)-N-(methyl-d3)pyridazine-3-carboxamide (7.7 mg, 0.017 mmol, 29.6% yield). MS (M+1) m/z: 444.2 (M+H)⁺. LC retention time 1.22 [C] $^1$H NMR (500 MHz, DMSO-d6) δ 11.48 (br s, 1H), 11.01 (s, 1H), 9.17 (s, 1H), 8.12 (s, 1H), 8.09 (s, 1H), 7.71 (d, J=7.3 Hz, 1H), 7.46 (br d, J=7.9 Hz, 1H), 7.29 (t, J=7.9 Hz, 1H), 5.00-4.80 (m, 1H), 4.24 (s, 3H), 3.66 (s, 3H), 2.68-2.58 (m, 1H), 1.61-1.48 (m, 1H), 1.25 (dq, J=13.3, 6.4 Hz, 1H).

Example 30

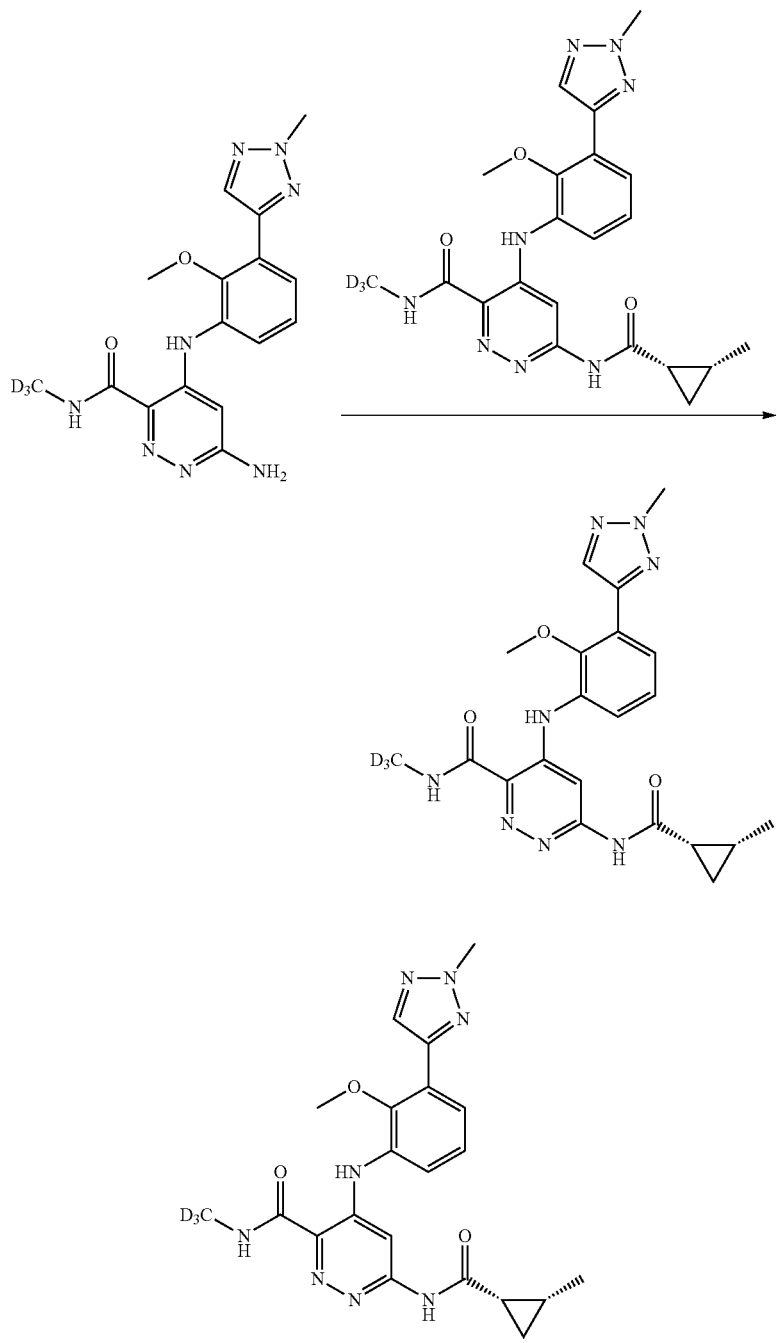

To a solution 6-amino-4-((2-methoxy-3-(2-methyl-2H-1,2,3-triazol-4-yl)phenyl)amino)-N-(methyl-d3)pyridazine-3-carboxamide (30 mg, 0.084 mmol), and 1-propanephosphonic anhydride, in 50% DMF solution (160 mg, 0.252 mmol) in DMF (1 mL) and TEA (0.059 mL, 0.420 mmol) was added to (1S,2R)-2-methylcyclopropane-1-carboxylic acid (21.01 mg, 0.210 mmol) and then the resulting mixture was stirred at 50° C. overnight, whereupon LC-MS indicated that the reaction was complete. Diluted to 2 mL with DMF, then filtered and purified by prep HPLC. Concentration of the pure fractions afforded 4-((2-methoxy-3-(2-methyl-2H-1,2,3-triazol-4-yl)phenyl)amino)-N-(methyl-d3)-6-((1S,2R)-2-methylcyclopropane-1-carboxamido)-pyridazine-3-carboxamide (12.8 mg, 0.029 mmol, 34.7% yield). MS (M+1) m/z: 440.4 (M+H)$^+$. LC retention time 1.20 [C]. $^1$H NMR (500 MHz, DMSO-d6) δ 11.21 (s, 1H), 11.02 (s, 1H), 9.14 (s, 1H), 8.17 (s, 1H), 8.12 (s, 1H), 7.70 (d, J=7.9 Hz, 1H), 7.49 (br d, J=7.3 Hz, 1H), 7.31 (t, J=7.8 Hz, 1H), 4.24 (s, 3H), 3.66 (s, 3H), 2.13-2.06 (m, 1H), 1.36-1.27 (m, 1H), 1.07 (d, J=6.1 Hz, 3H), 0.99 (td, J=7.8, 3.7 Hz, 1H), 0.78 (br d, J=5.5 Hz, 1H).

Example 31

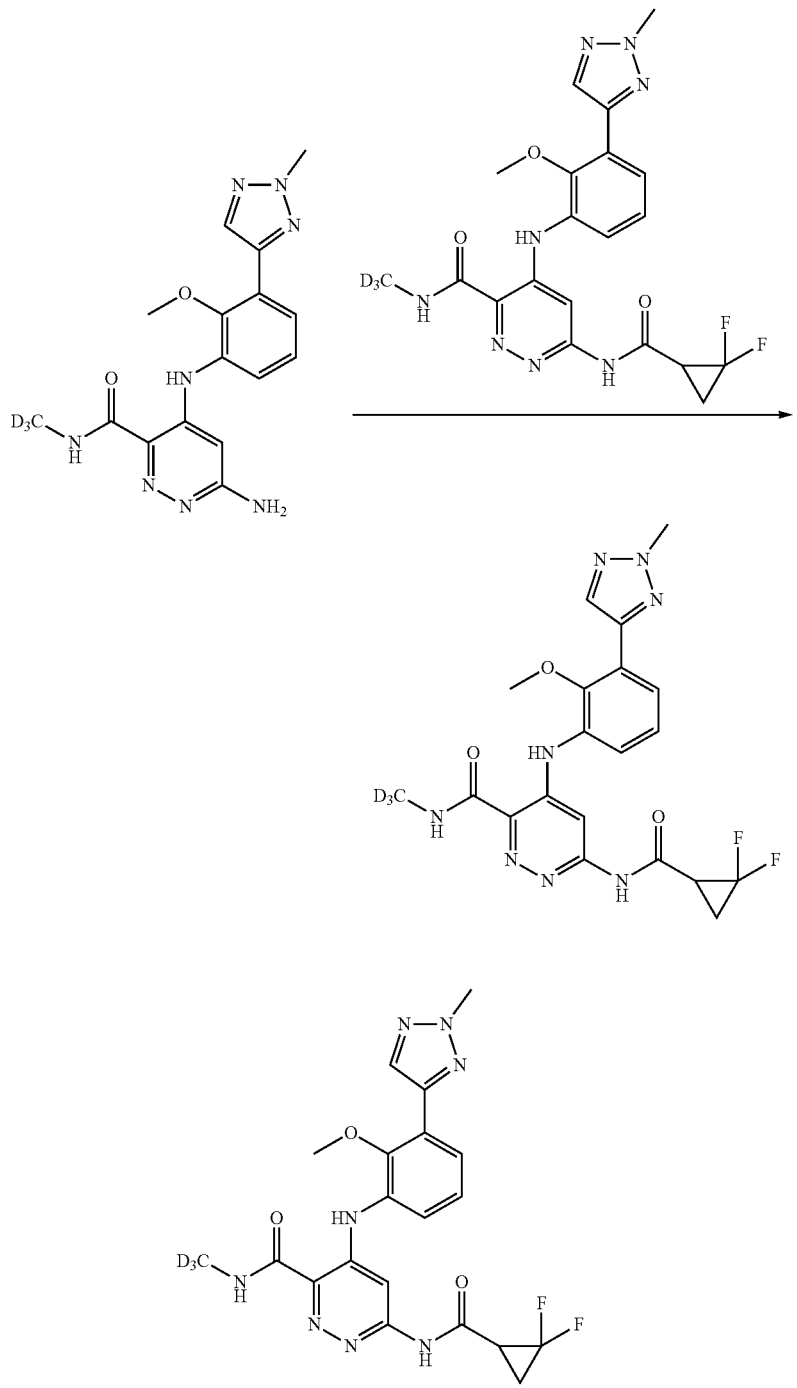

To a solution of 6-amino-4-((2-methoxy-3-(2-methyl-2H-1,2,3-triazol-4-yl)phenyl)amino)-N-(methyl-d3)pyridazine-3-carboxamide (30 mg, 0.084 mmol), and 1-Propanephosphonic anhydride, in 50% DMF solution (160 mg, 0.252 mmol) in DMF (1 mL) and TEA (0.059 mL, 0.420 mmol) was added to 2,2-difluorocyclopropane-1-carboxylic acid (15.37 mg, 0.126 mmol) and the resulting mixture was stirred at 50° C. for 1 h., whereupon LC-MS indicated the reaction was complete. The mixture was diluted to 2 mL with DMF, filtered and purified by prep HPLC. Concentration of the pure fractions afforded 6-(2,2-difluorocyclopropane-1-carboxamido)-4-((2-methoxy-3-(2-methyl-2H-1,2,3-triazol-4-yl)phenyl)amino)-N-(methyl-d3)pyridazine-3-carboxamide (10.3 mg, 0.022 mmol, 26.3% yield). MS (M+1) m/z: 462.4 (M+H)$^+$. LC retention time 1.28 [C] $^1$H NMR (500 MHz, DMSO-d6) δ 11.53 (s, 1H), 11.02 (s, 1H), 9.17 (s, 1H), 8.12 (s, 1H), 8.09 (s, 1H), 7.72 (d, J=7.6 Hz, 1H), 7.48 (d, J=7.9 Hz, 1H), 7.32 (t, J=7.9 Hz, 1H), 4.24 (s, 3H), 3.66 (s, 3H), 3.07-2.99 (m, 1H), 2.07-1.97 (m, 2H).

Example 32

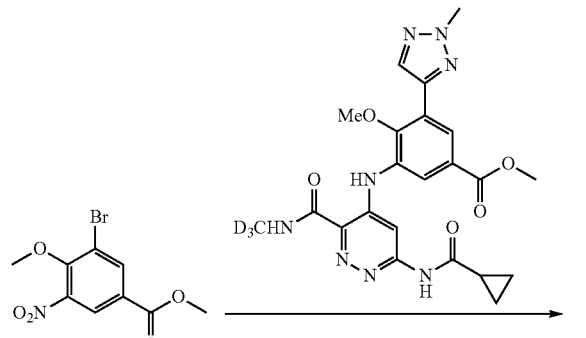

Step 1: 3-Amino-5-bromo-4-methoxybenzoate

A mixture of methyl 3-bromo-4-methoxy-5-nitrobenzoate (1000 mg, 3.45 mmol) and tin(II) chloride dihydrate (3112 mg, 13.79 mmol) in 35 ml of EtOAc was heated to reflux for 1 hr. After cooling to rt, the reaction mixture was diluted with 35 ml of EtOAc and was transferred to a separatory funnel, at which time, it was washed with 2.5N NaOH (3×50 ml), water (50 ml) and brine (25 ml). After drying over anhydrous sodium sulfate, the organic layer was concentrated to afford methyl 3-amino-5-bromo-4-methoxybenzoate (823 mg, 3.16 mmol, 92% yield) as an off-white oil. MS (M+1) m/z: 260.4/262.4 (M+H)+. LC retention time 0.96 [E]. $^1$H NMR (400 MHz, DMSO-d6) δ 7.32 (d, J=2.0 Hz, 1H), 7.24 (d, J=2.0 Hz, 1H), 5.58 (s, 2H), 3.80 (s, 3H), 3.71 (s, 3H).

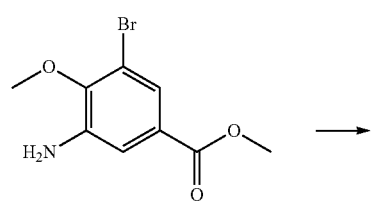

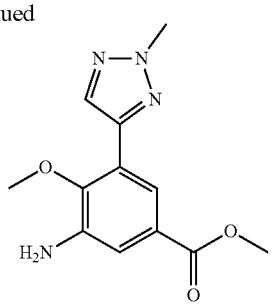

Step 2: Methyl 3-amino-4-methoxy-5-(2-methyl-2H-1,2,3-triazol-4-yl)benzoate

A stirred mixture of (2-methyl-2H-1,2,3-triazol-4-yl)boronic acid (73.2 mg, 0.577 mmol), methyl 3-amino-5-bromo-4-methoxybenzoate (100 mg, 0.384 mmol) and PdCl$_2$(dppf)-CH$_2$Cl$_2$-adduct (15.70 mg, 0.019 mmol) in Dioxane (2 mL) was degassed by bubbling nitrogen through the mixture for 5 minutes. 2M K$_3$PO$_4$ (aq) (0.577 mL, 1.153 mmol) was quickly added and the reaction mixture heated at 100° C. for 1 hr. After cooling to rt, the reaction mixture was partitioned between EtOAc (30 ml) and brine (20 ml). After drying over anhydrous sodium sulfate solution, the organic layer was concentrated and the residue was chromatographed on a 12 gm ISCO silica gel cartridge, eluting with a 0-70% EtOAc/Hex gradient. The pure fractions were concentrated to afford methyl 3-amino-4-methoxy-5-(2-methyl-2H-1,2,3-triazol-4-yl)benzoate (66 mg, 0.252 mmol, 65.5% yield) as a an off-white solid. MS (M+1) m/z: 263.5 (M+H)+. LC retention time 0.82 [E].

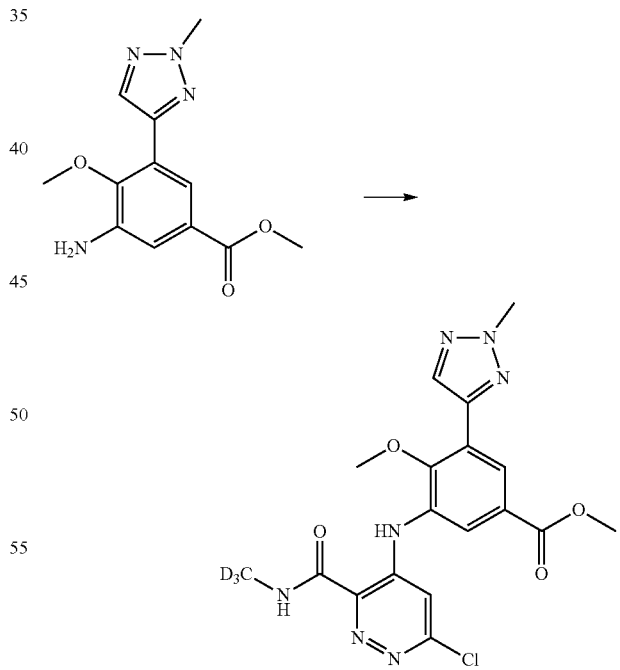

Step 3: Methyl 3-((6-chloro-3-((methyl-d3)carbamoyl)pyridazin-4-yl)amino)-4-methoxy-5-(2-methyl-2H-1,2,3-triazol-4-yl)benzoate To a solution of methyl 3-amino-4-methoxy-5-(2-methyl-2H-1,2,3-triazol-4-yl)benzoate (66 mg, 0.252 mmol) and 4,6-dichloro-N-(methyl-d3)pyridazine-3-carboxamide (52.6 mg, 0.252 mmol) in THF (1.5 mL) at rt was added, dropwise over 10 minutes, LiHMDS, 1M in THF (0.755 mL, 0.755 mmol). The reaction mixture was allowed to stir at rt for 30 minutes. After quenching with 2 ml of saturated ammonium chloride solution, the organics were removed. Additional water (~5 ml) was added and the suspensions was allowed to stand for 30 minutes. Filtration, rinsing the filter cake with waster and ethyl ether and drying afforded methyl 3-((6-chloro-3-((methyl-d3)carbamoyl)pyridazin-4-yl)amino)-4-methoxy-5-(2-methyl-2H-1,2,3-triazol-4-yl)benzoate (95 mg, 0.218 mmol, 87% yield) as a tan solid. MS (M+1) m/z: 435.6 (M+H)$^+$. LC retention time 0.98 [E].

Example 32

A mixture of methyl 3-((6-chloro-3-((methyl-d3)carbamoyl)pyridazin-4-yl)amino)-4-methoxy-5-(2-methyl-2H-1,2,3-triazol-4-yl)benzoate (95 mg, 0.218 mmol), cyclopropanecarboxamide (93 mg, 1.092 mmol), Pd$_2$(dba)$_3$, Chloroform adduct (22.57 mg, 0.022 mmol), xantphos (25.3 mg, 0.044 mmol) and Cs$_2$CO$_3$ (285 mg, 0.874 mmol) in dioxane (1.5 mL) was degassed by bubbling N$_2$ through the mixture for 5 minutes. The reaction vessel was sealed and heated to 130° C. for 30 minutes. The reaction mixture was concentrated to dryness and the residue was suspended in water. The pH was adjusted to ~2 with 1N HCl. The suspension was filtered and washed with water, followed by ethyl ether. Drying afforded a residue of 101 mg, of which 20 mg was dissolved in DMSO and was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 0-minute hold at 11% B, 11-61% B over 20 minutes, then a 0-minute hold at 100% B; Flow Rate: 20 mL/min; Column. Temperature: 25 C. Fraction collection was triggered by MS signals. Fractions containing the desired product were combined and dried via centrifugal evaporation to afford methyl 3-((6-(cyclopropanecarboxamido)-3-((methyl-d3)carbamoyl)-pyridazin-4-yl)amino)-4-methoxy-5-(2-methyl-2H-1,2,3-triazol-4-yl)benzoate (6.2 mg, 28.1% yield). MS (M+1) m/z: 484.1 (M+H)$^+$. LC retention time 1.56 [I]. $^1$H NMR (500 MHz, DMSO-d6) δ 11.33 (br s, 1H), 11.06 (br s, 1H), 9.15 (br s, 1H), 8.32 (br s, 1H), 8.15 (s, 1H), 8.08 (br s, 1H), 7.99 (br s, 1H), 4.25 (br s, 3H), 3.86 (br s, 3H), 3.73 (br s, 3H), 2.06 (br d, J=1.2 Hz, 1H), 0.90-0.71 (m, 4H).

Example 33

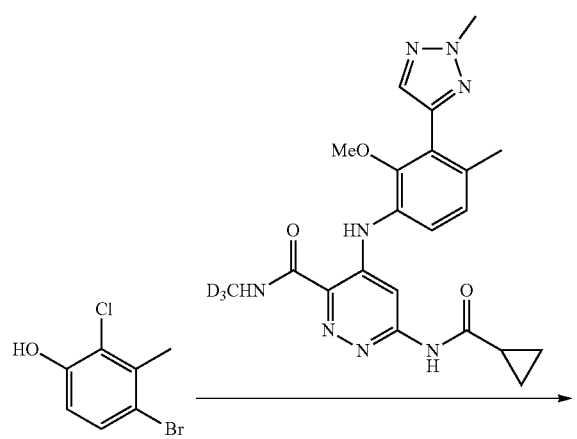

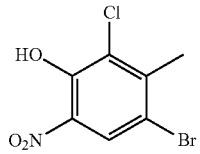

Step 1: 4-bromo-2-chloro-3-methyl-6-nitrophenol

All work was done behind a blast shield: To a solution of 4-bromo-2-chloro-3-methylphenol (500 mg, 2.258 mmol) in acetic acid (7 mL) in an ice bath was added dropwise over 5 minutes, nitric acid, 70 percent (0.216 mL, 3.39 mmol) in 1.5 ml of AcOH (prepared in an ice bath). After warming to rt, the reaction mixture was stirred 16 hr. The reaction mixture was partitioned between EtOAc (50) ml and 1.5M dibasic potassium phosphate solution (50 ml). The basic layer was acidified to pH<1 with 1N HCl and was extracted with EtOAc (150 ml). This organic layer was washed with brine (50 ml). The combined organics were dried over anhydrous magnesium sulfate and concentrated to afford 4-bromo-2-chloro-3-methyl-6-nitrophenol (602 mg, 99% yield) as a yellow solid. $^1$H NMR (400 MHz, chloroform-d) δ 11.03 (s, 1H), 8.28 (s, 1H), 2.62 (s, 3H).

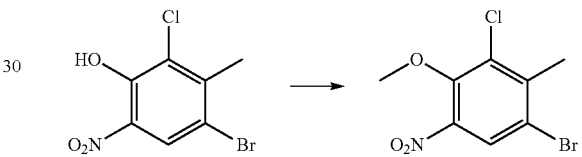

Step 2:
1-bromo-3-chloro-4-methoxy-2-methyl-5-nitrobenzene

A mixture of 4-bromo-2-chloro-3-methyl-6-nitrophenol (597 mg, 2.240 mmol), potassium carbonate (1548 mg, 11.20 mmol) and MeI (0.700 mL, 11.20 mmol) in DMF (10 mL) at rt was stirred for approximately 60 hours. The reaction mixture was partitioned between EtOAc (50 ml) and water (50 ml). The organic layer was washed with 10% LiCi solution (2×50 ml) and brine (50 ml). After drying over anhydrous sodium sulfate, the organic layer was concentrated to afford a residue that was chromatographed on a 24 gm ISCO silica gel cartridge, eluting with a 0-40% EtOAc/Hex gradient. The pure fractions were concentrated to afford 1-bromo-3-chloro-4-methoxy-2-methyl-5-nitrobenzene (510 mg, 81% yield) as a white solid. $^1$H NMR (400 MHz, chloroform-d) δ 8.00 (s, 1H), 4.01 (s, 3H), 2.59 (s, 3H).

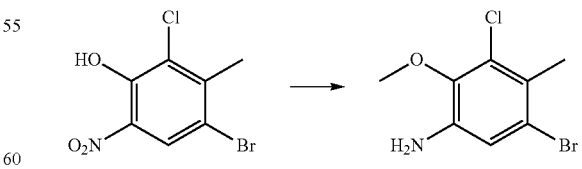

Step 3:
5-bromo-3-chloro-2-methoxy-4-methylaniline

To a mixture of 1-bromo-3-chloro-4-methoxy-2-methyl-5-nitrobenzene (405 mg, 1.444 mmol) and ammonium chloride (772 mg, 14.44 mmol) In EtOH (10 mL) and water (1.5 mL) at rt, zinc (944 mg, 14.44 mmol) was added portionwise over 10 minutes. The resulting heterogeneous mixture was stirred overnight at rt. The reaction mixture was diluted with DCM (200 ml) and was filtered through celite. The filtrate was washed with water (100 ml), dried over anhdrous sodium sulfate and concentrated to afford 5-bromo-3-chloro-2-methoxy-4-methylaniline (354 mg, 98% yield) as a yellow oil. $^1$H NMR (400 MHz, chloroform-d) δ 6.90 (s, 1H), 3.81 (s, 5H), 2.39 (s, 3H).

partitioned between EtOAc (30 ml) and brine (30 ml). The organic layer was dried over anhydrous sodium sulfate and was concentrated to a residue that was chromatographed on a 4 gm ISCO silica gel cartridge, eluting with a 0-100% EtOAc/Hex gradient. The pure fractions were concentrated to afford 2-methoxy-4-methyl-3-(2-methyl-2H-1,2,3-triazol-4-yl) aniline (14 mg, 0.064 mmol, 24.46% yield) as a yellow oil (impure). MS (M+1) m/z: 219.1 (M+H)$^+$. LC retention time 0.61 [E].

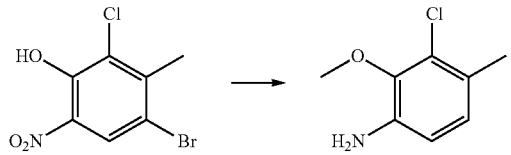

Step 4: 3-chloro-2-methoxy-4-methylaniline

To a solution of 5-bromo-3-chloro-2-methoxy-4-methylaniline (283 mg, 1.130 mmol) in THF (10 mL) at −78 C was added, dropwise over 5 minutes, n-BuLi, 2.5 M (0.994 mL, 2.485 mmol) and the resulting mixture was stirred at −78 C for 15 minutes. An additional aliquot of n-BuLi, 2.5 M (0.994 mL, 2.485 mmol) was added and the reaction was allowed to warm slowly to rt. The reaction mixture was partitioned between saturated ammonium chloride solution (40 ml) and EtOAc (40 ml). The organic layer was washed with brine (40 ml), dried over anhydrous sodium sulfate and concentrated to a complex mixture. The residue was chromatographed on a 12 gm ISCO silica gel cartridge, eluting with a 0-50% EtOAc/Hex gradient. The purest fractions were concentrated to afford 3-chloro-2-methoxy-4-methylaniline (45 mg, 0.262 mmol, 23.21% yield) as a yellow oil. The material is very impure and with be used as is. MS (M+1) m/z: 172.0 (174.0 chlorine pattern) (M+H)$^+$. LC retention time 0.76 [E].

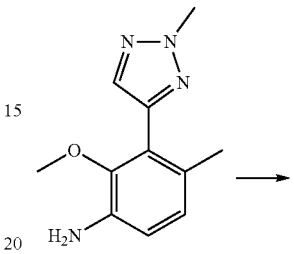

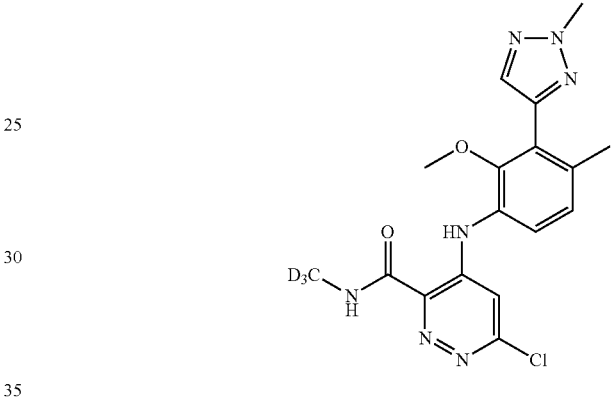

Step 6: 6-Chloro-4-((2-methoxy-4-methyl-3-(2-methyl-2H-1,2,3-triazol-4-yl)phenyl)amino)-N-(methyl-d3)pyridazine-3-carboxamide To a solution of 2-methoxy-4-methyl-3-(2-methyl-2H-1,2,3-triazol-4-yl) aniline (14 mg, 0.064 mmol) and 4,6-dichloro-N-(methyl-d3)pyridazine-3-carboxamide (20.11 mg, 0.096 mmol) in THF (0.75 mL) at rt was added, dropwise over 10 minutes, LiHMDS, 1M in THF (0.289 mL, 0.289 mmol). The reaction mixture was allowed to stir at rt for 30 minutes. After quenching with 2 ml of saturated ammonium chloride solution, the reaction mixture was partitioned between EtOAc (30 ml) and saturated ammonium chloride solution (20 ml). The organic layer was washed with brine (20 ml), dried over anhydrous sodium sulfate and concentrated to afford a brown solid that was chromatographed on a 4 gm ISCO silica gel cartridge, eluting with a 0-100% EtOAc/Hex gradient. The pure fractions were concentrated to afford 6-chloro-4-((2-methoxy-4-methyl-3-(2-methyl-2H-1,2,3-triazol-4-yl)phenyl)amino)-N-(methyl-d3)pyridazine-3-carboxamide (20 mg, 0.051 mmol, 80% yield) as a light yellow solid. MS (M+1) m/z: 391.3 (M+H)$^+$. LC retention time 1.00 [E].

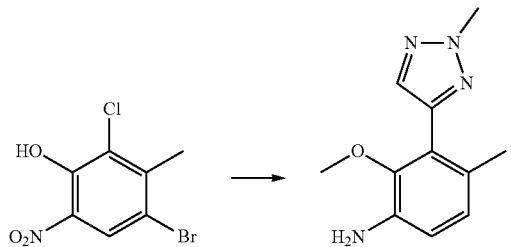

Step 5: 2-methoxy-4-methyl-3-(2-methyl-2H-1,2,3-triazol-4-yl) aniline

A degassed mixture of 3-chloro-2-methoxy-4-methylaniline (45 mg, 0.262 mmol), (2-methyl-2H-1,2,3-triazol-4-yl) boronic acid (66.6 mg, 0.524 mmol), 1,1'-bis(di-t-butylphosphino)ferrocene (12.44 mg, 0.026 mmol) and tribasic potassium phosphate, 2 M (0.393 mL, 0.787 mmol) in dioxane (2 mL) was stirred at 100° C. for 90 minutes. At this time, the reaction mixture was cooled and an addition 1/2 aliquot of boronic acid, catalyst and base were added and the reaction was degassed and heated to 100° C. for an additional 30 minutes. After cooling, the reaction mixture was Example 33: 6-(cyclopropanecarboxamido)-4-((2-methoxy-4-methyl-3-(2-methyl-2H-1,2,3-triazol-4-yl)phenyl)amino)-N-(methyl-d3)pyridazine-3-carboxamide A mixture of 6-chloro-4-((2-methoxy-4-methyl-3-(2-methyl-2H-1,2,3-triazol-4-yl)phenyl)amino)-N-(methyl-d3)

pyridazine-3-carboxamide (20 mg, 0.051 mmol), cyclopropanecarboxamide (8.71 mg, 0.102 mmol), Pd$_2$(dba)$_3$, chloroform adduct (5.29 mg, 5.12 µmol), xantphos (5.92 mg, 10.23 µmol) and Cs$_2$CO$_3$ (66.7 mg, 0.205 mmol) in dioxane (0.5 mL) was degassed by bubbling N2 through the mixture for 5 minutes. The reaction vessel was sealed and heated to 130° C. for 45 minutes. The reaction mixture was diluted with DMF. The mixture was filtered through a 0.45 micron nylon filter and the filtrate was purified via preparative LC/MS with the following conditions: Column: XBridge C18, 200 mm×19 mm, 5-µm
particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 13% B, 13-53% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to afford 6-(cyclopropanecarboxamido)-4-((2-methoxy-4-methyl-3-(2-methyl-2H-1,2,3-triazol-4-yl)phenyl)amino)-N-(methyl-d3)pyridazine-3-carboxamide (8.4 mg, 37.4%). MS (M+1) m/z: 440.3 (M+H)$^+$. LC retention time 1.48 [I]. $^1$H NMR (500 MHz, DMSO-d6) δ 11.28 (s, 1H), 10.79 (s, 1H), 9.09 (s, 1H), 8.08 (s, 1H), 7.86 (s, 1H), 7.39 (d, J=8.2 Hz, 1H), 7.16 (d, J=8.2 Hz, 1H), 4.22 (s, 3H), 3.41 (s, 3H), 2.19 (s, 3H), 2.12-2.04 (m, 1H), 0.87-0.77 (m, 4H).

Example 34

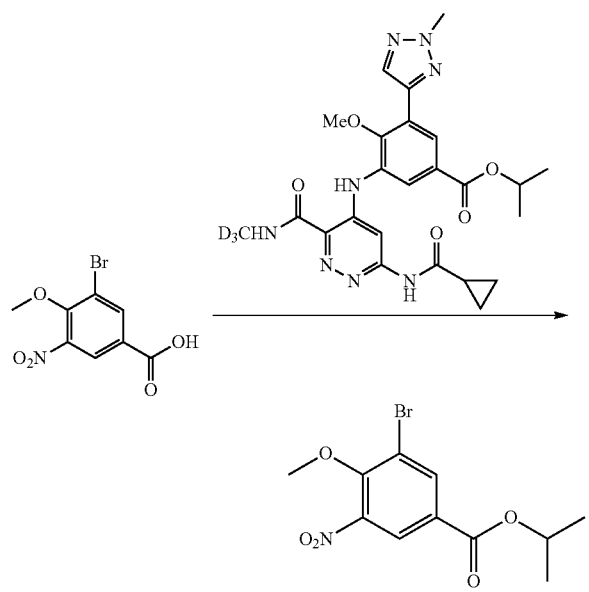

gm ISCO silica gel cartridge, eluting with a 0-40% EtOAc/Hex gradient. The pure fractions were concentrated to afford isopropyl 3-bromo-4-methoxy-5-nitrobenzoate (272 mg, 0.855 mmol, 99% yield) as a yellow oil. The product contains some reduced DIAD by NMR. $^1$H NMR (400 MHz, chloroform-d) δ 8.43 (d, J=2.1 Hz, 1H), 8.37 (d, J=2.1 Hz, 1H), 5.25 (m, J=10.3, 6.3 Hz, 1H), 4.06 (s, 3H), 1.38 (d, J=6.2 Hz, 6H).

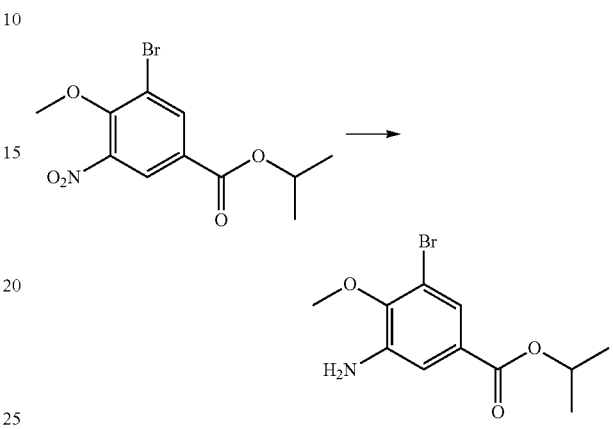

Step 2: Isopropyl
3-amino-5-bromo-4-methoxybenzoate

A mixture of isopropyl 3-bromo-4-methoxy-5-nitrobenzoate (272 mg, 0.855 mmol) and tin(II) chloride dihydrate (772 mg, 3.42 mmol) in ethyl acetate (10 mL) was refluxed for 90 min. After cooling to rt, the reaction mixture was diluted with 25 ml of EtOAc and was transferred to a separatory funnel. The organic layer was washed with 2.5N NaOH (3×30 ml), water (30 ml) and brine (30 ml). The organic layer was dried over anhydrous sodium sulfate and was concentrated to afford an oil that was chromatographed on a 12 gm ISCO silica gel cartridge, eluting with a 0-70% EtOAc/Hex gradient. The pure fractions were concentrated to afford isopropyl 3-amino-5-bromo-4-methoxybenzoate as a colorless oil. $^1$H NMR (400 MHz, chloroform-d) δ 7.59 (d, J=2.0 Hz, 1H), 7.35 (d, J=2.0 Hz, 1H), 5.20 (dt, J=12.5, 6.2 Hz, 1H), 4.01 (br s, 2H), 3.86 (s, 3H), 1.34 (d, J=6.2 Hz, 6H).

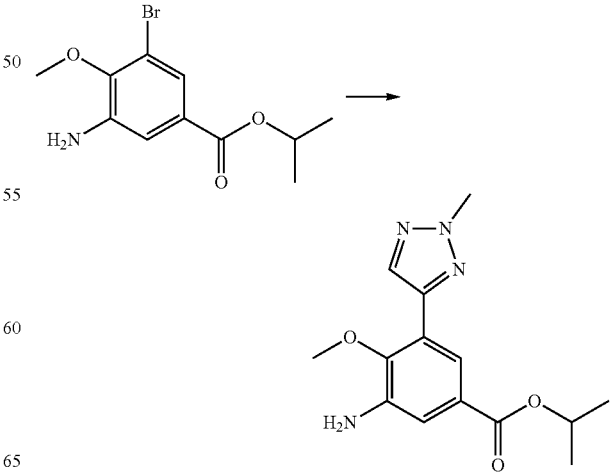

Step 1: Isopropyl
3-bromo-4-methoxy-5-nitrobenzoate

To a solution of 3-bromo-4-methoxy-5-nitrobenzoic acid (236 mg, 0.855 mmol), 2-propanol (0.198 mL, 2.56 mmol) and triphenylphosphine (336 mg, 1.282 mmol) in THF (5 mL) at 0° C. was added DIAD (0.249 mL, 1.282 mmol) dropwise over 5 minutes. The reaction mixture was allowed to warm to rt and stir overnight. The reaction mixture was concentrated and the residue was chromatographed on a 24

Step 3: Isopropyl 3-amino-4-methoxy-5-(2-methyl-2H-1,2,3-triazol-4-yl)benzoate A stirred mixture of (2-methyl-2H-1,2,3-triazol-4-yl)boronic acid (94 mg, 0.743 mmol), isopropyl 3-amino-5-bromo-4-methoxybenzoate (153 mg, 0.531 mmol), PdCl$_2$(dppf)-CH$_2$Cl$_2$ adduct (21.68 mg, 0.027 mmol) and 2M K$_3$PO$_4$ (aq) (0.796 mL, 1.593 mmol) in dioxane (4 mL) was degassed by bubbling nitrogen through the mixture for 5 minutes. The reaction mixture heated to 100° C. for 1 hr. After cooling to rt, the reaction mixture was partitioned between EtOAc (50 ml) and brine (20 ml). After drying over anhydrous sodium sulfate, the organic layer was concentrated and the residue was chromatographed on a 24 gm ISCO silica gel cartridge, eluting with a 0-100% EtOAc/Hex gradient. The pure fractions were concentrated to afford isopropyl 3-amino-4-methoxy-5-(2-methyl-2H-1,2,3-triazol-4-yl)benzoate (57 mg, 0.196 mmol, 37.0% yield) as a tan solid. MS (M+1) m/z: 291.0 (M+H)$^+$. LC retention time 0.84 [E].

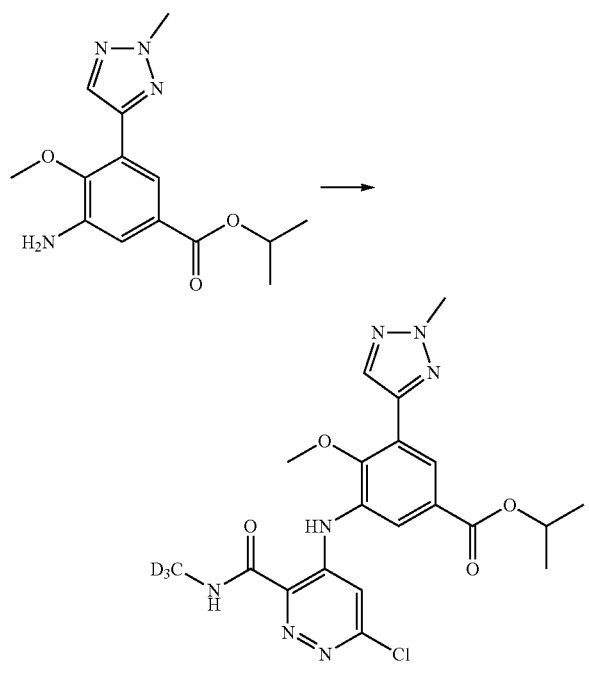

Step 4: Isopropyl 3-((6-chloro-3-((methyl-d3)carbamoyl)pyridazin-4-yl)amino)-4-methoxy-5-(2-methyl-2H-1,2,3-triazol-4-yl)benzoate To a solution of isopropyl 3-amino-4-methoxy-5-(2-methyl-2H-1,2,3-triazol-4-yl)benzoate (57 mg, 0.196 mmol) and 4,6-dichloro-N-(methyl-d3)pyridazine-3-carboxamide (65.7 mg, 0.314 mmol) in THF (2 mL) at rt was added, dropwise over 10 minutes, LiHMDS, 1M in THF (0.785 mL, 0.785 mmol). The reaction mixture was allowed to stir at rt for 30 minutes. After quenching with 2 ml of saturated ammonium chloride solution, the reaction mixture was partitioned between saturated ammonium chloride solution (20 ml) and EtOAc (20 ml). The organic layer was washed with brine (20 ml), dried over anhydrous sodium sulfate and concentrated to afford a residue that was chromatographed on a 12 gm ISCO silica gel cartridge, eluting with a 0-70% EtOAc/Hex gradient. The pure fractions were concentrated to afford isopropyl 3-((6-chloro-3-((methyl-d3)carbamoyl)pyridazin-4-yl)amino)-4-methoxy-5-(2-methyl-2H-1,2,3-triazol-4-yl)benzoate (71 mg, 78% yield) as a white solid. MS (M+1) m/z: 463.1 (465.1 chlorine pattern) (M+H)$^+$. LC retention time 0.97 [E].

Example 34: 3-((6-(Cyclopropanecarboxamido)-3-((methyl-d3)carbamoyl)pyridazin-4-yl)amino)-4-methoxy-5-(2-methyl-2H-1,2,3-triazol-4-yl)benzoate A mixture of isopropyl 3-((6-chloro-3-((methyl-d3)carbamoyl)pyridazin-4-yl)amino)-4-methoxy-5-(2-methyl-2H-1,2,3-triazol-4-yl)benzoate (40 mg, 0.086 mmol), cyclopropane-carboxamide (36.8 mg, 0.432 mmol), Pd$_2$(dba)$_3$, chloroform adduct (8.93 mg, 8.64 μmol), xantphos (10.00 mg, 0.017 mmol) and Cs$_2$CO$_3$ (113 mg, 0.346 mmol) in dioxane (0.6 mL) was degassed by bubbling N$_2$ through the mixture for 5 minutes. The reaction vessel was sealed and heated to 130° C. for 30 minutes. The reaction mixture was diluted with DMSO, filtered and purified by preparative HPLC. The pure fractions were concentrated to afford isopropyl 3-((6-(cyclopropanecarboxamido)-3-((methyl-d3)carbamoyl)pyridazin-4-yl)amino)-4-methoxy-5-(2-methyl-2H-1,2,3-triazol-4-yl)benzoate (17.5 mg; 39.6%). MS (M+1) m/z: 512.2 (M+H)$^+$. LC retention time 1.83 [I]. $^1$H NMR (500 MHz, DMSO-d6) δ 11.36 (s, 1H), 11.22 (s, 1H), 9.16 (s, 1H), 8.27 (d, J=2.0 Hz, 1H), 8.22 (s, 1H), 8.17 (s, 1H), 8.03 (d, J=2.0 Hz, 1H), 5.15 (quin, J=6.2 Hz, 1H), 4.26 (s, 3H), 3.73 (s, 3H), 2.15-2.01 (m, 1H), 1.32 (d, J=6.2 Hz, 6H), 0.89-0.74 (m, 4H).

Example 35

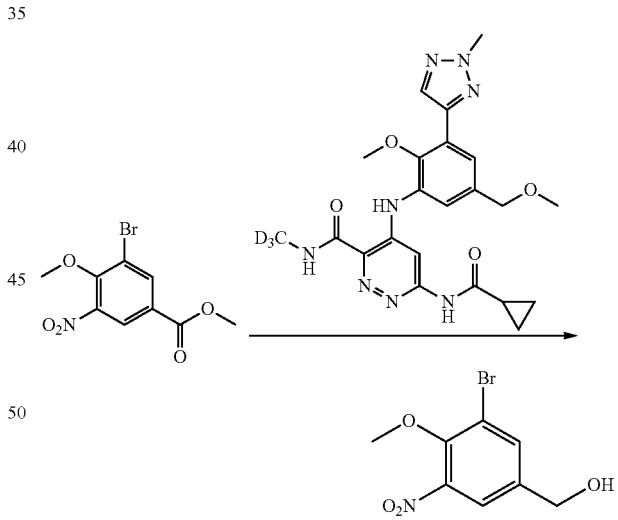

Step 1: (3-Bromo-4-methoxy-5-nitrophenyl)methanol

To a solution of methyl 3-bromo-4-methoxy-5-nitrobenzoate (1000 mg, 3.45 mmol) in dioxane (18 mL) and water (7.5 mL) at rt was added, portion wide over 10 minutes, sodium borohydride (913 mg, 24.13 mmol) and the resulting mixture was allowed to stir at rt overnight.

The reaction mixture was cooled to 0° C. and 1N HCl was added slowly to minimize gas evolution. When gas evolution ceased, the mixture was partitioned between EtOAc (50 ml) and water (50 ml). The organic layer was washed with brine (50 ml), dried over anhydrous sodium sulfate and concentrated to afford a residue that was chromatographed on a 24 gm ISCO silica gel cartridge, eluting with a 0-100% EtOAc/Hex gradient. The pure fractions were concentrated to afford (3-bromo-4-methoxy-5-nitrophenyl)methanol (406 mg, 1.549 mmol, 44.9% yield) as a light yellow solid. $^1$H NMR (400 MHz, chloroform-d) δ 7.83-7.79 (m, 1H), 7.78-7.74 (m, 1H), 4.72 (d, J=5.8 Hz, 2H), 4.01 (s, 3H), 1.90 (t, J=5.8 Hz, 1H).

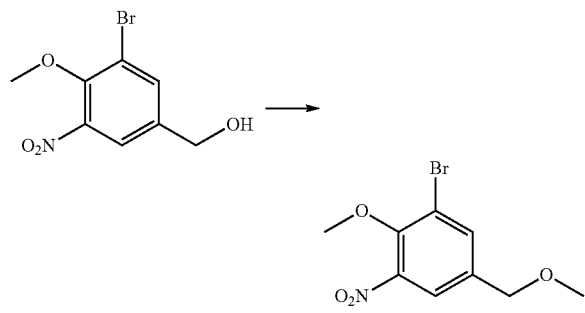

Step 2: 1-Bromo-2-methoxy-5-(methoxymethyl)-3-nitrobenzene

To a solution of (3-bromo-4-methoxy-5-nitrophenyl) methanol (200 mg, 0.763 mmol) in THF at 0° C. was added sodium hydride, 60% in mineral oil (61.0 mg, 1.526 mmol) over 5 min, portionwise. The reaction became dark brown. After stirring 30 minutes, MeI (0.095 mL, 1.526 mmol) was added and stirring was continued, while warming to rt for 90 minutes. At this time, the reaction was quenched with water and was partitioned between water (40 ml) and EtOAc (40 ml). The organic layer was washed with brine (25 ml), dried over anhydrous sodium sulfate and concentrated to a residue that was chromatographed on a 24 gm ISCO silica gel cartridge, eluting with a 0-100% EtOAc/Hex gradient. The pure fractions were concentrated to afford 1-bromo-2-methoxy-5-(methoxymethyl)-3-nitrobenzene (83 mg, 39.4% yield) as a colorless oil. $^1$H NMR (400 MHz, chloroform-d) δ 7.77 (d, J=2.1 Hz, 1H), 7.72 (d, J=2.0 Hz, 1H), 4.44 (s, 2H), 4.01 (s, 3H), 3.43 (s, 3H).

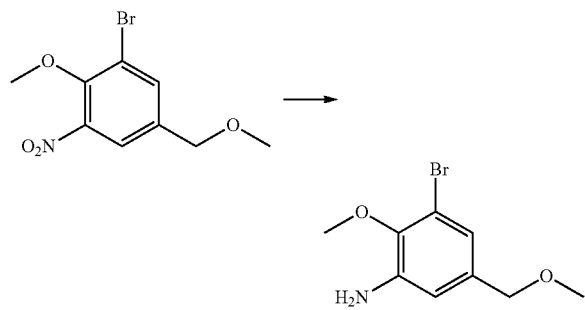

Step 3: 3-Bromo-2-methoxy-5-(methoxymethyl) aniline

A mixture of 1-bromo-2-methoxy-5-(methoxymethyl)-3-nitrobenzene (82 mg, 0.297 mmol) and tin(II) chloride dihydrate (268 mg, 1.188 mmol) in ethyl acetate (3 mL) was heated to reflux for 1 hr. After cooling to rt, the reaction mixture was diluted with 20 ml of EtOAc and was transferred to a separatory funnel. The organic layer was washed with 2.5M NaOH (2×25 ml), water (25 ml) and brine (25 ml). After drying over anhydrous sodium sulfate, the organic layer was concentrated and the residue was chromatographed on a 4 gm ISCO silica gel cartridge, eluting with a 0-70% EtOAc/Hex gradient. The pure fractions were concentrated to afford 3-bromo-2-methoxy-5-(methoxymethyl) aniline (36 mg, 49.3% yield) as a light yellow oil. MS (M+1) m/z: 245.9/247.9 (M+H)$^+$. LC retention time 0.83 [E].

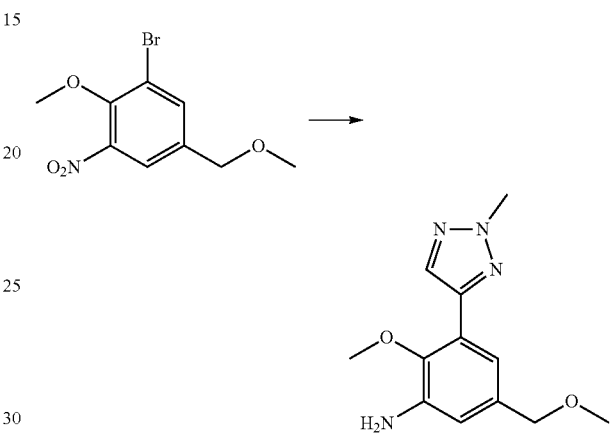

Step 4: 2-Methoxy-5-(methoxymethyl)-3-(2-methyl-2H-1,2,3-triazol-4-yl) aniline

A stirred mixture of (2-methyl-2H-1,2,3-triazol-4-yl)boronic acid (36.1 mg, 0.284 mmol), 3-bromo-2-methoxy-5-(methoxymethyl) aniline (35 mg, 0.142 mmol), PdCl$_2$(dppf)-CH$_2$Cl$_2$ adduct (5.81 mg, 7.11 μmol) and 2M K$_3$PO$_4$ (aq) (0.213 mL, 0.427 mmol) in dioxane (1 mL) was degassed by bubbling nitrogen through the mixture for 5 minutes. The reaction mixture heated at 100° C. for 0.75 hr. After cooling to rt, the reaction mixture was partitioned between EtOAc (50 ml) and brine (20 ml). After drying over anhydrous sodium sulfate solution, the organic layer was concentrated and the residue was chromatographed on a 4 gm ISCO silica gel cartridge, eluting with a 0-100% EtOAc/Hex gradient. The pure fractions were concentrated to afford 2-methoxy-5-(methoxymethyl)-3-(2-methyl-2H-1,2,3-triazol-4-yl) aniline (22 mg, 62.3% yield) as a yellow oil. MS (M+1) m/z: 249.1 (M+H)$^+$. LC retention time 0.69 [E].

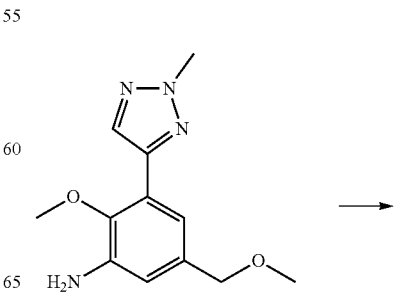

105
-continued

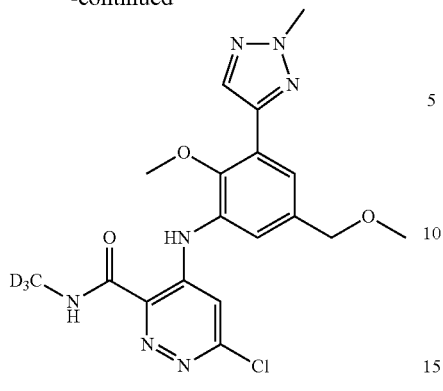

Step 5: 6-Chloro-4-((2-methoxy-5-(methoxymethyl)-3-(2-methyl-2H-1,2,3-triazol-4-yl)phenyl)amino)-N-(methyl-d3)pyridazine-3-carboxamide To a solution of 2-methoxy-5-(methoxymethyl)-3-(2-methyl-2H-1,2,3-triazol-4-yl) aniline (22 mg, 0.089 mmol) and 4,6-dichloro-N-(methyl-d3)pyridazine-3-carboxamide (37.0 mg, 0.177 mmol) in THF (1 mL) at rt was added, dropwise over 10 minutes, LiHMDS, 1M in THF (0.354 mL, 0.354 mmol). The reaction mixture was allowed to stir at rt for 30 minutes. After quenching with 2 ml of saturated ammonium chloride solution, the reaction mixture was partitioned between saturated ammonium chloride solution (20 ml) and EtOAc (20 ml). The organic layer was washed with brine (20 ml), dried over anhydrous sodium sulfate and concentrated to afford a residue that was chromatographed on a 4 gm ISCO silica gel cartridge, eluting with a 0-100% EtOAc/Hex gradient. The pure fractions were concentrated to afford 6-chloro-4-((2-methoxy-5-(methoxymethyl)-3-(2-methyl-2H-1,2,3-triazol-4-yl)phenyl)amino)-N-(methyl-d3)pyridazine-3-carboxamide (25 mg, 0.059 mmol, 67.0% yield) as a white solid. MS (M+1) m/z: 421.0 (M+H)$^+$. LC retention time 0.89 [E].

Example 35: 6-(Cyclopropanecarboxamido)-4-((2-methoxy-5-(methoxymethyl)-3-(2-methyl-2H-1,2,3-triazol-4-yl)phenyl)amino)-N-(methyl-d3)pyridazine-3-carboxamide A mixture of 6-chloro-4-((2-methoxy-5-(methoxymethyl)-3-(2-methyl-2H-1,2,3-triazol-4-yl)phenyl)amino)-N-(methyl-d3)pyridazine-3-carboxamide (25 mg, 0.059 mmol), cyclopropanecarboxamide (25.3 mg, 0.297 mmol), Pd$_2$(dba)$_3$, chloroform adduct (6.14 mg, 5.94 μmol), xantphos (6.87 mg, 0.012 mmol) and Cs$_2$CO$_3$ (77 mg, 0.238 mmol) in dioxane (0.5 mL) was degassed by bubbling N2 through the mixture for 5 minutes. The reaction vessel was sealed and heated to 130° C. for 30 minutes. The reaction mixture was diluted with DMSO, filtered and purified by prep. HPLC. The purfractions were concentrated to afford 6-(cyclopropane-carboxamido)-4-((2-methoxy-5-(methoxymethyl)-3-(2-methyl-2H-1,2,3-triazol-4-yl)phenyl)amino)-N-(methyl-d3)pyridazine-3-carboxamide (16.3 mg; 57.7%). MS (M+1) m/z: 470.0 (M+H)$^+$. LC retention time 1.46 [I]. $^1$H NMR (500 MHz, DMSO-d6) δ 11.29 (s, 1H), 10.95 (s, 1H), 9.13 (s, 1H), 8.10 (d, J=9.0 Hz, 2H), 7.67 (d, J=1.8 Hz, 1H), 7.39 (d, J=1.7 Hz, 1H), 4.42 (s, 2H), 4.23 (s, 3H), 3.64 (s, 3H), 3.30 (s, 3H), 2.14-2.00 (m, 1H), 0.87-0.73 (m, 4H).

106

Example 36

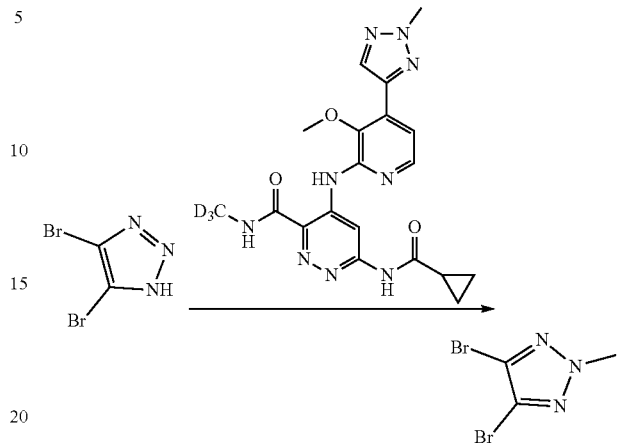

Step 1: (Also See Intermediate 19)

To a solution of 4,5-dibromo-1H-1,2,3-triazole (3.5 g, 15.43 mmol) in DMF (40 mL), at −10° C. (in an ice-water bath) was added potassium carbonate (4.69 g, 33.9 mmol). After stirring 15 minutes, iodomethane (1.929 mL, 30.9 mmol) was added dropwise. The reaction mixture was stirred overnight while warming to room temperature, at which time it was quenched with 10 mL water. After the mixture was extracted with EtOAc (2×50 ml), the combined organic layer was washed with 10% aq. LiCl and brine. After drying over anhydrous sodium sulfate, the organic layer was filtered and concentrated to a residue that was loaded onto a 40 g silica gel column for purification by flash chromatography, eluting with 0-100% ethyl acetate in hexanes. Concentration of the pure fractions afforded 4,5-dibromo-2-methyl-2H-1,2,3-triazole (2.17 g, 58.4% yield) as a white crystalline solid. LC retention time 1.24 [C] [the desired dibromo product does not ionize].

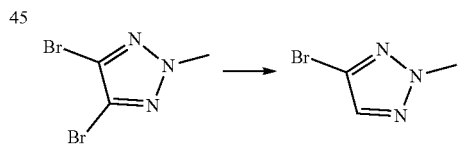

Step 2: (Also See Intermediate 19)

To a solution of 4,5-dibromo-2-methyl-2H-1,2,3-triazole (2.55 g, 10.59 mmol) in ether (18 mL) cooled to −20° C. was slowly added isopropyl magnesium chloride, 2M in THF (17.47 mL, 34.9 mmol). The reaction was stirred 30 minutes cold at −20° C. The reaction mixture was allowed to warm to 0° C. over 2 hours. After quenching with saturated ammonium chloride solution, the mixture was extracted with ether (2×50 ml). The combined organic layer was washed with brine (1×). After drying over anhydrous sodium sulfate, the organic layer was filtered, concentrated and purified by silica gel column chromatography, eluting with 0-100% ethyl acetate in hexanes. Concentration of the pure fractions afforded 4-bromo-2-methyl-2H-1,2,3-triazole (1.13 g, 65.9% yield) as a yellow oil. MS (M+1) m/z: 188.1 (M+H)+. LC retention time 0.87 [C].

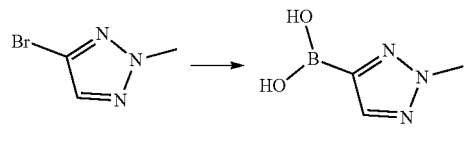

Step 3: (Also See Intermediate 19)

To a solution of 4-bromo-2-methyl-2H-1,2,3-triazole (1.59 g, 9.82 mmol) in THF (20 mL) cooled to 10° C. was slowly added isopropyl magnesium chloride-lithium chloride complex, 1.3 in THF (15.10 mL, 19.63 mmol). The reaction was stirred 2 h cold and was then cooled to −20° C. Trimethyl borate (3.29 mL, 29.4 mmol) was added and the resulting mixture was stirred 1 hour. After quenching with 1N HCl, the mixture was extracted with ethyl acetate (1×). The organic layer was washed with brine (1×) dried over anhydrous sodium sulfate, filtered and concentrated to afford (2-methyl-2H-1,2,3-triazol-4-yl)boronic acid (899 mg, 72.2% yield) as a white solid. LC retention time 0.95 [C]. $^1$H NMR (400 MHz, DMSO-d6) δ 8.31 (br s, 2H), 7.89 (s, 1H), 4.16 (s, 3H).

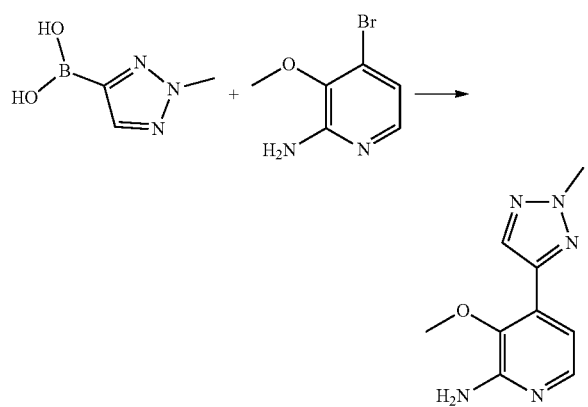

Step 4

A stirred mixture of (2-methyl-2H-1,2,3-triazol-4-yl)boronic acid (100 mg, 0.788 mmol), 4-bromo-3-methoxypyridin-2-amine (80 mg, 0.394 mmol) and PdCl$_2$(dppf)-dichloromethane adduct (16.09 mg, 0.020 mmol) in dioxane (2 mL) was degassed by bubbling nitrogen through the mixture for 5 minutes. 2M K$_3$PO$_4$ (aq) (0.591 mL, 1.182 mmol) was quickly added and the reaction mixture heated at 100° C. for 30 minutes. The reaction turned dark almost immediately. LC-MS showed complete consumption of the starting material. The reaction mixture was cooled to room temperature, then diluted with EtOAc (75 mL). This solution was then dried over anhydrous sodium sulfate, filtered, concentrated and purified by flash chromatography, eluting with 0-100% EtOAc in hexanes. Concentration of the pure fractions afforded 3-methoxy-4-(2-methyl-2H-1,2,3-triazol-4-yl)pyridin-2-amine (45 mg, 54.5% yield) as a yellow oil. MS (M+1) m/z: 206.1 (M+H)+. LC retention time 0.60 [C].

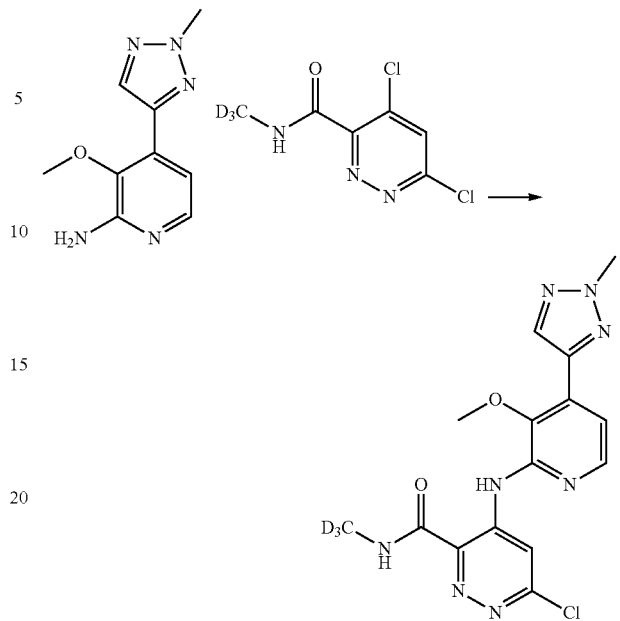

Step 5

To a solution of 4,6-dichloro-N-(methyl-d3)pyridazine-3-carboxamide (48.1 mg, 0.230 mmol) and 3-methoxy-4-(2-methyl-2H-1,2,3-triazol-4-yl)pyridin-2-amine (45 mg, 0.219 mmol) (re-purified) in THF (2 mL) was added lithium bis(trimethylsilyl)amide (0.548 mL, 0.548 mmol) in a dropwise manner (<5 min) using a syringe and the reaction was stirred until complete by LCMS. Sat. ammonium chloride (aq.) was added to quench the residual base whereupon a solid precipitated out of solution and was filtered off. The solid was the desired product. The reaction solution was partitioned between ethyl acetate and water. The water layer was extracted 1× with ethyl acetate, and then the combined organic layer was washed 1× with sat. ammonium chloride (aq.) and 1× with brine. The organic layer was then dried over anhydrous sodium sulfate, filtered and concentrated. No desired product was found in the residue. Only the filtered and dried solid was the product. Drying the solid afforded 6-chloro-4-((3-methoxy-4-(2-methyl-2H-1,2,3-triazol-4-yl)pyridin-2-yl)amino)-N-(methyl-d3)pyridazine-3-carboxamide (37 mg, 44.7% yield) as an off-white solid. MS (M+1) m/z: 378.1 (M+H)+. LC retention time 1.445 [C].

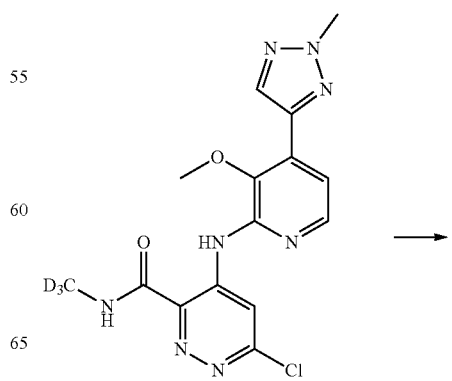

110

Example 36

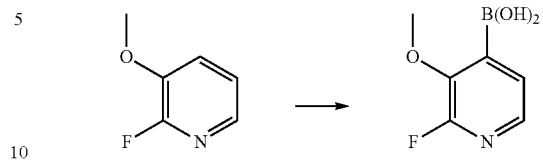

Step 1: 2-Fluoro-3-methoxypyridin-4-yl)boronic acid

To a solution of 2-fluoro-3-methoxypyridine (0.5 g, 3.93 mmol) in THF at −78° C. was added TMEDA (1.25 ml, 8.26 mmol) and n-BuLi (1.88 ml, 4.72 mmol). The mixture was stirred for 2 hr warming from −78° C. to −55° C., at which time the reaction mixture was re-cooled to −78° C. and triisopropyl borate (1.370 ml, 5.90 mmol) was added. The mixture was stirred for 2 hr while warming from −78° C. to −55° C., at which time it was quenched with water (2 ml) and allowed to warm to rt. The mixture was concentrated in vacuo and additional water (20 ml) was added. The resulting mixture was washed with ether (20 ml) and the separated aqueous layer was acidified to pH with AcOH. The aqueous layer was extracted with EtOAc (2×20 ml), dried over anhydrous sodium sulfate and concentrated in vacuo to afford 2-fluoro-3-methoxypyridin-4-yl)boronic acid (650 mg; 97% yield). MS (M+1) m/z: 172.1 (M+H)⁺. LC retention time 0.66 min [H]. ¹H NMR (400 MHz, CHLOROFORM-d) δ 7.93 (dd, J=4.7, 1.7 Hz, 1H), 7.55 (dd, J=4.7, 1.4 Hz, 1H), 6.25-5.41 (m, 2H), 4.09 (d, J=3.3 Hz, 3H).

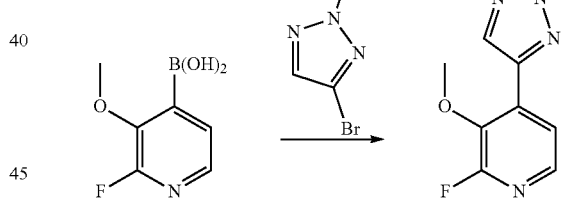

Step 2: 2-Fluoro-3-methoxy-4-(2-methyl-2H-1,2,3-triazol-4-yl)pyridine

A stirred mixture of 4-bromo-2-methyl-2H-1,2,3-triazole (Intermediate 19 and shown in first method) (281 mg, 1.738 mmol), (2-fluoro-3-methoxypyridin-4-yl)boronic acid (270 mg, 1.580 mmol) and PdCl₂(dppf)-CH₂Cl₂ adduct (64.5 mg, 0.079 mmol) in dioxane (6.9 ml) was degassed by bubbling nitrogen through the mixture for 5 minutes. 2M K₃PO₄ (aq) (2.4 ml, 4.74 mmol) was quickly added and the reaction mixture heated at 80° C. for 1 hr. The reaction turned dark almost immediately. The mixture was diluted with EtOAc (20 mL) and was filtered through a pad of celite. The filter cake was washed with EtOAc (2×) and the combined organic layer was washed with brine 20 ml, dried over sodium sulfate and concentrated in vacuo to afford a residue that was purified with isco column (24 g, AcOEt/Hexane=0-50%, gradient time=15 min flow rate=35 ml/min) Concentration of the pure fractions and drying afforded 2-fluoro-

109

-continued

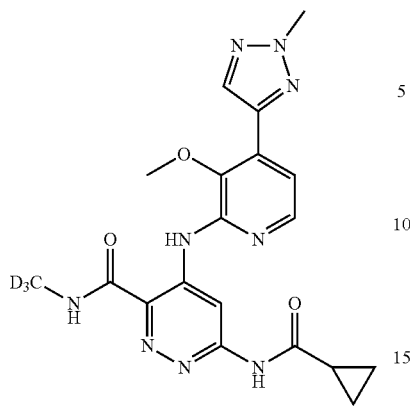

Step 6

A mixture of 6-chloro-4-((3-methoxy-4-(2-methyl-2H-1,2,3-triazol-4-yl)pyridin-2-yl)amino)-N-(methyl-d3)pyridazine-3-carboxamide (37 mg, 0.098 mmol), xantphos (11.33 mg, 0.020 mmol), and cyclopropanecarboxamide (41.7 mg, 0.490 mmol) in dioxane (1.5 mL) was degassed by bubbling nitrogen through it for 5 minutes. Cesium carbonate (128 mg, 0.392 mmol) and Pd₂(dba)₃ (8.97 mg, 9.79 μmol) were added, the vessel was sealed, and the reaction was stirred at 130° C. for 2 h. The reaction was complete by LC-MS. The reaction mixture was diluted to 2 mL with DMF, filtered and purified by prep HPLC. Concentration of the pure fractions afforded 6-(cyclopropanecarboxamido)-4-((3-methoxy-4-(2-methyl-2H-1,2,3-triazol-4-yl)pyridin-2-yl)amino)-N-(methyl-d3)pyridazine-3-carboxamide (11.5 mg, 27.3% yield). MS (M+1) m/z: 427.1 (M+H)⁺. LC retention time 1.16 [C]. ¹H NMR (500 MHz, DMSO-d6) δ 12.41 (s, 1H), 11.33 (s, 1H), 9.85 (s, 1H), 9.24 (s, 1H), 8.31 (s, 1H), 8.15 (d, J=5.2 Hz, 1H), 7.47 (d, J=5.5 Hz, 1H), 4.27 (s, 3H), 3.82 (s, 3H), 2.19-2.09 (m, 1H), 0.97-0.83 (m, 4H).

Alternate synthesis of Example 36: 6-(cyclopropanecarboxamido)-4-((3-methoxy-4-(2-methyl-2H-1,2,3-triazol-4-yl)pyridin-2-yl)amino)-N-(methyl-d3)pyridazine-3-carboxamide

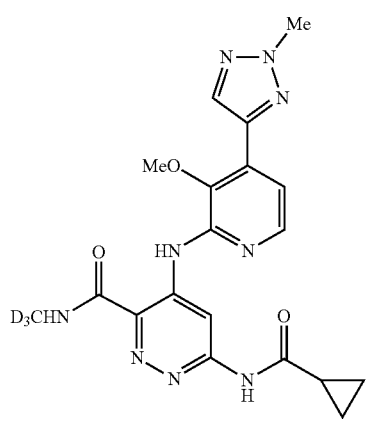

3-methoxy-4-(2-methyl-2H-1,2,3-triazol-4-yl)pyridine (245 mg; 74.5% yield). MS (M+1) m/z: 209.1 (M+H)⁺. LC retention time 0.81 min [H]. ¹H NMR (400 MHz, CHLOROFORM-d) δ 8.15 (s, 1H), 7.91 (dd, J=5.2, 1.5 Hz, 1H), 7.75 (d, J=5.2 Hz, 1H), 4.27 (s, 3H), 4.02 (d, J=2.6 Hz, 3H).

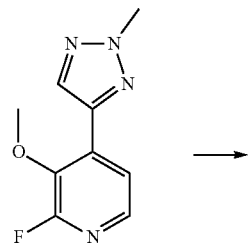

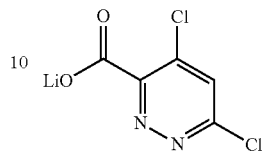

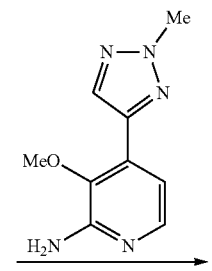

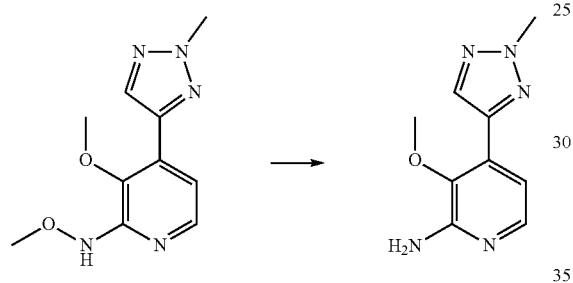

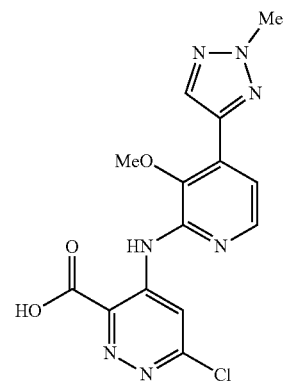

Step 3: 3-Methoxy-4-(2-methyl-2H-1,2,3-triazol-4-yl)pyridin-2-amine

A stirred mixture of 2-fluoro-3-methoxy-4-(2-methyl-2H-1,2,3-triazol-4-yl)pyridine (50 mg, 0.240 mmol), O-methylhydroxylamine, HCl (80 mg, 0.961 mmol) in n-BuOH (1044 µl) was stirred at 100° C. for 4 hr under N₂. After cooling, the solid, which was MeONH₂, HCl was filtered off and washed with EtOAc (2×1 ml). The filtrate and the washes were combined and extracted with 1N HCl (2×2 ml), the acidic layer was washed with EtOAc (2×1 ml) and basified with Na₂CO₃. The resulting mixture was extracted with EtOAc (2×3 ml) and the combined organic layers were washed with brine (2 ml), dried over anhydrous sodium sulfate and concentrated to a residue that was used as is. To a mixture of the residue in ethanol (1.5 ml) and AcOH (0.2 ml) was added zinc (62.8 mg, 0.961 mmol). The mixture was stirred at rt for 1 h. LC-MS indicated that the reaction was complete and the mixture was filtered and concentrated in vacuo to afford a residue that was taken up in EtOAc (10 ml) and washed with half saturated NaHCO₃ (10 ml) and brine (5 ml). Drying over anhydrous sodium sulfate and concentrated afforded 3-methoxy-4-(2-methyl-2H-1,2,3-triazol-4-yl)pyridin-2-amine (45 mg; 80% yield). MS (M+1) m/z: 206.1 (M+H)⁺. LC retention time 0.69 min [H]. ¹H NMR (400 MHz, CHLOROFORM-d) δ 8.09 (s, 1H), 7.87 (d, J=5.3 Hz, 1H), 7.17 (d, J=5.3 Hz, 1H), 4.74 (br s, 2H), 4.27 (s, 3H), 3.73 (s, 3H).

Step 4: 6-Chloro-4-((3-methoxy-4-(2-methyl-2H-1,2,3-triazol-4-yl)pyridin-2-yl)amino)pyridazine-3-carboxylic acid To a solution of 3-methoxy-4-(2-methyl-2H-1,2,3-triazol-4-yl)pyridin-2-amine (7 g, 34.1 mmol) and lithium 4,6-dichloropyridazine-3-carboxylate, lithium salt, H₂O (refer to patent: U.S. Pat. No. 10,899,745) (12.22 g, 54.6 mmol) in 2-Me-THF (227 ml) (new bottle) at rt was added 1M LiHMDS in THF (153 ml, 153 mmol) dropwise over 30 minutes. The inner temperature raised to 34° C. and the reaction mixture was heated with an oil bath of 45° C. (the inner temperature rose to 43° C. gradually) for 2 hr then heated to 50° C. with stirring for 30 min. After cooling, the mixture was quenched with water (50 ml) at 10-15° C. and then concentrated in vacuo to remove most of the solvents. To the residue was added 800 ml of water and citric acid (16.38 g, 85 mmol) and the mixture was stirred for 30 min at 10° C. The resulting suspension was filtered and the filter cake was washed with water (3×), (slow filtration), air dried o/n then at 50° C. under vacuum for 6 hr to afford 6-chloro-4-((3-methoxy-4-(2-methyl-2H-1,2,3-triazol-4-yl)pyridin-2-yl)amino)pyridazine-3-carboxylic acid (10.7 g; 87% yield). MS (M+1) m/z: 362.0 (364.0, chloro pattern) (M+H)+. LC retention time 0.89 min [H].

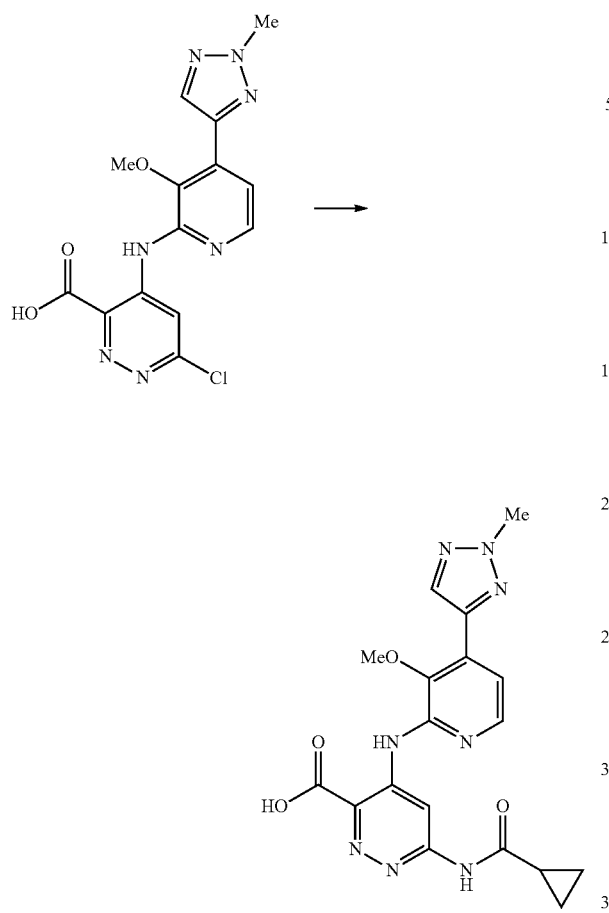

Step 5: 6-(Cyclopropanecarboxamido)-4-((3-methoxy-4-(2-methyl-2H-1,2,3-triazol-4-yl)pyridin-2-yl)amino)pyridazine-3-carboxylic acid In a 2000 ml 4 neck flask 6-chloro-4-((3-methoxy-4-(2-methyl-2H-1,2,3-triazol-4-yl)pyridin-2-yl)amino)pyridazine-3-carboxylic acid (31 g, 86 mmol) and cyclopropanecarboxamide (21.88 g, 257 mmol) were suspended in 2-Me-THF (714 ml). DBU (19.38 ml, 129 mmol) and sodium trifluoroacetate 98% (17.48 g, 129 mmol) were added and the mixture was purged with $N_2$ for 5 min. (R)-(−)-1-[(S)-2-(dicyclohexylphosphino)ferrocenyl]ethyldi-t-butylphosphine (2.091 g, 3.77 mmol) and allylpalladium chloride dimer, min. 98% (0.627 g, 1.714 mmol) were then added, the reaction mixture was purged with N2 for an additional 5 min and was then heated to 80-82° C. (inner temperature) with mechanical stirring under $N_2$ for 18 hr. LC-MS indicated that the starting material was consumed. The reaction mixture was cooled to rt, and a solution of citric acid (52.7 g, 274 mmol) in 300 ml of ACN and 600 ml of water was added. The mixture was stirred for 1 hr and then was allowed to stand for 1 hr. The suspension was filtered and the filter cake was washed with ACN (2×), water (3×), and ACN (2×). Vacuum drying at 45° C. overnight afforded 6-(cyclopropanecarboxamido)-4-((3-methoxy-4-(2-methyl-2H-1,2,3-triazol-4-yl)pyridin-2-yl)amino)pyridazine-3-carboxylic acid (31.3 g; 89% yield). MS (M+1) m/z: 411.1 (M+H)+. LC retention time 0.76 min [H].

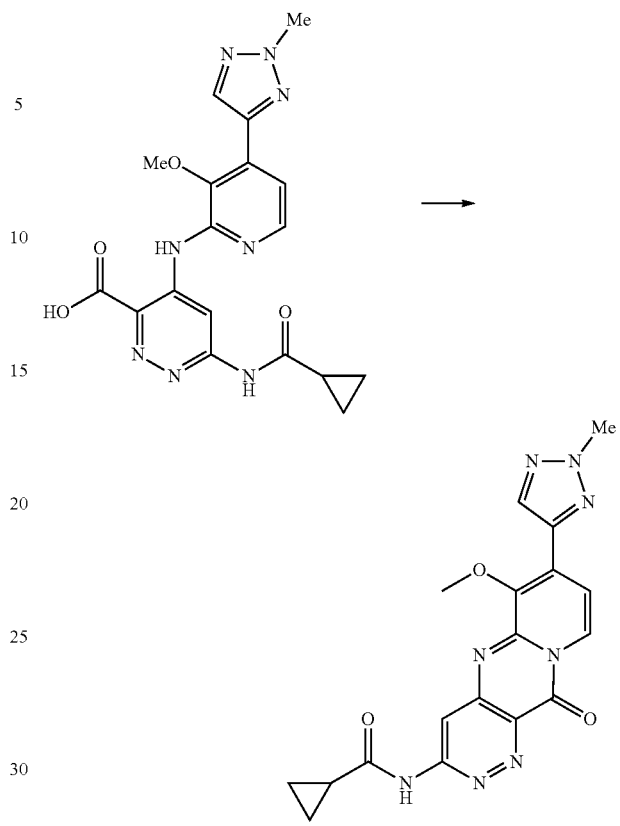

Step 6: N-(6-methoxy-7-(2-methyl-2H-1,2,3-triazol-4-yl)-11-oxo-11H-pyrido[1',2':1,2]pyrimido[5,4-c]pyridazin-3-yl)cyclopropanecarboxamide A mixture of 1-methylimidazole (1.259 ml, 15.79 mmol) and 6-(cyclopropanecarboxamido)-4-((3-methoxy-4-(2-methyl-2H-1,2,3-triazol-4-yl)pyridin-2-yl)amino)pyridazine-3-carboxylic acid (10.8 g, 26.3 mmol) in NMP/ACN (202 ml) (146/56 ml) was stirred at rt for 20 minutes. 1-hydroxybenzotriazole hydrate wetted with not less than 14 wt. % water 97% (2.252 g, 13.16 mmol) and N-(3-dimethylaminopropyl)-N'-ethylcarbodiimide hydrochloride (7.06 g, 36.8 mmol) were added and the reaction mixture was heated with an oil bath at 65° C. for 1.5 hr hours (the inner temperature raised to 74.5° C. at one point and stayed above 70° C.). The reaction mixture was cooled to rt and stirred for 30 minutes, after which time it was cooled with an ice water bath until the inner temperature was 6° C. After standing for 30 minutes, the suspension was filtered and the filter cake was washed with acetonitrile until no more color came through in the wash. Drying at 45° C. over for approximately 60 hours afforded N-(6-methoxy-7-(2-methyl-2H-1,2,3-triazol-4-yl)-11-oxo-11H-pyrido[1',2':1,2]pyrimido[5,4-c]pyridazin-3-yl)cyclopropanecarboxamide (8.78 g; 85% yield). MS (M+1) m/z: 393.1 (M+H)+. LC retention time 0.82 min [H]. 1H NMR (400 MHz, DMSO-d6) δ 11.95 (s, 1H), 8.75 (d, J=7.7 Hz, 1H), 8.43 (s, 1H), 8.39 (s, 1H), 7.60 (d, J=7.7 Hz, 1H), 4.31 (s, 3H), 4.14 (s, 3H), 2.24-2.12 (m, 1H), 0.94 (d, J=6.1 Hz, 4H).

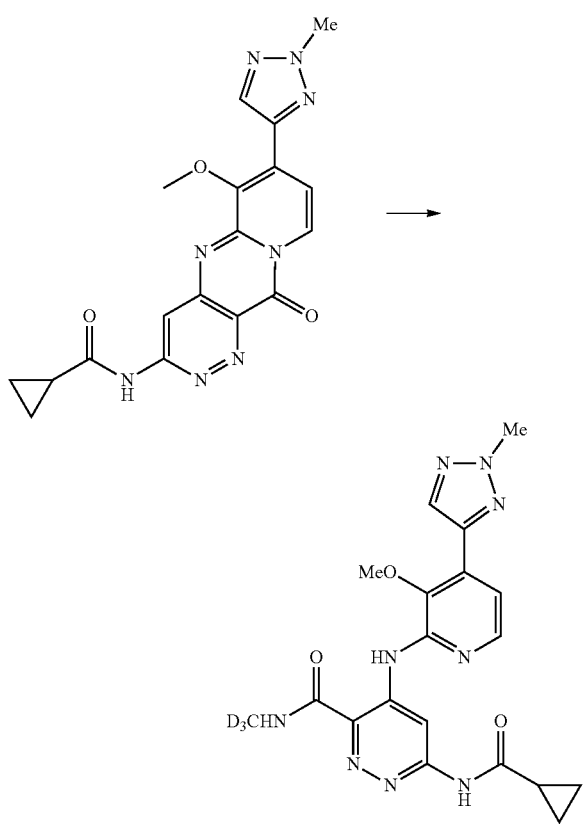

Step 7: 6-(Cyclopropanecarboxamido)-4-((3-methoxy-4-(2-methyl-2H-1,2,3-triazol-4-yl)pyridin-2-yl)amino)-N-(methyl-d3)pyridazine-3-carboxamide A mixture of N-(6-methoxy-7-(2-methyl-2H-1,2,3-triazol-4-yl)-11-oxo-11H-pyrido[1',2':1,2]pyrimido[5,4-c]pyridazin-3-yl)cyclopropanecarboxamide (8.77 g, 22.35 mmol), anhydrous DMSO (160 ml), DIEA (17.57 ml, 101 mmol) and methan-d3-amine, HCl (6.31 g, 89 mmol) was stirred at 100° C. (oil bath) in a pressure vessel for 15 hr. After cooling to rt, the mixture was filtered twice through glass filter paper and the container was washed with DMSO (2×5 ml and 3 ml). The clear filtrate was heated to 60° C. and water added slowly with stirring. A total of 21 ml of water was added. The mixture was cooled down slowly to rt and stirred for 1 hr. The resulting suspension was filtered and the filter cake was washed with DMSO (2×6 ml) and ACN (3×15 ml). After drying, the crude product was mixed with 75 ml of anhydrous DMSO and was stirred at 95° C. for 1 hr under N2. After cooling to 60° C., 10 ml of water was slowly added with stirring. After the water addition, the mixture was stirred and cooled to rt, filtered and the solid was washed with DMSO (5 ml) and acetonitrile (3×20 ml). Drying, under vacuum at 45° C. for approximately 60 hours afforded N-(6-methoxy-7-(2-methyl-2H-1,2,3-triazol-4-yl)-11-oxo-11H-pyrido[1',2':1,2]pyrimido[5,4-c]pyridazin-3-yl)cyclopropanecarboxamide (7.8 g; 82%). See other synthesis above for analytical data.

Example 37

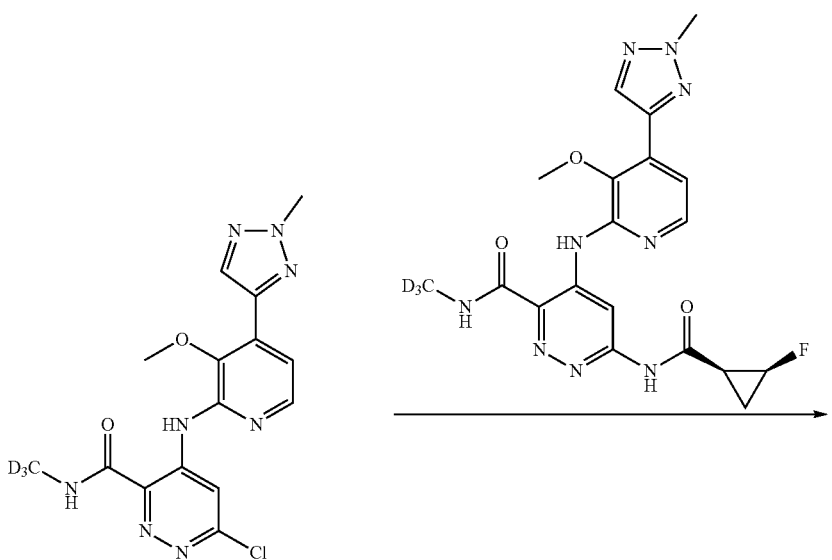

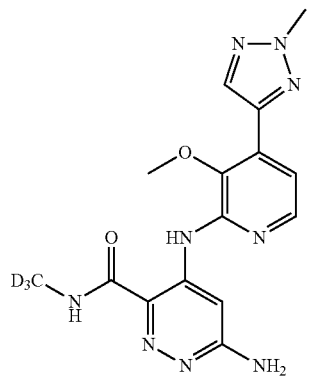

Step 1

A mixture of 6-chloro-4-((3-methoxy-4-(2-methyl-2H-1,2,3-triazol-4-yl)pyridin-2-yl)amino)-N-(methyl-d3) pyridazine-3-carboxamide (60 mg, 0.159 mmol), xantphos (18.38 mg, 0.032 mmol), and tert-butyl carbamate (74.4 mg, 0.635 mmol) in dioxane (1.3 mL) was degassed by bubbling nitrogen through it for 5 minutes. Then cesium carbonate (207 mg, 0.635 mmol) and Pd$_2$(dba)$_3$ (14.54 mg, 0.016 mmol) were added, the vessel was sealed, and the reaction was stirred at 130° C. for 2 h. The reaction was complete by LC-MS. The reaction mixture was directly purified using a small cartridge and silica gel column, eluting with 0-15% MeOH in DCM. Concentration of the pure fractions afforded 6-amino-4-((3-methoxy-4-(2-methyl-2H-1,2,3-triazol-4-yl)pyridin-2-yl)amino)-N-(methyl-d3)pyridazine-3-carboxamide (23 mg, 0.064 mmol, 40.4% yield). MS (M+1) m/z: 359.1 (M+H)$^+$. LC retention time 0.99 [C].

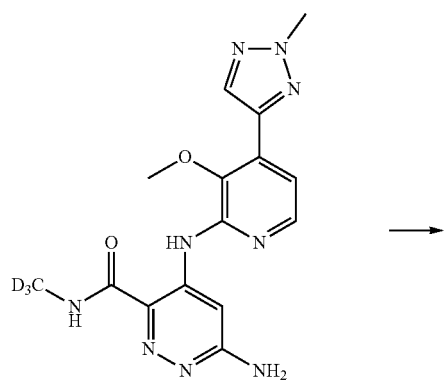

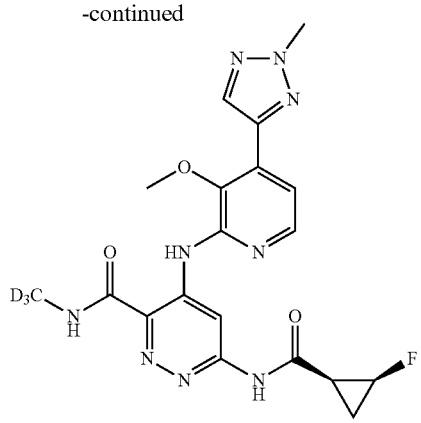

Step 2

A solution of (1S,2S)-2-fluorocyclopropane-1-carboxylic acid (8.02 mg, 0.077 mmol), and 1-propanephosphonic anhydride, in 50% DMF solution (123 mg, 0.193 mmol) in DMF (1 mL) and TEA (0.045 mL, 0.321 mmol) was added to 6-amino-4-((3-methoxy-4-(2-methyl-2H-1,2,3-triazol-4-yl)pyridin-2-yl)amino)-N-(methyl-d3)pyridazine-3-carboxamide (23 mg, 0.064 mmol) and the resulting mixture was stirred at 50° C. for 2 h. LC-MS indicated the reaction was complete. The mixture was diluted to 2 mL with DMF, filtered and purified by prep HPLC concentration of the pure fractions afforded 6-(((1S,2S)-2-fluorocyclopropane-1-carboxamido)-4-((3-methoxy-4-(2-methyl-2H-1,2,3-triazol-4-yl)pyridin-2-yl)amino)-N-(methyl-d3)pyridazine-3-carboxamide (4.6 mg, 15.47% yield) MS (M+1) m/z: 445.1 (M+H)$^+$. LC retention time 1.078 [C]. $^1$H NMR (500 MHz, DMSO-d6) δ 12.43 (s, 1H), 11.38 (s, 1H), 9.86 (s, 1H), 9.26 (s, 1H), 8.31 (s, 1H), 8.18 (d, J=5.2 Hz, 1H), 7.48 (d, J=5.5 Hz, 1H), 5.11-4.90 (m, 1H), 4.28 (s, 3H), 3.82 (s, 3H), 2.40-2.30 (m, 1H), 1.81-1.67 (m, 1H), 1.37-1.16 (m, 1H).

Example 38

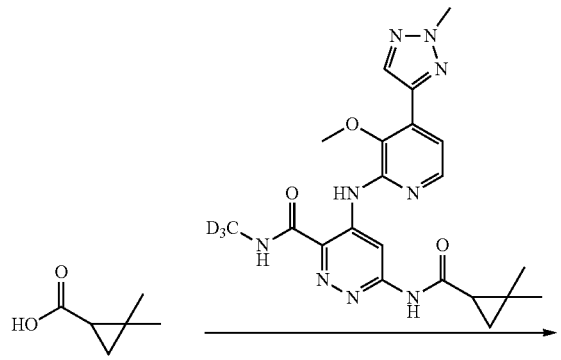

Step 1

To a solution of 2,2-dimethylcyclopropane-1-carboxylic acid (65 mg, 0.569 mmol) and oxalyl chloride (0.065 mL, 0.740 mmol) in DCM (5 mL) at rt was added 3 drops of DMF. Gas evolution was observed. The reaction mixture was stirred at rt for 45 minutes. The volatiles were removed in vacuo. The crude acid chloride was dissolved in DCM (5 mL) and was added slowly to a solution of ammonia, 0.5M in dioxane (7.12 mL, 2.85 mmol) and diisopropylethylamine (0.298 mL, 1.708 mmol). After stirring at rt for 1 hr, the reaction mixture was concentrated to a solid. Drying overnight afforded impure 2,2-dimethylcyclopropane-1-carboxamide (55 mg, 85% yield) as a white solid. Used as is in the next step.

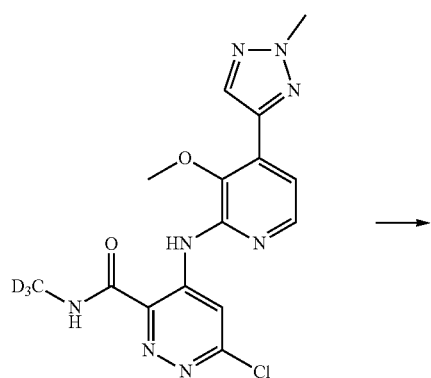

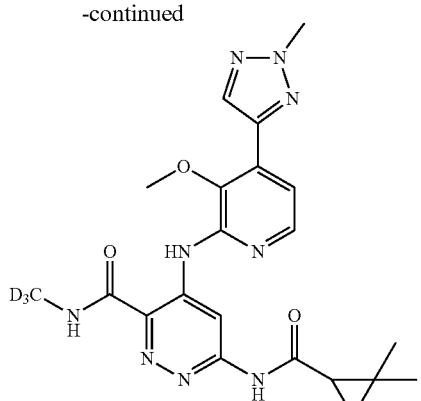

Step 2

A mixture of 6-chloro-4-((3-methoxy-4-(2-methyl-2H-1,2,3-triazol-4-yl)pyridin-2-yl)amino)-N-(methyl-d3) pyridazine-3-carboxamide (20 mg, 0.053 mmol), 2,2-dimethyl-cyclopropane-1-carboxamide (23.96 mg, 0.212 mmol), $Pd_2(dba)_3$, (5.47 mg, 5.29 μmol), xantphos (6.13 mg, 10.59 μmol) and cesium carbonate (69.0 mg, 0.212 mmol) in dioxane (1.0 mL) was degassed by bubbling nitrogen through the mixture for 5 minutes. The reaction vessel was sealed and heated to 130° C. for 90 minutes. The reaction mixture was diluted with DMF, filtered through a 0.45 micron nylon filter and the filtrate was purified by prep HPLC. Concentration of the pure fractions afforded 6-(2,2-dimethylcyclopropane-1-carboxamido)-4-((3-methoxy-4-(2-methyl-2H-1,2,3-triazol-4-yl)pyridin-2-yl)amino)-N-(methyl-d3)pyridazine-3-carboxamide (4.2 mg, 17.46% yield).

MS (M+1) m/z: 455.3 $(M+H)^+$. LC retention time 1.29 [C]. $^1$H NMR (500 MHz, DMSO-d6) δ 12.38 (s, 1H), 11.14 (s, 1H), 9.84 (s, 1H), 9.22 (s, 1H), 8.29 (s, 1H), 8.16 (d, J=5.2 Hz, 1H), 7.47 (d, J=5.2 Hz, 1H), 4.27 (s, 3H), 3.87-3.79 (m, 3H), 2.00 (br t, J=6.4 Hz, 1H), 1.17 (br d, J=10.7 Hz, 6H), 1.07 (br t, J=3.8 Hz, 1H), 0.87 (br dd, J=7.5, 3.5 Hz, 1H).

Example 39

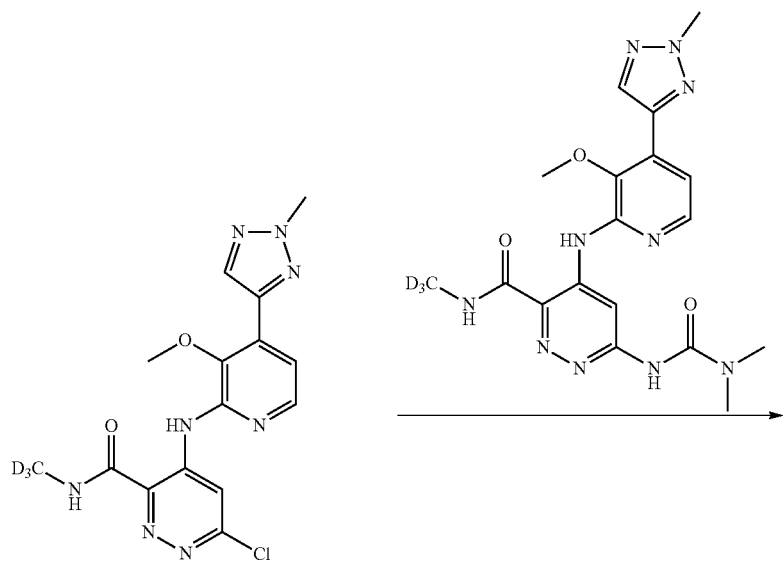

A mixture of 6-chloro-4-((3-methoxy-4-(2-methyl-2H-1,2,3-triazol-4-yl)pyridin-2-yl)amino)-N-(methyl-d3)pyridazine-3-carboxamide (20 mg, 0.053 mmol), 1,1-dimethylurea (23.32 mg, 0.265 mmol), Pd$_2$(dba)$_3$ (5.47 mg, 5.29 µmol), xantphos (6.13 mg, 10.59 µmol) and cesium carbonate (69.0 mg, 0.212 mmol) in dioxane (1.0 mL) was degassed by bubbling nitrogen through the mixture for 5 minutes. The reaction vessel was sealed and heated to 130° C. for 90 minutes. The reaction mixture was diluted with DMF. The mixture was filtered through a 0.45 micron nylon filter and the filtrate was purified by prep HPLC. Concentration of the pure fractions afforded 6-(3,3-dimethylureido)-4-((3-methoxy-4-(2-methyl-2H-1,2,3-triazol-4-yl)pyridin-2-yl)amino)-N-(methyl-d3)pyridazine-3-carboxamide (4 mg, 16.98% yield) MS (M+1) m/z: 430.2 (M+H)$^+$. LC retention time 1.07 [C]. $^1$H NMR (500 MHz, DMSO-d6) δ 12.34 (br s, 1H), 9.49 (s, 1H), 9.14 (br s, 1H), 8.30 (br d, J=0.8 Hz, 1H), 8.15 (br d, J=5.2 Hz, 1H), 7.46 (br d, J=5.2 Hz, 1H), 4.27 (s, 3H), 3.81 (s, 3H), 3.50 (m, 1H), 3.00 (s, 6H).

Example 40

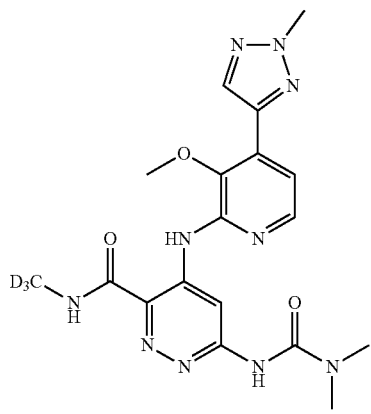

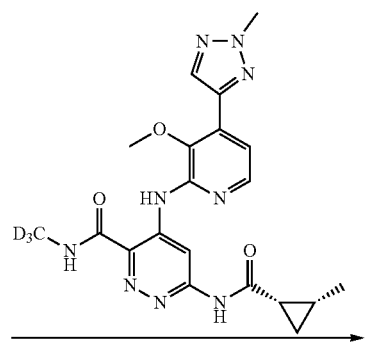

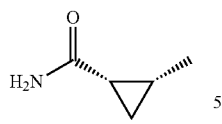

Step 1

To a solution of (1S,2R)-2-methylcyclopropane-1-carboxylic acid (82 mg, 0.819 mmol) in THF (2 mL) was added first TEA (0.171 mL, 1.229 mmol) and ethyl chloroformate (0.087 mL, 0.901 mmol). After stirring 1 hr, a white precipitate formed. This precipitate was filtered off and was subsequently suspended in 5 mL of THF. The suspension added ammonia in THF, 0.4M (10.24 mL, 4.10 mmol) and was stirred overnight at 25° C. The solvents were removed in vacuo to afford a white solid that was used as-is.

This method was utilized to prepare the carboxamides used in the preparation of each of the analogs listed below.

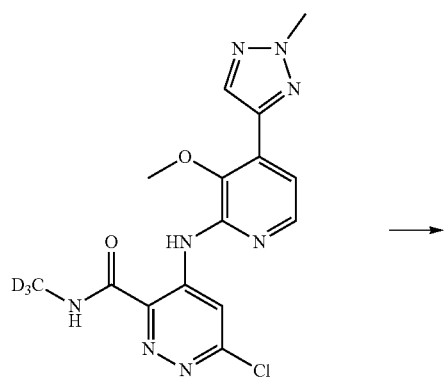

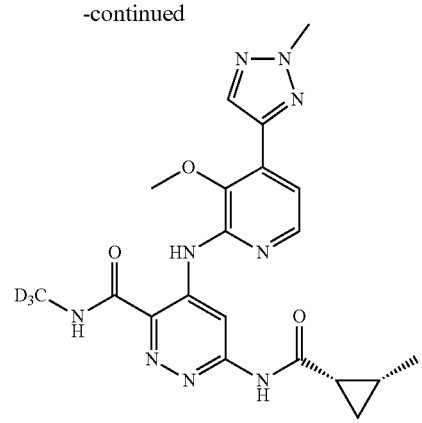

Step 2

A mixture of 6-chloro-4-((3-methoxy-4-(2-methyl-2H-1,2,3-triazol-4-yl)pyridin-2-yl)amino)-N-(methyl-d3) pyridazine-3-carboxamide (20 mg, 0.053 mmol), (1S,2R)-2-methylcyclopropane-1-carboxamide (20.99 mg, 0.212 mmol), Pd$_2$(dba)$_3$ (5.47 mg, 5.29 μmol), xantphos (6.13 mg, 10.59 μmol) and cesium carbonate (69.0 mg, 0.212 mmol) in dioxane (1.0 mL) was degassed by bubbling nitrogen through the mixture for 5 minutes. The reaction vessel was sealed and heated to 130° C. for 20 minutes. The reaction mixture was diluted with DMF. The mixture was filtered through a 0.45 micron nylon filter and the filtrate was purified by prep HPLC. Concentration of the pure fraction afforded 4-((3-methoxy-4-(2-methyl-2H-1,2,3-triazol-4-yl)pyridin-2-yl)amino)-N-(methyl-d3)-6-((1S,2R)-2-methylcyclopropane-1-carboxamido)pyridazine-3-carboxamide (3.1 mg, 13.29% yield). MS (M+1) m/z: 441.2 (M+H)$^+$. LC retention time 1.21 [C]. $^1$H NMR (500 MHz, DMSO-d6) δ 12.41 (s, 1H), 11.22 (s, 1H), 9.85 (s, 1H), 9.24 (s, 1H), 8.31 (s, 1H), 8.17 (br d, J=4.9 Hz, 1H), 7.48 (br d, J=4.9 Hz, 1H), 4.36-4.31 (m, 1H), 4.28 (s, 3H), 3.82 (s, 3H), 2.15 (br d, J=6.1 Hz, 1H), 1.39-1.29 (m, 1H), 1.15 (br d, J=5.8 Hz, 3H), 1.07-0.83 (m, 1H).

Example 41

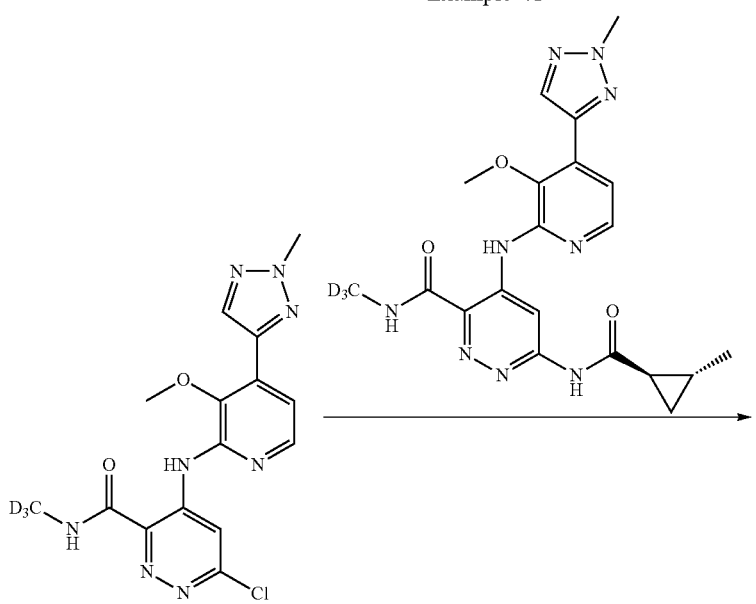

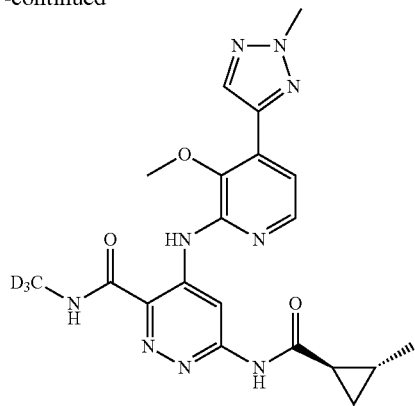

A mixture of 6-chloro-4-((3-methoxy-4-(2-methyl-2H-1,2,3-triazol-4-yl)pyridin-2-yl)amino)-N-(methyl-d3) pyridazine-3-carboxamide (20 mg, 0.053 mmol), (1R,2R)-2-methylcyclopropane-1-carboxamide (20.99 mg, 0.212 mmol), Pd$_2$(dba)$_3$ (5.47 mg, 5.29 μmol), xantphos (6.13 mg, 10.59 μmol) and cesium carbonate (69.0 mg, 0.212 mmol) in dioxane (1.0 mL) was degassed by bubbling nitrogen through the mixture for 5 minutes. The reaction vessel was sealed and heated to 130° C. for 90 minutes. The reaction mixture was diluted with DMF. The mixture was filtered through a 0.45 micron nylon filter and the filtrate was purified by prep HPLC. Concentration of the pure fractions afforded 4-((3-methoxy-4-(2-methyl-2H-1,2,3-triazol-4-yl) pyridin-2-yl)amino)-N-(methyl-d3)-6-((1R,2R)-2-methyl-cyclopropane-1-carboxamido)pyridazine-3-carboxamide (4.6 mg, 18.86% yield). MS (M+1) m/z: 441.2 (M+H)$^+$. LC retention time 1.25 [C]. $^1$H NMR (500 MHz, DMSO-d6) δ 12.35 (s, 1H), 11.21 (s, 1H), 9.81 (s, 1H), 9.19 (s, 1H), 8.28 (s, 1H), 8.14 (br d, J=5.5 Hz, 1H), 7.46 (br d, J=4.9 Hz, 1H), 4.25 (s, 3H), 3.84-3.77 (m, 1H), 3.62-3.54 (m, 3H), 1.84 (br dd, J=8.1, 4.4 Hz, 1H), 1.40-1.27 (m, 1H), 1.11 (br d, J=5.8 Hz, 3H), 0.74 (br s, 1H).

Example 42

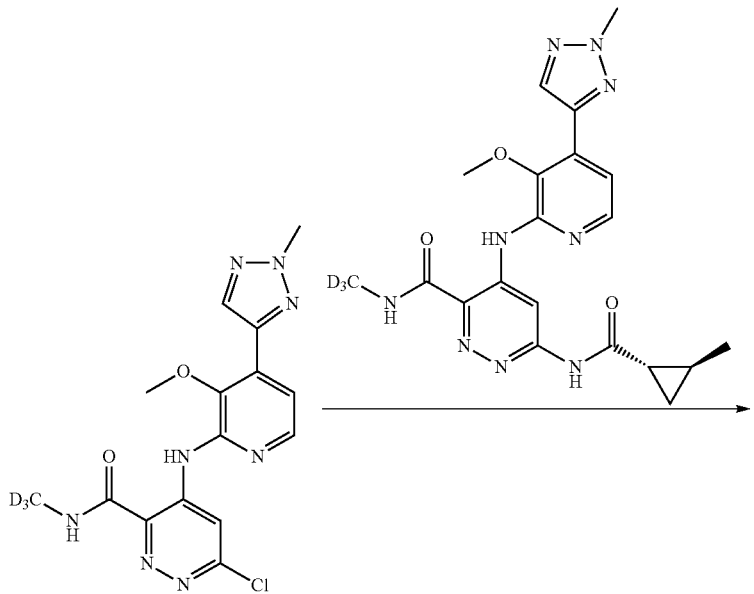

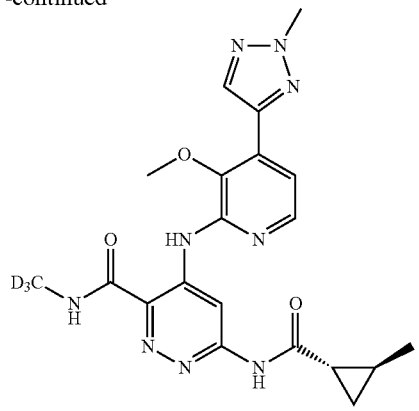

A mixture of 6-chloro-4-((3-methoxy-4-(2-methyl-2H-1,2,3-triazol-4-yl)pyridin-2-yl)amino)-N-(methyl-d3) pyridazine-3-carboxamide (50 mg, 0.132 mmol), (1S,2S)-2-methylcyclopropane-1-carboxamide (52.5 mg, 0.529 mmol), Pd$_2$(dba)$_3$ (13.67 mg, 0.013 mmol), xantphos (15.32 mg, 0.026 mmol) and cesium carbonate (172 mg, 0.529 mmol) in dioxane (1.0 mL) was degassed by bubbling nitrogen through the mixture for 5 minutes. The reaction vessel was sealed and heated to 130° C. for 30 minutes. The reaction mixture was diluted with DMSO. The mixture was filtered through a 0.45 micron nylon filter and the filtrate was purified by prep HPLC. Concentration of the pure fractions afforded 4-((3-methoxy-4-(2-methyl-2H-1,2,3-triazol-4-yl) pyridin-2-yl)amino)-N-(methyl-d3)-6-((1S,2S)-2-methylcyclopropane-1-carboxamido)pyridazine-3-carboxamide (6.7 mg, 10.92% yield) MS (M+1) m/z: 441.2 (M+H)$^+$. LC retention time 1.22 [C]. $^1$H NMR (500 MHz, DMSO-d6) δ 12.39 (s, 1H), 11.23 (s, 1H), 9.82 (s, 1H), 9.23 (s, 1H), 8.29 (s, 1H), 8.14 (d, J=5.3 Hz, 1H), 7.46 (d, J=5.3 Hz, 1H), 4.27 (s, 3H), 3.81 (s, 3H), 1.88 (dt, J=7.9, 4.2 Hz, 1H), 1.37-1.28 (m, 1H), 1.12 (d, J=6.0 Hz, 3H), 1.10 (br s, 1H), 0.73 (br dd, J=6.1, 4.3 Hz, 1H).

Example 43

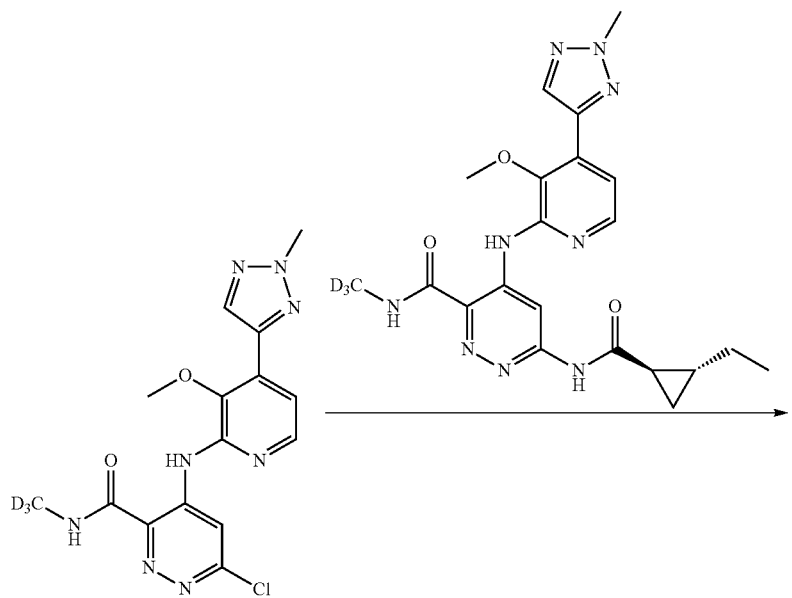

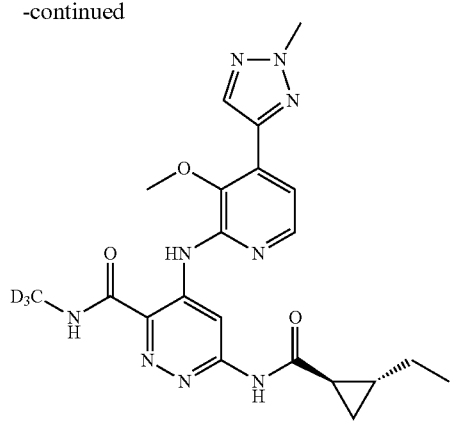

A mixture of 6-chloro-4-((3-methoxy-4-(2-methyl-2H-1,2,3-triazol-4-yl)pyridin-2-yl)amino)-N-(methyl-d3)pyridazine-3-carboxamide (50 mg, 0.132 mmol), (1R,2R)-2-ethylcyclopropane-1-carboxamide (59.9 mg, 0.529 mmol), Pd$_2$(dba)$_3$ (13.67 mg, 0.013 mmol), xantphos (15.32 mg, 0.026 mmol) and cesium carbonate (172 mg, 0.529 mmol) in dioxane (1.0 mL) was degassed by bubbling nitrogen through the mixture for 5 minutes. The reaction vessel was sealed and heated to 130° C. for 15 minutes. The reaction mixture was diluted with DMSO. The mixture was filtered through a 0.45 micron nylon filter and the filtrate was purified by prep HPLC. Concentration of the pure fractions afforded 6-((1R,2R)-2-ethylcyclopropane-1-carboxamido)-4-((3-methoxy-4-(2-methyl-2H-1,2,3-triazol-4-yl)pyridin-2-yl)amino)-N-(methyl-d3)pyridazine-3-carboxamide (14.2 mg, 0.031 mmol, 23.61% yield). MS (M+1) m/z: 455.3 (M+H)$^+$. LC retention time 1.33 [C]. $^1$H NMR (500 MHz, DMSO-d6) δ 12.40 (s, 1H), 11.25 (s, 1H), 9.84 (s, 1H), 9.24 (s, 1H), 8.30 (s, 1H), 8.15 (d, J=5.3 Hz, 1H), 7.47 (d, J=5.3 Hz, 1H), 4.27 (s, 3H), 3.81 (s, 3H), 1.93 (dt, J=7.8, 3.7 Hz, 1H), 1.45-1.38 (m, 1H), 1.33-1.26 (m, 2H), 1.12-1.05 (m, 1H), 0.97 (t, J=7.1 Hz, 3H), 0.80-0.73 (m, 1H).

Example 44

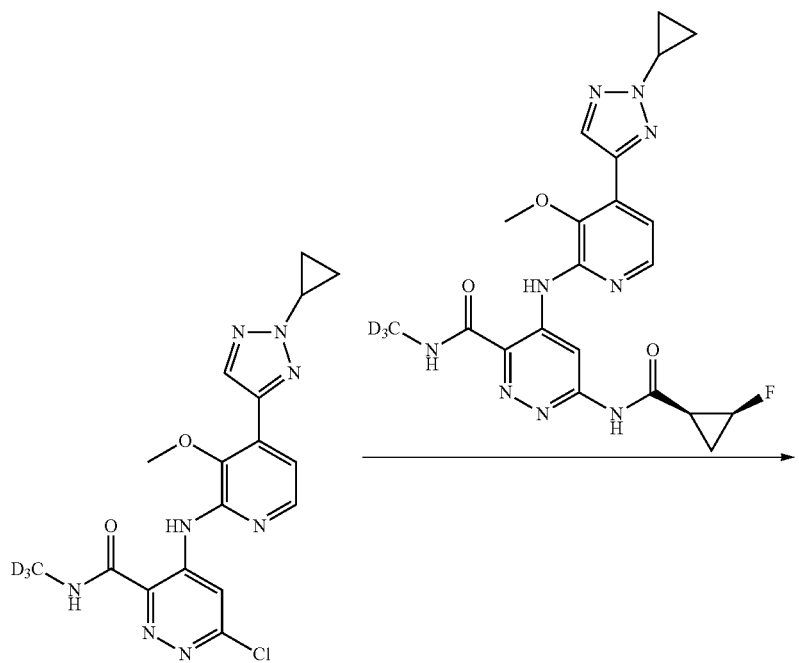

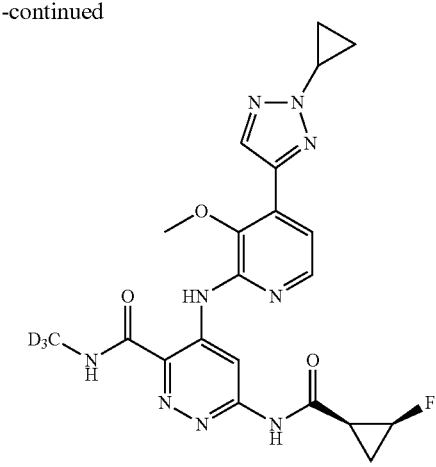

A mixture of 6-chloro-4-((4-(2-cyclopropyl-2H-1,2,3-triazol-4-yl)-3-methoxypyridin-2-yl)amino)-N-(methyl-d3)pyridazine-3-carboxamide (40 mg, 0.099 mmol), (1S,2S)-2-fluorocyclopropane-1-carboxamide (40.8 mg, 0.396 mmol), Pd$_2$(dba)$_3$ (10.23 mg, 9.90 μmol), xantphos (11.46 mg, 0.020 mmol) and cesium carbonate (129 mg, 0.396 mmol) in dioxane (1.0 mL) was degassed by bubbling nitrogen through the mixture for 5 minutes. The reaction vessel was sealed and heated to 130° C. for 20 minutes. The reaction mixture was diluted with DMSO. The mixture was filtered through a 0.45 micron nylon filter and the filtrate was purified by prep HPLC. Concentration of the pure fractions afforded 4-((4-(2-cyclopropyl-2H-1,2,3-triazol-4-yl)-3-methoxypyridin-2-yl)amino)-6-((1S,2S)-2-fluorocyclopropane-1-carboxamido)-N-(methyl-d3)pyridazine-3-carboxamide (8.2 mg, 0.016 mmol, 16.01% yield) MS (M+1) m/z: 471.2 (M+H)$^+$. LC retention time 1.31 [C]. $^1$H NMR (500 MHz, DMSO-d6) δ 12.43 (s, 1H), 11.38 (s, 1H), 9.87 (s, 1H), 9.25 (s, 1H), 8.30 (s, 1H), 8.17 (d, J=5.3 Hz, 1H), 7.48 (d, J=5.3 Hz, 1H), 5.10-4.89 (m, 1H), 4.26 (dt, J=7.4, 3.7 Hz, 1H), 3.81 (s, 3H), 2.39-2.29 (m, 1H), 1.78-1.67 (m, 1H), 1.33-1.28 (m, 2H), 1.27-1.21 (m, 1H), 1.17 (dd, J=7.4, 2.2 Hz, 2H).

Example 45

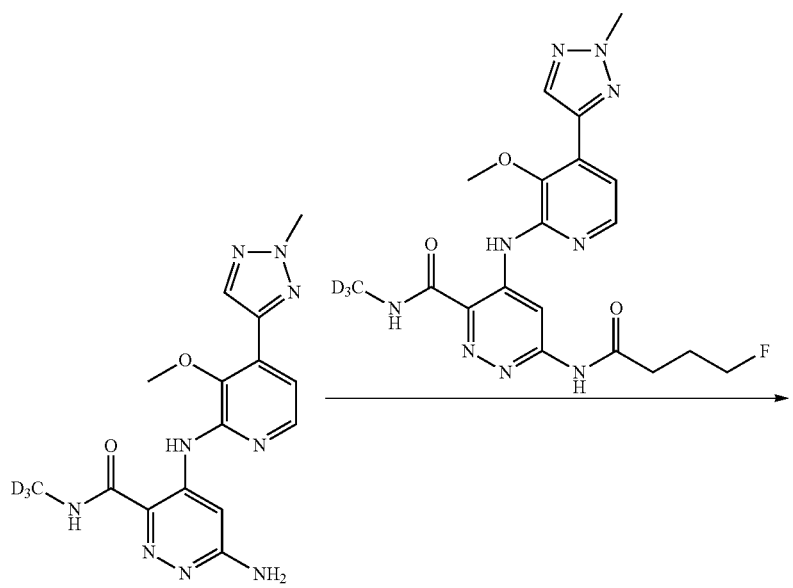

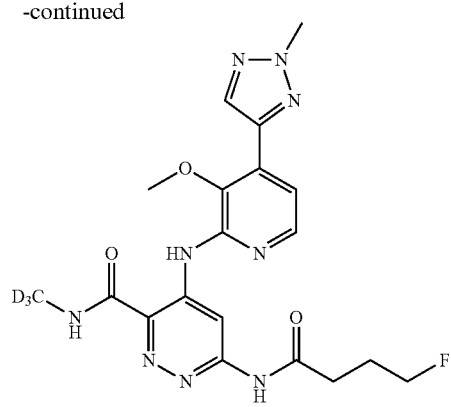

A solution of 4-fluorobutanoic acid (8.88 mg, 0.084 mmol), and 1-propanephosphonic anhydride, in 50% DMF solution (80 mg, 0.126 mmol) in DMF (0.5 mL) was stirred for 20 minutes and then was added to a mixture of 6-amino-4-((3-methoxy-4-(2-methyl-2H-1,2,3-triazol-4-yl)pyridin-2-yl)amino)-N-(methyl-d3)pyridazine-3-carboxamide (15 mg, 0.042 mmol) and DIEA (0.037 mL, 0.209 mmol) in 0.5 mL DMF. The resulting mixture was stirred at 50° C. overnight. The reaction was incomplete. A solution of 10 mg 4-fluorobutanoic acid and 200 uL 50% 1-propanephosphonic anhydride in DMF was prepared, stirred 20 minutes, then added to the reaction solution and stirring was continued at 50° C. for another night. After stirring a second night, LC-MS indicated that the reaction was complete. The reaction mixture was diluted to 2 mL with DMF, filtered and purified by prep HPLC. Concentration of the pure fractions afforded 6-((1S,2S)-2-fluorocyclopropane-1-carboxamido)-4-((3-methoxy-4-(2-methyl-2H-1,2,3-triazol-4-yl)pyridin-2-yl)amino)-N-(methyl-d3)pyridazine-3-carboxamide (2.9 mg, 6.50 μmol, 15.52% yield) MS (M+1) m/z: 447.2 (M+H)+. LC retention time 1.08 [C]. $^1$H NMR (500 MHz, DMSO-d6) δ 12.38 (s, 1H), 11.04 (s, 1H), 9.87 (s, 1H), 9.21 (s, 1H), 8.29 (s, 1H), 8.17 (d, J=5.2 Hz, 1H), 7.48 (d, J=5.3 Hz, 1H), 4.55 (t, J=6.1 Hz, 1H), 4.45 (br t, J=5.9 Hz, 1H), 4.26 (s, 3H), 3.80 (s, 3H), 2.66-2.59 (m, 2H), 2.07-1.93 (m, 2H).

Example 46

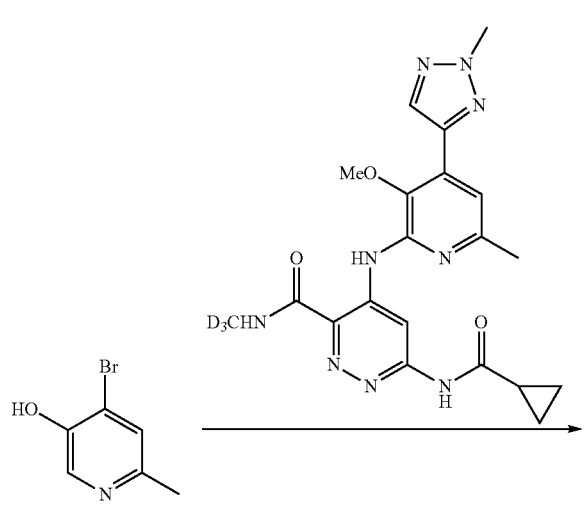

Step 1: 4-Bromo-6-methyl-2-nitropyridin-3-ol

Concentrated sulfuric acid (1 mL) was added dropwise to solid 4-bromo-6-methylpyridin-3-ol (0.267 g, 1.420 mmol) in a flask at −10° C. [in a salt and ice bath]. Subsequently, nitric acid, fuming (0.063 mL, 1.420 mmol) was added dropwise. The reaction mixture was stirred over night as the reaction slowly warmed to room temperature. The reaction mixture was poured onto ~50 gm of ice. After the ice melted, the mixture was transferred to a separatory funnel and was extracted with DCM (3×50 ml). The combined organic layers were dried over anhydrous sodium sulfate and concentrated to afford 4-bromo-6-methyl-2-nitropyridin-3-ol (165 mg, 0.708 mmol, 49.9% yield) as a yellow solid. $^1$H NMR (400 MHz, chloroform-d) δ 10.63 (s, 1H), 7.75 (s, 1H), 2.57 (s, 3H).

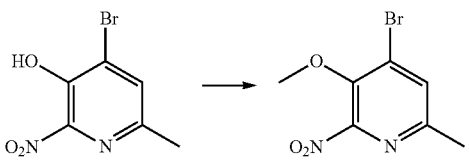

Step 2: 4-Bromo-3-methoxy-6-methy-2-nitropyridine

A mixture of 4-bromo-6-methyl-2-nitropyridin-3-ol (160 mg, 0.687 mmol), potassium carbonate (474 mg, 3.43 mmol) and MeI (0.215 mL, 3.43 mmol) in DMF was stirred at rt overnight. The reaction mixture was partitioned between EtOAc (30 ml) and water (30 ml). The organic layer was washed with 10% LiCl (2×30 ml) and brine (30 ml), dried over anhydrous sodium sulfate and concentrated to afford 4-bromo-3-methoxy-6-methyl-2-nitropyridine (133 mg, 0.538 mmol, 78% yield) as a brown solid. MS (M+1) m/z: 247.0 (249.0) (M+H)+. LC retention time 1.02 [E].

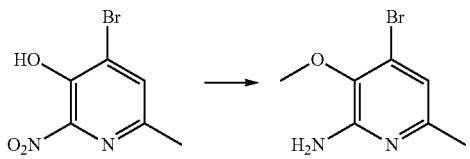

Step 3: 4-bromo-3-methoxy-6-methylpyridin-2-amine

To a solution of 4-bromo-3-methoxy-6-methyl-2-nitropyridine (133 mg, 0.538 mmol) in ethanol (0.6 mL), acetic acid (0.3 mL) and water (0.6 mL) stirring at 0° C. was added iron powder (210 mg, 3.77 mmol) and the resulting mixture was allowed to warm to rt and stir a total of 2 hr. The reaction mixture was filtered through Celite® and the filter cake was rinsed with EtOAc and water. The filtrate was transferred to a separatory funnel and 50 ml of 1.5M dibasic potassium phosphate were added. After shaking, the layers were separated and the organic layer was washed with brine (50 ml), dried over anhydrous sodium sulfate and concentrated to afford 4-bromo-3-methoxy-6-methylpyridin-2-amine (101 mg, 0.465 mmol, 86% yield) as a cream colored solid. MS (M+1) m/z: 217.0 (219.0) (M+H)$^+$. LC retention time 0.64 [E].

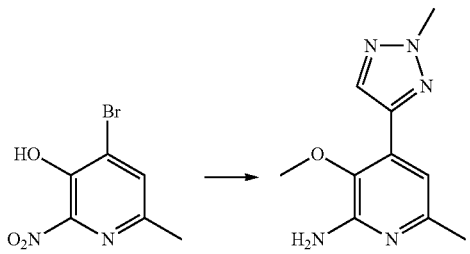

Step 4: 3-methoxy-6-methyl-4-(2-methyl-2H-1,2,3-triazol-4-yl)pyridin-2-amine A stirred mixture of (2-methyl-2H-1,2,3-triazol-4-yl)boronic acid (intermediate 19) (89 mg, 0.698 mmol), 4-bromo-3-methoxy-6-methylpyridin-2-amine (101 mg, 0.465 mmol) and PdCl$_2$(dppf)-CH$_2$Cl$_2$ adduct (19.00 mg, 0.023 mmol) in dioxane (3.5 mL) was degassed by bubbling nitrogen through the mixture for 5 minutes. 2M K$_3$PO$_4$ (aq) (0.698 mL, 1.396 mmol) was quickly added and the reaction mixture heated at 100° C. for 0.75 hr. After cooling to rt, the reaction mixture was partitioned between EtOAc (30 ml) and brine (20 ml). After drying over anhydrous sodium sulfate solution, the organic layer was concentrated and the residue was chromatographed on a 12 gm ISCO silica gel cartridge, eluting with a 0-100% EtOAc/Hex gradient. The pure fractions were concentrated to afford 3-methoxy-6-methyl-4-(2-methyl-2H-1,2,3-triazol-4-yl)pyridin-2-amine (75 mg, 0.342 mmol, 73.5% yield) as a an light yellow solid. MS (M+1) m/z: 220.2 (M+H)$^+$. LC retention time 0.68 [E].

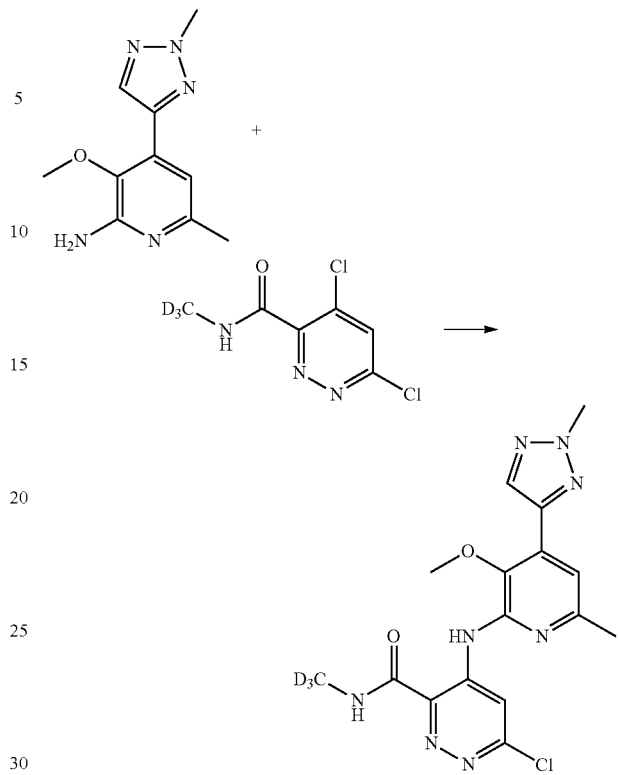

Step 5: 6-chloro-4-((3-methoxy-6-methyl-4-(2-methyl-2H-1,2,3-triazol-4-yl)pyridin-2-yl)amino)-N-(methyl-d3)pyridazine-3-carboxamide To a solution of 3-methoxy-6-methyl-4-(2-methyl-2H-1,2,3-triazol-4-yl)pyridin-2-amine (75 mg, 0.342 mmol) and 4,6-dichloro-N-(methyl-d3)pyridazine-3-carboxamide (143 mg, 0.684 mmol) in THF (3 mL) at rt was added, dropwise over 10 minutes, KHMDS, 1M in THF (1.539 mL, 1.539 mmol). The reaction mixture was allowed to stir at rt for 30 minutes. After quenching with 2 ml of saturated ammonium chloride solution, the organics were removed on the rotovap and the residue was diluted with water. Filtration, rinsing the filter cake with ethyl ether and drying afforded 6-chloro-4-((3-methoxy-6-methyl-4-(2-methyl-2H-1,2,3-triazol-4-yl)pyridin-2-yl)amino)-N-(methyl-d3)pyridazine-3-carboxamide (40 mg, 0.102 mmol, 29.8% yield) as a tan solid. MS (M+1) m/z: 392.2 (M+H)$^+$. LC retention time 1.13 [E].

Example 46: 6-(cyclopropanecarboxamido)-4-((3-methoxy-6-methyl-4-(2-methyl-2H-1,2,3-triazol-4-yl)pyridin-2-yl)amino)-N-(methyl-d3)pyridazine-3-carboxamide A mixture of 6-chloro-4-((2-methoxy-5-(methoxymethyl)-3-(2-methyl-2H-1,2,3-triazol-4-yl)phenyl)amino)-N-(methyl-d3)pyridazine-3-carboxamide (25 mg, 0.059 mmol), cyclopropanecarboxamide (25.3 mg, 0.297 mmol), Pd$_2$(dba)$_3$, Chloroform adduct (6.14 mg, 5.94 µmol), xantphos (6.87 mg, 0.012 mmol) and Cs$_2$CO$_3$ (77 mg, 0.238 mmol) in Dioxane (0.5 mL) was degassed by bubbling N2 through the mixture for 5 minutes. The reaction vessel was sealed and heated to 130° C. for 30 minutes. The reaction mixture was diluted with DMSO and filtered. The filtrate was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 15% B, 15-55% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to afford 6-(cyclopropanecarboxamido)-4-((3-methoxy-6-methyl-4-(2-methyl-2H-1,2,3-triazol-4-yl)pyridin-2-yl)amino)-N-(methyl-d3)pyridazine-3-carboxamide (18.3 mg; 40.7% yield). MS (M+1) m/z: 441.2 (M+H)$^+$. LC retention time 1.77 [G]. $^1$H NMR (500 MHz, DMSO-d6) δ 12.33 (s, 1H), 11.31 (s, 1H), 10.10 (s, 1H), 9.24 (s, 1H), 8.29 (s, 1H), 7.34 (s, 1H), 4.28 (s, 3H), 3.79 (s, 3H), 2.53 (br s, 3H), 2.22-1.96 (m, 1H), 1.19-0.84 (m, 4H).

The following examples were prepared using the same methods as example 46.

Example 47

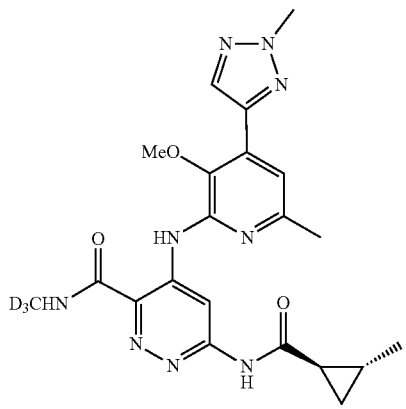

Example 47: 4-((3-methoxy-6-methyl-4-(2-methyl-2H-1,2,3-triazol-4-yl)pyridin-2-yl)amino)-N-(methyl-d3)-6-((1R,2R)-2-methylcyclopropane-1-carboxamido)pyridazine-3-carboxamide. MS (M+1) m/z: 455.3 (M+H)$^+$. LC retention time 1.69 [I]. $^1$H NMR (400 MHz, DMSO-d6) δ 12.31 (s, 1H), 11.21 (s, 1H), 10.07 (s, 1H), 9.23 (s, 1H), 8.27 (s, 1H), 7.32 (s, 1H), 4.26 (s, 3H), 3.77 (s, 3H), 2.47 (s, 3H), 1.90 (dt, J=8.0, 4.2 Hz, 1H), 1.38-1.25 (m, 1H), 1.19-1.04 (m, 4H), 0.72 (ddd, J=7.8, 6.2, 3.7 Hz, 1H).

Example 48

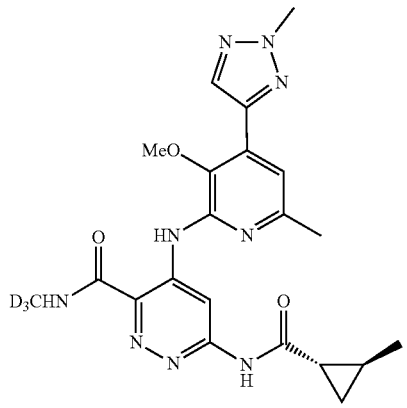

Example 48: 4-((3-methoxy-6-methyl-4-(2-methyl-2H-1,2,3-triazol-4-yl)pyridin-2-yl)amino)-N-(methyl-d3)-6-((1S,2S)-2-methylcyclopropane-1-carboxamido)pyridazine-3-carboxamide. MS (M+1) m/z: 455.3 (M+H)$^+$. LC retention time 1.69 [I]. $^1$H NMR (400 MHz, DMSO-d6) δ 12.31 (s, 1H), 11.21 (s, 1H), 10.07 (s, 1H), 9.23 (s, 1H), 8.27 (s, 1H), 7.32 (s, 1H), 4.26 (s, 3H), 3.77 (s, 3H), 2.48 (s, 3H), 1.95-1.86 (m, 1H), 1.40-1.25 (m, 1H), 1.18-1.05 (m, 4H), 0.77-0.68 (m, 1H).

Example 49

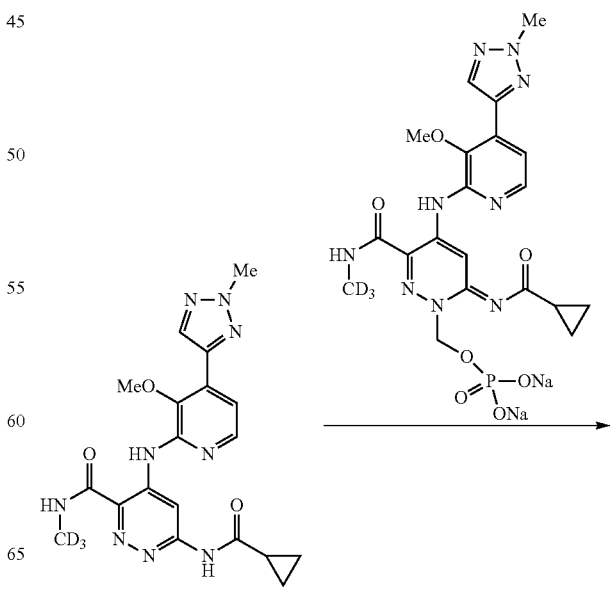

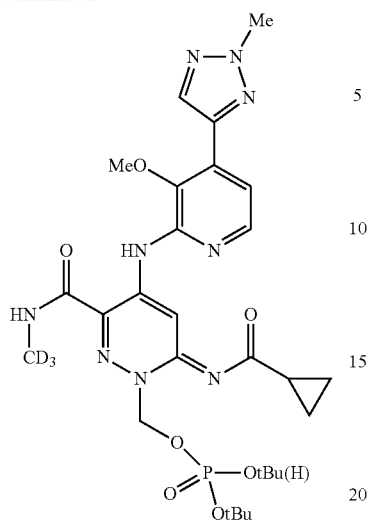

Step 1: (E)-di-tert-butyl (((6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl) phosphate To a suspension of 6-(cyclopropanecarboxamido)-4-((3-methoxy-4-(2-methyl-2H-1,2,3-triazol-4-yl)pyridin-2-yl)amino)-N-(methyl-d3)pyridazine-3-carboxamide (550 mg, 1.290 mmol) in DMF (7 mL) was added Cs$_2$CO$_3$ (2521 mg, 7.74 mmol) in one portion. After the reaction mixture was stirred at room temperature for 20 minutes, di-tert-butyl (chloromethyl) phosphate (1668 mg, 6.45 mmol) was added and stirring was continued at room temperature for 24 hr. The reaction mixture was poured into ice cold water (100 mL) and extracted with EtOAc (2×100 mL). The combined organic layers were washed with saturated brine solution (100 mL), dried over anhydrous sodium sulfate, filtered and concentrated under reduced pressure to afford the crude product which was used as a mixture in the next step.

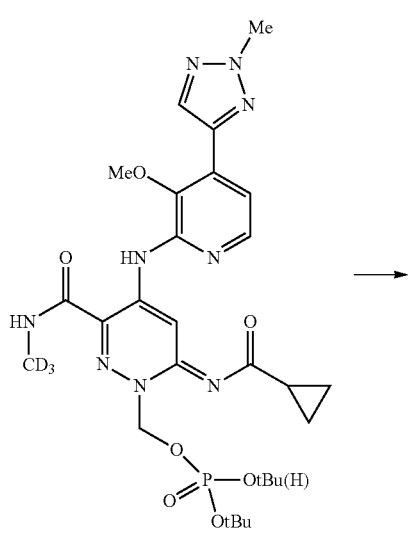

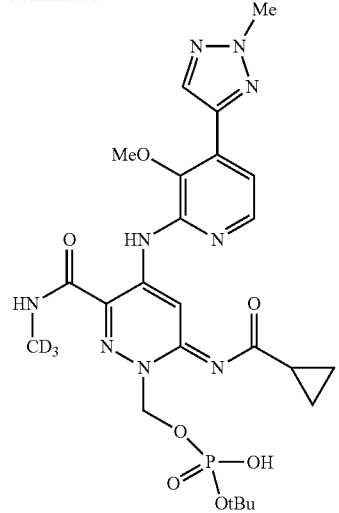

Step 2: (E)-tert-butyl (((6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl) hydrogen phosphate A solution of (E)-di-tert-butyl (((6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl) phosphate (2.1 g, 3.24 mmol) in 32 ml of acetone and 8 ml of AcOH was stirred at 30° C. for 16 hr and then 40° C. for 2 hr. The reaction mixture was cooled and diluted with ice water (100 ml) to which was added NaHCO$_3$ until the pH was adjusted to between 5 and 6. The resulting mixture was transferred to a separatory funnel and was extracted with EtOAc (4×80 ml). The combined org layers were washed with half sat. NaCl (100 ml), dried over anhydrous sodium sulfate and concentrated to afford a residue that was purified using an isco column (40 g, solid load, MeOH/DCM=0-10%, gradient time=20 min, flow rate=40 ml/min). Concentration of the pure fractions afforded (E)-tert-butyl (((6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl) hydrogen phosphate (1.15 g; 50.2% yield over 2 steps). MS (M+1) m/z: 593.2 (M+H)$^+$. LC retention time 0.79 min [H].

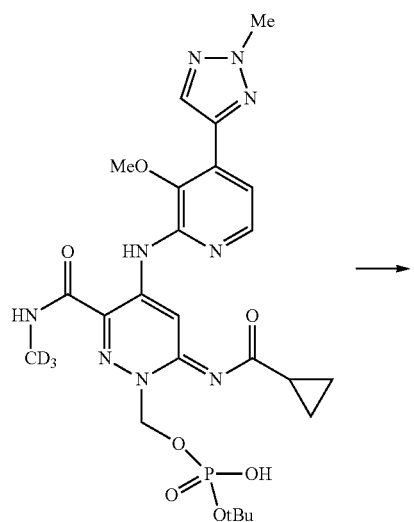

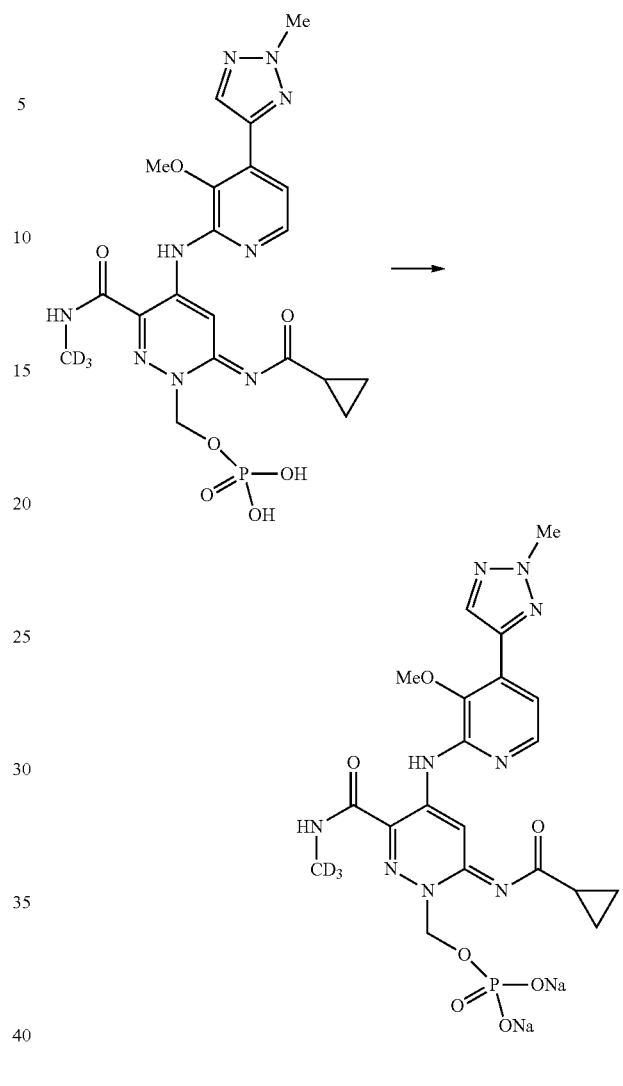

Example 48: (E)-(6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl dihydrogen phosphate, disodium salt

Step 3: (E)-(6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl dihydrogen phosphate A solution of (E)-tert-butyl ((6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl) hydrogen phosphate (0.88 g, 1.485 mmol) in 5.6 ml of AcOH and 5.6 ml of water was stirred at 45° C. for 5 hr. LC-MS indicated that the reaction was complete. The reaction mixture was cooled to room temperature, allowed to stand for 1 h and filtered. The solid was washed with water (3×), and vacuum dried to afford (E)-(6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl dihydrogen phosphate (680 mg; 85% yield). MS (M+1) m/z: 537.1 (M+H)$^+$. LC retention time 0.71 min [H].

To a solution of (E)-(6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl dihydrogen phosphate (680 mg, 1.268 mmol) in de-ionized water (7 ml) and acetonitrile (2 ml) was added NaOH (1N, 2535 μl, 2.54 mmol) dropwise with stirring at rt. After stirring for 10 minutes, the clear slight yellow solution was filtered through an acrodisc (0.45 um) filter with a syringe. The solution thus obtained was lyophilized overnight to afford (E)-(6-(((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl dihydrogen phosphate, disodium salt (735 mg; 100% yield) as a yellow solid.

MS (M+1) m/z: 537.1 (M+H)$^+$. LC retention time 0.71 min [H]. $^1$H NMR (400 MHz, deuterium oxide) δ 9.26 (br s, 1H), 8.25 (s, 1H), 8.11 (d, J=5.3 Hz, 1H), 7.41 (d, J=5.3 Hz, 1H), 5.89 (d, J=8.3 Hz, 2H), 4.28 (s, 3H), 3.77 (s, 3H), 2.07-1.74 (m, 1H), 1.16-0.91 (m, 4H).

Intermediate-22

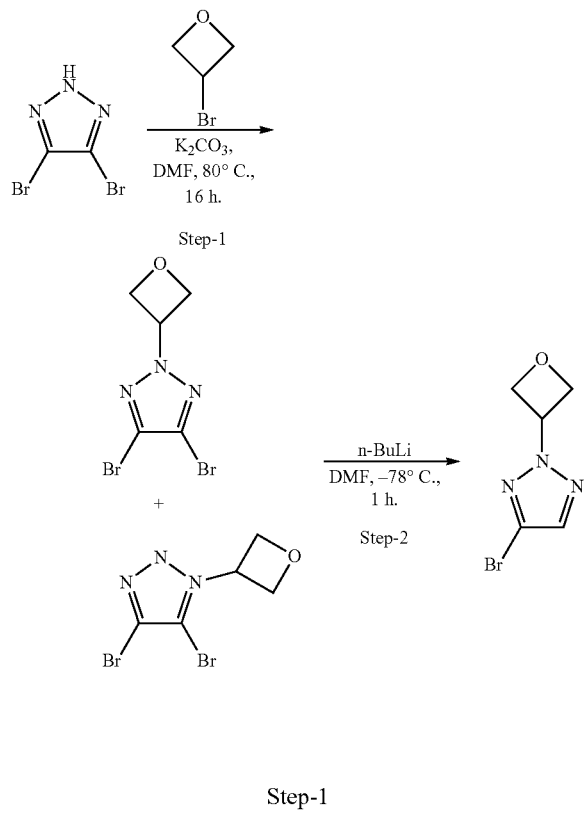

Step-1

To the solution of 4,5-dibromo-2H-1,2,3-triazole (0.5 g, 2.204 mmol) in DMF (3 mL) was added $K_2CO_3$ (1.217 g, 8.82 mmol) and 3-bromooxetane (0.302 g, 2.204 mmol). The reaction mixture was stirred at 80° C. for 16 h in the sealed tube. The reaction mixture was cooled to room temperature and extracted with EtOAc (2×50 mL). Organic layer was dried over $Na_2SO_4$ and concentrated to obtain crude which was purified by flash column chromatography using 0 to 10% EtOAc in Petroleum Ether to get desired 4,5-dibromo-2-(oxetan-3-yl)-2H-1,2,3-triazole (0.40 g, 1.414 mmol, 64.1% yield) as an oil. GCMS-EI [M] m/z: 282.9 (M)$^+$; GC retention time 7.57 Min.

Step-2

To the solution of 4,5-dibromo-2-(oxetan-3-yl)-2H-1,2,3-triazole (0.35 g, 1.237 mmol) in THF (3 mL) at −78° C. was added n-BuLi (0.773 mL, 1.237 mmol) dropwise and continued to stir for 1 h. The reaction mixture was warmed to 0° C. and quenched with saturated $NH_4Cl$ (10 mL) and extracted with diethyl ether (2×50 mL). Organic layers were dried over $Na_2SO_4$ and concentrated under reduced pressure at room temperature to get crude 4-bromo-2-(oxetan-3-yl)-2H-1,2,3-triazole (0.235 g, 1.152 mmol, 93% yield) which was used as such without further purification. $^1$H-NMR (400 MHz, DMSO-d6): δ 7.66 (s, 1H), 5.80-5.71 (m, 1H), 5.21-5.01 (m, 4H).

The following intermediates (22a-22b) were prepared in a similar manner to the preparation of intermediate 22.

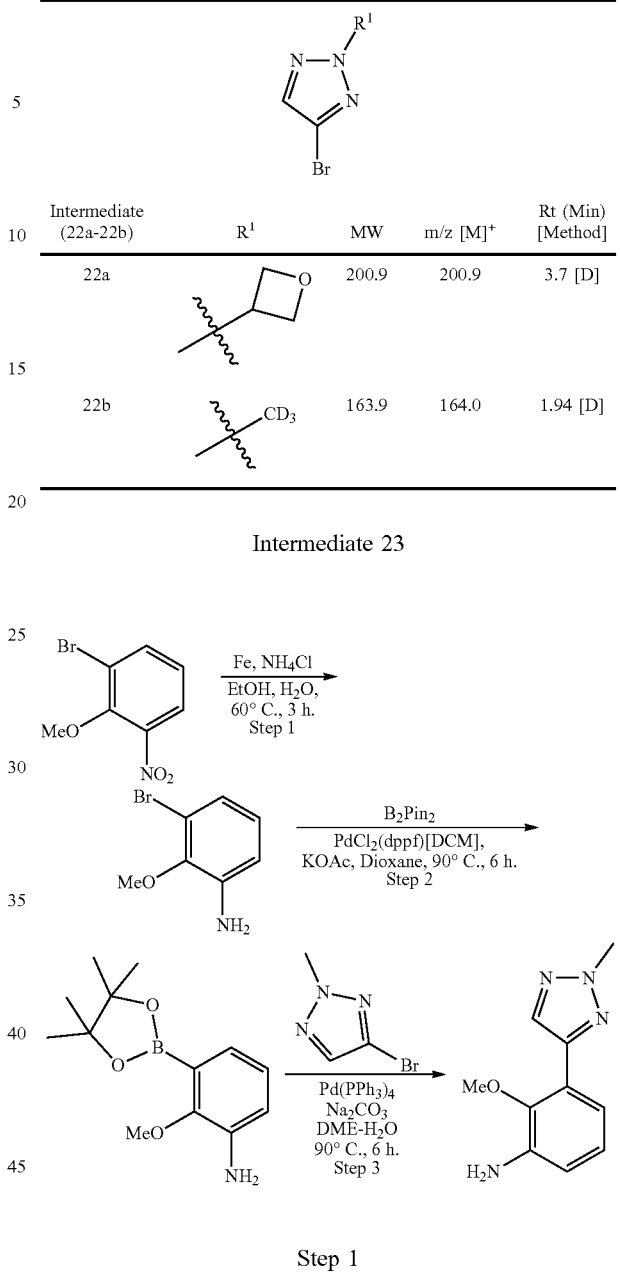

| Intermediate (22a-22b) | R$^1$ | MW | m/z [M]$^+$ | Rt (Min) [Method] |
|---|---|---|---|---|
| 22a | oxetan-3-yl | 200.9 | 200.9 | 3.7 [D] |
| 22b | CD$_3$ | 163.9 | 164.0 | 1.94 [D] |

Intermediate 23

Step 1

To a solution of 1-bromo-2-methoxy-3-nitrobenzene (2.0 g, 8.62 mmol) in Ethanol (20 mL) and water (5 mL) was added Iron powder (3.37 g, 60.3 mmol) and ammonium chloride (2.3 g, 43.3 mmol). The reaction was stirred at 60° C. for 3 h, diluted with ethanol (50 mL) and filtered through celite pad. The filtrate was concentrated under reduced pressure to afford crude product. The crude residue was diluted with EtOAc (100 mL) and washed with water (2×20 mL) and brine (2×20 mL). Combined organic layer was dried over anhydrous $Na_2SO_4$ and concentrated under reduced pressure to afford 3-bromo-2-methoxyaniline (1.8 g, 8.55 mmol, 99% yield) as a brown liquid. MS (M+1) m/z: 202.0 (M+H)$^+$. LC retention time 1.84 Min [Method A].

Step 2

To a stirred solution of 3-bromo-2-methoxyaniline (1.80 g, 8.91 mmol) in 1,4-dioxane (15 mL) in a sealed tube was added bis(pinacolato)diborone (3.39 g, 13.36 mmol) and KOAc (2.62 g, 26.7 mmol). The reaction was purged with N$_2$ gas for 5 min and then added PdCl$_2$(dppf).[DCM] (0.73 g, 0.89 mmol). The reaction mixture was stirred at 90° C. for 5 h, then cooled to rt and diluted with EtOAc (100 mL). Reaction mixture was filtered through celite pad and the filtrate was washed with water (2×50 mL) and brine (2×50 mL). Collected organic extract was dried over Na$_2$SO$_4$ and concentrated under reduced pressure to afford crude product which was purified by silica gel column chromatography (25% EtOAc in petroleum ether) to afford 2-methoxy-3-(4,4,5,5-tetramethyl-1,3,2-dioxaborolan-2-yl) aniline (1.8 g, 6.88 mmol, 77% yield) as a pale brown solid. MS (M+1) m/z: 250.4 (M+H)$^+$. LC retention time 2.11 Min [Method A].

Step 3

To a stirred solution of 2-methoxy-3-(4,4,5,5-tetramethyl-1,3,2-dioxaborolan-2-yl) aniline (2.31 g, 9.26 mmol) and 4-bromo-2-methyl-2H-1,2,3-triazole (1.50 g, 9.26 mmol) in DME (15 mL) and water (5 mL) was added Na$_2$CO$_3$ (2.45 mg, 23.15 mmol). The reaction mixture was purged with N$_2$ for 5 min and Pd(Ph$_3$P)$_4$ (1.07 g, 0.93 mmol) was added under N$_2$. The reaction mixture was stirred at 90° C. for 6 h. Filtered the reaction mixture through celite pad and washed with methanol (50 mL). Filtrate was then concentrated under reduced pressure. The crude residue was partitioned between ethyl acetate (150 mL) and water (150 mL). Collected organic layer was dried over anhydrous Na$_2$SO$_4$ and concentrated. The crude residue was purified by silica gel column chromatography (50% EtOAc in petroleum ether) to obtain desired 2-methoxy-3-(2-methyl-2H-1,2,3-triazol-4-yl) aniline (1.70 g, 7.67 mmol, 83% yield) as brown crystalline solid. MS (M+1) m/z: 205.2 (M+H)$^+$. LC retention time 1.20 Min [Method A].

The following intermediates (23a-23c) were prepared in a similar manner to the preparation of intermediate 23.

| Intermediate (23a-23c) | R$^1$ | MW | m/z [M + H]$^+$ | Rt (Min) [Method] |
|---|---|---|---|---|
| 23a | 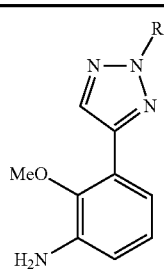 | 246.2 | 247.1 | 1.22 [A] |
| 23b | | 244.3 | 245.2 | 2.10 [A] |
| 23c | ⟶CD$_3$ | 207.2 | 207.8 | 1.22 [B] |

Intermediate-24

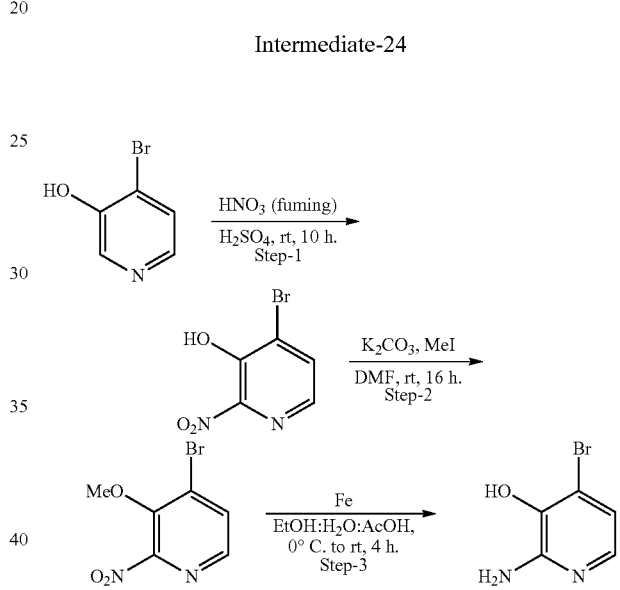

Step-1

To a −10° C. cooled 250 mL three neck round bottom flask was added 4-bromopyridin-3-ol (1.70 g, 9.77 mmol). Concentrated sulfuric acid (5 mL) was added dropwise over 10 min at −10° C. with slow stirring under N$_2$ atmosphere. The mixture was continued to stir at same temperature for 10 min, 4-bromopyridin-3-ol completely dissolves to form a clear solution. Nitric acid (fuming, 437 µL, 9.77 mmol) was added dropwise over 10 min at −10° C. The resulting mixture was allowed to attain room temperature gradually (~1.5 h) and stirred for 10 h. The reaction mixture was poured carefully into a crushed ice (~150 g). After complete quenching, the reaction mixture was extracted with CH$_2$Cl$_2$ (3×50 mL). The resulting organic layer was washed with saturated brine solution (30 mL), dried over anhydrous Na$_2$SO$_4$, filtered and concentrated under reduced pressure to give 4-bromo-2-nitropyridin-3-ol (1.01 g as crude), which was used for next step without further purification. GCMS (M) m/z: 218.0 [M]$^+$. GC retention time 7.36 Min. $^1$H-NMR (400 MHz, MeOH-d4): δ 8.00 (d, J=4.8 Hz, 1H), 7.94 (d, J=4.8 Hz, 1H).

Step-1

To a stirred solution of 4-bromo-2-methyl-2H-1,2,3-triazole (5.0 g, 30.9 mmol) in THF (50 mL) was slowly added isopropyl magnesium chloride Lithium chloride complex (3.17 g, 30.9 mmol) at 0° C. The reaction was stirred for 2 h at this temperature and then further cooled to −20° C. To this solution was then added trimethyl borate (0.64 mL, 5.7 mmol) slowly. The reaction was stirred at −20° C. for 1 h and then the reaction mixture was acidified with aqueous 1N HCl until pH~5. The resultant mixture was stirred for 10 min at 0° C. The reaction mixture was partitioned between EtOAc (50 mL) and water (50 mL). Organic layer was collected and aqueous layer was extracted again with EtOAc (2×100 mL) and the combined organic layers were washed with brine solution (50 mL) and then dried over anhydrous $Na_2SO_4$. Organic solvent was removed under reduced pressure to obtain the crude product. The resultant crude product was washed with 20 mL of n-Pentane to obtain the desired (2-methyl-2H-1,2,3-triazol-4-yl)boronic acid (2.6 g, 66.3% yield) as white solid. MS (M+1) m/z: 128.0 [M+H]$^+$. LC retention time 0.66 Min [Method B]. $^1$H-NMR (400 MHz, DMSO-d6): δ 8.34 (s, 2H), 7.89 (s, 1H), 4.12 (S, 3H).

Step-2

A 250 mL three neck round bottom flask with a stir bar was charged with 4-Bromo-2-nitropyridin-3-ol (6 g, 27.4 mmol) and DMF (100 mL). The reaction mixture was stirred at room temperature to form a clear solution (~5 min). $K_2CO_3$ (7.57 g, 54.8 mmol) was added to this solution portionwise and the mixture was stirred at room temperature for 10 min. Methyl iodide (3.43 mL, 54.8 mmol) was added dropwise over 5 min and the mixture was stirred at room temperature for 16 h. The reaction mixture was quenched with water (60 mL), extracted with EtOAc (3×100 mL). The combined organic layers was washed successively with ice cold water (2×100 mL) and saturated brine solution (100 mL). The resulting organic layer was dried over anhydrous $Na_2SO_4$, filtered and concentrated under reduced pressure to afford crude product. It was purified by silica column chromatography using 0-25% EtOAc in petroleum ether to afford 4-bromo-3-methoxy-2-nitropyridine as an off white solid (4.61 g, 71% yield). MS (M+1) m/z: 234.9 [M+H]$^+$. LC retention time 0.66 Min [Method B].
$^1$H-NMR (400 MHz, DMSO-d6): δ 8.25 (d, J=5.2 Hz, 1H), 8.20 (d, J=5.2 Hz, 1H), 3.97 (s, 3H).

Step-2

To the solution of 4-bromo-3-methoxypyridin-2-amine (0.3 g, 1.478 mmol) in 1,4-Dioxane (3 mL) and Water (0.5 ml) was added $Cs_2CO_3$ (0.963 g, 2.96 mmol), (2-methyl-2H-1,2,3-triazol-4-yl)boronic acid (0.281 g, 2.216 mmol) and purged under $N_2$ gas for 5 min, followed by addition of tetrakis(triphenylphosphine)palladium(0) (0.085 g, 0.074 mmol) then subjected to heating at 120° C. for 3 h in a sealed tube. The reaction mixture was cooled to room temperature, diluted with ethylacetate (25 mL), filtered through celite pad and washed with ethylacetate (25 mL). The filtrate was sequentially washed with water (25 mL) and saturated brine solution (20 mL), dried over anhydrous $Na_2SO_4$, filtered and concentrated under reduced pressure. The crude residue was purified by flash column chromatography by using 0 to 30% EtOAc in petroleum ether to get the desired product 3-methoxy-4-(2-methyl-2H-1,2,3-triazol-4-yl)pyridin-2-amine (0.22 g, 72.6% yield) as yellow solid. MS (M+1) m/z: 206.2 [M+1]$^+$. LC retention time 0.36 Min [Method A].

Step-3

A 250 mL three neck round bottom flask with a stir bar was charged with 4-Bromo-3-methoxy-2-nitropyridine (4.70 g, 21.5 mmol), AcOH (20 mL), EtOH (20 mL) and water (10 mL). The mixture was stirred at room temperature to form a clear solution (~5 min). The mixture was cooled to 0° C. Iron powder (12.0 g, 151 mmol) was added portion wise over 10 min at 0° C. The mixture was warmed to room temperature and stirred for 4 h. The mixture was filtered through celite pad, washed with EtOAc (100 mL). The filtrate was sequentially washed with saturated aqueous $NaHCO_3$ (100 mL) and saturated brine solution (50 mL), dried over anhydrous $Na_2SO_4$, filtered and concentrated under reduced pressure. The crude product was purified by silica column chromatography (230-400 mesh) using 0% to 60% EtOAc in petroleum ether to afford 4-bromo-3-methoxypyridin-2-amine (3.5 g, 80% yield) as an off white solid. MS (M+1) m/z: 205.0 [M+H]$^+$. LC retention time 0.66 Min [Method B].
$^1$H-NMR (400 MHz, DMSO-d6): δ 7.54 (d, J=5.2 Hz, 1H), 6.72 (d, J=5.2 Hz, 1H), 3.69 (s, 3H).

Intermediate-24

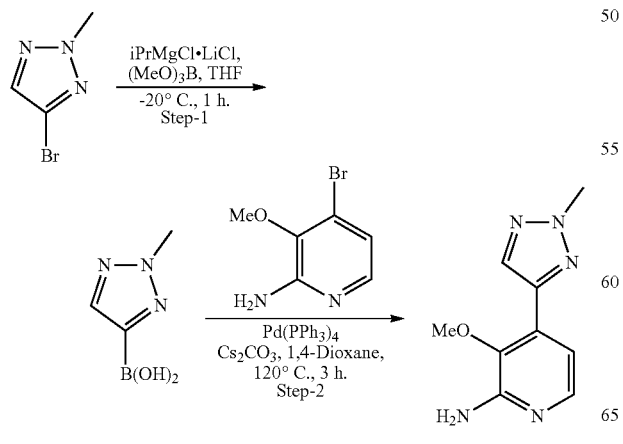

Intermediate 25

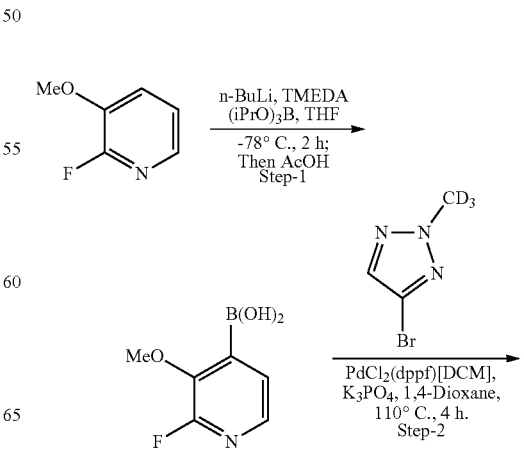

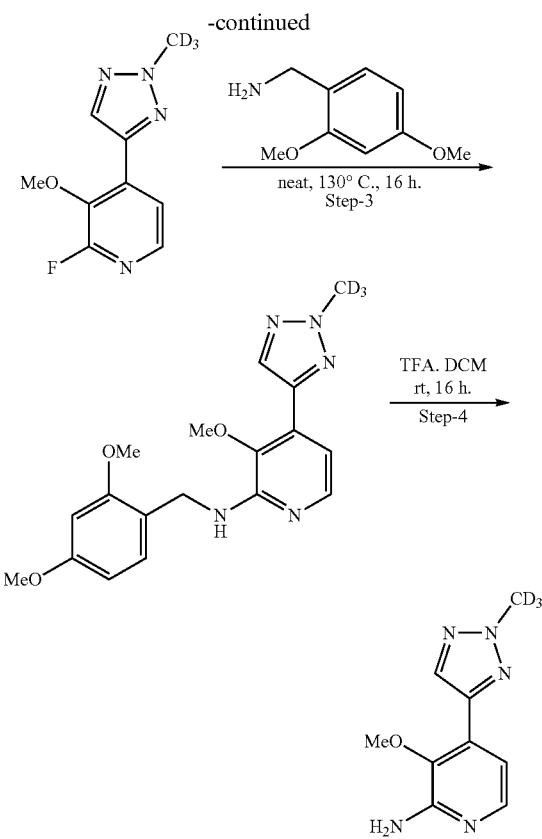

Step 1

To a stirred solution of 2-fluoro-3-methoxypyridine (5.0 g, 39.3 mmol) and TMEDA (11.87 mL, 79 mmol) in THF (50 mL) was added n-butyllithium (29.5 mL, 47.2 mmol) at −78° C. Then, it was stirred at same temperature for 2 h. Triisopropyl borate (13.70 mL, 59.0 mmol) was added to the reaction mixture at −78° C. and stirred for 2 h. The reaction mixture was quenched with water (20 mL), then it was extracted with diethyl ether (2×50 mL). The aqueous layer was acidified with AcOH (Ph~4) and extracted with ethyl acetate (2×100 mL). The combined organic layer was washed with brine (50 mL), dried over anhydrous $Na_2SO_4$ and concentrated. The desired product (2-fluoro-3-methoxy-pyridin-4-yl)boronic acid (6 g, 33.7 mmol, 86% yield) obtained as an off white solid. MS (M+1) m/z: 172.2 [M+1]$^+$. LC retention time 0.63 Min [Method J].

Step 2

To a stirred solution of (2-fluoro-3-methoxypyridin-4-yl) boronic acid (0.35 g, 2.048 mmol) and 4-bromo-2-(methyl-d3)-2H-1,2,3-triazole (0.399 g, 2.416 mmol) in 1,4-Di-oxane:water (8 mL: 2 mL) in a 40 mL sealed vessel were added $K_3PO_4$ (1.304 g, 6.14 mmol) and $PdCl_2$(dppf).[DCM] (0.167 g, 0.205 mmol) and the reaction mixture was degassed with $N_2$ for 10 min. The resultant reaction mixture was heated to 110° C. for 4 h. After 4 h, reaction mixture was diluted with ethyl acetate (100 mL), filtered through celite pad and washed with ethyl acetate (100 mL). Filtrate was washed with water (100 mL) followed by brine (100 mL) and dried over $Na_2SO_4$. Solvent was evaporated under reduced pressure and the resultant crude residue was purified by reverse phase column chromatography (c18 column, ammonium formate method) to give 2-fluoro-3-methoxy-4-(2-(methyl-d3)-2H-1,2,3-triazol-4-yl)pyridine (0.25 g, 1.095 mmol, 53.5% yield) as an off-white solid. MS (M+1) m/z: 212.0 [M+1]$^+$. LC retention time 1.50 Min [Method J].

Step 3

To a 2-fluoro-3-methoxy-4-(2-(methyl-d3)-2H-1,2,3-tri-azol-4-yl)pyridine (0.2 g, 0.947 mmol) in 8 mL pressure release vial was added (2,4-dimethoxyphenyl)methanamine (1.583 g, 9.47 mmol). The resultant reaction mixture was heated to 130° C. for 16 h. After 16 h, reaction mixture was diluted with ethyl acetate (30 mL) and washed with water (2×10 mL) followed by brine (20 mL) and dried over $Na_2SO_4$, filtered and concentrated under reduced pressure to get the crude residue. The obtained crude product was purified by silica gel column chromatography using 30-40% EtOAc in petroleum ether to give N-(2,4-dimethoxybenzyl)-3-methoxy-4-(2-(methyl-d3)-2H-1,2,3-triazol-4-yl)pyridin-2-amine (220 mg, 0.528 mmol, 55.8% yield) as an off-white solid. MS (M+1) m/z: 359.2 [M+1]$^+$. LC retention time 1.41 Min [Method J].

Step 4

To a stirred solution of N-(2,4-dimethoxybenzyl)-3-methoxy-4-(2-(methyl-d3)-2H-1,2,3-triazol-4-yl)pyridin-2-amine (0.22 g, 0.614 mmol) in a 20 mL DCM was added TFA (0.142 mL, 1.841 mmol) at 0° C. under nitrogen. The resultant reaction mixture was stirred at room temperature for 16 h. After completion of the reaction, solvent was evaporated under reduced pressure and the resultant crude was diluted with DCM (100 mL) and washed with saturated $NaHCO_3$ solution (50 mL) followed by brine (50 mL) and dried over $Na_2SO_4$, filtered and concentrated under reduced pressure to get crude. The obtained crude mixture was washed with n-pentane (25 mL) to afford 3-methoxy-4-(2-(methyl-d3)-2H-1,2,3-triazol-4-yl)pyridin-2-amine (100 mg, 0.437 mmol, 71.1% yield) as a pale brown solid. MS (M+1) m/z: 209.2 [M+1]$^+$. LC retention time 1.44 Min [Method B].

Intermediate-26

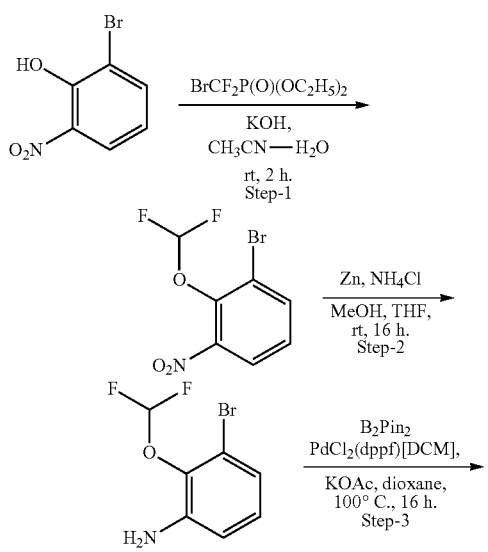

151

-continued

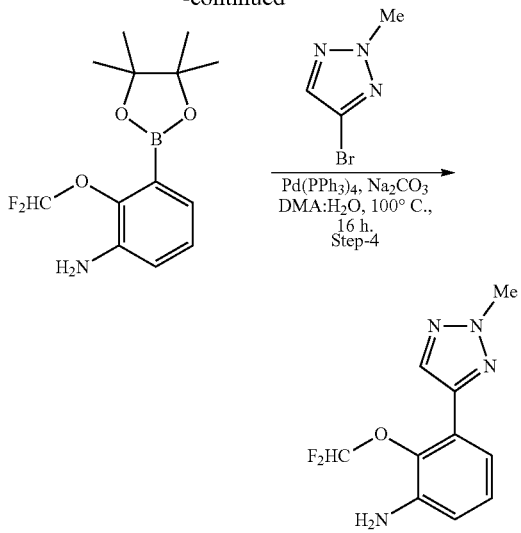

Step 1

To a stirred solution of 2-bromo-6-nitrophenol (1 g, 4.59 mmol) and KOH (3.86 g, 68.8 mmol) in acetonitrile (15 mL) and water (5 mL) were added diethyl(bromodifluoromethyl)phosphonate (1.47 g, 5.50 mmol) at 0° C. The reaction mixture was stirred at rt for 2 h. The reaction mixture was concentrated under reduced pressure. The crude product was partitioned between ethyl acetate (50 mL) and water (50 mL). Organic layer collected, dried over anhydrous $Na_2SO_4$ and concentrated. The crude product was purified by silica gel (230-400 mesh) column chromatography using 25% EtOAc in petroleum ether as eluent to obtain desired 1-bromo-2-(difluoromethoxy)-3-nitrobenzene (1.1 g, 3.86 mmol, 84% yield) as a brown solid. MS (M+1) m/z: 269.0 [M+1]$^+$; LC retention time: 2.58 Min [Method A].

$^1$H NMR (400 MHz, DMSO-d6) δ 8.16 (dd, J=1.6, 8.0 Hz, 1H), 8.11 (dd, J=1.4, 8.2 Hz, 1H), 7.55 (t, J=8.0 Hz, 1H), 7.26 (t, J=71.6 Hz, 1H).

Step 2

To a stirred solution of 1-bromo-2-(difluoromethoxy)-3-nitrobenzene (1.0 g, 3.73 mmol) in methanol (10 mL) and THF (5 mL) were added ammonium chloride (1.397 g, 26.1 mmol) and zinc powder (3.66 g, 56.0 mmol) at ambient temperature. Then, it was stirred at rt for 16 h. The reaction mixture was filtered through celite pad and washed with ethyl acetate (100 mL). The collected filtrate was concentrated under reduced pressure. The crude product was washed with hexane and dried to obtain 3-bromo-2-(difluoromethoxy) aniline (900 mg, 3.14 mmol, 84% yield) as a brown solid. MS (M+1) m/z: 239.9 [M+1]$^+$; LC retention time: 2.35 Min [Method A].

Step 3

To a stirred solution of 3-bromo-2-(difluoromethoxy) aniline (0.8 g, 3.36 mmol) in 1,4-dioxane (15 mL) were added bis(pinacolato)diboron (1.71 g, 6.72 mmol) and KOAc (0.82 g, 8.40 mmol) at ambient temperature. The reaction mixture was degassed for under $N_2$ 5 min. $PdCl_2$(dppf).[DCM] (549 mg, 0.672 mmol) was added to the reaction mixture and degassed for 5 minutes. The resultant reaction mixture was heated at 100° C. for 16 h in sealed tube. The reaction mixture was filtered through celite pad under reduced pressure and washed with ethyl acetate (100 mL). The crude was concentrated under reduced pressure and used as such without further purification. MS (M+1) m/z: 286.2 [M+1]$^+$; LC retention time: 2.83 Min [Method A]

Step 4

To a stirred solution of 4-bromo-2-methyl-2H-1,2,3-triazole (0.70 g, 4.32 mmol) in DMA (10 mL) and water (1.0 mL) were added $Na_2CO_3$ (1.14 g, 10.80 mmol) and 2-(difluoromethoxy)-3-(4,4,5,5-tetramethyl-1,3,2-dioxaborolan-2-yl) aniline (1.85 g, 6.48 mmol) at room temperature, then it was degassed under $N_2$ for 10 min. Tetrakis(triphenylphosphine)palladium(0) (1.0 g, 0.864 mmol) was added to the reaction mixture degassed for 5 minutes. The reaction mixture was stirred at 100° C. for 16 h in a sealed tube. The reaction mixture was filtered through celite pad and washed with ethyl acetate (100 mL). The collected filtrate was washed with brine, dried over anhydrous $Na_2SO_4$ and concentrated. The crude product was purified by silica gel (230-400 mesh) column chromatography using 40% EtOAc in petroleum ether to obtain 2-(difluoromethoxy)-3-(2-methyl-2H-1,2,3-triazol-4-yl) aniline (400 mg, 1.332 mmol, 30.8% yield)) as a pale brown solid. MS (M+1) m/z: 241.1 [M+1]$^+$. LC retention time 1.45 Min [Method B].

Intermediate-77

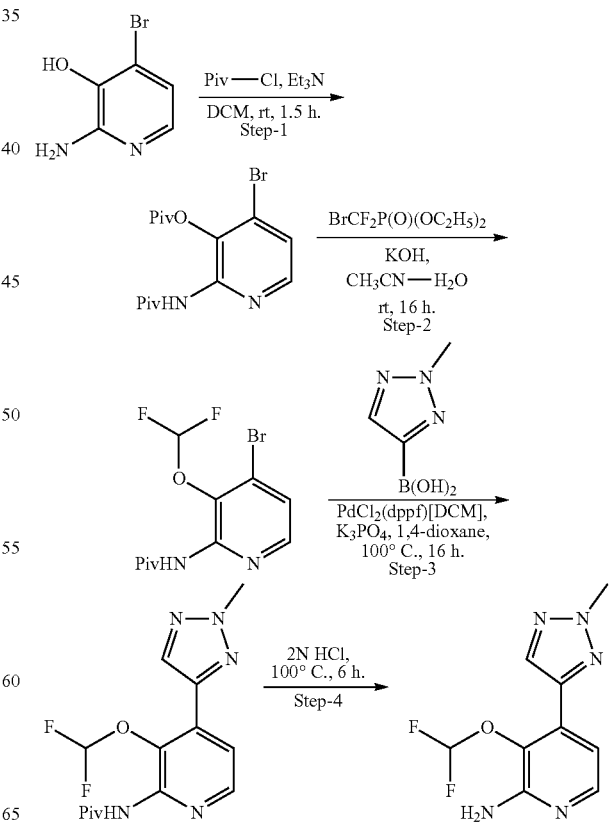

Step 1

To a stirred solution of 2-amino-4-bromopyridin-3-ol (5 g, 26.5 mmol) in DCM (80 mL) and N,N-dimethylformamide (5 mL) were added triethylamine (22.12 mL, 159 mmol) followed by pivaloyl chloride (6.38 g, 52.9 mmol) at 0° C. The reaction mixture was stirred at ambient temperature for 1.5 h. The reaction mixture was quenched with water, then it was extracted with DCM (2×200 mL). The combined organic layer was washed with brine (10 mL), dried over anhydrous $Na_2SO_4$ and concentrated. The crude product was purified by silica gel (230-400 mesh) column chromatography using 25% EtOAc in petroleum ether to obtain 4-bromo-2-pivalamidopyridin-3-yl pivalate (2.7 g, 34.0% yield) as an off white solid. MS (M+1) m/z: 357.2 $[M+1]^+$. LC retention time 2.27 Min [Method A].

Step 2

To a stirred solution of 4-bromo-2-pivalamidopyridin-3-yl pivalate (2.7 g, 7.56 mmol) in acetonitrile (30 mL) and water (6 mL) were added KOH (6.36 g, 113 mmol) followed by diethyl (bromodifluoromethyl)phosphonate (8.07 g, 30.2 mmol) at 0° C. The reaction mixture was stirred at ambient temperature for 16 h. The reaction mixture was concentrated under reduced pressure. The crude product was partitioned between ethyl acetate (100 mL) and water (100 mL). Organic layer collected, dried over anhydrous $Na_2SO_4$ and concentrated under reduced pressure. The crude product was purified by silica gel (230-400 mesh) column chromatography eluted using 35% ethyl acetate in petroleum ether to obtain N-(4-bromo-3-(difluoromethoxy)pyridin-2-yl)pivalamide (580 mg, 21.37% yield) as an off white solid.

MS (M+1) m/z: 323.0; LC retention time: 1.98 Min [Method A].

Step 3

To a stirred solution of N-(4-bromo-3-(difluoromethoxy) pyridin-2-yl)pivalamide (640 mg, 1.981 mmol) and (2-methyl-2H-1,2,3-triazol-4-yl)boronic acid (302 mg, 2.377 mmol) in 1,4-dioxane (8 mL) water (2 mL) were added $K_3PO_4$ (862 mg, 4.95 mmol) at ambient temperature, then it was degassed for 10 min under $N_2$. $PdCl_2(dppf)$.[DCM] (323 mg, 0.396 mmol) was added to the reaction mixture. The resultant mixture was degassed for another 5 minutes and subsequently heated to 100° C. for 16 h in a sealed tube. The reaction mixture was filtered through celite pad and washed with ethyl acetate (100 mL). The collected filtrate was washed with brine, dried over anhydrous $Na_2SO_4$ and concentrated. The concentrated product was purified by silica gel (230-400 mesh) column chromatography using 40% EtOAc in petroleum ether to obtain N-(3-(difluoromethoxy)-4-(2-methyl-2H-1,2,3-triazol-4-yl)pyridin-2-yl)pivalamide (450 mg, 65.7% yield) as an off white solid. MS (M+1) m/z: 326.2; LC retention time 1.71 Min [Method A] $^1$H NMR (400 MHz, DMSO-d6): δ 9.71 (s, 1H), 8.44 (d, J=4.8 Hz, 1H), 8.21 (s, 1H), 7.85 (d, J=5.2 Hz, 1H), 6.87 (t, J=73.2 Hz, 1H), 4.28 (s, 3H), 1.24 (s, 9H).

Step 4

To a stirred solution of N-(3-(difluoromethoxy)-4-(2-methyl-2H-1,2,3-triazol-4-yl)pyridin-2-yl)pivalamide (460 mg, 1.414 mmol) in aqueous 2N HCl (8 mL, 16.00 mmol) was heated to 100° C. for 6 h. Then the reaction mixture was concentrated under reduced pressure. The concentrated crude product was neutralized with 10% $NaHCO_3$ solution extracted with ethyl acetate (2×50 mL). The combined organic layer was washed with brine, dried over anhydrous $Na_2SO_4$ and concentrated. The crude product was purified by silica gel (230-400 mesh) column chromatography using 70% in EtOAc in petroleum ether to obtain 3-(difluoromethoxy)-4-(2-methyl-2H-1,2,3-triazol-4-yl)pyridin-2-amine (260 mg, 69.4% yield) as an off white solid. MS (M+1) m/z: 242.0; LC retention time 0.77 Min [Method A].

Intermediate-28

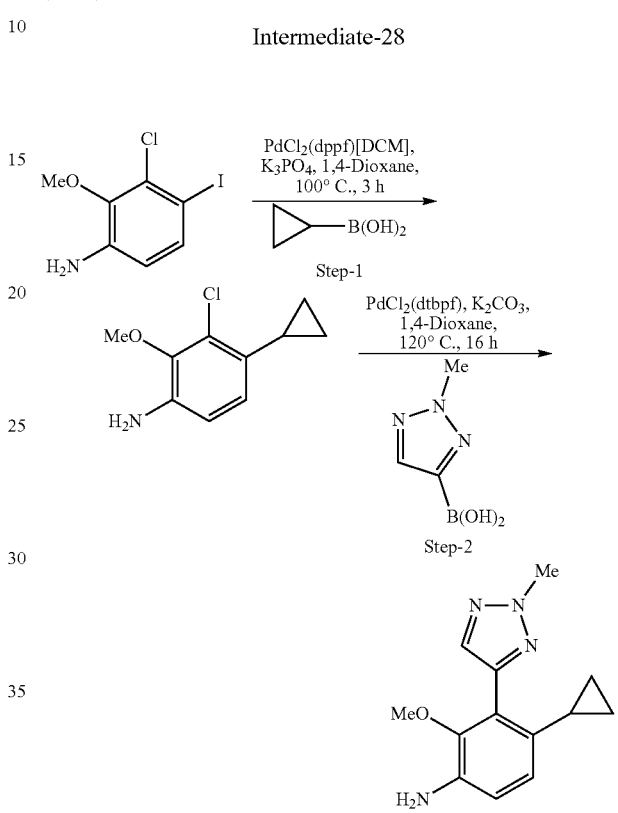

Step 1

To a stirred solution of 3-chloro-4-iodo-2-methoxyaniline (3 g, 10.58 mmol) in 1,4-Dioxane (60 mL), water (10 mL) in a 250 mL sealed tube were added cyclopropylboronic acid (1.091 g, 12.70 mmol) and $K_3PO_4$ (2.246 g, 10.58 mmol) followed by $PdCl_2(dppf)[DCM](8.64$ g, 10.58 mmol). The reaction mixture was degassed with $N_2$ for 10 min. The resultant reaction mixture was heated to 100° C. for 3 h. After completion of reaction, the reaction mixture was diluted with ethyl acetate (100 mL), filtrated through celite pad and washed with ethyl acetate (200 mL). Filtrate was washed with water (200 mL) followed by brine (200 mL) and dried over $Na_2SO_4$. Solvent was evaporated under reduced pressure and the resultant crude residue was purified by reverse phase column chromatography (c18 column) using 60% acetonitrile in 0.1% aqueous ammonium formate solution to get 3-chloro-4-cyclopropyl-2-methoxyaniline (400 mg, 1.922 mmol, 18.17% yield) as a brown liquid. MS (M+1) m/z: 198.0 $[M+H]^+$, LC retention time 2.21 Min [Method A].

Step 2

To a stirred solution of 3-chloro-4-cyclopropyl-2-methoxyaniline (0.2 g, 1.012 mmol) in 1,4-dioxane (15 mL)

water (3 mL) in a 50 mL sealed tube were added (2-methyl-2H-1,2,3-triazol-4-yl)boronic acid (0.257 g, 2.024 mmol) and $K_2CO_3$ (0.280 g, 2.024 mmol) followed by $PdCl_2(dtbpf)$ (0.033 g, 0.051 mmol). The reaction mixture was degassed under $N_2$ for 10 min. The resultant reaction mixture was heated to 120° C. for 16 h. The reaction mixture was cooled to room temperature, diluted with ethyl acetate (100 mL) filtrated through celite pad and washed with ethyl acetate (100 mL). Filtrate was washed with water (2×100 mL) followed by brine (100 mL) and dried over $Na_2SO_4$. Solvent was evaporated under reduced pressure and the resultant crude residue was purified by column chromatography on silica gel (230-400 mesh) using 12 to 20% EtOAc in petroleum ether to get 4-cyclopropyl-2-methoxy-3-(2-methyl-2H-1,2,3-triazol-4-yl) aniline (50 mg, 0.164 mmol, 16.18% yield) as a pale brown solid. MS (M+1) m/z: 245.1 [M+H]+, LC retention time 1.43 Min [Method B].

Intermediate 29

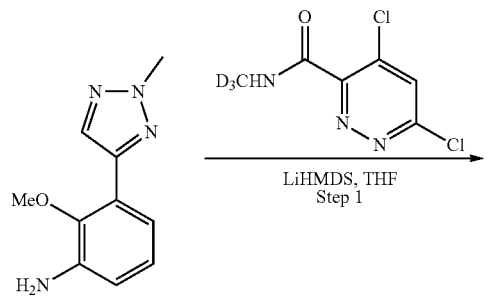

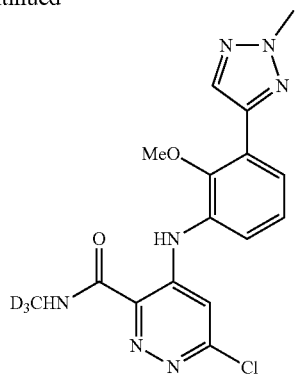

Step 1

To a solution of 4,6-dichloro-N-(methyl-d3)pyridazine-3-carboxamide (0.35 g, 1.67 mmol) and 2-methoxy-3-(2-methyl-2H-1,2,3-triazol-4-yl) aniline (0.41 g, 2.01 mmol) in THF (10 mL) at 0° C. was added LiHMDS (6.70 mL, 6.70 mmol, 1M solution in THF) dropwise and stirred at rt for 2 h. The reaction mixture was quenched with saturated ammonium chloride solution and extracted with ethyl acetate (2×30 mL). Combined organic layer was dried over anhydrous sodium sulfate and concentrated under reduced pressure. The crude residue was purified by silica gel column chromatography (40% EtOAc in petroleum ether) to afford desired 6-chloro-4-((2-methoxy-3-(2-methyl-2H-1,2,3-triazol-4-yl)phenyl)amino)-N-(methyl-d3)pyridazine-3-carboxamide (0.37 g, 0.97 mmol, 58.2% yield) as a light brown solid. MS (M+1) m/z: 377.2 (M+H)+. LC retention time 2.16 Min [Method A].

The following intermediates (29a-29e) were prepared in a similar manner to the preparation of intermediate 29.

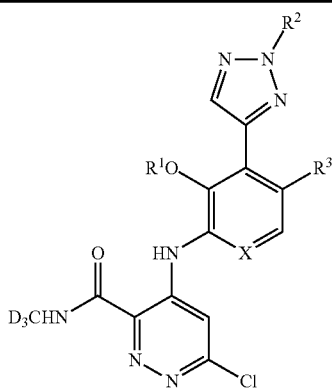

| Intermediate (29a-29e) | X | $R^1$ | $R^2$ | $R^3$ | m/z [M + H]+ | Rt (min) [Method] |
|---|---|---|---|---|---|---|
| 29a | CH | Me | $CD_3$ | H | 379.7 | 2.05 [B] |
| 29b | CH | Me | 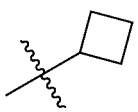 [SMILES: *C1CCC1] | H | 417.1 | 2.62 [B] |
| 29c | CH | Me | 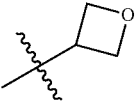 | H | 419.2 | 2.25 [A] |

-continued

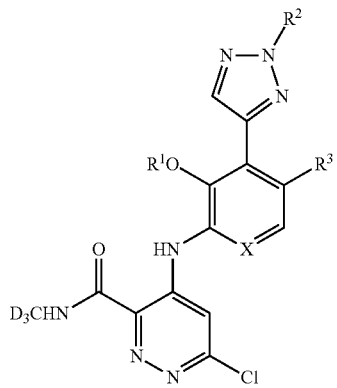

| Intermediate (29a-29e) | X | R¹ | R² | R³ | | m/z [M + H]⁺ | Rt (min) [Method] |
|---|---|---|---|---|---|---|---|
| 29d | CH | CHF₂ | Me | H | | 414.0 | 2.39 [A] |
| 29e | CH | Me | Me | 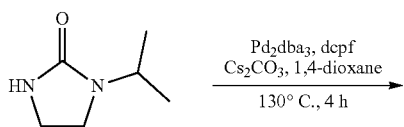 | | 417.0 | 2.31 [B] |
| 29f | N | Me | CD₃ | H | | 381.2 | 1.49 [J] |
| 29g | N | CHF₂ | Me | H | | 414.0 | 2.39 [A] |

Example-50

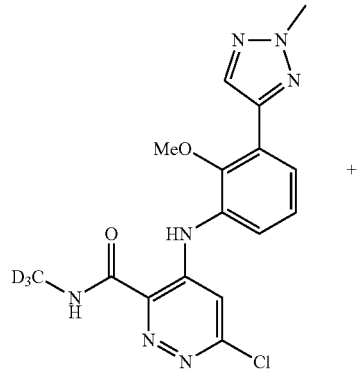

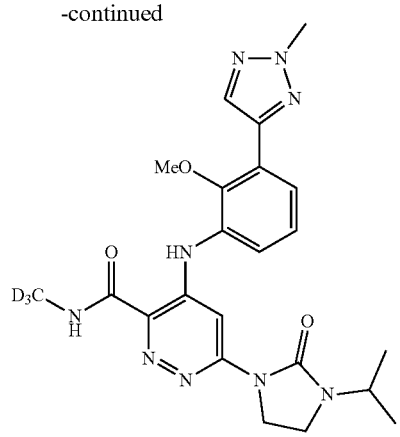

To a stirred solution 6-chloro-4-((2-methoxy-3-(2-methyl-2H-1,2,3-triazol-4-yl)phenyl)amino)-N-(methyl-d3) pyridazine-3-carboxamide (150 mg, 0.398 mmol) in 1,4-Dioxane (10 mL) in a 50 mL sealed tube added 1-isopropylimidazolidin-2-one (61.2 mg, 0.478 mmol), Cs₂CO₃ (130 mg, 0.398 mmol). Then the reaction mixture was purged with N₂ for 10 min then added 1,1-bis(dicyclohexylphosphino)ferrocene (23.01 mg, 0.040 mmol), Pd₂(dba)₃ (18.23 mg, 0.020 mmol) and the resultant reaction mixture allowed to stir at 130° C. for 4 h. After completion of reaction, the reaction mixture was filtered through celite pad and washed with ethyl acetate (100 mL). Solvent was evaporated under reduced pressure and the resultant crude residue was purified by reverse phase column chromatography (c18 column) using 70% acetonitrile in 0.1% aqueous ammonium acetate solution to obtain 6-(3-isopropyl-2-oxo-imidazolidin-1-yl)-4-((2-methoxy-3-(2-methyl-2H-1,2,3-triazol-4-yl)phenyl)amino)-N-(methyl-d3)pyridazine-3-carboxamide (100 mg, 52.1% yield) as white solid. MS (M+1) m/z: 469.2 [M+H]⁺, LC retention time 2.194 Min [Method A]. ¹H-NMR (400 MHz, DMSO-D6): δ 10.93 (s, 1H), 9.20 (s, 1H), 8.30 (s, 1H), 8.14 (s, 1H), 7.69 (dd, J=1.60, 7.80 Hz, 1H), 7.49 (dd, J=1.20, 7.80 Hz, 1H), 7.30 (t, J=7.60 Hz, 1H), 4.24 (s, 3H), 4.13-4.02 (m, 3H), 3.66 (s, 3H), 3.46 (t, J=7.60 Hz, 2H), 1.12 (d, J=6.80 Hz, 6H).

The following examples (51-56) were prepared in a similar manner to the preparation of example 50.

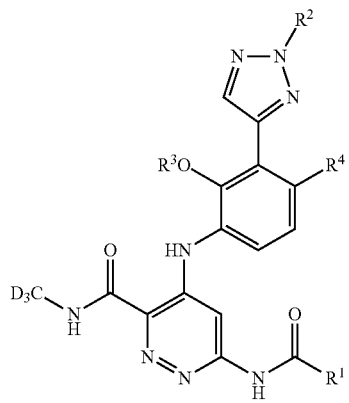

| Example (51-56) | R¹ | R² | R³ | R⁴ | MW | m/z [M + H]⁺ | Rt (min) [Method] | Reaction conditions |
|---|---|---|---|---|---|---|---|---|
| 51 | ⌇N⌐ (azetidine) | Me | Me | H | 440.4 | 441.2 | 1.80 [A] | Dcpf, 120° C., 2 h. |
| 52 | ⌇△ (cyclopropyl) | CD₃ | Me | H | 416.9 | 429.2 | 1.89 [B] | XantPhos, 130° C., 3 h. |
| 53 | ⌇△ | ⌇□O (oxetanyl) | Me | H | 468.2 | 468.2 | 2.20 [A] | XantPhos, 110° C., 1 h |
| 54 | ⌇△ | ⌇□ (cyclobutyl) | Me | H | 466.2 | 466.2 | 2.29 [B] | XantPhos, 110° C., 1 h |
| 55 | ⌇△ | Me | Me | ⌇△ (cyclopropyl) | 465.5 | 466.1 | 1.91 [B] | Dcpf, 130° C., 3 h. |
| 56 | ⌇△ | Me | CHF₂ | H | 462.1 | 462.1 | 2.05 [B] | Dcpf, MW, 100° C., 2 h. |

Example-57

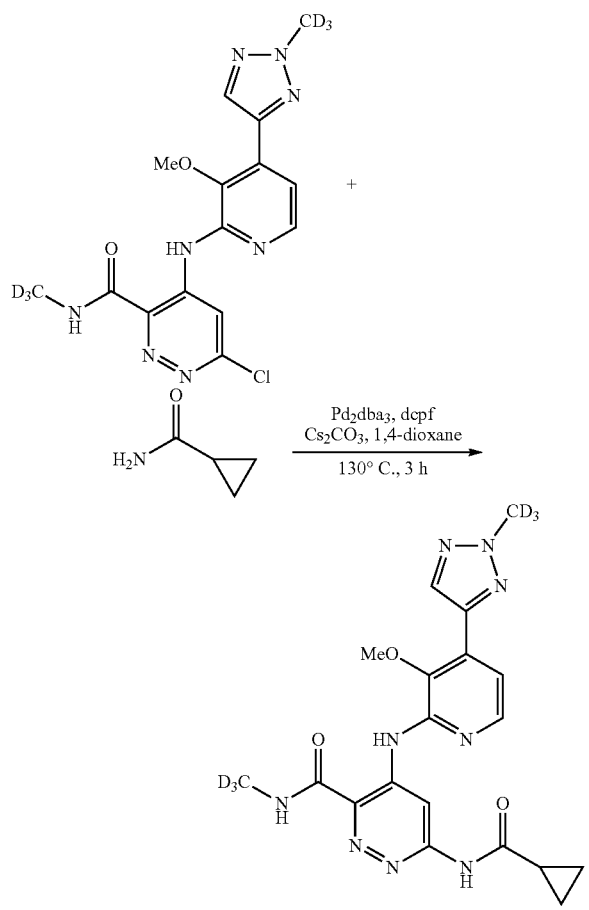

To a stirred solution of 6-chloro-4-((3-methoxy-4-(2-(methyl-d3)-2H-1,2,3-triazol-4-yl)pyridin-2-yl)amino)-N-(methyl-d3)pyridazine-3-carboxamide (0.15 g, 0.150 mmol) in 1,4-dioxane (5 mL) in a 20 mL pressure release vial were added cyclopropanecarboxamide (0.013 g, 0.150 mmol) and Pd$_2$(dba)$_3$ (6.85 mg, 7.48 μmol), 1,1'-bis(dicyclohexylphosphino)-ferrocene (4.33 mg, 7.48 μmol) followed by Cs$_2$CO$_3$ (0.098 g, 0.299 mmol). The reaction mixture was degassed with N$_2$ for 5 min. The resultant reaction mixture was heated to 110° C. for 3 h, cooled to rt and diluted with ethyl acetate (50 mL), filtrated through celite pad and washed with ethyl acetate (100 mL). Filtrate was washed with water (2×50 mL) followed by brine (50 mL) and dried over Na$_2$SO$_4$. Solvent was evaporated under reduced pressure and the resultant crude residue was purified by reverse phase column (C18) chromatography using 45-50% water (0.1% ammonium formate) in acetonitrile to give 6-(cyclopropane-carboxamido)-4-((3-methoxy-4-(2-(methyl-d3)-2H-1,2,3-triazol-4-yl)pyridin-2-yl)amino)-N-(methyl-d3)pyridazine-3-carboxamide (21 mg, 0.046 mmol, 30.7% yield) as an off-white solid.

MS (M+1) m/z: 430.2 [M+H]$^+$, LC retention time 2.18 Min [Method A]. $^1$H-NMR (400 MHz, DMSO-d6): δ 12.43 (s, 1H), 11.35 (s, 1H), 9.86 (s, 1H), 9.27 (s, 1H), 8.32 (s, 1H), 8.15 (d, J=5.20 Hz, 1H), 7.47 (d, J=5.20 Hz, 1H), 3.82 (s, 3H), 2.17-2.09 (m, 1H), 0.90-0.87 (in, 4H).

The following examples (58-60) were prepared in a similar manner to the preparation of example 57.

| Example (58-60) | R$^1$ | R$^2$ | R$^3$ | MW | m/z [M + H]$^+$ | Rt (min) [Method] | Reaction conditions |
|---|---|---|---|---|---|---|---|
| 58 | ⟨N-Et⟩ | Me | Me | 443.4 | 444.2 | 2.01 [A] | XantPhos, 110° C., 3 h. |
| 59 | ⟨N-iPr⟩ | Me | Me | 457.5 | 458.2 | 2.08 [A] | XantPhos, 110° C., 1 h |
| 60 | ⟨cyclopropyl⟩ | Me | CHF$_2$ | 463.2 | 463.2 | 2.31 [A] | Dcpf, MW, 120° C., 2 h. |

| Example No. | $^1$H NMR |
|---|---|
| 51 | $^1$H-NMR (400 MHz, DMSO-D$_6$): 10.96 (s, 1H), 9.65 (s, 1H), 9.06 (s, 1H), 8.14 (s, 1H), 8.04 (s, 1H), 7.68 (dd, J = 1.60, 7.80 Hz, 1H), 7.47 (dd, J = 1.20, 7.80 Hz, 1H), 7.29 (t, J = 8.00 Hz, 1H), 4.24 (s, 3H), 4.00 (bs, 4H), 3.66 (s, 3H), 2.20-2.10 (m, 2H). |
| 52 | $^1$H NMR (400 MHz, DMSO-d$_6$): δ 11.35 (s, 1H), 11.01 (s, 1H), 9.17 (s, 1H), 8.15 (d, J = 14.80 Hz, 2H), 7.70 (dd, J = 7.80 Hz, 1.20, 1H), 7.47 (dd, J = 1.20, 8.00 Hz, 1H), 7.30 (t, J = 8.00 Hz, 1H), 3.65 (s, 3H), 2.11-2.05 (m, 1H), 0.88-0.81 (m, 4H). |
| 53 | $^1$H-NMR (400 MHz, DMSO-d$_6$): δ 11.33 (s, 1H), 11.02 (s, 1H), 9.16 (s, 1H), 8.28 (s, 1H), 8.16 (s, 1H), 7.75 (m, 1H), 7.49 (m, 1H), 7.32 (t, J = 8.00 Hz, 1H), 5.95 (m, 1H), 5.03 (m, 4H), 3.68 (s, 3H), 2.08 (m, 1H), 0.82 (m, 4H). |

-continued

| Example No. | $^1$H NMR |
|---|---|
| 54 | $^1$H-NMR (400 MHz, DMSO-$d_6$): δ 11.35 (s, 1H), 11.02 (s, 1H), 9.17 (s, 1H), 8.16 (s, 2H), 7.73 (dd, J = 7.80, 1.60 Hz, 1H), 7.47 (dd, J = 8.00, 1.20 Hz, 1H), 7.30 (t, J = 8.00 Hz, 1H), 5.23 (m, 1H), 3.67 (s, 3H), 2.63 (m, 4H), 2.08 (m, 1H), 1.82 (m, 2H), 0.82 (m, 4H). |
| 55 | $^1$H-NMR (400 MHz, DMSO-$d_6$): δ 11.30 (s, 1H), 10.84 (s, 1H), 9.11 (s, 1H), 8.08 (s, 1H), 7.87 (s, 1H), 7.41 (d, J = 8.80 Hz, 1H), 6.84 (d, J = 8.80 Hz, 1H), 4.24 (s, 3H), 3.42 (s, 3H) 2.09-2.07 (m, 1H), 1.77-1.75 (m, 1H), 0.85-0.81 (m, 6H), 0.79-0.77 (m, 2H). |
| 56 | $^1$H NMR (400 MHz, DMSO-$d_6$) δ 11.35 (s, 1H), 10.90 (s, 1H), 9.14 (s, 1H), 8.08 (s, 1H), 8.01 (s, 1H), 7.77 (dd, J = 1.6, 8.0 Hz, 1H), 7.56 (dd, J = 1.6, 8.0 Hz, 1H), 7.49 (t, J = 8.0 Hz, 1H), 6.98 (t, J = 73.2 Hz, 1H), 4.24 (s, 3H), 2.04-2.11 (m, 1H), 0.76-0.87 (m, 4H). |
| 58 | $^1$H NMR (400 MHz, MeOH-$d_4$) δ 9.77 (s, 1H), 8.23 (d, J = 5.20 Hz, 1H), 8.21 (s, 1H), 7.74 (s, 2H), 7.50 (d, J = 5.60 Hz, 1H), 4.29 (s, 3H), 3.89 (s, 3H), 3.52 (q, J = 7.20 Hz, 2H), 3.11 (s, 3H), 1.26 (t, J = 7.20 Hz, 3H). |
| 59 | $^1$H NMR (400 MHz, DMSO-$d_6$) δ 12.37 (s, 1H), 9.50 (s, 1H), 9.38 (s, 1H), 9.18 (s, 1H), 8.32 (s, 1H), 8.15 (d, J = 5.60 Hz, 1H), 7.46 (d, J = 5.60 Hz, 1H), 4.54-4.51 (m, 1H), 4.28 (s, 3H), 3.82 (s, 3H), 2.88 (s, 3H), 1.12 (d, J = 6.80 Hz, 6H). |
| 60 | $^1$H NMR (400 MHz, DMSO-$d_6$) δ 12.47 (s, 1H), 11.39 (s, 1H), 9.77 (s, 1H), 9.26 (s, 1H), 8.33 (d, J = 5.2 Hz, 1H), 8.27 (s, 1H), 7.54 (d, J = 5.2 Hz, 1H), 7.15 (t, J = 72.8 Hz, 1H), 4.28 (s, 3H), 2.10-2.18 (m, 1H), 0.85-0.92 (m, 4H). |

Example 61

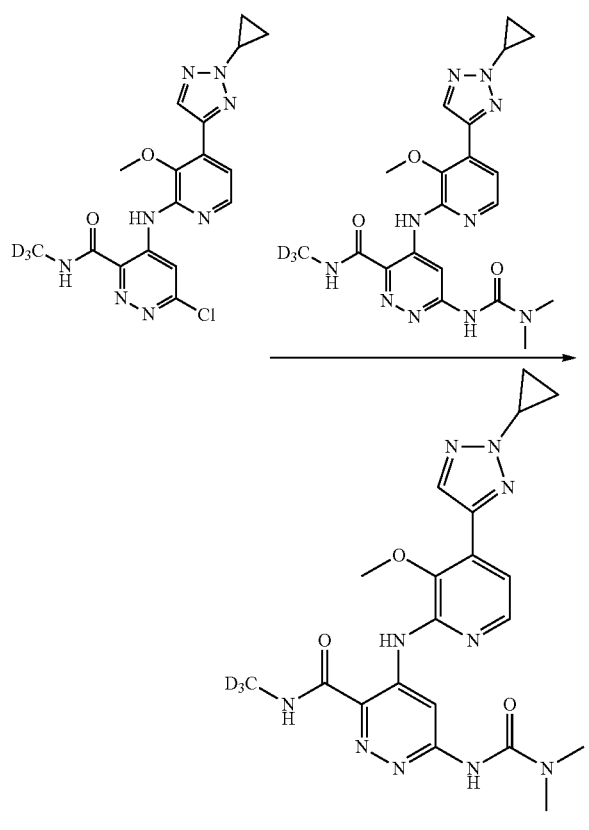

A mixture of 6-chloro-4-((4-(2-cyclopropyl-2H-1,2,3-triazol-4-yl)-3-methoxypyridin-2-yl)amino)-N-(methyl-d3)pyridazine-3-carboxamide (44 mg, 0.109 mmol), 1,1-dimethylurea (38.4 mg, 0.436 mmol), Pd$_2$(dba)$_3$ (11.26 mg, 10.90 μmol), 1,1'-bis(discyclohexylphosphino)ferrocene (12.61 mg, 0.022 mmol) and cesium carbonate (142 mg, 0.426 mmol) in dioxane (1.0 mL) was degassed by bubbling nitrogen through the mixture for 5 minutes. The reaction vessel was sealed and heated to 130° C. for 30 minutes. No reaction was detected by LCMS. Methanesulfonato(2-dicyclohexyl-phosphino-2',4',6'-tri-i-propyl-1,1'-biphenyl)(2'-methylamino-1, i-biphenyl-2-yl)palladium(II) (X-phos, gen 4) (12 mg, 0.014 mmol) was added, the reaction mixture was re-degassed and was then heated to 125° C. for 30 minutes. After cooling to rt, the reaction mixture was diluted with DMSO. The mixture was filtered through a 0.45 micron nylon filter and the filtrate was purified by prep HPLC. Concentration of the pure fractions afforded 4-((4-(2-cyclopropyl-2H-1,2,3-triazol-4-yl)-3-methoxypyridin-2-yl)amino)-6-(3,3-dimethylureido)-N-(methyl-d3)pyridazine-3-carboxamide (7.7 mg, 14.17% yield). MS (M+1) m/z: 456.0 (M+H)$^+$. LC retention time 1.40 [I]. $^1$H NMR (500 MHz, DMSO-d6) δ 12.34 (s, 1H), 9.48 (s, 1H), 9.46 (s, 1H), 9.14 (s, 1H), 8.30 (s, 1H), 8.14 (d, J=5.3 Hz, 1H), 7.45 (d, J=5.2 Hz, 1H), 4.25 (tt, J=7.5, 3.7 Hz, 1H), 3.81 (s, 3H), 3.00 (s, 6H), 1.33-1.25 (m, 2H), 1.19-1.11 (m, 2H).

Example 62

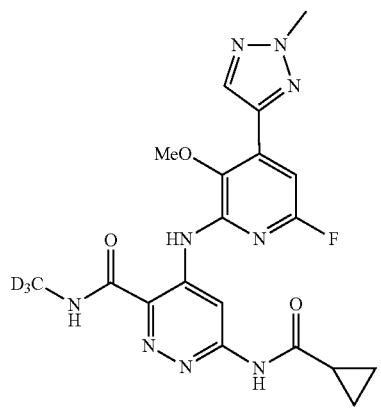 [SMILES: [2H]C([2H])([2H])NC(=O)c1nnc(NC(=O)C2CC2)cc1Nc1nc(F)cc(-c2cnn(C)n2)c1OC]

6-(Cyclopropanecarboxamido)-4-((6-fluoro-3-methoxy-4-(2-methyl-2H-1,2,3-triazol-4-yl)pyridin-2-yl)amino)-N-(methyl-d₃)pyridazine-3-carboxamide

6-Fluoro-3-methoxy-4-(2-methyl-2H-1,2,3-triazol-4-yl)pyridin-2-amine

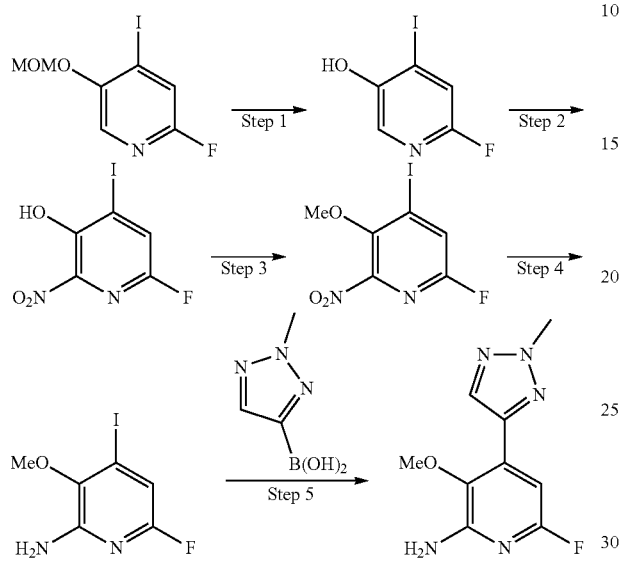

Synthesis of 6-fluoro-4-iodopyridin-3-ol (Step 1)

In a 100 mL round bottom flask, HCl (1.5 M in H₂O, 15 mL) was added to a solution of 2-fluoro-4-iodo-5-methoxymethoxy-pyridine (5 g, 17.67 mmol) in THF (40 mL). The mixture was stirred at 60° C. for 3 hours. The mixture was cooled down to room temperature and the pH was adjusted to 7 with the slow addition of saturated aqueous NaHCO₃ solution. The mixture was extracted with EtOAc (3×100 mL). The combined organic layer was washed with saturated brine solution. The resulting organic layer was dried over anhydrous Na₂SO₄, filtered and concentrated under reduced pressure to afford the title compound (4.15 g crude) as a yellow solid which was used for the next reaction without further purification. MS (EI) m/z 240 [M+1]⁺.

Synthesis of 6-fluoro-4-iodo-2-nitropyridin-3-ol (Step 2)

To a stirred solution of 6-fluoro-4-iodopyridin-3-ol (500 mg, 2.09 mmol) in acetonitrile (20 mL) was added nitronium tetrafluoroborate (1.10 g, 8.37 mmol) at 0° C. Then the reaction mixture was stirred for 16 h at room temperature. After completion, ice cold water (50 mL) was added to the reaction and the mixture was extracted with ethyl acetate (300 mL). The organic layer was dried over anhydrous Na₂SO₄, filtered and concentrated under reduced pressure to afford crude title compound (700 mg). GC-MS (EI) m/z 283 [M⁺].

6-fluoro-4-iodo-3-methoxy-2-nitropyridine (Step 3)

To a stirred solution of 6-fluoro-4-iodo-2-nitropyridin-3-ol (2.8 g, 9.86 mmol) in DMF (10 mL) was added K₂CO₃ (4.09 g, 29.6 mmol) and methyl iodide (1.850 mL, 29.6 mmol) at 0° C. Reaction mixture was stirred at room temperature for 16 h. The reaction mixture was added with ice cold water (100 mL) and extracted with EtOAc (2×200 mL). The combined organic layer was dried over anhydrous Na₂SO₄ and concentrated under reduced pressure to afford crude product which was purified on neutral alumina column using EtOAc in petroleum ther as a mobile phase (0-30%) to afford 6-fluoro-4-iodo-3-methoxy-2-nitropyridine (650 mg, 1.963 mmol, 19.91% yield) as white solid.

6-fluoro-4-iodo-3-methoxypyridin-2-amine (Step 4)

To a stirred solution of 6-fluoro-4-iodo-3-methoxy-2-nitropyridine (650 mg, 2.181 mmol) in EtOH (4 mL), AcOH (4 mL) & H₂O (2 mL) iron powder was added (853 mg, 15.27 mmol) slowly at 0° C. The reaction was stirred for 1 h at room temperature. After complete disappearance of starting material (as monitored by TLC), reaction mixture was filtered, and the filtrate was concentrated to obtain sticky crude mass. This sticky mass was dissolved with EtOAc (150 mL) and water (50 mL), then pH was adjusted to 9 using solid NaHCO₃. The organic layer was separated and washed with brine (40 mL). The resulting organic layer was dried over anhydrous Na₂SO₄, filtered and concentrated to obtain the title compound (550 mg crude) which was used for next step without further purification. LCMS (EI) m/z=269 [M+1].

6-Fluoro-3-methoxy-4-(2-methyl-2H-1,2,3-triazol-4-yl)pyridin-2-amine (Step 5)

In a 50 mL sealed tube, to a solution of 6-fluoro-4-iodo-3-methoxypyridin-2-amine (550 mg, 2.05 mmol), (2-methyl-2H-1,2,3-triazol-4-yl)boronic acid (260 mg, 2.05 mmol) (intermediate 19) in 1,4-dioxane (8 mL) were added PdCl₂(dppf)-CH₂Cl₂-adduct (168 mg, 0.21 mmol), K₃PO₄ (1.31 g, 6.16 mmol). The reaction mixture was degassed under N₂ for 5 mins. The sealed tubed was capped and the mixture was stirred at 110° C. for 1.5 h. The reaction mixture was filtered through Celite pad and the Celite pad was washed with MeOH (50 mL). The filtrate was concentrated under reduced pressure to afford crude product which was purified under neutral alumina column chromatography (0-50% EtOAc in petroleum ether) to obtain desired product 6-fluoro-3-methoxy-4-(2-methyl-2H-1,2,3-triazol-4-yl)pyridin-2-amine (450 mg, 1.855 mmol, 90% yield) as white solid. LCMS: (EI) m/z=224 [M+1]. ¹H-NMR (400 MHz, DMSO-d6): δ 8.18 (s, 1H), 6.48 (m, 3H), 4.23 (s, 3H), 3.61 (s, 3H).

6-Chloro-4-((6-fluoro-3-methoxy-4-(2-methyl-2H-1,2,3-triazol-4-yl)pyridin-2-yl)amino)-N-(methyl-d₃)pyridazine-3-carboxamide (Step 6)

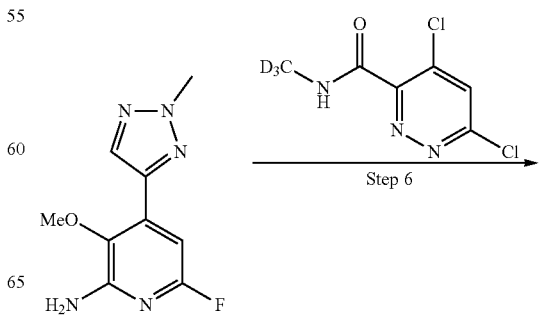

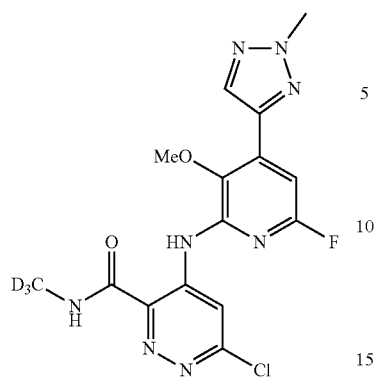

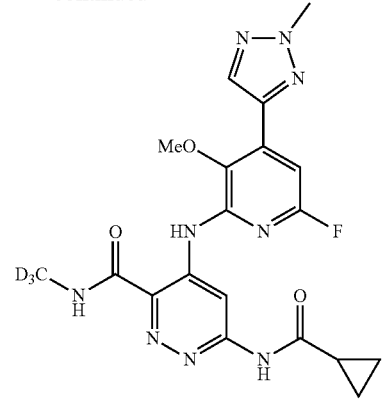

6-(Cyclopropanecarboxamido)-4-((6-fluoro-3-methoxy-4-(2-methyl-2H-1,2,3-triazol-4-yl)pyridin-2-yl)amino)-N-(methyl-d₃)pyridazine-3-carboxamide

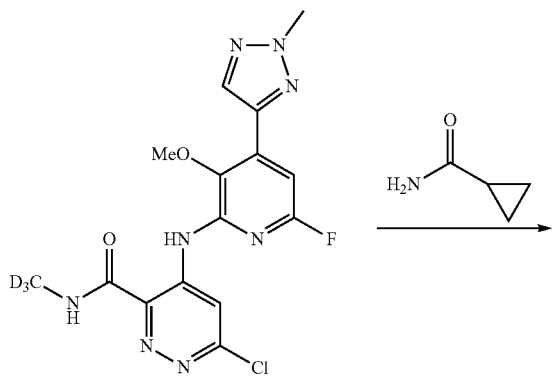

In a 50 mL round bottom flask, To a stirred solution of 6-fluoro-3-methoxy-4-(2-methyl-2H-1,2,3-triazol-4-yl) pyridin-2-amine (200 mg, 0.90 mmol) and 4,6-dichloro-N-(methyl-d3)pyridazine-3-carboxamide (281 mg, 1.34 mmol) in THF (10 mL) was added LiHMDS (600 mg, 3.58 mmol, 1M in THF) at 0° C. Then the reaction mixture was stirred at room temperature for 4 h. After the completion of reaction, ice cold water (60 mL) was added, and extracted with EtOAc (2×100 mL). The combined organic layers was washed with brine solution (100 mL). The resulting organic layer was dried over anhydrous Na₂SO₄, filtered and concentrated under reduced pressure to afford the crude product. To remove the impurities, the reaction mass was triturated with 50% EtOAc in petroleum ether three times (60 mL each), petroleum ether (20 mL) and finally with Et₂O (20 mL) to afford 250 mg of brown solid (72% desired product by LCMS).

In a 50 mL sealed tube containing a solution of 6-chloro-4-((6-fluoro-3-methoxy-4-(2-methyl-2H-1,2,3-triazol-4-yl) pyridin-2-yl)amino)-N-(methyl-d3)pyridazine-3-carboxamide (100 mg, 0.253 mmol), cyclopropanecarboxamide (64.55 mg, 0.758 mmol) in 1,4-dioxane (10 mL) and DMA (1 mL) were added Cs₂CO₃ (247 mg, 0.758 mmol) and 1,1-Bis(dicyclohexylphosphino)ferrocene (29.3 mg, 0.051 mmol) in a sealed tube. The reaction mixture was degassed under N₂ for 5 mins and Pd₂(dba)₃ (23.15 mg, 0.025 mmol) was added. The resulting mixture was stirred at 110° C. for 8 h. The reaction mixture was filtered through Celite pad; the Celite pad was washed with MeOH (50 mL). The filtrate was concentrated under reduced pressure to afford crude product.

Yield of product: 19% (after RP PREP HPLC purification). LCMS: (EI) m/z=445.2 [M+1]. ¹H-NMR (400 MHz, DMSO-d6): δ 12.64 (s, 1H), 11.43 (s, 1H), 9.68 (s, 1H), 9.34 (s, 1H), 8.37 (s, 1H), 7.09 (m, 1H), 4.29 (s, 3H), 3.82 (s, 3H), 2.18-2.08 (m, 1H), 0.92-0.87 (m, 4H).

RP PREP HPLC Purification Method:
Column: Sun fire C18 (19*150 mm*5)
Mobile Phase A: 0.1% TFA in water
Mobile Phase B: ACN
LCMS: m/z: [M+1]: 445.2, RT: 2.421 min
Column: XBridge C18 (50×4.6 mm) 5 µm
Mobile phase: A: 0.1% TFA in H₂O
Mobile phase: B: 0.1% TFA in ACN, Flow Rate: 1.0 ml/min.
Purity: 94.55%.
HPLC:
HPLC Method 1:
Column: Kinetex Biphenyl (100×4.6) mm, 2.6 µm
Mobile phase: A: 0.05% TFA in H₂O:ACN (95:5),
Mobile phase: B: ACN: 0.05% TFA in H₂O (95:5)
Flow: 1.0 mL/min.
Purity: 97.76%.
HPLC Method 2:
Column: Kinetex EVO C18 (100×4.6) mm, 2.6 µm
Mobile phase: A: 0.05% TFA IN Water:ACN
Mobile phase: B: 0.05% TFA IN ACN:Water
Flow: 1.0 mL/min
Purity: 97.30%.

Example 63

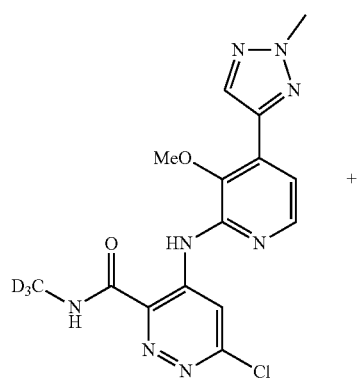

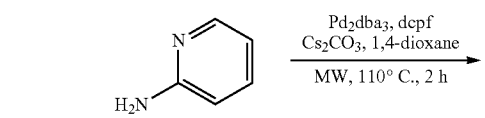

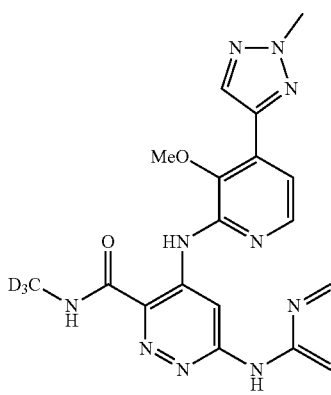

To a stirred solution of 6-chloro-4-((3-methoxy-4-(2-methyl-2H-1,2,3-triazol-4-yl)pyridin-2-yl)amino)-N-(methyl-d3)pyridazine-3-carboxamide (100 mg, 0.265 mmol) in 1,4-Dioxane (15 mL) and DMA (1.5 mL) were added and Cs$_2$CO$_3$ (216 mg, 0.662 mmol) at ambient temperature. The reaction mixture was degassed for 5 min under N$_2$. Pyridin-2-amine (29.9 mg, 0.318 mmol) and Pd$_2$dba$_3$ (36.4 mg, 0.040 mmol) and 1,1'-Bis(dicyclohexylphosphino)ferrocene (22.96 mg, 0.040 mmol) were added to reaction mixture and degassed for 5 min. The resultant reaction mixture was heated at 110° C. for 2 h under microwave conditions. The reaction mixture was filtered through celite pad under reduced pressure and washed with ethyl acetate (100 mL). The filtrate was concentrated under reduced pressure. The crude product was purified by silica gel (230-400 mesh) column chromatography using 2-3% MeOH in DCM as an eluent to obtained 4-((3-methoxy-4-(2-methyl-2H-1,2,3-triazol-4-yl)pyridin-2-yl)amino)-N-(methyl-d3)-6-(pyridin-2-ylamino)pyridazine-3-carboxamide (26.98 mg, 0.061 mmol, 23.17% yield) as an off white solid.

MS (M+1) m/z: 436.0 [M+H]$^+$, LC retention time 1.34 Min [Method A].

$^1$H-NMR (400 MHz, DMSO-d6): δ 12.35 (s, 1H), 10.28 (s, 1H), 9.79 (s, 1H), 9.20 (s, 1H), 8.34 (d, J=4.0 Hz, 1H), 8.31 (s, 1H), 8.20 (d, J=5.2 Hz, 1H), 7.73-7.75 (m, 1H), 7.65-7.71 (m, 1H), 7.46-7.47 (m, 1H), 6.99-6.97 (m, 1H) 4.28 (s, 3H), 3.83 (s, 3H).

The following examples were prepared in a similar manner to the preparation of example 63.

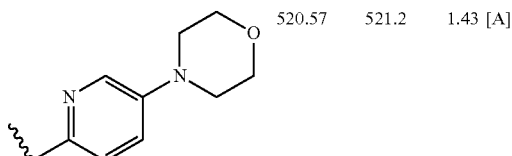

| Example | R | MW | m/z [M + H]$^+$ | Rt (min) [Method] |
|---|---|---|---|---|
| 64 | 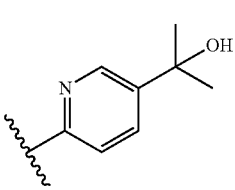 | 464.51 | 465.2 | 2.01 [B] |
| 65 | | 493.55 | 494.2 | 2.07 [B] |
| 66 | | 520.57 | 521.2 | 1.43 [A] |

| | 171 -continued | | | |
|---|---|---|---|---|

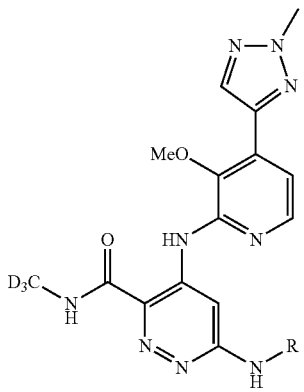

| Example | R | MW | m/z [M + H]+ | Rt (min) [Method] |
|---|---|---|---|---|
| 67 | (2-pyridyl-4-(2-hydroxypropan-2-yl)) | 493.55 | 494.3 | 2.13 [B] |

| | 172 -continued | | | |
|---|---|---|---|---|

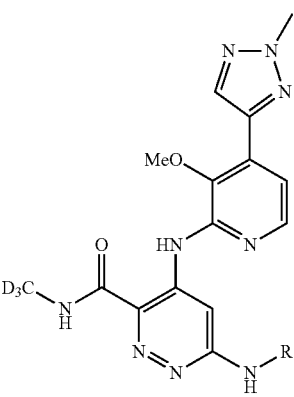

| Example | R | MW | m/z [M + H]+ | Rt (min) [Method] |
|---|---|---|---|---|
| 68 | (1,5-dimethyl-1H-pyrazol-3-yl) | 452.50 | 453.3 | 2.22 [B] |

| Example No. | $^1$H NMR |
|---|---|
| 64 | $^1$H-NMR (400 MHz, DMSO-$d_6$): δ 12.45 (s, 1H), 10.57 (s, 1H), 9.96 (s, 1H), 9.79 (s, 1H), 8.57 (s, 1H), 8.36 (s, 1H), 7.55 (d, J = 5.2 Hz, 1H), 7.35-7.38 (m, 1H), 4.29 (s, 3H), 3.83 (s, 3H), 2.57 (s, 3H), 2.35 (s, 3H). |
| 65 | $^1$H NMR (400 MHz, DMSO-$d_6$): δ 12.34 (s, 1H), 10.22 (s, 1H), 9.72 (s, 1H), 9.21 (s, 1H), 8.41 (d, J = 2.0 Hz, 1H), 8.31 (s, 1H), 8.2 (d, J = 5.2 Hz, 1H), 7.80 (d, J = 8.4 Hz, 1H), 7.63 (d, J = 8.4 Hz, 1H), 7.47 (d, J = 5.2 Hz, 1H), 5.10 (s, 1H), 4.28 (s, 3H), 3.83 (s, 3H), 1.47 (s, 6H). |
| 66 | $^1$H-NMR (400 MHz, DMSO-$d_6$): δ 12.32 (s, 1H), 10.04 (s, 1H), 9.59 (s, 1H), 9.17 (s, 1H), 8.31 (s, 1H), 8.21 (s, 1H), 8.03 (d, J = 2.8 Hz, 1H), 7.60 (d, J = 8.8 Hz, 1H), 7.47 (d, J = 2.8 Hz, 1H), 7.45 (d, J = 5.2 Hz, 1H), 4.28 (s, 3H), 3.82 (s, 3H), 3.75-3.78 (m, 4H), 3.10-3.12 (m, 4H). |
| 67 | $^1$H-NMR (400 MHz, DMSO-$d_6$): δ 12.35 (s, 1H), 10.21 (s, 1H), 9.75 (s, 1H), 9.24 (s, 1H), 8.32 (s, 1H), 8.24 (d, J = 5.2 Hz, 1H), 8.19 (d, J = 5.2 Hz, 1H), 7.82 (d, J = 0.8 Hz, 1H), 7.47 (d, J = 5.2 Hz, 1H), 7.04 (d, J = 5.2 Hz, 1H), 5.21 (s, 1H), 4.29 (s, 3H), 3.83 (s, 3H), 1.44 (s, 6H). |
| 68 | $^1$H NMR (400 MHz, DMSO-$d_6$) δ 12.32 (s, 1H), 9.79 (s, 1H), 9.28 (s, 1H), 9.13 (s, 1H), 8.31 (s, 1H), 8.17 (d, J = 5.20 Hz, 1H), 7.45 (d, J = 5.20 Hz, 1H), , 6.11 (s, 1H), 4.28 (s, 3H), 3.82 (s, 3H), 3.69 (s, 3H), 2.34 (s, 3H). |

Example 69

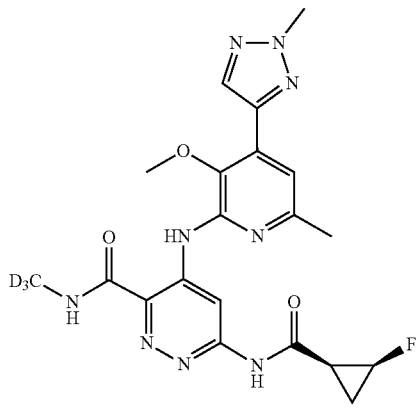 [SMILES: [2H]C([2H])([2H])NC(=O)c1nnc(NC(=O)[C@@H]2C[C@@H]2F)cc1Nc1nc(C)cc(-c2cnn(C)n2)c1OC]

Example 69 was prepared in the same way as example 46, from an amide prepared from the appropriate, commercially available, carboxylic acid, in the same way as described in example 40 to afford 6-((1S,2S)-2-fluorocyclopropane-1-carboxamido)-4-((3-methoxy-6-methyl-4-(2-methyl-2H-1,2,3-triazol-4-yl)pyridin-2-yl)amino)-N-(methyl-d3) pyridazine-3-carboxamide, 12 mg, 18.46% yield. MS (M+1) m/z: 459.3 (M+H)$^+$. LC retention time 1.20 [C]. $^1$H NMR (400 MHz, DMSO-d6) δ 12.34 (s, 1H), 11.35 (s, 1H), 10.10 (s, 1H), 9.25 (s, 1H), 8.28 (s, 1H), 7.34 (s, 1H), 5.29-4.65 (m, 1H), 4.27 (s, 3H), 3.78 (s, 3H), 2.38-2.28 (m, 1H), 1.83-1.61 (m, 1H), 1.34-1.15 (m, 1H) one methyl peak is buried under solvent.

The table below shows additional prodrugs (A-I) that can be made to potentially enhance certain properties of Example 36.

| Pro-drug | Structure | Molecular Weight |
|---|---|---|
| A | 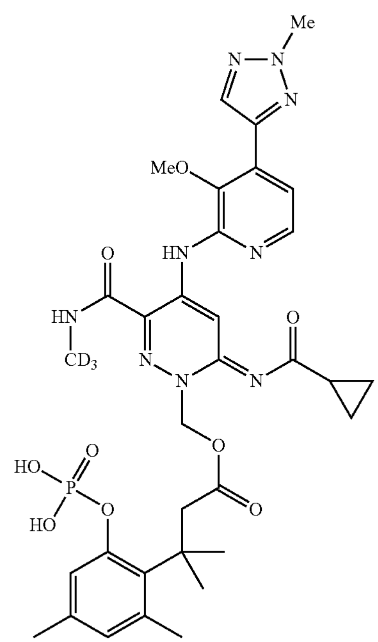 [SMILES: [2H]C([2H])([2H])NC(=O)c1nn(COC(=O)CC(C)(C)c2c(C)cc(C)cc2OP(=O)(O)O)/c(=N/C(=O)C2CC2)cc1Nc1nccc(-c2cnn(C)n2)c1OC] | 740.29 |

-continued
| Pro-drug | Structure | Molecular Weight |
|---|---|---|
| B | 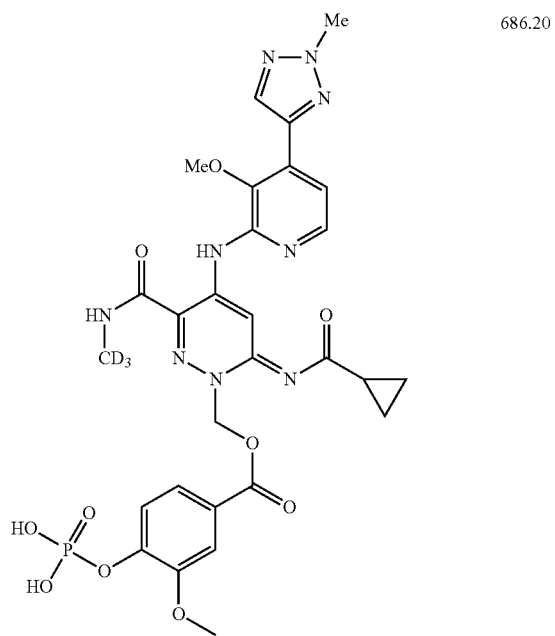 | 686.20 |
| C | 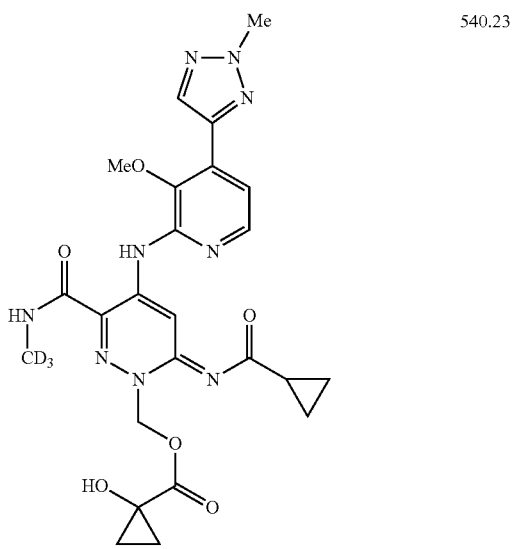 | 540.23 |

-continued
| Pro-drug | Structure | Molecular Weight |
|---|---|---|
| D | 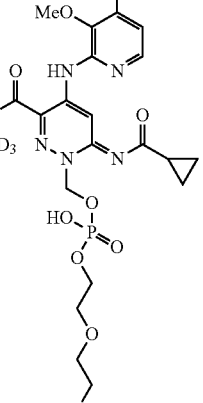 | 638.24 |
| E | 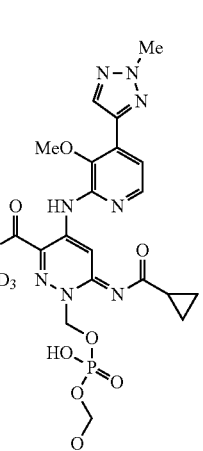 | 650.24 |
| F | 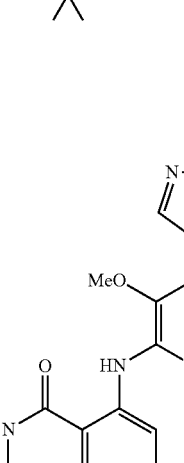 | 536.17 |

-continued

| Pro-drug | Structure | Molecular Weight |
|---|---|---|
| G | 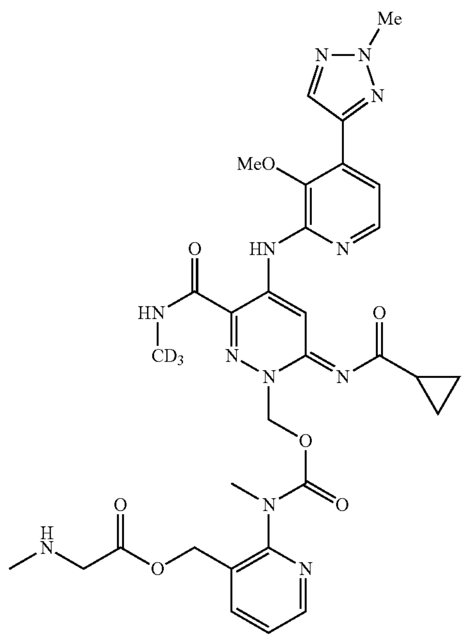 [SMILES: [2H]C([2H])([2H])NC(=O)c1nn(COC(=O)N(C)c2ncccc2COC(=O)CNC)/c(=N/C(=O)C2CC2)cc1Nc1nccc(-c2cnn(C)n2)c1OC] | 691.30 |
| H | 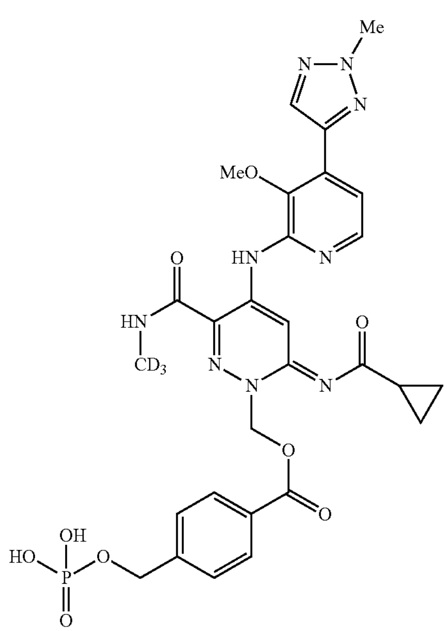 [SMILES: [2H]C([2H])([2H])NC(=O)c1nn(COC(=O)c2ccc(COP(=O)(O)O)cc2)/c(=N/C(=O)C2CC2)cc1Nc1nccc(-c2cnn(C)n2)c1OC] | 670.21 |

| Pro-drug | Structure | Molecular Weight |
|---|---|---|
| I | (structure shown) | 686.20 |

Biological Assays

The following assays are used to show the activity for compounds of the invention.

Brain Penetration In Vivo Assay

A pharmacokinetic study was performed using C57BL6 wild-type mice (n=3 per experiment) to determine brain and plasma exposure of compounds of the invention. The compound was administered orally in a solution of 5% ETHANOL: 90% PEG 300; 5% TPGS at 5 mL/kg for a final concentration of 10 mg/kg. Nice were euthanized 1 hour post-dose and plasma and brain were collected and frozen for analysis. Brain tissues were homogenized in a 1:1 volume of blank C57BL6 mouse plasma. Concentrations of the compound in plasma and brain homogenate were determined by LC-MS analysis.

$MOG_{1-125}$ EAE Model of Multiple Sclerosis: In-Life and Ex Vivo

Female C57BL/6J mice (Jackson Labs #000664) were approximately 10-11 weeks old at study initiation. After at least one week of acclimation, disease was induced by subcutaneous (SC) immunization with an emulsion containing human recombinant myelin oligodendrocyte glycoprotein 1-125 ($MOG_{1-125}$) in complete Freund's adjuvant (two dorsal sites were injected with 0.1 mL emulsion per site). Pertussis toxin (PTX) was then injected intraperitoneally (approximately 4 and 24 hours after SC emulsion injection) with each injection containing the same dose of PTX. Mice were then monitored for the development of disease using a standard clinical disease score and randomized into treatment groups (N=12) approximately 11 days later with once-daily treatment of vehicle or test compound commencing after the onset of disease. The duration of treatment was 21 days with daily measurement of body weight and clinical disease score. Tissue samples were collected at various times after the last dose for pharmacokinetic assessment of compound levels in plasma and brain. In addition, the spinal cord was collected at various times after the last dose for assessment of inflammatory and target-related parameters by flow cytometry analysis, Western blotting and other laboratory techniques. Spinal cords were analyzed ex vivo as follows:

JESS Western Blot: snap-frozen tissues were homogenized in RIPA with protease/phosphatase inhibitors and centrifuged to remove debris. Protein concentration was measured using the BCA assay and lysates were normalized to 0.5 mg/mL, mixed with loading buffer and denatured. These were then run on the JESS for markers of inflammation and pathway activation. Antibodies for pStat1 were used at 1:50 dilution with a control protein (usually alpha/beta tubulin at 1:1500 dilution).

FACS Analysis: single cell suspensions were prepared using Miltenyi's ABDK protocol and divided as per the number of panels. FACS panels assessing surface markers and transcription factors employed a standard protocol (eBioscience Protocol B: One-step protocol: intracellular (nuclear) proteins) and panels assessing pStat1 or other phosphoproteins also used a standard protocol (BioLegend's True-Phos protocol). Assessment of cytokine by FACS was performed by culturing cells for 18 hours in microglia media+brefelin-A+P/S and then staining was performed using a standard protocol (Biolegend CytoFix/Perm or CytoLast) for staining.

Results are shown in FIG. 1. Oral treatment started on Day 12 and continued until Day 35.

IFNα-Induced STAT Phosphorylation in Human Whole Blood

After an hour long incubation with compound, human whole blood (drawn with ACD-A as anticoagulant) was stimulated with 1000 U/mL recombinant human IFNα A/D (R&D Systems 11200-2) for 15 min. The stimulation was stopped by adding Fix/Lyse buffer (BD 558049). Cells were stained with a CD3 FITC antibody (BD 555916), washed, and permeabilized on ice using Perm III buffer (BD 558050). Cells were then stained with an Alexa-Fluor 647 pSTAT5 (pY694) antibody (BD 612599) for 60 min prior to analysis on the iQue Plus. The amount of pSTAT5 expression was quantitated by median fluorescence intensity after gating on the CD3 positive population.

Bidirectional Permeability Assay in Caco-2 Cells

Overview

Compounds described were tested in the Caco-2 Bidirectional Permeability Assay to assess its permeability and efflux substrate potential. Compounds (at 3 µM in triplicate) were incubated with Caco-2 cells in the assay buffer at pH 7.4 (containing 0.5% bovine serum albumin [BSA]) for 2 hours at 37° C. and then was extracted for LC-MS analysis to determine its concentration in reaction mixtures and to calculate permeability coefficient, efflux ratio, and recovery.

Materials and Methods

Caco-2 (Caucasian colon adenocarcinoma) cells were obtained from the American Type Culture Collection (Manassas, Virginia). Dulbecco's Modified Eagle's Medium (DMEM), N-2-hydroxyethylpiperazine-N'-2-ethanesulfonic acid (HEPES) buffer, nonessential amino acids, L-glutamine, penicillin-G-streptomycin, and heat-inactivated fetal bovine serum (FBS) were purchased from GIBCO/Invitrogen (Carlsbad, California). Transwell plates with 96 wells (surface area: 0.11 $cm^2$) with a 0.4-µm pore size polycarbonate membrane and low-binding transwell cluster plates, were purchased from Sigma Aldrich (Saint Louis, Missouri). Low binding 96-well plates were purchased from Corning (Corning, New York). Modified Hank's Balanced Salt Solution (MHBSS) was prepared by adjusting Hank's Balanced Salt Solution (HBSS) with HEPES to pH 7.4. HBSS, digoxin, and bovine serum albumin (BSA) were purchased from Sigma (Saint Louis, Missouri). Filtration blocks (2 mL, 96 well) were purchased from Whatman (Freiburg, Germany). All solvents were analytical grade.

Cell Preparation

Fourteen (14) to 28 days prior to assay, Caco-2 cells were seeded onto polycarbonate filter membranes in 96-well transwell plates at a density of $1.8 \times 10^5$ cells/$cm^2$, approximately $2.0 \times 10^4$ cells per well. The cells were grown in culture medium consisting of DMEM supplemented with 10% fetal bovine serum, 10 mM HEPES, 1% nonessential amino acids, 2 mM L-glutamine, 100 U/mL penicillin-G, and 100 µg/mL streptomycin. The culture medium was replaced every 3 days and the cells maintained at 37° C. in a 95% relative humidity and 5% $CO_2$ atmosphere. The cells were evaluated for tight junction formation just prior to assay (see Quality Control section below).

Compound Preparation

Compounds were solubilized to 10 mM in 100% DMSO. Following visual confirmation of complete solubilization, 10 mM stock of the compounds were plated into a 96-well plate and further serially diluted in 100% DMSO to create a 100× stock concentration of 0.3 mM. Four (4) control compounds were tested alongside described compounds, they were plated at a 100× concentration of 0.3 mM in quadruplicate.

Permeability Assessment

Compounds described were tested in triplicate in a single experiment at a final concentration of 3 µM. Cell passage used in the assay have passed QC criteria (see Quality Control section below). The study was conducted with Caco-2 cell monolayers cultured for 14 to 28 days, with cell passage numbers between 20 and 80. Assay (transport) buffer consisted of MHBSS, adjusted to pH 7.4, and 0.5% BSA. From the 100× compound plate, 8 µL of 100% DMSO stock solution of compounds were added to 800 µL assay buffer, mixed well, and filtered to remove any precipitate as a final preparation step before assay incubation. Targeted final test concentration of compounds described and control compounds was 3 µM. The filtrate represented the initial stock compound solution that was used as the donor solution for the assay (in both directions). The receiver solution was the assay buffer only.

Right before assay execution, each cell monolayer was washed 3 times with assay buffer to remove all traces of culture media. Permeability studies were initiated by adding 100 µL assay buffer plus/minus compound to the apical transwell compartment and 200 µL assay buffer plus/minus compound to the basolateral compartment of the 96-well transwell low-binding cluster plate. For apical-to-basolateral (A→B) permeability (absorptive direction), buffer containing compounds or control compounds (1× donor solution) were placed in the apical compartments (donor wells), while buffer alone was placed in the corresponding basolateral compartments (receiver wells). For basolateral-to-apical (B→A) permeability (secretive direction), buffer containing compounds or control compounds (1× donor solution) were placed in the basolateral compartments (donor wells), while buffer alone was placed in the corresponding apical compartments (receiver wells). Transwells were then incubated for 2 hours at 37° C. in a 95% relative humidity and 5% $CO_2$ atmosphere. Following incubation, 75 µL was removed from each apical and basolateral compartment and transferred to 96-well low-binding plates that had been previously loaded with 75 µL/well of acetonitrile containing 250 nM propranolol, 250 nM diclofenac, and 500 nM tolbutamide as internal standards. The samples were subsequently analyzed by LC-MS/MS to determine concentrations of compounds described and control compounds.

Analysis of Assay Samples

The concentrations of compounds described and control compounds in the assay samples were determined by LC-MS/MS. The AB Sciex 4500/5500/6500 multiplexed systems consisted of 2 sets of binary Shimadzu 20ADvp pumps with SCL-20Avp controllers for gradient elution, and LS1 autosampler, and an AB Sciex 4500/5500/6500 triple quadrupole mass spectrometer operated under electrospray ionization (ESI) mode. To obtain the optimum SRM conditions for sample analysis, MS/MS optimization for each compound was performed using DiscoveryQuant™ (AB Sciex) featuring saturation control with 5 µM standard solutions in a mixture of methanol and water (1:1, v/v) prepared from compound stock solutions. The optimization was performed using a flow injection analysis with an injection volume of 40 µL under isocratic elution of 75% of mobile phase B (0.2% formic acid in acetonitrile) and 25% mobile phase A (0.2% formic acid in water).

A 5-µL aliquot of sample was injected and then separated on a Kinetex XB-C18, 2.6 µm, 2.1×30 mm column under a gradient elution using mobile phase consisting of A (0.2% formic acid in water) and B (0.2% formic acid in acetonitrile).

TABLE A

Bidirectional Permeability in Caco-2 Cells Assay-
Mobile Phase Gradient for Sample Analysis

| Time (s) | Length (s) | Flow (mL/min) | Gradient | % A | % B |
|---|---|---|---|---|---|
| 0 | 5 | 0.7 | Step | 98 | 2 |
| 5 | 25 | 0.7 | Ramp | 2 | 98 |

TABLE A-continued

Bidirectional Permeability in Caco-2 Cells Assay-
Mobile Phase Gradient for Sample Analysis

| Time (s) | Length (s) | Flow (mL/min) | Gradient | % A | % B |
|---|---|---|---|---|---|
| 30 | 20 | 0.7 | Step | 2 | 98 |
| 50 | 30 | 0.7 | Step | 98 | 2 |

A = 0.2% formic acid in water;
B = 0.2% formic acid in acetonitrile

DiscoveryQuant™ automatically determined the optimal ionization polarity (positive or negative), precursor and product ions, declustering potential, and collision energy for compounds described and reference compounds. The optimized SRM MS/MS conditions were used for sample analysis. The peak area ratios of compounds described or control compound to internal standard were used for quantification. The peak area ratio of compound in the dosing solution was used to determine the compound concentration in the sample.

Data Analysis

The following results were reported for compounds described: permeability coefficient (Pc [nanometers per second]), efflux ratio and percent recovery.

The Pc value was calculated using the following equation:

$$Pc = \frac{C_{At} \times V_A}{S \times C_{D0} \times t}$$

Where:
$C_{At}$=concentration of the test compound in acceptor well after time t,
$V_A$=volume in acceptor well,
S=surface area of the membrane (0.11 cm$^2$),
$C_{D0}$=initial concentration of the test compound in donor well,
t=incubation time.

The efflux ratio was calculated as:

$$\text{Efflux Ratio} = \frac{Pc_{(B \to A)}}{Pc_{(A \to B)}}$$

Recovery (%) was calculated by expressing the total amount (nmol) of test compound present in the donor and receiver assay compartments at the end of incubation time (combined) as a fraction (percentage) of the total amount (nmol) of test compound added to the donor compartment before assay incubation. It was calculated using the following equation:

$$\% \text{ Recovery} = \frac{C_{Dt} \times V_D + C_{At} \times V_A}{C_{D0} \times V_D} \times 100$$

Where:
$C_{D0}$=initial concentration of the test compound in donor well,
$V_D$=volume in donor well,
$C_{Dt}$=concentration in donor well after time t,
$C_{At}$=concentration in acceptor well after time t,
$V_A$=volume in acceptor well.

Quality Control

The Caco-2 cells in one of the transwell plates used on the day of assay were evaluated for tight junction formation using trans-epithelial electrical resistance (TEER) measurement. TEER evaluation was performed using the EVOM resistance meter (World Precision Instruments, Sarasota, Florida). Each well of the transwell plate demonstrated a TEER value>600 Ω·cm$^2$, and the cell passage and all the plates of this plating batch were accepted for the assay.

Four (4) control compounds, with Pc values covering a range of permeability, were tested alongside the compounds described in each experiment. Acceptance criteria for this assay require that the results for the control compounds at 3 μM are within acceptable historical ranges. The acceptable ranges of the Pc values and efflux ratios observed historically for these 4 controls are shown in table B.

In these studies, the results for all control compounds were within their respective historical ranges. Thus, the assay data were accepted for the data analysis and evaluation of the compounds described bidirectional permeability in Caco-2 cells.

TABLE B

Bidirectional Permeability in Caco-2 Cells Assay -
Historical Results for Control Compounds

| Compound | Pc (A→B) (nm/s) | Pc (B→A) (nm/s) | Efflux Ratio |
|---|---|---|---|
| Digoxin | 18 ± 7 | 265 ± 74 | 14.7 |
| Nadolol | 20 ± 9 | 25 ± 11 | 1.3 |
| Atenolol | 19 ± 8 | 27 ± 10 | 1.4 |
| Verapamil | 120 ± 20 | 160 ± 40 | 1.3 |

Values are Mean ± Standard Deviation.
Pc = permeability coefficient.
A→B = apical-to-basolateral.
B→A = basolateral-to-apical.

TABLE 2

Potency and permiability data of exemplified compounds in
human whole blood assay and CACO2 permeability assay.

| Example number | Human Whole blood IFNa pSTAT5 IC$_{50}$ (μM) | CACO2 (A-B) (nm/s) | Efflux Ratio |
|---|---|---|---|
| 1 | 0.26 | 291 | 0.8 |
| 2 | 0.03 | 427 | 0.8 |
| 3 | 0.22 | 368 | 0.7 |
| 4 | 0.29 | 327 | 0.6 |
| 5 | 0.06 | 209 | 0.9 |
| 6 | 0.02 | 74 | 0.9 |
| 7 | 0.39 | 416 | 0.4 |
| 8 | 0.23 | 19 | <0.8 |
| 9 | 0.10 | 140 | 0.3 |
| 10 | 0.29 | 340 | 0.6 |
| 11 | 0.12 | 97 | 0.7 |
| 12 | 0.23 | 173 | 0.3 |
| 13 | 0.17 | 251 | 0.7 |
| 14 | 0.19 | 446 | 0.5 |
| 15 | 0.47 | 63 | 0.4 |
| 16 | 1.40 | 392 | 0.5 |
| 17 | 0.04 | 282 | 0.7 |
| 18 | 0.23 | 654 | 0.8 |
| 19 | 0.43 | 188 | 0.7 |
| 20 | 0.21 | 170 | 1.1 |
| 21 | 0.23 | 336 | 0.5 |
| 22 | 0.33 | 511 | 0.7 |
| 23 | 0.18 | 295 | 1.2 |
| 24 | 0.12 | 330 | 0.5 |
| 25 | 0.06 | 19 | 1.2 |
| 26 | 0.06 | 334 | 0.6 |
| 27 | 0.21 | 205 | 0.8 |

TABLE 2-continued

Potency and permiability data of exemplified compounds in human whole blood assay and CACO2 permeability assay.

| Example number | Human Whole blood IFNa pSTAT5 IC$_{50}$ (μM) | CACO2 (A-B) (nm/s) | Efflux Ratio |
|---|---|---|---|
| 28 | 0.37 | 280 | 0.5 |
| 29 | 0.05 | 379 | 0.5 |
| 30 | 0.06 | 299 | 0.7 |
| 31 | 0.11 | 313 | 0.8 |
| 32 | 0.22 | 195 | 0.9 |
| 33 | 0.08 | 345 | 0.8 |
| 34 | 0.16 | 209 | 0.3 |
| 35 | 0.02 | 429 | 0.6 |
| 36 | 0.05 | 328 | 0.6 |
| 37 | 0.02 | 494 | 0.9 |
| 38 | 0.44 | 330 | 0.4 |
| 39 | 0.42 | 188 | 0.4 |
| 40 | 0.04 | 259 | 0.8 |
| 41 | 0.08 | 339 | 0.5 |
| 42 | 0.05 | 287 | 0.4 |
| 43 | 0.28 | 134 | 0.6 |
| 44 | 0.04 | 246 | 0.5 |
| 45 | 0.06 | 58 | 0.5 |
| 46 | 0.01 | 381 | 0.4 |
| 47 | 0.11 | 340 | 0.3 |
| 48 | 6.80 | 301 | 0.3 |
| 49 | Pro-drug | — | — |
| 50 | 0.17 | 265 | 0.4 |
| 51 | 0.11 | 429 | 0.9 |
| 52 | 0.02 | 482 | 0.6 |
| 53 | 0.17 | 425 | 0.7 |
| 54 | 0.49 | 180 | 0.4 |
| 55 | 0.48 | 507 | 0.6 |
| 56 | 0.29 | 432 | 0.6 |
| 57 | 0.01 | 816 | 0.4 |
| 58 | 0.23 | 314 | 0.6 |
| 59 | 0.25 | 351 | 0.8 |
| 60 | 0.13 | 340 | 0.5 |
| 61 | 0.48 | 383 | 0.4 |
| 62 | 0.12 | 432 | 0.4 |
| 63 | 0.02 | 39 | <0.4 |
| 64 | 0.25 | 17 | <0.9 |
| 65 | 0.004 | 117 | 1.6 |
| 66 | 0.0002 | 222 | 0.3 |
| 67 | 0.086 | 286 | 0.9 |
| 68 | 0.29 | 594 | 0.4 |
| 69 | 0.003 | 362 | 0.6 |

TABLE 3

Ratio of measured concentrations of example compounds in brain and plasma homogenate after 1 hr of oral administration 10 mpk compound

| Example number | Ratio of exposure in brain to plasma (mouse) (1 h, 10 mpk, po) |
|---|---|
| 1 | 0.7 |
| 2 | 0.1* |
| 3 | 0.3 |
| 4 | 0.8 |
| 5 | 0.2 |
| 7 | 0.5** |
| 9 | 0.2 |
| 10 | 0.1 |
| 11 | 0.5 |
| 12 | 0.7 |
| 13 | 0.4 |
| 14 | 0.8 |
| 17 | 0.2*** |
| 24 | 0.2 |
| 36 | 0.8 |
| 37 | 0.1 |
| 41 | 0.3 |
| 49 | 0.6**** |
| 62 | 0.6***** |

*Example compound was administered as a 2 mpk iv solution dose.
**Example compound was administered as a 2 mpk iv solution dose and the exposures were measured at 40 minutes.
***Example compound was administrated as a nanosuspension in a vehicle of 0.5% methocel A4M; 0.1% tween 80; 99.4% water
****Example 49 is a prodrug of Example 36; thus, exposure was measured as the concentration of Example 36 observed. Dosing was done at a parent equivalent of 5 mpk and was done as a solution in vehicle: 0.5% methocel; 0.1% tween 80; 99.4% water
*****Example compound was administered as a 2 mpk iv solution dose and the exposures were measured at 90 minutes.

TABLE 4

Comparison of CNS penetration profiles of Examples 36 and 11 and prior art:

Example 36

A (Example 1 of US2021/0032220)

Example 11

B (Example 58 of WO 2020156311 A1)

| Compound | Ratio of exposure in brain to plasma (mouse) (1 h, 10 mpk, po) |
|---|---|
| Example 36 | 0.8 |
| A | 0.06 |
| Example 11 | 0.5 |
| B | 0.02 |

It has surprisingly been found that the 1,2,3-substituted triazoles compounds of the invention have a significantly higher brain to plasma ration than structurally similar 1,2,4-substituted triazole compounds. Thus, the compounds of the invention are able to penetrate the blood-brain barrier and may be useful for the treatment of certain neurological disorders.
We claim:
1. A compound having the structure
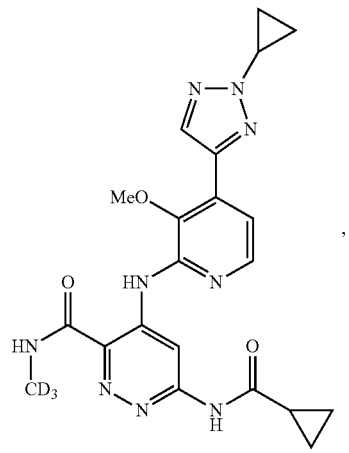 [SMILES: [2H]C([2H])([2H])NC(=O)c1nnc(NC(=O)C2CC2)cc1Nc1nccc(-c2cnn(C3CC3)n2)c1OC]
,
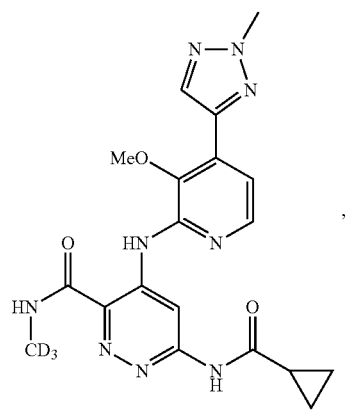 [SMILES: [2H]C([2H])([2H])NC(=O)c1nnc(NC(=O)C2CC2)cc1Nc1nccc(-c2cnn(C)n2)c1OC]
,
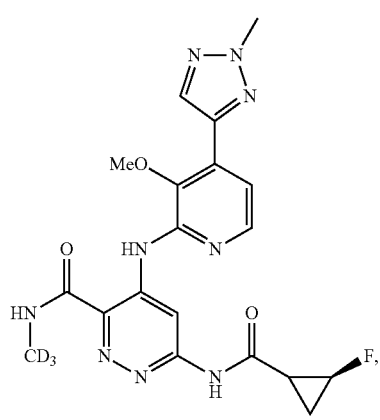
,
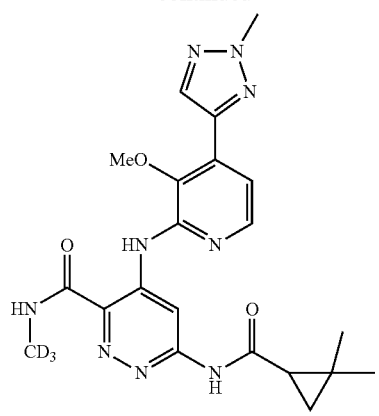
,
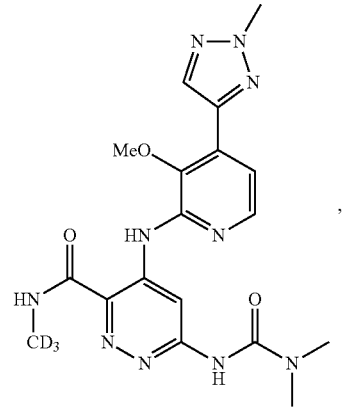 [SMILES: [2H]C([2H])([2H])NC(=O)c1nnc(NC(=O)N(C)C)cc1Nc1nccc(-c2cnn(C)n2)c1OC]
,
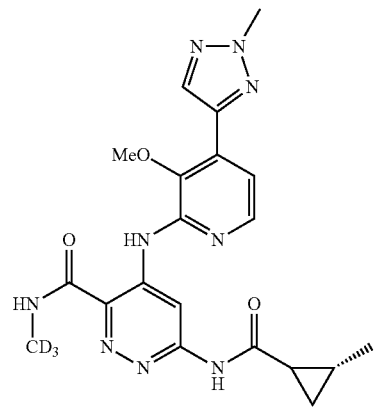
,
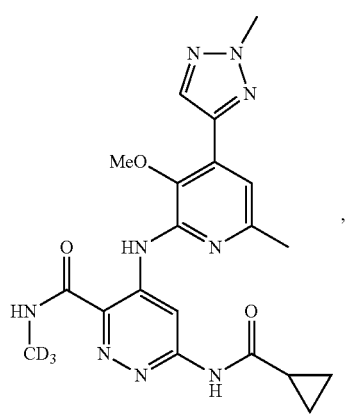 [SMILES: [2H]C([2H])([2H])NC(=O)c1nnc(NC(=O)C2CC2)cc1Nc1nc(C)cc(-c2cnn(C)n2)c1OC]
, -continued
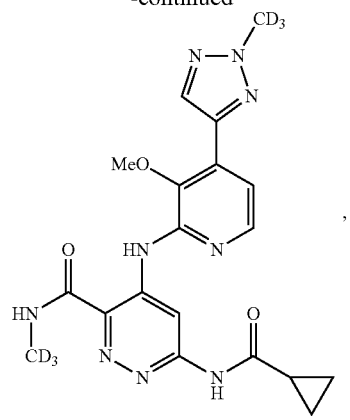
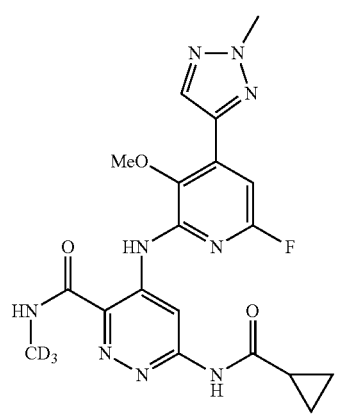
or,
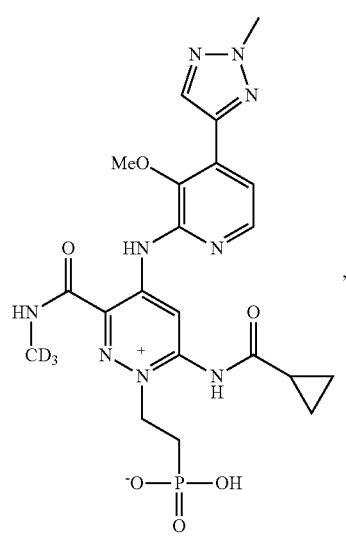,
or a pharmaceutically-acceptable salt thereof.
2. The compound according to claim 1 which is
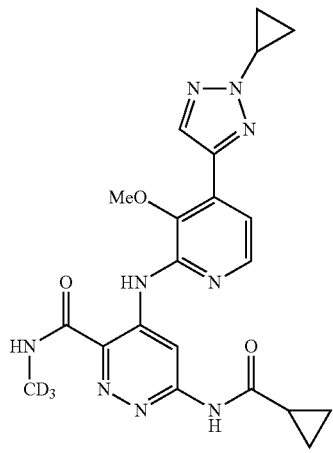,
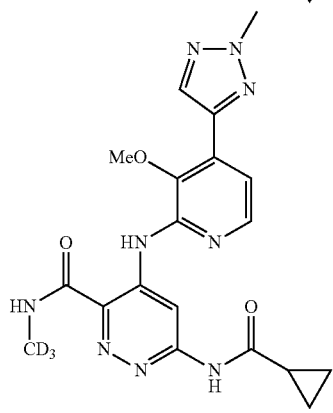,

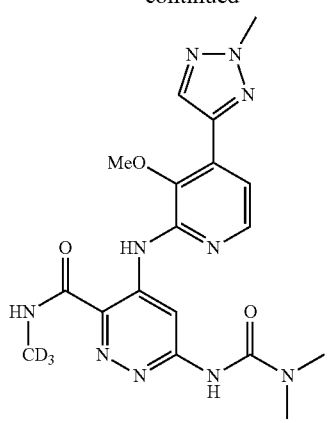
or
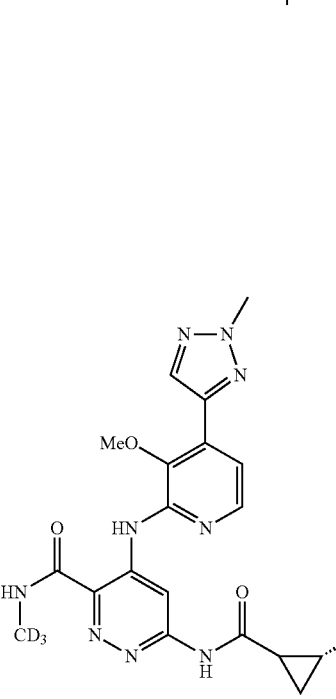
or a pharmaceutically-acceptable salt thereof.
3. The compound according to claim 1 which is
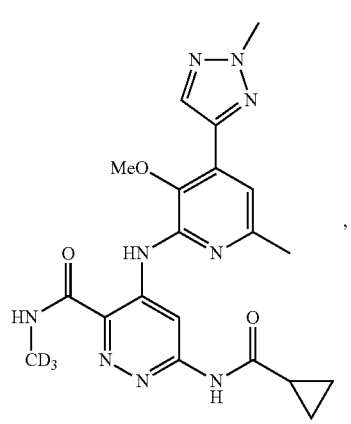
,
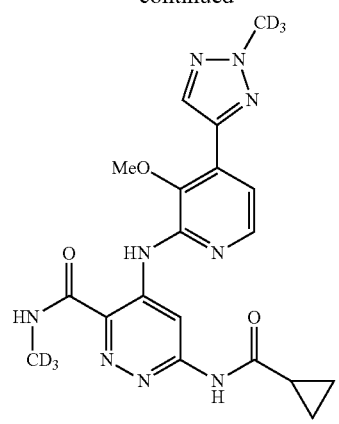
,
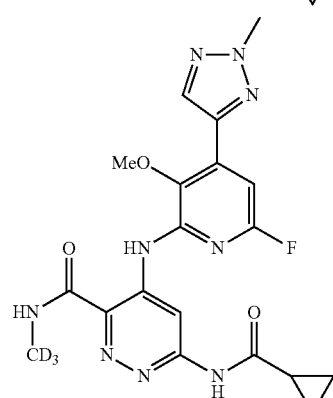
,
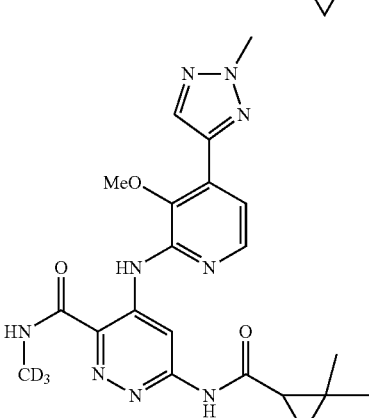
,
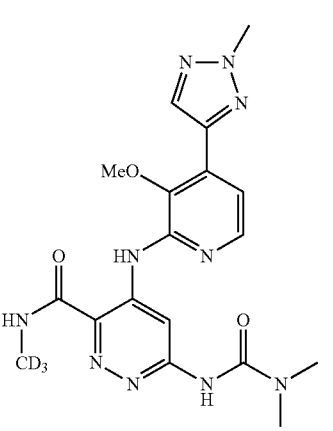
or

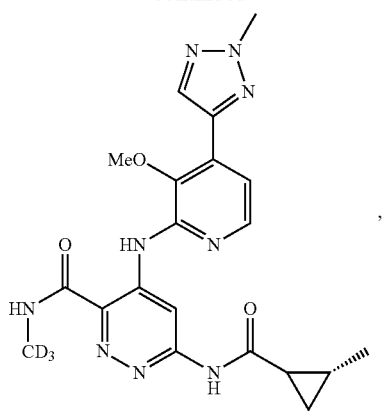
or a pharmaceutically-acceptable salt thereof.
4. The compound according to claim 2 which is
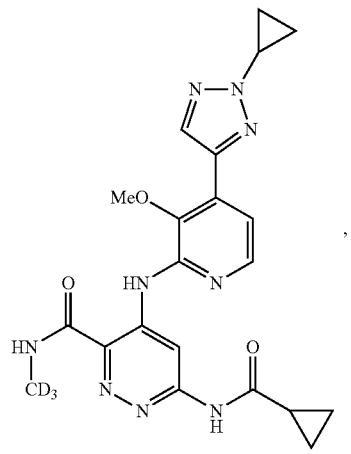
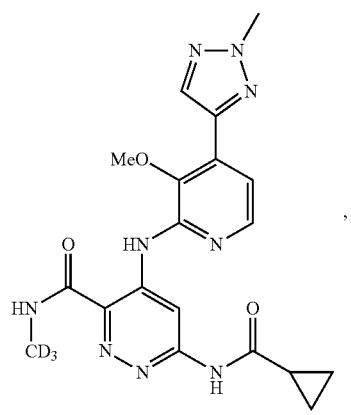
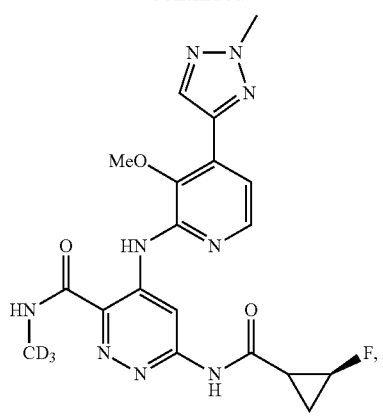
or a pharmaceutically-acceptable salt thereof.
5. The compound according to claim 2 which is
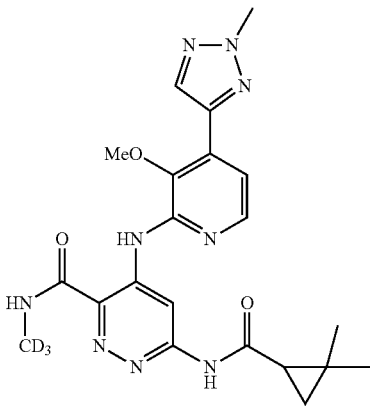
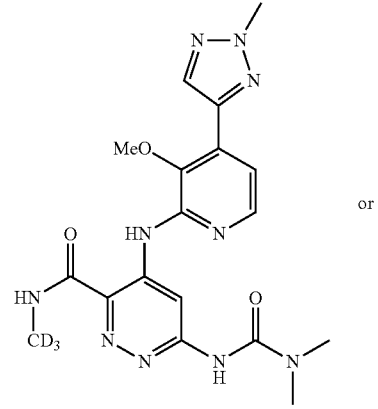

-continued
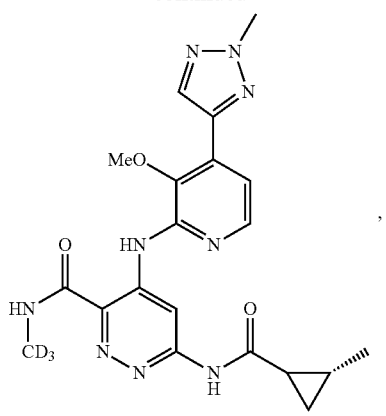
or a pharmaceutically-acceptable salt thereof.
6. The compound according to claim 3 which is
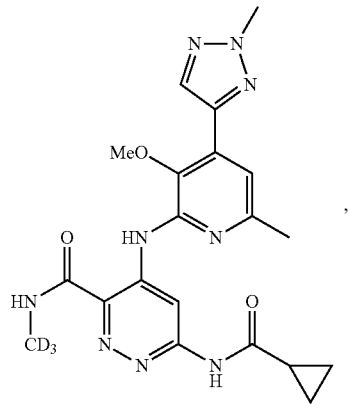
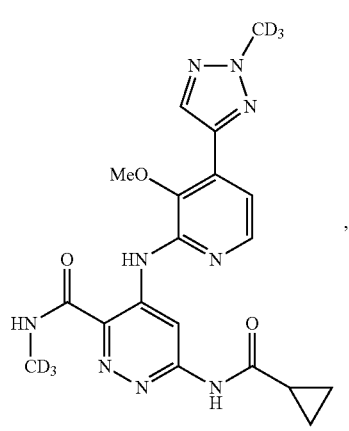
-continued
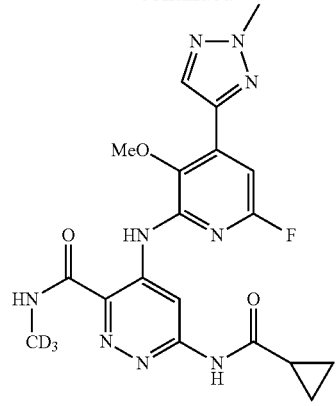
or a pharmaceutically-acceptable salt thereof.
7. The compound according to claim 4 having the structure
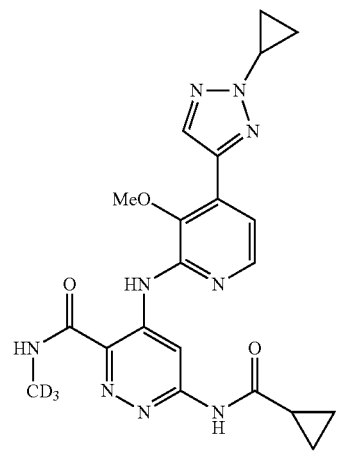
8. The compound according to claim 4 having the structure
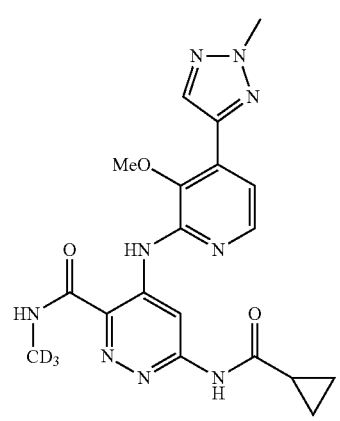

9. The compound according to claim 4 having the structure
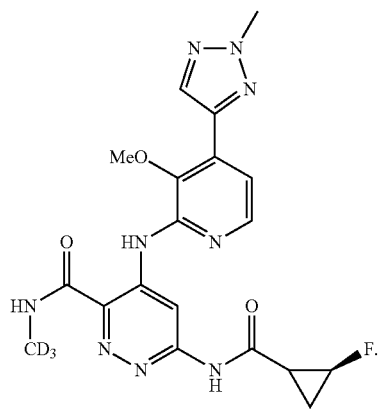
10. The compound according to claim 5 having the structure
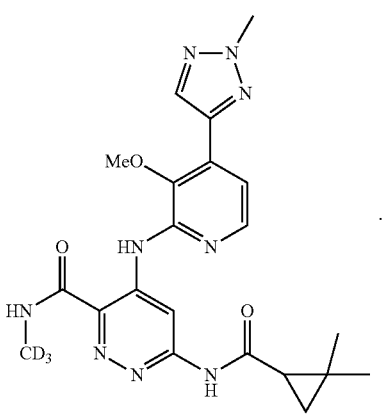
11. The compound according to claim 5 having the structure
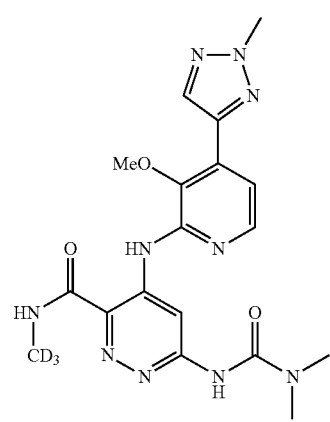
12. The compound according to claim 5 having the structure
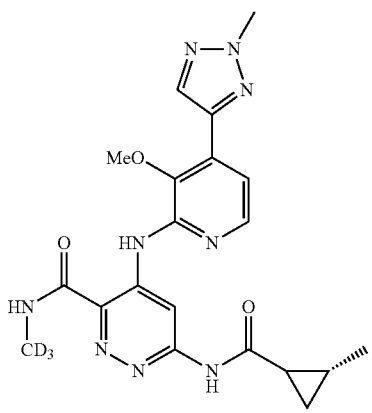
13. The compound according to claim 6 having the structure
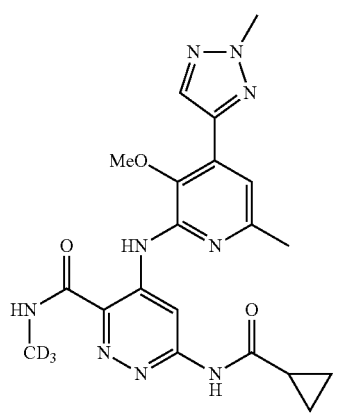
14. The compound according to claim 6 having the structure
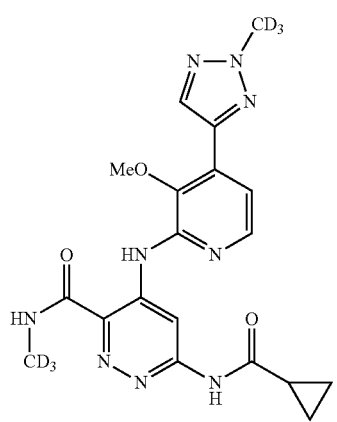

15. The compound according to claim 6 having the structure

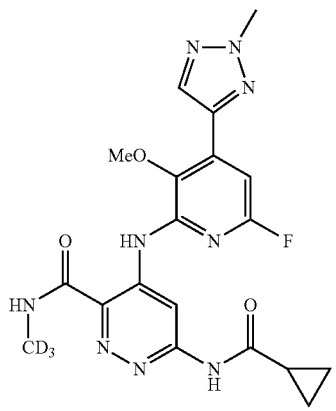

16. The compound according to claim 1 having the structure

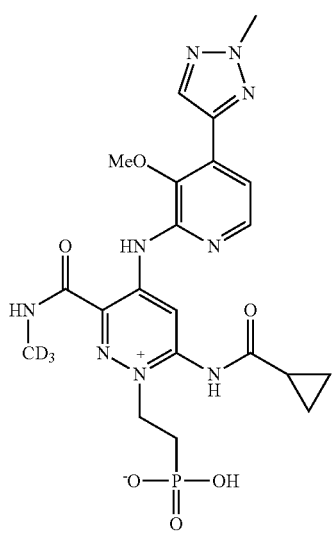

17. A compound having the structure

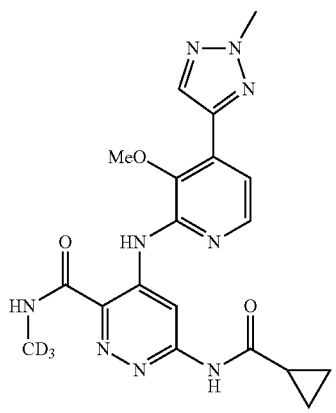

18. A pharmaceutically acceptable salt of a compound having the structure

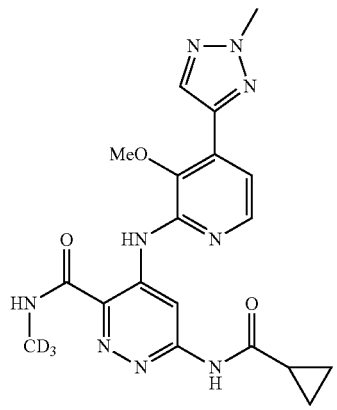

19. A compound having the structure

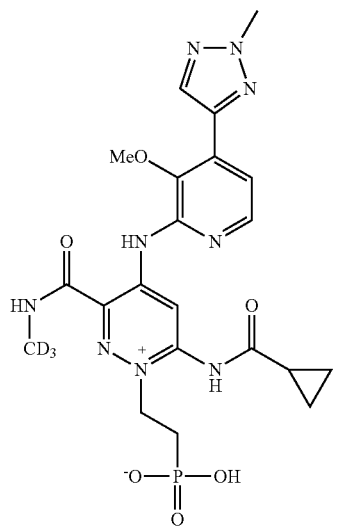

20. A compound or a pharmaceutically acceptable salt thereof selected from
6-cyclopropaneamido-4-{[4-(2-cyclopropyl-2H-1,2,3-triazol-4-yl)-3-methoxypyridin-2-yl]amino}-N—($^2$H3) methylpyridazine-3-carboxamide,
6-(cyclopropanecarboxamido)-4-((3-methoxy-4-(2-methyl-2H-1,2,3-triazol-4-yl)pyridin-2-yl)amino)-N-(methyl-d3)pyridazine-3-carboxamide,
6-((1S,2S)-2-fluorocyclopropane-1-carboxamido)-4-((3-methoxy-4-(2-methyl-2H-1,2,3-triazol-4-yl)pyridin-2-yl)amino)-N-(methyl-d$_3$)pyridazine-3-carboxamide,
6-(2,2-dimethylcyclopropane-1-carboxamido)-4-((3-methoxy-4-(2-methyl-2H-1,2,3-triazol-4-yl)pyridin-2-yl)amino)-N-(methyl-d$_3$)pyridazine-3-carboxamide,
6-(3,3-dimethylureido)-4-((3-methoxy-4-(2-methyl-2H-1,2,3-triazol-4-yl)pyridin-2-yl)amino)-N-(methyl-d$_3$) pyridazine-3-carboxamide,
4-((3-methoxy-4-(2-methyl-2H-1,2,3-triazol-4-yl)pyridin-2-yl)amino)-N-(methyl-d$_3$)-6-((1S,2R)-2-methylcyclopropane-1-carboxamido)pyridazine-3-carboxamide, 6-(cyclopropanecarboxamido)-4-((3-methoxy-6-methyl-4-(2-methyl-2H-1,2,3-triazol-4-yl)pyridin-2-yl)amino)-N-(methyl-d$_3$)pyridazine-3-carboxamide, (E)-(6-((cyclopropanecarbonyl)imino)-4-((3-methoxy-4-(2-methyl-2H-1,2,3-triazol-4-yl)pyridin-2-yl)amino)-3-((methyl-d3)carbamoyl)pyridazin-1(6H)-yl)methyl dihydrogen phosphate, 6-(cyclopropane-carboxamido)-4-((3-methoxy-4-(2-(methyl-d$_3$)-2H-1,2,3-triazol-4-yl)pyridin-2-yl)amino)-N-(methyl-d$_3$)pyridazine-3-carboxamide, or 6-(Cyclopropanecarboxamido)-4-((6-fluoro-3-methoxy-4-(2-methyl-2H-1,2,3-triazol-4-yl)pyridin-2-yl)amino)-N-(methyl-d$_3$)pyridazine-3-carboxamide.

21. A pharmaceutical composition comprising one or more compounds according to claim 1 and a pharmaceutically acceptable carrier or diluent.

22. A method of treating a disease, comprising administering to a patient in need of such treatment a therapeutically effective amount of a compound according to claim 1, wherein the disease is a neurodegenerative disease.

23. A method of treating a disease, comprising administering to a patient in need of such treatment a therapeutically effective amount of a compound according to claim 22, wherein the disease is a neurodegenerative disease selected from Alzheimer's disease, Parkinson's disease, ALS or multiple sclerosis.

* * * * *

UNITED STATES PATENT AND TRADEMARK OFFICE
CERTIFICATE OF CORRECTION

| | |
|---|---|
| PATENT NO. | : 11,866,414 B2 |
| APPLICATION NO. | : 17/743557 |
| DATED | : January 9, 2024 |
| INVENTOR(S) | : Steven Spergel et al. |

It is certified that error appears in the above-identified patent and that said Letters Patent is hereby corrected as shown below:

In the Specification

Column 1, Line 9, Delete "63/318,148," and insert -- 63/318,149, --.

Signed and Sealed this
Twenty-seventh Day of February, 2024

Katherine Kelly Vidal
*Director of the United States Patent and Trademark Office*